US007517531B2

(12) United States Patent
Whitehead et al.

(10) Patent No.: US 7,517,531 B2
(45) Date of Patent: Apr. 14, 2009

(54) DENGUE TETRAVALENT VACCINE CONTAINING A COMMON 30 NUCLEOTIDE DELETION IN THE 3'-UTR OF DENGUE TYPES 1,2,3, AND 4, OR ANTIGENIC CHIMERIC DENGUE VIRUSES 1,2,3, AND 4

(75) Inventors: Stephen S. Whitehead, Montgomery Village, MD (US); Brian R. Murphy, Bethesda, MD (US); Lewis Markoff, Bethesda, MD (US); Barry Falgout, Rockville, MD (US); Joseph Blaney, Frederick, MD (US); Kathryn Hanley, Las Cruces, NM (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 635 days.

(21) Appl. No.: 10/970,640

(22) Filed: Oct. 21, 2004

(65) Prior Publication Data

US 2007/0009552 A1 Jan. 11, 2007

Related U.S. Application Data

(63) Continuation of application No. PCT/US03/13279, filed on Apr. 25, 2003.

(60) Provisional application No. 60/377,860, filed on May 3, 2002, provisional application No. 60/436,500, filed on Dec. 23, 2002.

(51) Int. Cl.
*A61K 39/295* (2006.01)
*C12N 7/04* (2006.01)

(52) U.S. Cl. .............. 424/202.1; 424/218.1; 424/199.1; 424/205.1; 435/235.1; 435/320.1; 435/236

(58) Field of Classification Search ....................... None
See application file for complete search history.

(56) References Cited

FOREIGN PATENT DOCUMENTS

WO    WO 02/095075    11/2002

OTHER PUBLICATIONS

Durbin et al (American Journal of Tropical Medicine and Hygiene 65:405-413, 2001; cited in IDS).*
Lai et al (Clinical and Diagnostic Virology 10:173-179, 1998).*
Olsthoorn et al (RNA 7:1370-1377, 2001).*
Blaney et al (Journal of Virology 79:5516-5528, 2005, not prior art).*
Proutski et al (Virus Reseach 64:107-123, 1999).*
An, J. et al. 1999 "Development of a novel mouse model for dengue virus infection." *Virology* 263:70-77.
Barrett, A.D.T. 1997 "Yellow fever vaccines" *Biologicals* 25:17-25.

(Continued)

*Primary Examiner*—Mary E Mosher
(74) *Attorney, Agent, or Firm*—Knobbe, Martens, Olson & Bear LLP

(57) ABSTRACT

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

42 Claims, 15 Drawing Sheets

OTHER PUBLICATIONS

Blackwell, J.L. et al. 1997 "Translation elongation factor-1 alpha interacts with the 3' stem-loop region of West Nile virus genomic RNA" *J. Virol.* 71:6433-44.

Blaney, J.E. Jr. et al. 2001 "Chemical mutagenesis of dengue virus type 4 yields mutant viruses which are temperature sensitive in vero cells or human liver cells and attenuated in mice" *J. Virol.* 75:9731-40.

Blaney, J.E. Jr. et al. 2002 "Genetic basis of attenuation of dengue virus type 4 small plaque mutants with restricted replication in suckling mice and in SCID mice transplanted with human liver cells." *Virology* 300:125-139.

Blaney, J.E Jr. et al. 2003 "Mutations which enhance the replication of dengue virus type 4 and an antigenic chimeric dengue virus type 2/4 vaccine candidate in Vero cells" *Vaccine* 21:4317-27.

Blaney, J.E. Jr. et al. 2004 "Genetically modified, live attenuated dengue virus type 3 vaccine candidates." *Am. J. Trop. Med. Hyg.* 71:811-821.

Blaney, J.E. Jr. et al. 2004 "Vaccine candidates derived from a novel infectious cDNA clone of an American genotype dengue virus type 2." *BMC Infect. Dis.* 4:39 (10 pages).

Blok, J. et al. 1992 "Comparison of a dengue-2 virus and its candidate vaccine derivative: sequence relationships with the flaviviruses and other viruses" *Virology* 187:573-90.

Bray, M. et al. 1991 "Construction of intertypic chimeric dengue viruses by substitution of structural protein genes" *PNAS USA* 88:10342-6.

Bray, M. et al. 1996 "Monkeys immunized with intertypic chimeric dengue viruses are protected against wild-type virus challenge" *J. Virol.* 70:4162-6.

Bray, M. et al. 1998 "Genetic determinants responsible for acquisition of dengue type 2 virus mouse neurovirulence" *J. Virol.* 72:1647-51.

Brinton, M.A. et al. 1986 "The 3'-nucleotides of flavivirus genomic RNA form a conserved secondary structure," *Virology* 153:113-121.

Burke, D.S. et al. 1988 "A prospective study of dengue infections in Bangkok" *Am. J. Trop. Med. Hyg.* 38:172-80.

Butrapet, S. et al. 2000 "Attenuation markers of a candidate dengue type 2 vaccine virus, strain 16681 (PDK-53), are defined by mutations in the 5' noncoding region and nonstructural proteins 1 and 3." *J. Virol.* 74:3011-3019.

Chambers, T.J. et al. 2003 "Yellow fever virus/dengue-2 virus and yellow fever virus/dengue-4 virus chimeras: biological characterization, immunogenicity, and protection against dengue encephalitis in the mouse model" *J. Virol.* 77:3655-68.

Chen, W. et al. 1995 "Construction of intertypic chimeric dengue viruses exhibition type 3 antigenicity and neurovirulence for mice" *J. Virol.* 69:5186-5190.

Durbin, A.P. et al. 2001 "Attenuation and immunogenicity in humans of a live dengue virus type-4 vaccine candidate with a 30 nucleotide deletion in its 3'-untranslated region." *Am J. Trop. Med. Hyg.* 65:405-413.

Gubler, D.J. et al. 1999 "Impact of dengue/dengue hemorrhagic fever on the developing world." *Adv. Virus Res.* 53:35-70.

Guillot, S. et al. 2000 "Natural genetic exchanges between vaccine and wild poliovirus strains in humans." *J. Virol.* 74:8434-8443.

Guirakhoo, F. et al. 2001 "Construction, safety, and immunogenicity in nonhuman primates of a chimeric yellow fever-dengue virus tetravalent vaccine." *J. Virol.* 75:7290-7304.

Guirakhoo, F. et al. 2002 "Viremia and immunogenicity in nonhuman primates of a tetravalent yellow fever-dengue chimeric vaccine: genetic reconstructions, dose adjustment, and antibody responses against wild-type dengue virus isolates" *Virology* 298:146-59.

Hahn, C.S. et al. 1987 "Conserved elements in the 3' untranslated region of flavivirus RNAs and potential cyclization sequences." *J. Mol. Biol.* 198:33-41.

Hanley, K.A. et al. 2004 "Introduction of mutations into the non-structural genes or 3' untranslated region of an attenuated dengue virus type 4 vaccine candidate further decreases replication in rhesus monkeys while retaining protective immunity." *Vaccine* 22:3440-3448.

Huang, C.Y.-H. et al. 2000 "Chimeric dengue type 2 (vaccine strain PDK-53)/dengue type 1 virus as a potential candidate dengue type 1 virus vaccine." *J. Virol.* 74:3020-3028.

Kew, O. et al. 2002 "Outbreak of poliomyelitis in Hispaniola associated with circulating type 1 vaccine-derived poliovirus" *Science* 296:356-9.

Khromykh, A.A. et al. 1996 "RNA binding properties of core protein of the flavivirus Kunjin" *Arch. Virol.* 141:685-99.

Lai, C.J. et al. 1991 "Infectious RNA transcribed from stably cloned full-length cDNA of dengue type 4 virus" *PNAS USA* 88:5139-43.

Markoff, L. et al. 1997 "A conserved internal hydrophobic domain mediates the stable membrane integration of the dengue virus capsid protein" *Virology* 233:105-17.

Markoff, L. et al. 2002 "Derivation and characterization of a dengue type 1 host range-restricted mutant virus that is attenuated and highly immunogenic in monkeys." *J. Virol.* 76:3318-3328.

Mathew, A. et al. 1998 "Predominance of HLA-restricted cytotoxic T-lymphocyte responses to serotype-cross-reactive epitopes on nonstructual proteins following natural secondary dengue virus infection." *J. Virol.* 72:3999-4004.

Men, R. et al. 1996 "Dengue type 4 virus mutants containing deletions in the 3' noncoding region of the RNA genome: analysis of growth restriction in cell culture and altered viremia pattern and immunogenicity in rhesus monkeys." *J. Virol.* 70:3930-3937.

Pletnev, A.G. et al. 1992 "Construction and characterization of chimeric tick-borne encepalitis/dengue type 4 viruses" *PNAS USA* 89:10532-6.

Pletnev, A.G. et al. 1993 "Chimeric tick-borne encephalitis and dengue type 4 viruses: effects of mutations on neurovirulence in mice" *J. Virol.* 67:4956-63.

Pletnev, A.G. et al. 1998 "Attenuation of the Langat tick-borne flavivirus by chimerization with mosquito-borne flavivirus dengue type 4" *PNAS USA* 95:1746-51.

Pletnev, A.G. et al. 2002 "West Nile virus/dengue type 4 virus chimeras that are reduced in neurovirulence and peripheral virulence without loss of immunogenicity or protective efficacy" *PNAS USA* 99:3036-41.

Polo, S. et al. 1997 "Infectious RNA transcripts from full-length dengue virus type 2 cDNA clones made in yeast." *J. Virol.* 71:5366-5374.

Proutski, V. et al. 1997 "Secondary structure of the 3' untranslated region of flaviviruses: similarities and differences." *Nucleic Acids Res.* 25:1194-1202.

Puri, B. et al. 1997 "Molecular analysis of dengue virus attenuation after serial passage in primary dog kidney cells." *J. Gen. Virol.* 78:2287-2291.

Puri, B. et al. 2000 "Construction of a full length infectious clone for dengue-1 virus Western Pacific, 74 strain." *Virus Genes* 20:57-63.

Rauscher, S. et al. 1997 "Secondary structure of the 3'-noncoding region of flavivirus genomes: comparative analysis of base pairing probabilities." *RNA* 3:779-791.

Rice, C.M. et al. 1985 "Nucleotide sequence of yellow fever virus: implications for flavivirus gene expression and evolution" *Science* 229:726-33.

Rosen, L. et al. 1985 "Comparative susceptibility of mosquito species and strains to oral and parenteral infection with dengue and Japanese encephalitis viruses." *Am. J. Trop. Med. Hyg.* 34:603-615.

Rosen, L. et al. 1985 "Comparative susceptibility of five species of *Toxrhynchites* mosquitoes to parenteral infection with dengue and other flaviviruses." *Am. J. Trop. Med. Hyg.* 34:805-809.

Ta, M. et al. 2000 "Mov34 protein from mouse brain interacts with the 3' noncoding region of Japanese encephalitis virus" *J. Virol.* 74:5108-15.

Thein, S. et al. 1997 "Risk factors in dengue shock syndrome" *Am. J. Trop. Med. Hyg.* 56:566-72.

Troyer, J.M. et al. 2001 "A live attenuated recombinant dengue-4 virus vaccine candidate with restricted capacity for dissemination in mosquitoes and lack of transmission from vaccines to mosquitoes." *Am. J. Trop. Med. Hyg.* 65:414-419.

Whitehead, S.S. et al. 2003 "A live, attenuated dengue virus type 1 vaccine candidate with a 30-nucleotide deletion in the 3' untranslated region is highly attenuated and immunogenic in monkeys" *J. Virol.* 77:1653-1657.

Whitehead, S.S. et al. 2003 "Substitution of the structural genes of dengue virus type 4 with those of type 2 results in chimeric vaccine candidates which are attenuated for mosquitoes, mice, and rhesus monkeys." *Vaccine* 21:4307-4316.

Worobey, M. et al. 1999 "Widespread intra-serotype recombinant in natural populations of dengue virus." *PNAS USA* 96:7352-7357.

Zeng, L. et al. 1998 "Identification of specific nucleotide sequence within the conserved 3'-SL in the dengue type 2 virus genome required for replication." *J. Virol.* 72:7510-7522.

Bhamarapravati, N. et al., 2000, "Live attenuated tetravalent dengue vaccine," Vaccine 18: 44-47.

Blaney, Jr, J.E. et al., 2006, "Development of a Live Attenuated Dengue Virus Vaccine Using Reverse Genetics," Viral Immunol. 19:10-32.

Durbin, A.P. et al., 2003, "The Recombinant Live Attenuated Dengue 4 Candidate Vaccine rDEN4delta30 is Safe, Immunogenic, and Highly Infectious in Healthy Adults," Am. J. Trop. Med. Hyg. p. 361, Abstract 379.

Hanley, K.A. et al., 2002, "Paired Charge-to-Alanine Mutagenesis of Dengue Virus Type 4 NS5 Generates Mutants with Temperature-Sensitive, Host Range, and Mouse Attenuation Phenotypes," J. Virol. 76: 525-531.

Kanesa-Thasan, N. et al., 2001, "Safety and immunogenicity of attenuated dengue virus vaccines (Aventis Pasteur) in human volunteers," Vaccine 19: 3179-3188.

* cited by examiner

FIG. 12B

```
             DEN4                 BglII           DEN1
Junction 1: -CAGTTTGTTTGAATAGAGAGCAGATCTCTGGAAAAATGAACAACCAACGG-
                                                   MetAsnAsnGlnArg DEN1                    XhoI           DEN4
Junction 2: -CTGCTGACATGGCTAGGATTAAACTCGAGGAACACTTCAATGGCTATGACG-
             LeuLeuThrTrpLeuGlyLeuAsnSerArgAsnThrSerMetAlaMetThr DEN4                   PstI            DEN1
Junction 3: -ATCTTGAACGGGAGAAAAAGGTCTGCAGCCATGCTCCTCATGCTGCTGCCC-
             IleLeuAsnGlyArgLysArgSerAlaAlaMetLeuLeuMetLeuLeuPro
```

DENGUE TETRAVALENT VACCINE CONTAINING A COMMON 30 NUCLEOTIDE DELETION IN THE 3'-UTR OF DENGUE TYPES 1,2,3, AND 4, OR ANTIGENIC CHIMERIC DENGUE VIRUSES 1,2,3, AND 4

RELATED APPLICATIONS

This application is a continuation and claims the benefit of priority of International Application No. PCT/US03/13279 filed Apr. 25, 2003, designating the United States of America and published in English on Nov. 13, 2003, as WO 03/092592, which claims the benefit of priority of U.S. Provisional Application No. 60/377,860 filed May 3, 2002 and U.S. Provisional Application No. 60/436,500 filed Dec. 23, 2002, all of which are hereby expressly incorporated by reference in their entireties.

FIELD OF THE INVENTION

The invention relates to a dengue virus tetravalent vaccine containing a common 30 nucleotide deletion ($\Delta 30$) in the 3'-untranslated region of the genome of dengue virus serotypes 1, 2, 3, and 4, or antigenic chimeric dengue viruses of serotypes 1, 2, 3, and 4.

BACKGROUND OF THE INVENTION

Dengue virus is a positive-sense RNA virus belonging to the *Flavivirus* genus of the family Flaviviridae. Dengue virus is widely distributed throughout the tropical and semitropical regions of the world and is transmitted to humans by mosquito vectors. Dengue virus is a leading cause of hospitalization and death in children in at least eight tropical Asian countries (WHO 1997 *Dengue Haemorrhagic Fever: Diagnosis, Treatment, Prevention, and Control* 2nd Edition, Geneva). There are four serotypes of dengue virus (DEN1, DEN2, DEN3, and DEN4) that annually cause an estimated 50-100 million cases of dengue fever and 500,000 cases of the more severe form of dengue virus infection known as dengue hemorrhagic fever/dengue shock syndrome (DHF/DSS) (Gubler, D. J. and Meltzer, M. 1999 *Adv Virus Res* 53:35-70). This latter disease is seen predominantly in children and adults experiencing a second dengue virus infection with a serotype different than that of their first dengue virus infection and in primary infection of infants who still have circulating dengue-specific maternal antibody (Burke, D. S. et al. 1988 *Am J Trop Med Hyg* 38:172-180; Halstead, S. B. et al. 1969 *Am J Trop Med Hyg* 18:997-1021; Thein, S. et al. 1997 *Am J Trop Med Hyg* 56:566-575). A dengue vaccine is needed to lessen disease burden caused by dengue virus, but none is licensed. Because of the association of more severe disease with secondary dengue virus infection, a successful vaccine must simultaneously induce immunity to all four serotypes. Immunity is primarily mediated by neutralizing antibody directed against the envelope (E) glycoprotein, a virion structural protein. Infection with one serotype induces long-lived homotypic immunity and a short-lived heterotypic immunity (Sabin, A. 1955 *Am J Trop Med Hyg* 4:198-207). Therefore, the goal of immunization is to induce a long-lived neutralizing antibody response against DEN1, DEN2, DEN3, and DEN4, which can best be achieved economically using live attenuated virus vaccines. This is a reasonable goal since a live attenuated vaccine has already been developed for the related yellow fever virus, another mosquito-borne flavivirus present in tropical and semitropical regions of the world (Monath, T. P. and Heinz, F. X. 1996 in: *Fields Virology*, Fields, D. M et al. eds. Philadelphia: Lippincott-Raven Publishers, pp. 961-1034).

Several live attenuated dengue vaccine candidates have been developed and evaluated in humans and non-human primates. The first live attenuated dengue vaccine candidates were host range mutants developed by serial passage of wild-type dengue viruses in the brains of mice and selection of mutants attenuated for humans (Kimura, R. and Hotta, S. 1944 *Jpn J Bacteriol* 1:96-99; Sabin, A. B. and Schlesinger, R. W. 1945 *Science* 101:640; Wisserman, C. L. et al. 1963 *Am J Trop Med Hyg* 12:620-623). Although these candidate vaccine viruses were immunogenic in humans, their poor growth in cell culture discouraged further development. Additional live attenuated DEN1, DEN2, DEN3, and DEN4 vaccine candidates have been developed by serial passage in non-human tissue culture (Angsubhakorn, S. et al. 1994 *Southeast Asian J Trop Med Public Health* 25:554-559; Bancroft, W. H. et al. 1981 *Infect Immun* 31:698-703; Bhamarapravati, N. et al. 1987 *Bull World Health Organ* 65:189-195; Eckels, K. H. et al. 1984 *Am J Trop Med Hyg* 33:684-698; Hoke, C. H. Jr. et al. 1990 *Am J Trop Med Hyg* 43:219-226; Kanesa-Thasan, N. et al. 2001 *Vaccine* 19:3179-3188) or by chemical mutagenesis (McKee, K. T. et al. 1987 *Am J Trop Med Hyg* 36:435-442). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-Thasan, N. et al. 2001 *Vaccine* 19:3179-3188; Bhamarapravati, N. and Sutee, Y. 2000 *Vaccine* 18:44-47).

Two major advances using recombinant DNA technology have recently made it possible to develop additional promising live attenuated dengue virus vaccine candidates. First, methods have been developed to recover infectious dengue virus from cells transfected with RNA transcripts derived from a full-length cDNA clone of the dengue virus genome, thus making it possible to derive infectious viruses bearing attenuating mutations that have been introduced into the cDNA clone by site-directed mutagenesis (Lai, C. J. et al. 1991 *PNAS USA* 88:5139-5143). Second, it is possible to produce antigenic chimeric viruses in which the structural protein coding region of the full-length cDNA clone of dengue virus is replaced by that of a different dengue virus serotype or from a more divergent flavivirus (Bray, M. and Lai, C. J. 1991 *PNAS USA* 88:10342-10346; Chen, W. et al. 1995 *J Virol* 69:5186-5190; Huang, C. Y. et al. 2000 *J Virol* 74:3020-3028; Pletnev, A. G. and Men, R. 1998 *PNAS USA* 95:1746-1751). These techniques have been used to construct intertypic chimeric dengue viruses that have been shown to be effective in protecting monkeys against homologous dengue virus challenge (Bray, M. et al. 1996 *J Virol* 70:4162-4166). A similar strategy is also being used to develop attenuated antigenic chimeric dengue virus vaccines based on the attenuation of the yellow fever vaccine virus or the attenuation of the cell-culture passaged dengue viruses (Monath, T. P. et al. 1999 *Vaccine* 17:1869-1882; Huang, C. Y. et al. 2000 *J Virol* 74:3020-3028).

Another study examined the level of attenuation for humans of a DEN4 mutant bearing a 30-nucleotide deletion ($\Delta 30$) introduced into its 3'-untranslated region by site-directed mutagenesis and that was found previously to be attenuated for rhesus monkeys (Men, R. et al. 1996 *J Virol* 70:3930-3937). Additional studies were carried out to examine whether this $\Delta 30$ mutation present in the DEN4 vaccine candidate was the major determinant of its attenuation for monkeys. It was found that the $\Delta 30$ mutation was indeed the major determinant of attenuation for monkeys, and that it specified a satisfactory balance between attenuation and immunogenicity for humans (Durbin, A. P. et al. 2001 *Am J Trop Med Hyg* 65:405-13).

SUMMARY OF THE INVENTION

The previously identified Δ30 attenuating mutation, created in dengue virus type 4 (DEN4) by the removal of 30 nucleotides from the 3'-UTR, is also capable of attenuating a wild-type strain of dengue virus type 1 (DEN1). Removal of 30 nucleotides from the DEN1 3'-UTR in a highly conserved region homologous to the DEN4 region encompassing the Δ30 mutation yielded a recombinant virus attenuated in rhesus monkeys to a level similar to recombinant virus DEN4Δ30. This establishes the transportability of the Δ30 mutation and its attenuation phenotype to a dengue virus type other than DEN4. The effective transferability of the Δ30 mutation, described by this work, establishes the usefulness of the Δ30 mutation to attenuate and improve the safety of commercializable dengue virus vaccines of any serotype. We envision a tetravalent dengue virus vaccine containing dengue virus types 1, 2, 3, and 4 each attenuated by the Δ30 mutation. We also envision a tetravalent dengue virus vaccine containing recombinant antigenic chimeric viruses in which the structural genes of dengue virus types 1, 2, and 3 replace those of DEN4Δ30; 1, 2, and 4 replace those of DEN3Δ30; 1, 3, and 4 replace those of DEN2Δ30; and 2, 3, and 4 replace those of DEN1Δ30. In some instances, such chimeric dengue viruses are attenuated not only by the Δ30 mutation, but also by their chimeric nature. The presence of the Δ30 attenuating mutation in each virus component precludes the reversion to a wild-type virus by intertypic recombination. In addition, because of the inherent genetic stability of deletion mutations, the Δ30 mutation represents an excellent alternative for use as a common mutation shared among each component of a tetravalent vaccine.

Brief Description of the Sequences

| Serotype | GenBank Accession No. or description |
|---|---|
| DEN1 | U88535 |
| DEN2 | Tonga/74 |
| DEN3 | Sleman/78 |
| DEN4 | AF326825 |

Brief Description of the SEQ ID NOs

Figures 2A, 2B, 2C:
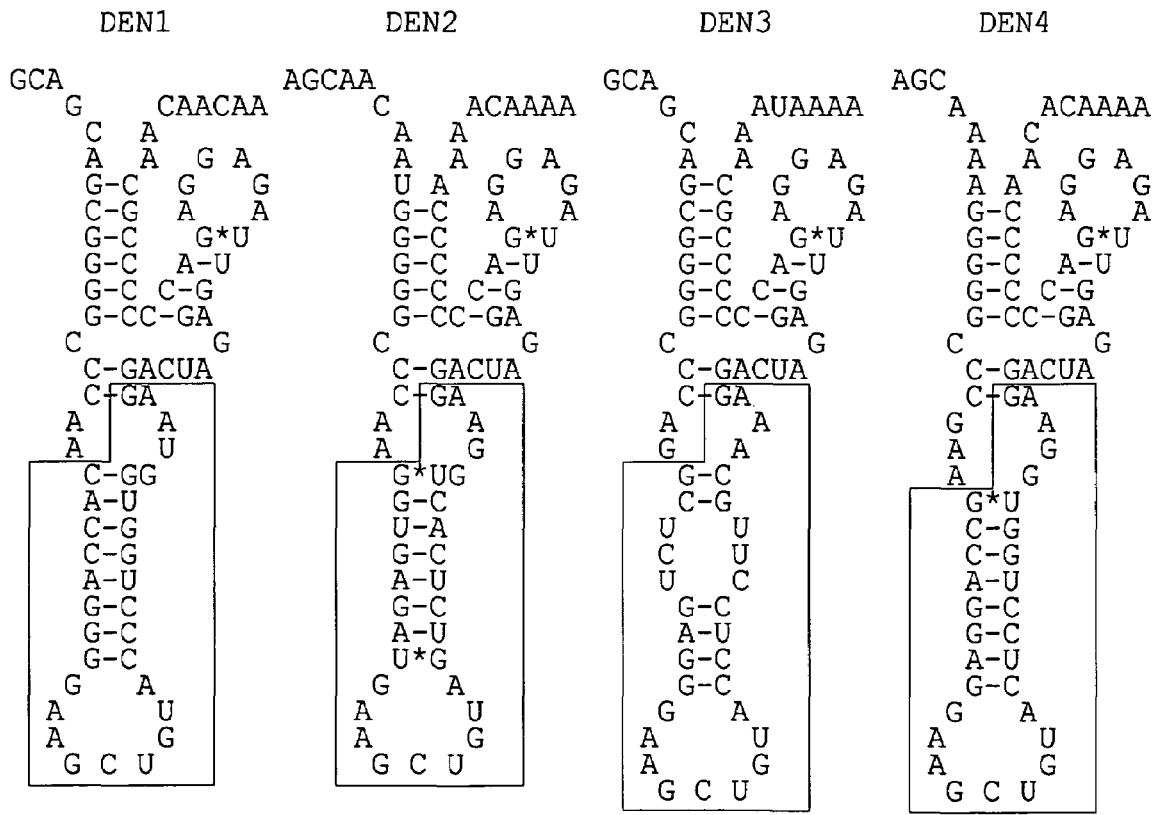
FIG. 2. A. The Δ30 mutation removes 30 contiguous nucleotides (shaded) from the 3' UTR of DEN4. Nucleotides are numbered from the 3' terminus. B. Nucleotide sequence alignment of the TL2 region of DEN1, DEN2, DEN3, and DEN4 and their Δ30 derivatives. Also shown is the corresponding region for each of the four DEN serotypes. Upper case letters indicate sequence homology among all 4 serotypes, underlining indicates nucleotide pairing to form the stem structure. C. Predicted secondary structure of the TL2 region of each DEN serotype. Nucleotides that are removed by the Δ30 mutation are boxed (DEN1—between nts 10562-10591, DEN2 Tonga/74—between nts 10541-10570, DEN3 Sleman/78—between nts 10535-10565, and DEN4—between nts 10478-10507).

| Identification | Figure, Table, or Appendix | SEQ ID NO. |
|---|---|---|
| TL2 region of DEN1 | FIG. 2C | 1 |
| TL2 region of DEN2 | FIG. 2C | 2 |
| TL2 region of DEN3 | FIG. 2C | 3 |
| TL2 region of DEN4 | FIG. 2C | 4 |
| TL2 region of DEN1Δ30 | FIG. 2B | 5 |
| TL2 region of DEN2Δ30 | FIG. 2B | 6 |
| TL2 region of DEN3Δ30 | FIG. 2B | 7 |
| TL2 region of DEN4Δ30 | FIG. 2B | 8 |
| TL2 region ofp2 | FIG. 6B | 9 |
| TL2 region of p2Δ30 | FIG. 6B | 10 |
| TL2 region of p3 | FIG. 8B | 11 |
| TL2 region of p3Δ30 | FIG. 8B | 12 |
| Spe1 linker in p3 | FIG. 8A | 13 |
| rDEN2/4 junction 1 | FIG. 9B | 14-nt, 15-aa |
| rDEN2/4 junction 2 | FIG. 9B | 16-nt, 17-aa |
| rDEN2/4 junction 3 | FIG. 9B | 18-nt, 19-aa |
| rDEN3/4 junction 1 | FIG. 11B | 20-nt, 21-aa |
| rDEN3/4 junction 2 | FIG. 11B | 22-nt, 23-aa |
| rDEN3/4 junction 3 | FIG. 11B | 24-nt, 25-aa |
| rDEN1/4 junction 1 | FIG. 12B | 26-nt, 27-aa |
| rDEN1/4 junction 2 | FIG. 12B | 28-nt, 29-aa |
| rDEN1/4 junction 3 | FIG. 12B | 30-nt, 31-aa |
| D4 selected NS4B region | Table 15 | 32-nt, 33-aa |
| D1 selected NS4B region | Table 15 | 34-nt, 35-aa |
| D2 selected NS4B region | Table 15 | 36-nt, 37-aa |

-continued

Brief Description of the SEQ ID NOs

| Identification | Figure, Table, or Appendix | SEQ ID NO. |
|---|---|---|
| D3 selected NS4B region | Table 15 | 38-nt, 39-aa |
| CCACGGGCGCCGT | Table 26 | 40 |
| AAGGCCTGGA | Table 26 | 41 |
| TATCCCCGGGAC | Table 26 | 42 |
| AGAGCTCTCTC | Table 26 | 43 |
| GAATCTCCACCCGGA | Table 26 | 44 |
| CTGTCGAATC | Table 26 | 45 |
| DEN2 (Tonga/74) cDNA plasmid p2 | Appendix 1 | 46-nt, 47-aa |
| DEN3 (Sleman/78) cDNA plasmid p3 | Appendix 2 | 48-nt, 49-aa |
| DEN1 (Puerto Rico/94) CME chimeric region | Appendix 3 | 50-nt, 51-aa |
| DEN1 (Puerto Rico/94) ME chimeric region | Appendix 4 | 52-nt, 53-aa |

DETAILED DESCRIPTION OF THE PREFERRED EMBODIMENT

Introduction

A molecular approach is herewith used to develop a genetically stable live attenuated tetravalent dengue virus vaccine. Each component of the tetravalent vaccine, namely, DEN1, DEN2, DEN3, and DEN4, must be attenuated, genetically stable, and immunogenic. A tetravalent vaccine is needed to ensure simultaneous protection against each of the four dengue viruses, thereby precluding the possibility of developing the more serious illnesses dengue hemorrhagic fever/dengue shock syndrome (DHF/DSS), which occur in humans during secondary infection with a heterotypic wild-type dengue virus. Since dengue viruses can undergo genetic recombination in nature (Worobey, M. et al. 1999 *PNAS USA* 96:7352-7), the tetravalent vaccine should be genetically incapable of undergoing a recombination event between its four virus components that could lead to the generation of viruses lacking attenuating mutations. Previous approaches to develop a tetravalent dengue virus vaccine have been based on independently deriving each of the four virus components through separate mutagenic procedures, such as passage in tissue culture cells derived from a heterologous host. This strategy has yielded attenuated vaccine candidates (Bhamarapravati, N. and Sutee, Y. 2000 *Vaccine* 18:44-7). However, it is possible that gene exchanges among the four components of these independently derived tetravalent vaccines could occur in vaccinees, possibly creating a virulent recombinant virus. Virulent polioviruses derived from recombination have been generated in vaccinees following administration of a trivalent poliovirus vaccine (Guillot, S. et al. 2000 *J Virol* 74:8434-43).

The present invention describes: (1) improvements to the previously described rDEN4Δ30 vaccine candidate, 2) attenuated rDEN1Δ30, rDEN2Δ30, and rDEN3Δ30 recombinant viruses containing a 30 nucleotide deletion (Δ30) in a section of the 3' untranslated region (UTR) that is homologous to that in the rDEN4Δ30 recombinant virus, (3) a method to generate a tetravalent dengue virus vaccine composed of rDEN1Δ30, rDEN2Δ30, rDEN3Δ30, and rDEN4Δ30, 4) attenuated antigenic chimeric viruses, rDEN1/4Δ30, rDEN2/4Δ30, and rDEN3/4Δ30, for which the CME, ME, or E gene regions of rDEN4Δ30 have been replaced with those derived from DEN1, DEN2, or DEN3; alternatively rDEN1/3Δ30, rDEN2/3Δ30, and rDEN4/3Δ30 for which CME, ME, or E gene regions of rDEN3Δ30 have been replaced with those derived from DEN1, 2, or 4; alternatively rDEN1/2Δ30, rDEN3/2Δ30, and rDEN4/2Δ30 for which CME, ME, or E gene regions of rDEN2Δ30 have been replaced with those derived from DEN1, 3, or, 4; and alternatively rDEN2/1Δ30, rDEN3/1Δ30, and rDEN4/1Δ30 for which CME, ME, or E gene regions of rDEN1Δ30 have been replaced with those derived from DEN2, 3, or 4, and 5) a method to generate a tetravalent dengue virus vaccine composed of rDEN1/4Δ30, rDEN2/4Δ30, rDEN3/4Δ30, and rDEN4Δ30, alternatively rDEN1/3Δ30, rDEN2/3Δ30, rDEN4/3Δ30, and rDEN3Δ30, alternatively rDEN1/2Δ30, rDEN3/2Δ30, rDEN4/2Δ30, and rDEN2Δ30, and alternatively rDEN2/1Δ30, rDEN3/1Δ30, rDEN4/1Δ30, and rDEN1Δ30. These tetravalent vaccines are unique since they contain a common shared attenuating mutation which eliminates the possibility of generating a virulent wild-type virus in a vaccinee since each component of the vaccine possesses the same Δ30 attenuating deletion mutation. In addition, the rDEN1Δ30, rDEN2Δ30, rDEN3Δ30, rDEN4Δ30 tetravalent vaccine is the first to combine the stability of the Δ30 mutation with broad antigenicity. Since the Δ30 deletion mutation is in the 3' UTR of each virus, all of the proteins of the four component viruses are available to induce a protective immune response. Thus, the method provides a mechanism of attenuation that maintains each of the proteins of DEN1, DEN2, DEN3, and DEN4 viruses in a state that preserves the full capability of each of the proteins of the four viruses to induce humoral and cellular immune responses against all of the structural and non-structural proteins present in each dengue virus serotype.

Figure 1:
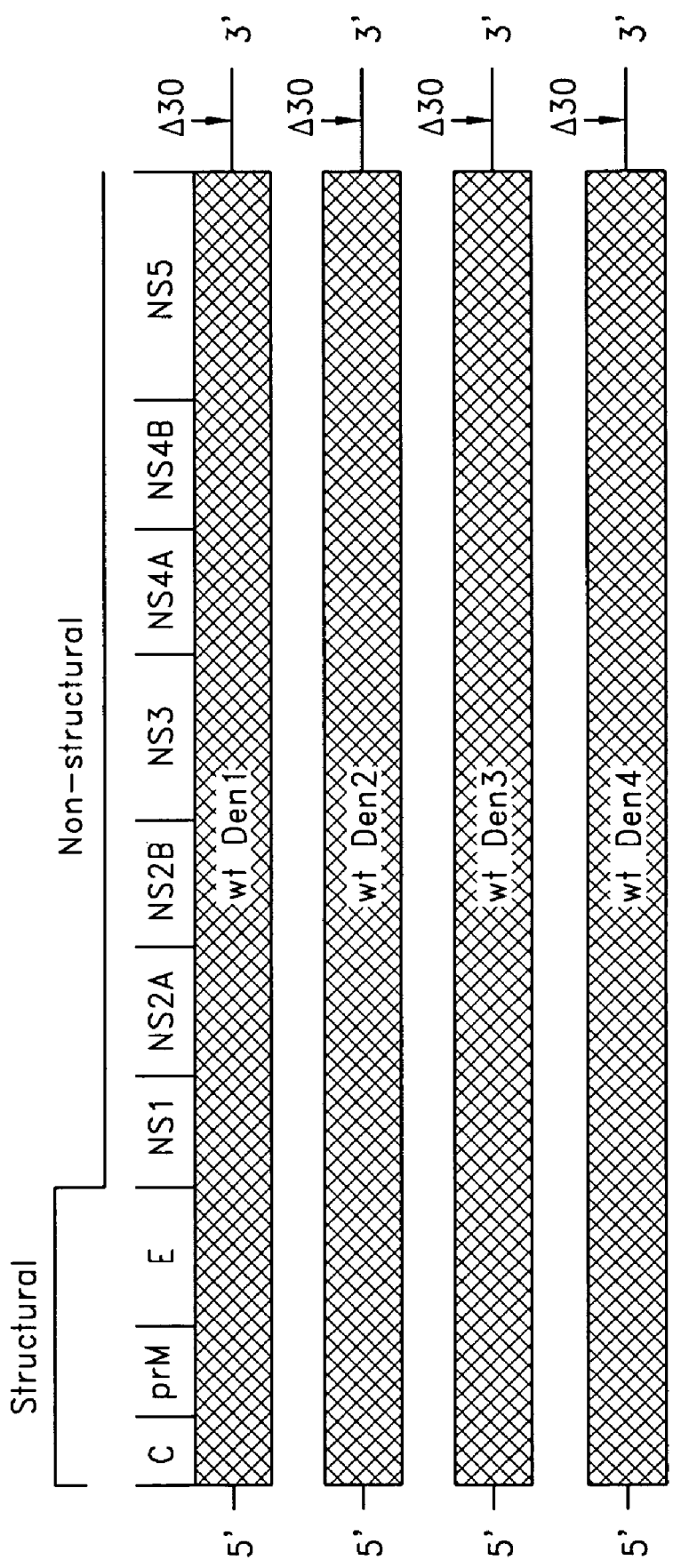
FIG. 1. The live attenuated tetravalent dengue virus vaccine contains dengue viruses representing each of the 4 serotypes, with each serotype containing its full set of unaltered wild-type structural and non-structural proteins and a shared Δ30 attenuating mutation. The relative location of the Δ30 mutation in the 3' untranslated region (UTR) of each component is indicated by an arrow.

As previously described, the DEN4 recombinant virus, rDEN4Δ30 (previously referred to as 2AΔ30), was engineered to contain a 30 nucleotide deletion in the 3' UTR of the viral genome (Durbin, A. P. et al. 2001 *Am J Trop Med Hyg* 65:405-13; Men, R. et al. 1996 *J Virol* 70:3930-7). Evaluation in rhesus monkeys showed the virus to be significantly attenuated relative to wild-type parental virus, yet highly immunogenic and completely protective. Also, a phase I clinical trial with adult human volunteers showed the rDEN4Δ30 recombinant virus to be safe and satisfactorily immunogenic (Durbin, A. P. et al. 2001 *Am J Trop Med Hyg* 65:405-13). To develop a tetravalent vaccine bearing a shared attenuating mutation in a untranslated region, we selected the Δ30 mutation to attenuate wild-type dengue viruses of serotypes 1, 2, and 3 since it attenuated wild-type DEN4 virus for rhesus monkeys and was safe in humans (FIG. 1).

The Δ30 mutation was first described and characterized in the DEN4 virus (Men, R. et al. 1996 *J Virol* 70:3930-7). In DEN4, the mutation consists of the removal of 30 contiguous nucleotides comprising nucleotides 10478-10507 of the 3' UTR (FIG. 2A) which form a putative stem-loop structure referred to as TL2 (Proutski, V. et al. 1997 *Nucleic Acids Res* 25:1194-202). Among the flaviviruses, large portions of the UTR form highly conserved secondary structures (Hahn, C. S. et al. 1987 *J Mol Biol* 198:33-41; Proutski, V. et al. 1997 *Nucleic Acids Res* 25:1194-202). Although the individual nucleotides are not necessarily conserved in these regions, appropriate base pairing preserves the stem-loop structure in each serotype, a fact that is not readily apparent when only considering the primary sequence (FIG. 2B, C).

Immunogenic Dengue Chimeras and Methods for their Preparation

Immunogenic dengue chimeras and methods for preparing the dengue chimeras are provided herein. The immunogenic dengue chimeras are useful, alone or in combination, in a pharmaceutically acceptable carrier as immunogenic compositions to minimize, inhibit, or immunize individuals and animals against infection by dengue virus.

Chimeras of the present invention comprise nucleotide sequences encoding the immunogenicity of a dengue virus of one serotype and further nucleotide sequences selected from the backbone of a dengue virus of a different serotype. These chimeras can be used to induce an immunogenic response against dengue virus.

In another embodiment, the preferred chimera is a nucleic acid chimera comprising a first nucleotide sequence encoding at least one structural protein from a dengue virus of a first serotype, and a second nucleotide sequence encoding non-structural proteins from a dengue virus of a second serotype different from the first. In another embodiment the dengue virus of the second serotype is DEN4. In another embodiment, the structural protein can be the C protein of a dengue virus of the first serotype, the prM protein of a dengue virus of the first serotype, the E protein of a dengue virus of the first serotype, or any combination thereof.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As used herein, the terms "virus chimera," "chimeric virus," "dengue chimera" and "chimeric dengue virus" means an infectious construct of the invention comprising nucleotide sequences encoding the immunogenicity of a dengue virus of one serotype and further nucleotide sequences derived from the backbone of a dengue virus of a different serotype.

As used herein, "infectious construct" indicates a virus, a viral construct, a viral chimera, a nucleic acid derived from a virus or any portion thereof, which may be used to infect a cell.

As used herein, "nucleic acid chimera" means a construct of the invention comprising nucleic acid comprising nucleotide sequences encoding the immunogenicity of a dengue virus of one serotype and further nucleotide sequences derived from the backbone of a dengue virus of a different serotype. Correspondingly, any chimeric virus or virus chimera of the invention is to be recognized as an example of a nucleic acid chimera.

The structural and nonstructural proteins of the invention are to be understood to include any protein comprising or any gene encoding the sequence of the complete protein, an epitope of the protein, or any fragment comprising, for example, three or more amino acid residues thereof.

Dengue Chimeras

Dengue virus is a mosquito-borne flavivirus pathogen. The dengue virus genome contains a 5' untranslated region (5' UTR), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' untranslated region (3' UTR). The viral structural proteins are C, prM and E, and the nonstructural proteins are NS1-NS5. The structural and nonstructural proteins are translated as a single polyprotein and processed by cellular and viral proteases.

The dengue chimeras of the invention are constructs formed by fusing structural protein genes from a dengue virus of one serotype, e.g. DEN1, DEN2, DEN3, or DEN4, with non-structural protein genes from a dengue virus of a different serotype, e.g., DEN1, DEN2, DEN3, or DEN4.

The attenuated, immunogenic dengue chimeras provided herein contain one or more of the structural protein genes, or antigenic portions thereof, of the dengue virus of one serotype against which immunogenicity is to be conferred, and the nonstructural protein genes of a dengue virus of a different serotype.

The chimera of the invention contains a dengue virus genome of one serotype as the backbone, in which the structural protein gene(s) encoding C, prM, or E protein(s) of the dengue genome, or combinations thereof, are replaced with the corresponding structural protein gene(s) from a dengue virus of a different serotype that is to be protected against. The resulting viral chimera has the properties, by virtue of being chimerized with a dengue virus of another serotype, of attenuation and is therefore reduced in virulence, but expresses antigenic epitopes of the structural gene products and is therefore immunogenic.

The genome of any dengue virus can be used as the backbone in the attenuated chimeras described herein. The backbone can contain mutations that contribute to the attenuation phenotype of the dengue virus or that facilitate replication in the cell substrate used for manufacture, e.g., Vero cells. The mutations can be in the nucleotide sequence encoding nonstructural proteins, the 5' untranslated region or the 3' untranslated region. The backbone can also contain further mutations to maintain the stability of the attenuation phenotype and to reduce the possibility that the attenuated virus or chimera might revert back to the virulent wild-type virus. For example, a first mutation in the 3' untranslated region and a second mutation in the 5' untranslated region will provide additional attenuation phenotype stability, if desired. In particular, a mutation that is a deletion of 30 nts from the 3' untranslated region of the DEN4 genome between nts 10478-10507 results in attenuation of the DEN4 virus (Men et al. 1996 *J. Virology* 70:3930-3933; Durbin et al. 2001 *Am J Trop Med* 65:405-413, 2001). Therefore, the genome of any dengue type 4 virus containing such a mutation at this locus can be used as the backbone in the attenuated chimeras described herein. Furthermore, other dengue virus genomes containing an analogous deletion mutation in the 3' untranslated region of the genomes of other dengue virus serotypes may also be used as the backbone structure of this invention.

Such mutations may be achieved by site-directed mutagenesis using techniques known to those skilled in the art. It will be understood by those skilled in the art that the virulence screening assays, as described herein and as are well known in the art, can be used to distinguish between virulent and attenuated backbone structures.

Construction of Dengue Chimeras

The dengue virus chimeras described herein can be produced by substituting at least one of the structural protein genes of the dengue virus of one serotype against which immunity is desired into a dengue virus genome backbone of a different serotype, using recombinant engineering techniques well known to those skilled in the art, namely, removing a designated dengue virus gene of one serotype and replacing it with the desired corresponding gene of dengue virus of a different serotype. Alternatively, using the sequences provided in GenBank, the nucleic acid molecules encoding the dengue proteins may be synthesized using known nucleic acid synthesis techniques and inserted into an appropriate vector. Attenuated, immunogenic virus is therefore produced using recombinant engineering techniques known to those skilled in the art.

As mentioned above, the gene to be inserted into the backbone encodes a dengue structural protein of one serotype. Preferably the dengue gene of a different serotype to be inserted is a gene encoding a C protein, a prM protein and/or an E protein. The sequence inserted into the dengue virus backbone can encode both the prM and E structural proteins of the other serotype. The sequence inserted into the dengue virus backbone can encode the C, prM and E structural proteins of the other serotype. The dengue virus backbone is the DEN1, DEN2, DEN3, or DEN4 virus genome, or an attenuated dengue virus genome of any of these serotypes, and includes the substituted gene(s) that encode the C, prM and/or E structural protein(s) of a dengue virus of a different serotype, or the substituted gene(s) that encode the prM and/or E structural protein(s) of a dengue virus of a different serotype.

Suitable chimeric viruses or nucleic acid chimeras containing nucleotide sequences encoding structural proteins of dengue virus of any of the serotypes can be evaluated for usefulness as vaccines by screening them for phenotypic markers of attenuation that indicate reduction in virulence with retention of immunogenicity. Antigenicity and immunogenicity can be evaluated using in vitro or in vivo reactivity with dengue antibodies or immunoreactive serum using routine screening procedures known to those skilled in the art.

Dengue Vaccines

The preferred chimeric viruses and nucleic acid chimeras provide live, attenuated viruses useful as immunogens or vaccines. In a preferred embodiment, the chimeras exhibit high immunogenicity while at the same time not producing dangerous pathogenic or lethal effects.

The chimeric viruses or nucleic acid chimeras of this invention can comprise the structural genes of a dengue virus of one serotype in a wild-type or an attenuated dengue virus backbone of a different serotype. For example, the chimera may express the structural protein genes of a dengue virus of one serotype in either of a dengue virus or an attenuated dengue virus background of a different serotype.

The strategy described herein of using a genetic background that contains nonstructural regions of a dengue virus genome of one serotype, and, by chimerization, the properties of attenuation, to express the structural protein genes of a dengue virus of a different serotype has lead to the development of live, attenuated dengue vaccine candidates that express structural protein genes of desired immunogenicity. Thus, vaccine candidates for control of dengue pathogens can be designed.

Viruses used in the chimeras described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Chimeric infectious clones are constructed from various dengue serotypes. The cloning of virus-specific cDNA fragments can also be accomplished, if desired. The cDNA fragments containing the structural protein or nonstructural protein genes are amplified by reverse transcriptase-polymerase chain reaction (RT-PCR) from dengue RNA with various primers. Amplified fragments are cloned into the cleavage sites of other intermediate clones. Intermediate, chimeric dengue clones are then sequenced to verify the sequence of the inserted dengue-specific cDNA.

Full genome-length chimeric plasmids constructed by inserting the structural or nonstructural protein gene region of dengue viruses into vectors are obtainable using recombinant techniques well known to those skilled in the art.

Methods of Administration

The viral chimeras described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nanoparticles and liposomes. It is expected that from about 1 to about 5 doses may be required per immunization schedule. Initial doses may range from about 100 to about 100,000 PFU or FFU, with a preferred dosage range of about 500 to about 20,000 PFU or FFU, a more preferred dosage range of from about 1000 to about 12,000 PFU or FFU and a most preferred dosage range of about 1000 to about 4000 PFU or FFU. Booster injections may range in dosage from about 100 to about 20,000 PFU or FFU, with a preferred dosage range of about 500 to about 15,000, a more preferred dosage range of about 500 to about 10,000 PFU or FFU, and a most preferred dosage range of about 1000 to about 5000 PFU or FFU. For example, the volume of administration will vary depending on the route of administration. Intramuscular injections may range in volume from about 0.1 ml to 1.0 ml.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

Administration Schedule

The immunogenic or vaccine composition described herein may be administered to humans, especially individuals travelling to regions where dengue virus infection is present, and also to inhabitants of those regions. The optimal time for administration of the composition is about one to three months before the initial exposure to the dengue virus. However, the composition may also be administered after initial infection to ameliorate disease progression, or after initial infection to treat the disease.

Adjuvants

A variety of adjuvants known to one of ordinary skill in the art may be administered in conjunction with the chimeric virus in the immunogen or vaccine composition of this invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof.

Nucleic Acid Sequences

Nucleic acid sequences of dengue virus of one serotype and dengue virus of a different serotype are useful for designing nucleic acid probes and primers for the detection of dengue virus chimeras in a sample or specimen with high sensitivity and specificity. Probes or primers corresponding to dengue virus can be used to detect the presence of a vaccine virus. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding dengue virus or complementary sequences thereof. By "selective" or "selectively" is meant a sequence which does not hybridize with other nucleic acids to prevent adequate detection of the dengue virus sequence. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in Molecular Cloning: A Laboratory Manual, 2nd ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of dengue virus, the degree of complementarity between the hybridizing nucleic acid (probe or primer) and the sequence to which it hybridizes is at least enough to distinguish hybridization with a nucleic acid from other organisms.

The nucleic acid sequences encoding dengue virus can be inserted into a vector, such as a plasmid, and recombinantly expressed in a living organism to produce recombinant dengue virus peptide and/or polypeptides.

The nucleic acid sequences of the invention include a diagnostic probe that serves to report the detection of a cDNA amplicon amplified from the viral genomic RNA template by using a reverse-transcription/polymerase chain reaction (RT/PCR), as well as forward and reverse amplimers that are designed to amplify the cDNA amplicon. In certain instances, one of the amplimers is designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer, 1996 *Nature Biotechnology* 14:303-308). Molecular beacon assays employ quencher and reporter dyes that differ from those used in the TaqMan assay. These and other detection systems may used by one skilled in the art.

EXAMPLE 1

Improvement of Dengue Virus Vaccine Candidate rDEN4Δ30

The safety of recombinant live-attenuated dengue-4 vaccine candidate rDEN4Δ30 was evaluated in twenty human volunteers who received a dose of 5.0 $\log_{10}$plaque forming units (PFU) (Durbin A. P. et al. 2001 *Am J Trop Med Hyg* 65:405-413). The vaccine candidate was found to be safe, well-tolerated and immunogenic in all of the vaccinees. However, five of the vaccinees experienced a transient elevation in alanine aminotransferase levels, three experienced neutropenia and ten vaccinees developed an asymptomatic macular rash, suggesting that it may be necessary to further attenuate this vaccine candidate.

Currently, a randomized, double-blind, placebo-controlled, dose de-escalation study is being conducted to determine the human infectious dose 50 ($HID_{50}$) of rDEN4Δ30. Each dose cohort consists of approximately twenty vaccinees and four placebo recipients. To date, complete data for doses of 3.0 $\log_{10}$PFU and 2.0 $\log_{10}$PFU has been collected. rDEN4Δ30 infected 100% of vaccinees when 3.0 $\log_{10}$PFU was administered and 95% of vaccinees when 2.0 $\log_{10}$PFU was administered (Table 1). The vaccine candidate caused no symptomatic illness at either dose (Table 1). One vaccinee who received 3.0 $\log_{10}$PFU experienced a transient elevation in alanine aminotransferase levels and approximately one fourth of the vaccinees experienced neutropenia at both doses (Table 1). Neutropenia was transient and mild. More than half of the vaccinees developed a macular rash at both doses; the occurrence of rash was not correlated with vaccination dose or with viremia (Table 1 and Table 2). Neither peak titer nor onset of viremia differed between the 3.0 $\log_{10}$PFU and 2.0 $\log_{10}$PFU doses, though both measures of viremia were significantly lower for these doses than for a dose of 5.0 $\log_{10}$PFU (Table 3). The vaccine candidate was immunogenic in 95% of vaccinees at both doses and neutralizing antibody did not decline between days 28 and 42 post-vaccination (Table 4). Although the $HID_{50}$ has not been determined yet, it is clearly less than 2.0 $\log_{10}$PFU. Interestingly, decreases in the dose of vaccine have had no consistent effect on immunogenicity, viremia, benign neutropenia or the occurrence of rash. Thus will not necessarily be possible to further attenuate rDEN4Δ30 by decreasing the dose of virus administered, and other approaches must be developed.

TABLE 1 rDEN4Δ30 clinical summary

| No. of subjects | Dose[a] | No. infected | No. with viremia | Mean peak titer[b] | Fever | Rash | Neutropenia[c] | ↑ALT |
|---|---|---|---|---|---|---|---|---|
| 20 | 5.0 | 20 | 14 | 1.2 (0.2) | 1[d] | 10 | 3 | 5 |
| 20 | 3.0 | 20 | 7 | 0.4 (0.0) | 0 | 11 | 5 | 1[e] |
| 20 | 2.0 | 19 | 11 | 0.6 (0.1) | 1[d] | 16 | 4 | 0 |
| 8 | 0 | 0 | 0 | 0 | 0 | 0 | 0 | 0 |

[a]$\log_{10}$ pfu
[b]$\log_{10}$ pfu/mL
[c]Neutropenia defined as ANC < 1500/dl
[d]T Max in volunteer = 100.4° F.
[e]ALT day 0 = 78, ALT max = 91 (day 14)

TABLE 2

Pattern of rash in vaccinees

| Dose[a] | No. with viremia | No. with rash | Viremia &rash | Viremia no rash | Mean day of onset ± SD | Mean duration (days ± SD) |
|---|---|---|---|---|---|---|
| 5 | 14/20 | 10/20 | 9/20 | 5/20 | 8.1 ± 1.3 [A][b] | 3.6 ± 2.0 [A] |
| 3 | 7/20 | 11/20 | 6/20 | 1/20 | 12.2 ± 1.4 [B] | 5.0 ± 2.1 [A] |
| 2 | 11/20 | 16/20 | 9/20 | 2/20 | 11.2 ± 1.4 [B] | 6.9 ± 1.7 [B] |

[a]$\log_{10}$ pfu
[b]Means in each column with different letters are significantly different (α = 0.05)

TABLE 3 rDEN4Δ30 viremia summary

| Dose[a] | # with viremia | Mean peak titer ($\log_{10}$ pfu/mL) | Mean onset of viremia (day ± SD) | Mean duration of viremia (day ± SD) |
|---|---|---|---|---|
| 5 | 14 | 1.2 ± 0.2 [A] | 5.8 ± 2.4 [A][b] | 4.4 ± 2.4 [A] |
| 3 | 7 | 0.4 ± 0.0 [B] | 9.1 ± 2.5 [B] | 1.6 ± 1.0 [B] |
| 2 | 11 | 0.6 ± 0.1 [B] | 8.7 ± 2.4 [B] | 2.6 ± 2.0 [A] |

[a]$\log_{10}$ pfu
[b]Means in each column with different letters are significantly different (α = 0.05)

TABLE 4

Immunogenicity of rDEN4Δ30

| No. of subjects | Dose ($\log_{10}$) | No. infected | Geometric mean serum neutralizing antibody titer (range) Day 28 | Day 42 | % seroconversion |
|---|---|---|---|---|---|
| 20 | 5.0 | 20 | 567 (72-2455) | 399 (45-1230) | 100 |
| 20 | 3.0 | 20 | 156 (5-2365) | 158 (25-1222) | 95 |
| 20 | 2.0 | 19 | 163 (5-943) | 165 (5-764) | 95 |
| 8 | 0 | 0 | 0 | 0 | 0 |

Two approaches have been taken to further attenuate rDEN4Δ30. This first is the generation and characterization of attenuating point mutations in rDEN4 using 5' fluorouracil mutagenesis (Blaney, J. E. Jr. et al. 2002 *Virology* 300: 125-139; Blaney, J. E. Jr. et al. 2001 *J. Virol.* 75: 9731-9740). This approach has identified a panel of point mutations that confer a range of temperature sensitivity (ts) and small plaque (sp) phenotypes in Vero and HuH-7 cells and attenuation (att) phenotypes in suckling mouse brain and SCID mice engrafted with HuH-7 cells (SCID-HuH-7 mice). In this example, a subset of these mutations has been introduced to rDEN4Δ30 and the phenotypes of the resulting viruses evaluated.

A second approach was to create a series of paired charge-to-alanine mutations in contiguous pairs of charged amino acid residues in the rDEN4 NS5 gene. As demonstrated previously, mutation of 32 individual contiguous pairs of charged amino acid residues in rDEN4 NS5 conferred a range of ts phenotypes in Vero and HuH-7 cells and a range of att phenotypes in suckling mouse brain (Hanley, K. H. et al. 2002 *J. Virol.* 76 525-531). As demonstrated below, these mutations also confer an att phenotype in SCID-HuH-7 mice. These mutations have been introduced, either as single pairs or sets of two pairs, into rDEN4Δ30 to determine whether they are compatible with the Δ30 mutation and whether they enhance the att phenotypes of rDEN4Δ30.

A panel of rDEN4 viruses bearing individual point mutations have been characterized which possess temperature sensitive and/or small plaque phenotypes in tissue culture and varying levels of attenuated replication in suckling mouse brain when compared to wild type rDEN4 virus (Blaney, J. E. et al. 2002 *Virology* 300:125-139; Blaney, J. E. et al. 2001 *J Virol.* 75:9731-9740). Three mutations have been selected to combine with the Δ30 deletion mutation to evaluate their ability to further restrict replication of rDEN4Δ30 in rhesus monkeys. First, the missense mutation in NS3 at nucleotide 4995 (Ser>Pro) which confers temperature sensitivity in Vero and HuH-7 cells and restricted replication in suckling mouse brain was previously combined with the Δ30 mutation (Blaney, J. E. et al. 2001 *J Virol.* 75:9731-9740). The resulting virus, rDEN4Δ30-4995, was found to be more restricted (1,000-fold) in mouse brain replication than rDEN4Δ30 virus (<5-fold) when compared to wild type rDEN4 virus. Second, a missense mutation at nucleotide 8092 (Glu>Gly) which also confers temperature sensitivity in Vero and HuH-7 cells and 10,000-fold restricted replication in suckling mouse brain was combined with the Δ30 mutation here. Third, a substitution in the 3' UTR at nucleotide 10634 which confers temperature sensitivity in Vero and HuH-7 cells, small plaque size in HuH-7 cells, and approximately 1,000-fold restricted replication in suckling mouse brain and SCID mice transplanted with HuH-7 cells was combined with the Δ30 mutation here (Blaney, J. E. et al. 2002 *Virology* 300:125-139).

For the present investigation, subcloned fragments of p4 (Durbin, A. P. et al. 2001 *Am J Trop Med Hyg* 65:405-13) containing the above mutations were introduced into the p4Δ30 cDNA clone. For transcription and recovery of virus, cDNA was linearized with Acc65I (isoschizomer of KpnI which cleaves leaving only a single 3' nucleotide) and used as template for transcription by SP6 RNA polymerase as previously described (Blaney, J. E. et al. 2002 *Virology* 300:125-139). C6/36 mosquito cells were transfected using liposome-mediated transfection and cell culture supernatants were harvested between days five and seven. Recovered virus was terminally diluted twice in Vero cells and passaged two (rDEN4Δ30-4995) or three (rDEN4Δ30-8092 and rDEN4Δ30-10634) times in Vero cells.

The complete genomic sequences of rDEN4Δ30-4995, rDEN4Δ30-8092, and rDEN4Δ30-10634 viruses were determined as previously described (Durbin et al. 2001 *Am. J. Trop. Med. Hyg.* 65:405-413). As expected, each rDEN4Δ30 virus derivative contained the Δ30 mutation. Unexpectedly, in rDEN4Δ30-4995 virus, the nucleotide changes in the codon containing nucleotide 4995, resulted in a Ser>Leu amino acid change rather than a Ser>Pro change since the p4Δ30-4995 cDNA was designed to introduce the Ser>Pro change (Table 5). The p4Δ30-4995 cDNA clone was indeed found to encode a Ser>Pro change at nucleotide 4995, so it is unclear how the virus population acquired the Ser>Leu mutation. Nevertheless, this virus was evaluated to assess the phenotype specified by this missense mutation. rDEN4Δ30-4995 virus was also found to contain an incidental mutation at nucleotides 4725-6 which resulted in a single amino acid change (Ser>Asp). The rDEN4Δ30-8092 and rDEN4Δ30-10634 viruses contained the appropriate nucleotide substitutions as well as additional incidental mutations in E, NS4B and NS4B, respectively (Table 5).

brain, groups of six seven-day-old mice were inoculated intracerebrally with 4.0 $\log_{10}$PFU of virus and the brain of each mouse was removed five days later. Clarified supernatants of 10% brain suspensions were then frozen at −70° C., and the virus titer was determined by plaque assay in Vero cells. For analysis of DEN4 virus replication in SCID-HuH-7 mice, four to six week-old SCID mice were injected intraperitoneally with $10^7$ HuH-7 cells. Five to six weeks after transplantation, mice were infected by direct inoculation into the tumor with 4.0 $\log_{10}$PFU of virus, and serum for virus titration was obtained by tail-nicking on day 7. The virus titer was determined by plaque assay in Vero cells.

Wild type rDEN4 virus replicated to 6.0 $\log_{10}$PFU/g in suckling mouse brain, and rDEN4Δ30 was restricted in replication by 0.7 $\log_{10}$PFU/g, which is similar to previous observations (Table 6) (Blaney, J. E. et al. 2001 *J Virol.* 75:9731-9740). rDEN4Δ30-4995, rDEN4Δ30-8092, and rDEN4Δ30-10634 viruses were found to have restricted replication in suckling mouse brain when compared to rDEN4 virus of 3.3, 2.8, and 2.4 $\log_{10}$PFU/g, respectively. These results indicate that the additional attenuating mutations serve to further restrict replication of the rDEN4Δ30 virus in mouse brain ranging from 50-fold (rDEN4Δ30-10634) to 400-fold (rDEN4Δ30-4995). In SCID-HuH-7 mice, virus titer of rDEN4Δ30 virus was 0.4 $\log_{10}$PFU/ml lower than rDEN4 virus, which is also similar to previous studies (Blaney, J. E. et al. 2002 *Virology* 300:125-139). Each modified rDEN4Δ30 virus was found to be further restricted in replication in SCID-HuH-7 mice (Table 6). rDEN4Δ30-4995, rDEN4Δ30-8092, and rDEN4Δ30-10634 viruses had restricted replication in SCID-HuH-7 mice when compared to rDEN4 virus of 2.9, 1.1, and 2.3 $\log_{10}$PFU/g below the level of wild type rDEN4 virus, respectively. Two important

TABLE 5

Missense and UTR mutations present in rDEN4Δ30 virus derivatives bearing introduced point mutations.

| Virus | Gene | Nucleotide position | Nucleotide substitution | Amino acid position[a] | Amino acid change |
|---|---|---|---|---|---|
| rDEN4Δ30-4995 | NS3 | 4725 | U > G | 1542 | Ser > Asp |
| | NS3 | 4726 | C > A | 1542 | Ser > Asp |
| | NS3 | 4995[b] | U > C | 1632 | Ser > Leu |
| rDEN4Δ30-8092 | E | 1612 | A > C | 504 | Asp > Ala |
| | NS4B | 7131 | A > G | 2344 | Thr > Ala |
| | NS5 | 8092[b] | A > G | 2664 | Glu > Gly |
| rDEN4Δ30-10634 | NS4B | 6969 | A > U | 2290 | Met > Leu |
| | NS4B | 7182 | G > C | 2361 | Gly > Arg |
| | 3' UTR | 10634[b] | U > C | none | none |

[a]Amino acid position in DEN4 polyprotein beginning with the methionine residue of the C protein (nucleotides 102-104) as position 1.
[b]Mutation restricts replication in mouse models of DEN4 infection which were introduced by Kunkel mutagenesis.

Replication of the three modified rDEN4Δ30 viruses were compared to rDEN4Δ30 and wild type rDEN4 virus in the suckling mouse brain model and SCID mice transplanted with HuH-7 cells (SCID-HuH-7 mice). Experiments were conducted as previously described (Blaney, J. E. et al. 2002 *Virology* 300:125-139; Blaney, J. E. et al. 2001 *J Virol.* 75:9731-9740). Briefly, for infection of suckling mouse observations were made: (1) The 4995, 8092 and 10634 mutations were compatible for viability with the Δ30 mutation, and (2) These three modified rDEN4Δ30 viruses had between a 10 and 1,000-fold reduction in replication in comparison to rDEN4 wild-type virus, which allows viruses with a wide range of attenuation in this model to be further evaluated in monkeys or humans.

TABLE 6

Addition of point mutations in NS3, NS5, or the 3' UTR to rDEN4Δ30 virus further attenuates the virus for suckling mouse brain and SCID-HuH-7 mice.

| | Replication in suckling mouse brain[a] | | | Replication in SCID-HuH-7 mice[c] | | |
|---|---|---|---|---|---|---|
| Virus | No. of mice | Virus titer ± SE $\log_{10}$ PFU/g brain | Mean $\log_{10}$-unit reduction from wt[b] | No. of mice | Virus titer ± SE $\log_{10}$ PFU/ml serum | Mean $\log_{10}$-unit reduction from wt[b] |
| rDEN4 | 12 | 6.0 ± 0.1 | — | 13 | 6.4 ± 0.2 | — |
| rDEN4Δ30 | 12 | 5.3 ± 0.1 | 0.7 | 20 | 6.0 ± 0.2 | 0.4 |
| rDEN4Δ30-4995 | 6 | 2.7 ± 0.4 | 3.3 | 5 | 3.5 ± 0.3 | 2.9 |
| rDEN4Δ30-8092 | 6 | 3.2 ± 0.2 | 2.8 | 7 | 5.0 ± 0.4 | 1.1 |
| rDEN4Δ30-10634 | 12 | 3.6 ± 0.1 | 2.4 | 5 | 4.4 ± 0.3 | 2.3 |

[a]Groups of 6 suckling mice were inoculated i.c. with $10^4$ PFU of virus. Brains were removed 5 days later, homogenized, and titered in Vero cells.
[b]Comparison of mean virus titers of mice inoculated with mutant virus and concurrent rDEN4 wt control.
[c]Groups of HuH-7-SCID mice were inoculated directly into the tumor with $10^4$ PFU virus. Serum was collected on day 6 and 7 and titered in Vero cells.

Based on the findings in the two mouse models of DEN4 virus infection, each of the rDEN4Δ30-4995, rDEN4Δ30-8092, and rDEN4Δ30-10634 viruses was evaluated in the rhesus macaque model of DEN4 infection which has been previously described (Durbin et al. 2001 *Am. J. Trop. Med. Hyg.* 65:405-413). Briefly, groups of four (rDEN4Δ30-4995, rDEN4Δ30-8092, and rDEN4Δ30-10634) or two (rDEN4, rDEN4Δ30, mock) monkeys were inoculated with 5.0 $\log_{10}$PFU virus subcutaneously. Monkeys were observed daily and serum was collected on days 0 to 6, 8, 10, and 12, and virus titers were determined by plaque assay in Vero cells for measurement of viremia. On day 28, serum was drawn and the level of neutralizing antibodies was tested by plaque reduction assay in Vero cells as previously described (Durbin et al. 2001 *Am. J. Trop. Med. Hyg.* 65:405-413).

Figure 3:
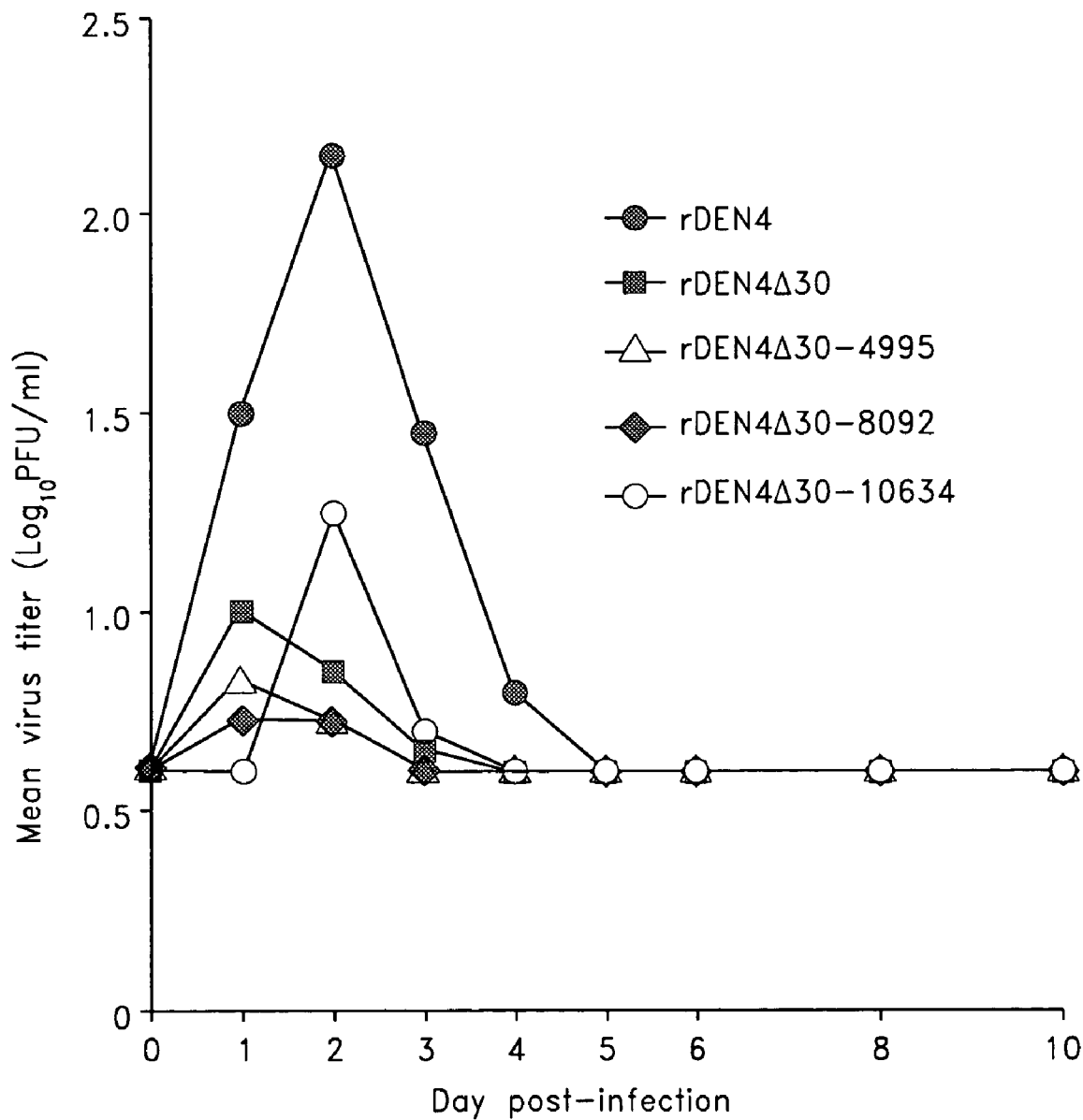
FIG. 3. Viremia levels in rhesus monkeys inoculated with rDEN4 vaccine candidates bearing 5-FU derived mutations. Groups of four or two (rDEN4 and rDEN4Δ30) monkeys were inoculated with 5.0 $\log_{10}$PFU virus subcutaneously. Serum was collected daily and virus titers were determined by plaque assay in Vero cells. The limit of virus detection was 0.7 $\log_{10}$PFU/ml. Mean virus titers are indicated for each group.

Viremia was detected beginning on day 1 post-infection and ended by day 4 in all monkeys (Table 7, FIG. 3). Viremia was present in each monkey infected with rDEN4, rDEN4Δ30, or rDEN4Δ30-10634 virus, but only 2 out of 4 monkeys infected with rDEN4Δ30-4995 or rDEN4Δ30-8092 virus had detectable viremia. As expected, infection with rDEN4 virus resulted in the highest mean number of viremic days per monkey (3.0 days) as well as mean peak virus titer (2.2 $\log_{10}$PFU/ml). Monkeys infected with rDEN4Δ30 virus had both a lower mean number of viremic days per monkey (2.0 days) and mean peak virus titer (1.1 $\log_{10}$PFU/ml) compared to rDEN4 virus. Groups of monkeys infected with each of the modified rDEN4Δ30 viruses had a further restricted mean number of viremic days with those inoculated with rDEN4Δ30-8092 virus having the lowest value, 0.5 days, a 4-fold reduction compared to rDEN4Δ30 virus. The mean peak virus titer of monkeys infected with rDEN4Δ30-4995 (0.9 $\log_{10}$PFU/ml) or rDEN4Δ30-8092 (0.7 $\log_{10}$PFU/ml) was also lower than those infected with rDEN4Δ30 virus. However, the mean peak virus titer of monkeys infected with rDEN4Δ30-10634 (1.3 $\log_{10}$PFU/ml) was slightly higher than those infected with rDEN4Δ30 particularly on day 2 (FIG. 3).

TABLE 7

Addition of point mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <10 | <10 |
| rDEN4 | 2 | 2 | 3.0 | 2.2 ± 0.6 | <10 | 398 |
| rDEN4Δ30 | 2 | 2 | 2.0 | 1.1 ± 0.4 | <10 | 181 |
| rDEN4Δ30-4995 | 4 | 2 | 0.8 | 0.9 ± 0.2 | <10 | 78 |
| rDEN4Δ30-8092 | 4 | 2 | 0.5 | 0.7 ± 0.1 | <10 | 61 |
| rDEN4Δ30-10634 | 4 | 4 | 1.3 | 1.3 ± 0.2 | <10 | 107 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

Serum collected on day 0 and 28 was tested for the level of neutralizing antibodies against rDEN4. No detectable neutralizing antibodies were found against DEN4 on day 0, as expected, since the monkeys were pre-screened to be negative for neutralizing antibodies against flaviviruses (Table 7). On day 28, monkeys infected with rDEN4 had a mean serum neutralizing antibody titer (reciprocal dilution) of 398 which was approximately two-fold higher than monkeys infected with rDEN4Δ30 virus (1:181). This result and the two-fold higher level of viremia in rDEN4 virus-infected monkeys are similar to results obtained previously (Durbin et al. 2001 Am. J. Trop. Med. Hyg. 65:405-413). Monkeys infected with rDEN4Δ30-4995 (1:78), rDEN4Δ30-8092 (1:61), and rDEN4Δ30-10634 (1:107) viruses each had a reduced mean serum neutralizing antibody titer compared to monkeys infected with rDEN4Δ30 virus. The four monkeys which had no detectable viremia did have serum neutralizing antibody titers indicating that they were indeed infected. Despite the slight increase in mean peak virus titer of rDEN4Δ30-10634 virus compared with rDEN4Δ30 virus, rDEN4Δ30-10634 virus had a lower mean serum neutralizing antibody titer compared to monkeys infected with rDEN4Δ30 virus. This and the lower mean number of viremic days per monkey suggests that the 10634 mutation can attenuate the replication of rDEN4Δ30 virus in monkeys.

On day 28 after inoculation, all monkeys were challenged with 5.0 $\log_{10}$PFU wild type rDEN4 virus subcutaneously. Monkeys were observed daily and serum was collected on days 28 to 34, 36, and 38, and virus titers were determined by plaque assay in Vero cells for measurement of viremia after challenge. Twenty eight days after rDEN4 virus challenge, serum was drawn and the level of neutralizing antibodies was tested by plaque reduction assay in Vero cells. Mock-inoculated monkeys had a mean peak virus titer of 2.3 $\log_{10}$PFU/ml after challenge with a mean number of viremic days of 3.5 (Table 8). However, monkeys inoculated with rDEN4, rDEN4Δ30, or each of the modified rDEN4Δ30 viruses had no detectable viremia, indicating that despite the decreased replication and immunogenicity of rDEN4Δ30-4995, rDEN4Δ30-8092, and rDEN4Δ30-10634 viruses, each was sufficiently immunogenic to induce protection against wild type rDEN4. Increases in mean neutralizing antibody titer were minimal (<3-fold) following challenge in all inoculation groups except mock-infected providing further evidence that the monkeys were protected from the challenge.

Taken together, these results indicate that the three point mutations, 4995, 8092, and 10634) described above do further attenuate the rDEN4Δ30 vaccine candidate in suckling mouse brain, SCID-HuH-7 mice, and rhesus monkeys. Because of additional incidental mutations (Table 4) present in each modified rDEN4Δ30 virus, the phenotypes cannot be directly attributed to the individual 4995, 8092, and 10634 point mutations. However, the presence of similar mouse-attenuation phenotypes in other rDEN4 viruses bearing one of these three mutations supports the contention that the 4995, 8092, and 10634 point mutations are responsible for the att phenotypes of the modified rDEN4Δ30 viruses. Since rDEN4Δ30-4995, rDEN4Δ30-8092, and rDEN4Δ30-10634 virus demonstrated decreased replication in rhesus monkeys while retaining sufficient immunogenicity to confer protective immunity, these viruses are contemplated as dengue vaccines for humans.

DEN4 viruses carrying both Δ30 and charge-to-alanine mutations were next generated. A subset of seven groups of charge-to-alanine mutations described above were identified that conferred between a 10-fold and 1,000-fold decrease in replication in SCID-HuH-7 mice and whose unmutated sequence was well-conserved across the four dengue serotypes. These mutations were introduced as single pairs and as two sets of pairs to rDEN4Δ30 using conventional cloning techniques. Transcription and recovery of virus and terminal dilution of viruses were conducted as described above. Assay of the level of temperature sensitivity of the charge-cluster-to-alanine mutant viruses in Vero and HuH-7 cells, level of replication in the brain of suckling mice and level of replication in SCID-HuH-7 mice was conducted as described above.

Introduction of one pair of charge-to-alanine mutations to rDEN4 produced recoverable virus in all cases (Table 9). Introduction of two pairs of charge-to-alanine mutations produced recoverable virus in two out of three cases (rDEN4Δ30-436-437-808-809 was not recoverable).

rDEN4Δ30 is not ts in Vero or HuH-7 cells. In contrast, seven of the seven sets of charge-to-alanine mutations used in this example conferred a ts phenotype in HuH-7 cells and five also conferred a ts phenotype in Vero cells. All six viruses carrying both Δ30 and charge-to-alanine mutations showed a ts phenotype in both Vero and HuH-7 cells (Table 9). rDEN4Δ30 is not attenuated in suckling mouse brain, whereas five of the seven sets of charge-to-alanine mutations conferred an att phenotype in suckling mouse brain (Table

TABLE 8 rDEN4Δ30 containing additional point mutations protects rhesus monkeys from wt DEN4 virus challenge

| Virus[a] | No. of monkeys | Mean no. of viremic days per monkey after rDEN4 challenge | Mean peak virus titer ($\log_{10}$ PFU/ml ± SE) | Geometric mean serum neutralizing antibody titer (reciprocal dilution) | |
|---|---|---|---|---|---|
| | | | | Day 28 | Day 56 |
| Mock | 2 | 3.5 | 2.3 ± 0.1 | <10 | 358 |
| rDEN4 | 2 | 0.0 | <0.7 | 398 | 753 |
| rDEN4Δ30 | 2 | 0.0 | <0.7 | 181 | 202 |
| rDEN4Δ30-4995 | 4 | 0.0 | <0.7 | 78 | 170 |
| rDEN4Δ30-8092 | 4 | 0.0 | <0.7 | 61 | 131 |
| rDEN4Δ30-10634 | 4 | 0.0 | <0.7 | 107 | 177 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 38, and 56. Virus titer was determined by plaque assay in Vero cells.

10). Four of the viruses carrying both Δ30 and charge-to-alanine mutations were attenuated in suckling mouse brain (Table 10). In one case (rDEN4Δ30-23-24-396-397) combination of two mutations that did not attenuate alone resulted in an attenuated virus. Generally, viruses carrying both Δ30 and charge-to-alanine mutations showed levels of replication in the suckling mouse brain more similar to their charge-to-alanine mutant parent virus than to rDEN4Δ30.

rDEN4Δ30 is attenuated in SCID-HuH-7 mice, as are six of the seven charge-to-alanine mutant viruses used in this example. Viruses carrying both Δ30 and charge-to-alanine mutations tended to show similar or slightly lower levels of replication in SCID-HuH-7 mice compared to their charge-to-alanine mutant parent virus (Table 10). In three cases, viruses carrying both Δ30 and charge-to-alanine mutations showed at least a fivefold greater reduction in SCID-HuH-7 mice than rDEN4Δ30.

The complete genomic sequence of five viruses (rDEN4-200-201, rDEN4Δ30-200-201, rDEN4-436-437 [clone 1], rDEN4Δ30-436-437, and rDEN4-23-24-200-201) that replicated to >10$^5$ PFU/ml in Vero cells at 35° C. and that showed a hundredfold or greater reduction in replication in SCID-HuH-7 mice was determined (Table 11). Each of the five contained one or more incidental mutations. In one virus, rDEN4Δ30-436-437, the one additional mutation has been previously associated with Vero cell adaptation (Blaney, J. E. Jr. et al. 2002 *Virology* 300:125-139). Each of the remaining viruses contained at least one incidental mutation whose phenotypic effect is unknown. Consequently, the phenotypes described cannot be directly attributed to the charge-to-alanine mutations. However, the fact that rDEN4 and rDEN4Δ30 viruses carrying the same charge-to-alanine mutations shared similar phenotypes provides strong support for the ability of charge-to-alanine mutations to enhance the attenuation of rDEN4Δ30. Because rDEN4-436-437 [clone 1] contained 4 incidental mutations, a second clone of this virus was prepared. rDEN4-436-437 [clone2] contained only one incidental mutation (Table 11), and showed the same phenotypes as rDEN4-436-437 in cell culture and SCID-HuH-7 mice. rDEN4-436-437 [clone 2] was used in the rhesus monkey study described below.

TABLE 9

Addition of charge-to-alanine mutations to rDEN4Δ30 confers a ts phenotype in both Vero and HuH-7 cells.

| Virus | AA changed[b] | No. nt changed | Vero 35 | 37 | 38 | 39 | Δ[c] | HuH-7 35 | 37 | 38 | 39 | Δ |
|---|---|---|---|---|---|---|---|---|---|---|---|---|
| rDEN4 | none | 0 | 7.4 | 7.1 | 7.7 | 7.2 | 0.2 | 7.7 | 7.5 | 7.5 | 7.4 | 0.3 |
| rDEN4Δ30 | none | 30 | 6.6 | 6.6 | 6.5 | 6.5 | 0.1 | 7.4 | 6.9 | 7.0 | 6.4 | 1.0 |
| rDEN4-23-24 | KE | 3 | 6.7 | 6.6 | 6.0 | 6.5 | 0.2 | 7.1 | 7.3 | 5.6 | ≤1.7 | >5.4 |
| rDEN4Δ30-23-24 | | | 6.1 | 5.5 | 4.9 | ≤1.7 | 4.4 | 6.5 | 5.9 | 4.7 | ≤1.7 | >4.2 |
| rDEN4-200-201 | KH | 4 | 5.3 | 4.8 | 4.8 | 4.3 | 1.0 | 5.7 | 5.4 | 2.7 | ≤1.7 | >4.0 |
| rDEN4Δ30-200-201 | | | 6.0 | 5.3 | 5.6 | ≤1.7 | >4.3 | 5.8 | 5.0 | 5.9 | ≤1.7 | >4.1 |
| rDEN4-436-437 | DK | 4 | 5.2 | 4.2 | 3.4 | 1.9 | 3.3 | 5.9 | 4.9 | 3.2 | ≤1.7 | >4.2 |
| rDEN4Δ30-436-437 [clone1] | | | 6.3 | 5.7 | 5.5 | ≤1.7 | >4.6 | 6.5 | 5.7 | 5.1 | ≤1.7 | >4.8 |
| rDEN4-808-809 | ED | 3 | 4.6 | 4.1 | ≤1.7 | ≤1.7 | >2.9 | 5.2 | ≤1.7 | ≤1.7 | ≤1.7 | >3.5 |
| rDEN4Δ30-808-809 | | | 5.6 | 4.9 | 4.9 | ≤1.7 | >3.9 | 5.9 | 4.8 | 5.1 | ≤1.7 | >4.2 |
| rDEN4-23-24-200-201 | KE, KH | 7 | 6.0 | 5.2 | 4.2 | ≤1.7 | >4.3 | 6.9 | 6.3 | ≤1.7 | ≤1.7 | >5.2 |
| rDEN4Δ30-23-24-200-201 | | | 4.5 | 4.2 | 4.8 | ≤1.7 | >2.8 | 4.9 | 4.5 | 2.9 | ≤1.7 | >3.2 |
| rDEN4-23-24-396-397 | KE, RE | 7 | 6.5 | 5.8 | 5.5 | ≤1.7 | >4.8 | 7.1 | 5.9 | 5.4 | ≤1.7 | >5.4 |
| rDEN4Δ30-23-24-396-397 | | | 6.1 | 5.2 | 4.8 | ≤1.7 | >4.4 | 6.9 | 5.4 | 4.9 | ≤1.7 | >5.2 |
| rDEN-436-437-808-809 | DK, ED | 7 | 4.9 | 4.9 | 5.1 | ≤1.7 | >3.2 | 5.5 | 3.2 | ≤1.7 | ≤1.7 | >3.8 |

[a]Underlined values indicate a 2.5 or 3.5 log$_{10}$ PFU/ml reduction in titer in Vero or HuH-7 cells, respectively, at the indicated temperature when compared to the permissive temperature (35° C.).
[b]Amino acid pair(s) changed to pair of Ala residues.
[c]Reduction in titer (log$_{10}$ pfu/ml) compared to the permissive temperature (35° C.).

TABLE 10

Addition of charge-to-alanine mutations attenuates rDEN4Δ30 in suckling mouse brain and enhances attenuation in SCID-HuH-7 mice.

| Virus | Replication in suckling mice[a] | | | Replication in SCID-HuH-7 mice[c] | | |
|---|---|---|---|---|---|---|
| | n | Mean virus titer ± SE (log$_{10}$ PFU/g brain) | Mean log reduction from wt[b] | n | Mean virus titer ± SE (log$_{10}$ PFU/ml serum) | Mean log reduction from wt[d] |
| rDEN4 | 18 | 6.2 ± 0.4 | — | 33 | 5.4 ± 0.3 | — |
| rDEN4Δ30 | 12 | 5.9 ± 0.8 | 0.2 | 8 | 3.4 ± 0.3 | 2.3 |
| rDEN4-23-24 | 18 | 4.7 ± 0.1 | 1.6 | 19 | 4.7 ± 0.5 | 1.3 |
| rDEN4Δ30-23-24 | 6 | 5.6 ± 0.3 | 0.7 | 7 | 4.6 ± 0.4 | 1.5 |
| rDEN4-200-201 | 12 | 5.5 ± 0.5 | 0.6 | 12 | 3.7 ± 0.2 | 2.6 |
| rDEN4Δ30-200-201 | 6 | 5.5 ± 0.6 | 0.1 | 4 | 3.3 ± 0.6 | 1.8 |
| rDEN4-436-437 | 18 | 2.7 ± 0.4 | 3.5 | 10 | 2.9 ± 0.7 | 2.5 |
| rDEN4Δ30-436-437 [clone 1] | 6 | 2.9 ± 0.3 | 3.4 | 4 | 2.3 ± 0.4 | 2.8 |
| rDEN4-808-809 | 6 | 1.8 ± 0.1 | 3.1 | 8 | 3.2 ± 0.4 | 3.0 |
| rDEN4Δ30-808-809 | 12 | 3.9 ± 0.7 | 2.1 | 4 | 3.7 ± 0.6 | 2.4 |

TABLE 10-continued

Addition of charge-to-alanine mutations attenuates rDEN4Δ30 in suckling mouse brain and enhances attenuation in SCID-HuH-7 mice.

| | | Replication in suckling mice[a] | | | Replication in SCID-HuH-7 mice[c] | |
|---|---|---|---|---|---|---|
| Virus | n | Mean virus titer ± SE ($\log_{10}$ PFU/g brain) | Mean log reduction from wt[b] | n | Mean virus titer ± SE ($\log_{10}$ PFU/ml serum) | Mean log reduction from wt[d] |
| rDEN4-23-24-200-201 | 12 | 5.3 ± 0.5 | 0.7 | 13 | 3.4 ± 0.1 | 2.9 |
| rDEN4Δ30-23-24-200-201 | 6 | 3.0 ± 0.2 | 2.6 | 5 | 1.8 ± 0.1 | 3.3 |
| rDEN4-23-24-396-397 | 12 | 4.6 ± 0.9 | 1.5 | 8 | 3.6 ± 0.3 | 2.3 |
| rDEN4Δ30-23-24-396-397 | 6 | 3.0 ± 0.2 | 2.6 | 5 | 2.2 ± 0.3 | 2.9 |
| rDEN4-36-437-808-809 | 6 | <1.7 ± 0.0 | 3.6 | 8 | 2.1 ± 0.3 | 2.4 |

[a]Groups of six suckling mice were inoculated i.c. with $10^4$ PFU virus in a 30 μl inoculum. The brain was removed 5 days later, homogenized, and virus was quantitated by titration in Vero cells.
[b]Determined by comparing the mean viral titers in mice inoculated with sample virus and concurrent wt controls (n = 6). The attenuation (att) phenotype is defined as a reduction of ≧1.5 $\log_{10}$ PFU/g compared to wt virus; reductions of ≧1.5 are listed in boldface.
[c]Groups of SCID-HuH-7 mice were inoculated directly into the tumor with $10^4$ PFU virus.
[d]Determined by comparing mean viral titers in mice inoculated with sample virus and concurrent wt controls.

The attenuation phenotype is defined as a reduction of ≧1.5 $\log_{10}$ PFU/g compared to wt virus; reductions of ≧1.5 are listed in boldface.

with rDEN4 showed the highest mean peak virus titer; and in each case viruses carrying the Δ30 mutation showed an approximately 0.5 log decrease in mean peak virus titer rela-

TABLE 11

Missense and UTR mutations present in rDEN4 virus derivatives bearing charge-to-alanine and the Δ30 mutation.

| Virus | Gene[a,b] | Nucleotide position | Nucleotide substitution | Amino acid position[c] | Amino acid change[b] |
|---|---|---|---|---|---|
| rDEN4-200-201 | prM | 626 | A > T | 61 | Glu > Asp |
| | NS4A | 6659 | C > T | 93 | Leu > Phe |
| | NS5 | 8160-8165 | AAACA > GCAGC | 200-201 | LysHis > AlaAla |
| rDEN4Δ30-200-201 | NS3 | 4830 | G > A | 102 | Gly > Arg |
| | NS5 | 8106 | G > A | 181 | Val > Ile |
| | NS5 | 8160-8165 | AAACA > GCAGC | 200-201 | LysHis > AlaAla |
| | 3′ UTR | 10478-10507 | Δ30 deletion | None | None |
| rDEN4-436-437 [clone 1] | E | 2331 | T > G | 464 | Trp > Gly |
| | NS1 | 2845 | C > T | 140 | Ser > Phe |
| | NS3* | 4891 | T > C | 122 | Ile > Thr |
| | NS5 | 8869-8873 | GACAA > GCAGC | 436-437 | AspLys > AlaAla |
| | NS5 | 9659 | A > G | 699 | Lys > Arg |
| rDEN4-436-437 [clone 2] | NS4B | 7153 | T > C | 108 | Val > Ala |
| | NS5 | 8869-8873 | GACAA > GCAGC | 436-437 | AspLys > AlaAla |
| rDEN4Δ30-436-437 | NS4B* | 7163 | A > C | 111 | Leu > Phe |
| | NS5 | 8869-73 | GACAA > GCAGC | 436-437 | AspLys > AlaAla |
| | 3′ UTR | 10478-10507 | Δ30 deletion | None | None |
| rDEN4-23-24-200-201 | NS3 | 6751 | A > C | 124 | Lys > Thr |
| | NS5 | 7629-7633 | AAAGA > GCAGC | 23-24 | LysGlu > AlaAla |
| | NS5 | 8160-8165 | AAACA > GCAGC | 200-201 | LysHis > AlaAla |

[a]Asterisk indicates previously identified Vero cell adaptation mutation.
[b]Bold values indicate mutations designed to occur in the designated virus.
[c]Amino acid position in the protein product of the designated DEN4 gene; numbering starts with the amino terminus of the protein.

Figure 4:
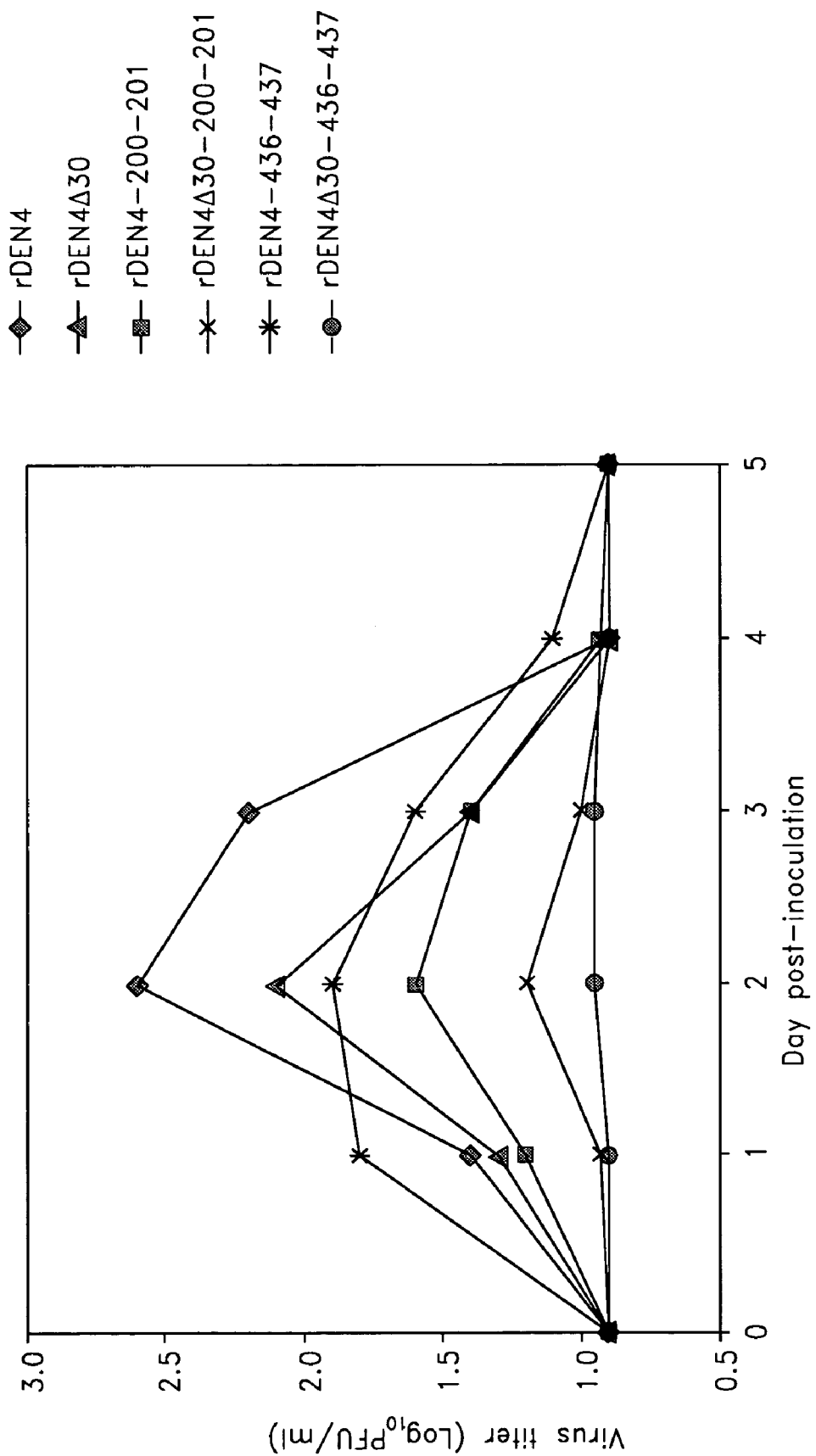
FIG. 4. Viremia levels in rhesus monkeys inoculated with rDEN4 vaccine candidates bearing pairs of charge-to-alanine mutations in NS5. Groups of four or two (rDEN4 and rDEN4Δ30) monkeys were inoculated with 5.0 $\log_{10}$PFU virus subcutaneously. Serum was collected daily and virus titers were determined by plaque assay in Vero cells. The limit of virus detection was 1.0 $\log_{10}$PFU/ml. Mean virus titers are indicated for each group. Viremia was not detected in any monkey after day 4.

Based on the attenuation in the SCID-HuH7 mouse model, four of the charge-to-alanine mutant viruses (rDEN4-200-201, rDEN4Δ30-200-201, rDEN4-436-437 [clone 2], rDEN4Δ30-436-437) were evaluated in rhesus macaques as described above. As with the study of viruses carrying attenuating point mutations, viremia was detected on day 1 post-infection and ended by day 4 in all monkeys (FIG. 4, Table 12). Viremia was detected in most of the monkeys infected; only one of the four monkeys infected with rDEN4Δ30-200-201 and one of the four monkeys infected with rDEN4Δ30-436-437 showed no detectable viremia. Monkeys infected with rDEN4 showed the highest mean peak virus titer; and in each case viruses carrying the Δ30 mutation showed an approximately 0.5 log decrease in mean peak virus titer relative to their parental viruses and a 0.5 to 2 day decrease in mean number of viremic days per monkey. Monkeys infected with viruses carrying both the Δ30 and charge-to-alanine mutations showed a two-fold reduction in mean peak viremia relative to those infected with rDEN4Δ30. This suggests that addition of the charge-to-alanine mutations further attenuates rDEN4Δ30 for rhesus macaques.

As expected, none of the monkeys in this study showed detectable levels of neutralizing antibody on day 0. On day 28, every monkey infected with a virus showed a detectable levels of neutralizing antibody, indicating that all of the monkeys, even those that showed no detectable viremia, had indeed been infected. As in the study of attenuating point mutations, monkeys infected with rDEN4 had a mean serum neutralizing antibody titer (reciprocal dilution) which was approximately twice that of monkeys that had been infected with rDEN4Δ30. Monkeys infected with rDEN4-200-201 and rDEN4-436-437 [clone 2] had similar mean neutralizing antibody titers to rDEN4, and those infected with rDEN4Δ30-200-201 and rDEN4Δ30-436-437 had similar mean neutralizing antibody titers to rDEN4. In each case the addition of the Δ30 mutation to a virus resulted in a two-fold decrease in neutralizing antibody. Thus, although the addition of charge-to-alanine mutations to rDEN4Δ30 decreased mean peak viremia below that of rDEN4Δ30 alone, it did not affect levels of neutralizing antibody.

TABLE 12

Addition of paired charge-to-alanine mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <5 | <5 |
| rDEN4 | 2 | 2 | 2.5 | 2.6 ± 0.3 | <5 | 276 |
| rDEN4Δ30 | 2 | 2 | 2.0 | 2.1 ± 0.1 | <5 | 131 |
| rDEN4-200, 201 | 4 | 4 | 2.3 | 1.8 ± 0.3 | <5 | 212 |
| rDEN4Δ30-200, 201 | 4 | 3 | 1.5 | 1.3 ± 0.2 | <5 | 139 |
| rDEN4-436, 437 [cl 2] | 4 | 4 | 3.3 | 1.8 ± 0.2 | <5 | 273 |
| rDEN4Δ30-436, 437 | 4 | 3 | 1.3 | 1.0 ± 0.0 | <5 | 143 |

[a]Groups of rhesus monkeys were inoculated subcutaneously with $10^5$ PFU of the indicated virus in a 1 ml dose. Serum was collected on days 0 to 6, 8, 10 and 28. Virus titer was determined by plaque assay in Vero cells.
[b]Viremia was not detected in any monkey after day 4.

After challenge with rDEN4 on day 28, mock-infected monkeys had a mean peak virus titer of 1.5 $\log_{10}$PFU/ml and a mean number of viremic days of 3.0 (Table 13). However, none of the monkeys previously inoculated with rDEN4, rDEN4Δ30 or the charge-to-alanine mutant viruses showed detectable viremia. Additionally, none of the monkeys showed a greater than four-fold increase in serum neutralizing antibody titer. Together these data indicate that infection with any of the viruses, including those carrying both Δ30 and the charge-to-alanine mutations, protected rhesus macaques from challenge with rDEN4.

TABLE 13 rDEN4Δ30 containing charge-to-alanine mutations protects rhesus monkeys from wt DEN4 virus challenge

| Virus[a] | No. of monkeys | Mean no. of viremic days per monkey after rDEN4 challenge | Mean peak virus titer ($\log_{10}$ PFU/ml ± SE) | Geometric mean serum neutralizing antibody titer (reciprocal dilution) | |
|---|---|---|---|---|---|
| | | | | Day 28 | Day 56 |
| mock | 2 | 3.0 | 1.5 ± 0.7 | <5 | 284 |
| rDEN4 | 2 | 0.0 | <0.7 | 276 | 316 |
| rDEN4Δ30 | 2 | 0.0 | <0.7 | 131 | 96 |
| rDEN4-200, 201 | 4 | 0.0 | <0.7 | 212 | 356 |
| rDEN4Δ30-200, 201 | 4 | 0.0 | <0.7 | 139 | 132 |
| rDEN4-436, 437 [cl 2] | 4 | 0.0 | <0.7 | 273 | 401 |
| rDEN4Δ30-436, 437 | 4 | 0.0 | <0.7 | 143 | 182 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 10, and 56. Virus titer was determined by plaque assay in Vero cells.

Addition of charge-to-alanine mutations to rDEN4Δ30 can confer a range of ts phenotypes in both Vero and HuH-7 cells and att phenotypes in suckling mouse brain and can either enhance or leave unchanged attenuation in SCID-HuH-7 mice. Most importantly, addition of these mutations can decrease the viremia produced by rDEN4Δ30 in rhesus macaques without decreasing neutralizing antibody titer or protective efficacy. Thus addition of such mutations to rDEN4Δ30 is contemplated as enhancing attenuation in humans. Also, mutations are contemplated as being added that do not change the overall level of attenuation, but stabilize the attenuation phenotype because they themselves are independently attenuating even in the absence of the Δ30 mutation. Charge-to-alanine mutations are particularly useful because they occur outside of the structural gene regions, and so can be used to attenuate structural gene chimeric viruses. Moreover, they involve at least three nucleotide changes, making them unlikely to revert to wild type sequence.

A series of point mutations that enhance the replication of rDEN4 in Vero cells tissue culture have been identified; these are primarily located in the NS4B gene (Blaney, J. E. et. al. 2002 *Virology* 300:125-139; Blaney, J. E. et al. 2001 *J Virol* 75:9731-9740). Vero cell adaptation mutations confer two desirable features upon a vaccine candidate. First, they enhance virus yield in Vero cells, the intended substrate for vaccine production, and thus render vaccine production more cost-effective. Second, although each of these Vero adaptation mutations are point mutations, they are likely to be extremely stable during vaccine manufacture, because they give a selective advantage in Vero cells. At least one Vero cell adaptation mutation, at position 7129, was also shown to decrease mosquito infectivity of rDEN4; poor mosquito infectivity is another desirable characteristic of a dengue vaccine candidate. To investigate the generality of this finding, we tested the effect of the remaining Vero cell adaptation mutations on the ability of rDEN4 to infect *Aedes aegypti* mosquitoes fed on an infectious bloodmeal. Table 14 shows the infectivity of each virus carrying a single Vero cell adaptation mutation at high titer. Of these, only one mutation, at position 7182, was associated with a large decrease in mosquito infectivity. Thus 7182 may be a particularly valuable mutation to include in an rDEN4 vaccine candidate, as it has opposite effects on replication in Vero cells and in mosquitoes.

TABLE 14

Effect of Vero cell adaptation mutations on rDEN4 mosquito infectivity

| Virus | *Aedes aegypti* (oral infection) | | | |
|---|---|---|---|---|
| | Dose[a] | | % infected[b] | |
| | (log$_{10}$ pfu) | No. tested | Midgut | Head |
| rDEN4 | 4.3 | 27 | 70 | 25 |
| rDEN4-4891 | 4.4 | 23 | 74 | 13 |
| rDEN4-4995 | 4.8 | 20 | 80 | 50 |
| rDEN4-7153 | 4.8 | 20 | 80 | 30 |
| rDEN4-7546 | 4.6 | 20 | 55 | 10 |
| rDEN4-7162 | 5.0 | 20 | 55 | 25 |
| rDEN4-7163 | 4.9 | 15 | 73 | 72 |
| rDEN4-7182 | 5.0 | 20 | 20 | 0 |
| rDEN4-7630 | 4.3 | 10 | 70 | 10 |

[a]Virus titer ingested, assuming a 2 μl bloodmeal.
[b]Percentage of mosquitoes with IFA detectable antigen in midgut or head tissue prepared 21 days after oral infection.

EXAMPLE 2

Generation and Characterization of a Recombinant DEN1 Virus Containing the Δ30 Mutation We first sought to determine if the Δ30 mutation was able to satisfactorily attenuate a wild-type DEN virus other than the DEN4 serotype. To do this, the Δ30 mutation was introduced into the cDNA for DEN1 (Western Pacific). The pRS424DEN1WP cDNA clone (Puri, B. et al. 2000 *Virus Genes* 20:57-63) was digested with BamHI and used as template in a PCR using Pfu polymerase with forward primer 30 (DEN1 nt 10515-10561 and 10592-10607) and the M13 reverse sequencing primer (101 nt beyond the 3' end of DEN1 genome sequence). The resulting PCR product was 292 bp and contained the Δ30 mutation. The pRS424DEN1WP cDNA was partially digested with Apa I, then digested to completion with Sac II and the vector was gel isolated, mixed with PCR product, and used to transform yeast strain YPH857 to yield growth on plates lacking tryptophan (Polo, S. et al. 1997 *J Virol* 71:5366-74). Positive yeast colonies were confirmed by PCR and restriction enzyme analysis. DNA isolated from two independent yeast colonies was used to transform *E. coli* strain STBL2. Plasmid DNA suitable for generating RNA transcripts was prepared and the presence of the Δ30 mutation was verified by sequence analysis.

For transcription and generation of virus, cDNA (designated pRS424DEN1Δ30) that was linearized with Sac II was used as template in a transcription reaction using SP6 RNA polymerase as described (Polo, S. et al. 1997 *J Virol* 71:5366-74). Transcription reactions were electroporated into LLC-MK2 cells and infection was confirmed by observation of CPE and immunofluorescence and harvested on day 14. Virus stocks were amplified on C6/36 mosquito cells and titered on LLC-MK2 cells. The genome of the resulting virus, rDEN1Δ30, was sequenced to confirm the presence of the Δ30 mutation. The Δ30 mutation removes nucleotides 10562-10591 of DEN1 (FIG. 2B, C), which corresponds to the TL2 of DEN1. The virus replicates efficiently in Vero cell culture to titers of 6.5 log$_{10}$PFU/ml, indicating that the Δ30 mutation is compatible with efficient growth of DEN1 in cell culture, a property essential for manufacture of the vaccine. Using similar techniques, parent virus rDEN1 was generated. Incidental mutations arising from virus passage in tissue culture were identified in both rDEN1 and rDEN1Δ30 using sequence analysis and are listed in Table 15. An additional rDEN1Δ30 virus was derived by transfection and amplification in Vero cells. Although this virus was not evaluated in the studies described below, its sequence analysis is included in Table 15. The properties of rDEN1Δ30 as a vaccine in vivo were next examined.

TABLE 15

Missense mutations present among the recombinant DEN1 viruses and correlation of NS4B region mutations with those found in DEN4

| Virus | Transfection cell type | Gene | Nucleotide position | Nucleotide change | Amino acid position | Amino acid change |
|---|---|---|---|---|---|---|
| wt rDEN1 | LLC-MK2 | prM | 816 | C > U | 241 | Ala > Val |
|  |  | NS4B | 7165[a] | U > G | 2357 | Phe > Leu |
|  |  | NS4B | 7173[b] | U > C | 2360 | Val > Ala |
| rDEN1Δ30 | LLC-MK2 | E | 1748 | A > U | 552 | Thr > Ser |
| rDEN1Δ30 | Vero | E | 1545 | A > G | 484 | Lys > Arg |

[a]Same nucleotide as 7154 in rDEN4.
[b]Same nucleotide as 7162 in rDEN4

\* Nucleotide and amino acid comparison of selected NS4B region:

```
              7              7              7              7              7              7
DEN4          1              1              1              1              1              1 base          3              4              5              6              7              8

Number:  89012345678901234567890123456789012345678901234567890123456 7
          ++       ++   + +++++   +   +   +   + ++   +      ++++++++ ++  ++  ++  ++

D4 7128- CCAACAACCUUGACAGCAUCCUUAGUCAUGCUUUUAGUCCAUUAUGCAAUAAUAGGCCCA
          P   T   T   L   T   A   S   L   V   M   L   L   V   H   T   A   I   I   G   P

D1 7139- CCGCUGACGCUGACAGCGGCGGUAUUUAUGCUAGUGGCUCAUUAUGCCAUAAUUGGACCC
          P   L   T   L   T   A   A   V   P   M   L   V   A   H   T   A   I   I   G   P

D2 7135- CCUAUAACCCUCACAGCGGCUCUUCUUUUAUUGGUAGCACAUUAUGCCAUCAUAGGACCG
          P   I   T   L   T   A   A   L   L   L   L   V   A   H   T   A   I   I   G   P

D3 7130- CCACUAACUCUCACAGCGGCAGUUCUCCUGCUAGUCACGCAUUAUGCUAUUAUAGGUCCA
          P   L   T   L   T   A   A   V   L   L   L   V   T   H   T   A   I   I   G   P
          +   +   +   +   +           +           +   +   +   +   +   +   +
D4 = rDEN4
D1 = rDEN1(WP)
D2 = rDEN2(Tonga/74)
D3 = rDEN3(Sleman/78)
+Homology among all four serotypes
Nucleotides are underlined in even multiples of 10.
```

Figure 5:
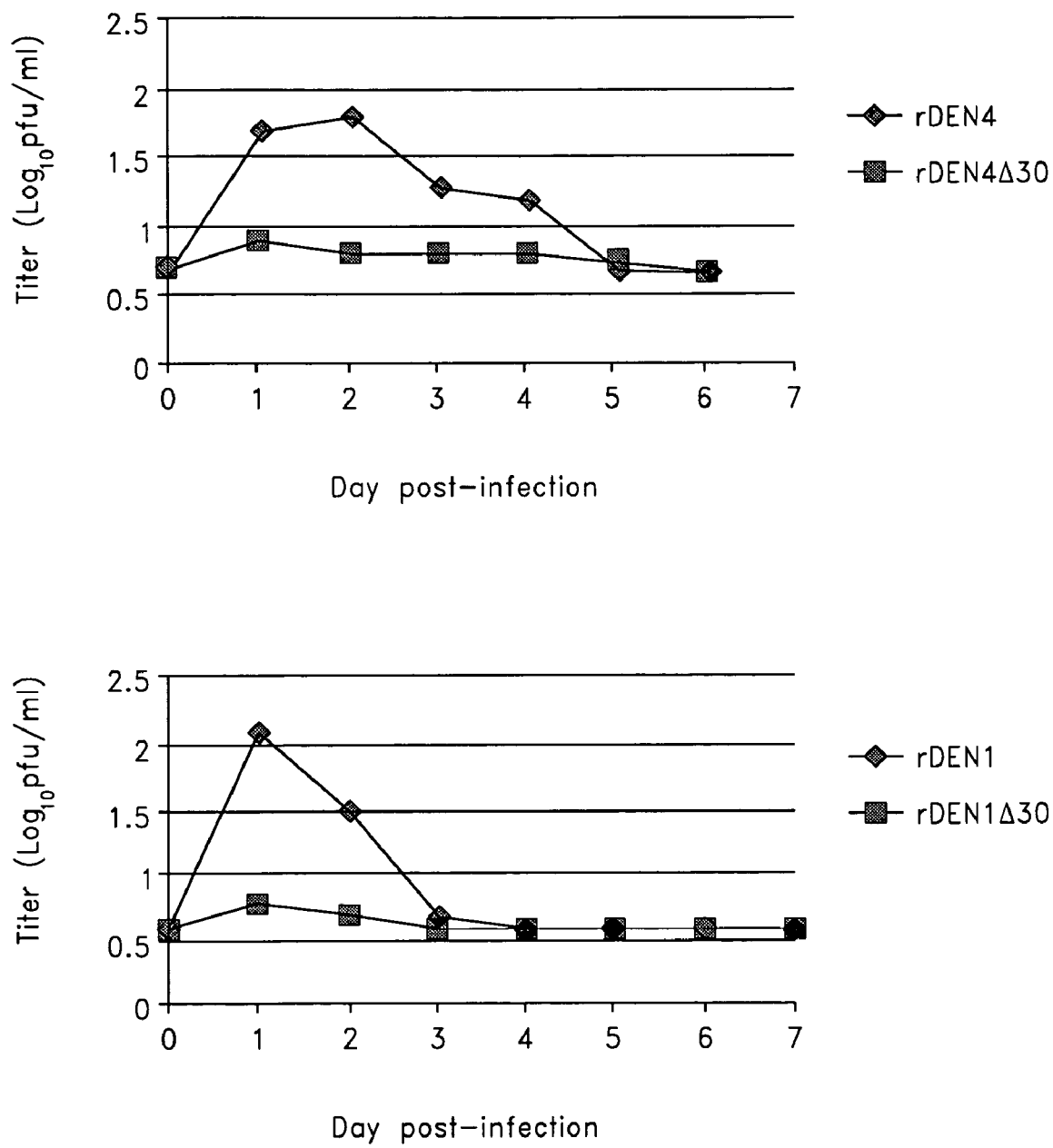
FIG. 5. The Δ30 mutation attenuates both DEN1 and DEN4 for rhesus monkeys. Groups of 4 monkeys were immunized subcutaneously with 5.0 $\log_{10}$PFU of the indicated virus. Serum was collected each day following immunization and virus titers were determined and are shown as mean $\log_{10}$PFU/ml.

Evaluation of the replication, immunogenicity, and protective efficacy of rDEN1Δ30 and wild-type parental rDEN1 virus (derived from the pRS424DEN1WP cDNA) in juvenile rhesus monkeys was performed as follows. Dengue virus-seronegative monkeys were injected subcutaneously with 5.0 $\log_{10}$PFU of virus in a 1 ml dose divided between two injections in each side of the upper shoulder area. Monkeys were observed daily and blood was collected on days 0-10 and 28 and serum was stored at −70° C. Titer of virus in serum samples was determined by plaque assay in Vero cells as described previously (Durbin, A. P. et al. 2001 *Am J Trop Med Hyg* 65:405-13). Plaque reduction neutralization titers were determined for the day 28 serum samples as previously described (Durbin, A. P. et al. 2001 *Am J Trop Med Hyg* 65:405-13). All monkeys were challenged on day 28 with a single dose of 5.0 $\log_{10}$PFU of wild-type rDEN1 and blood was collected for 10 days. Virus titer in post-challenge sera was determined by plaque assay in Vero cells. Monkeys inoculated with full-length wild-type rDEN1 were viremic for 2-3 days with a mean peak titer of 2.1 $\log_{10}$PFU/ml (Table 16), and monkeys inoculated with rDEN1Δ30 were viremic for less than 1 day with a mean peak titer of 0.8 $\log_{10}$PFU/ml, indicating that the Δ30 mutation is capable of attenuating DEN1. As expected for an attenuated virus, the immune response, as measured by neutralizing antibody titer, was lower following inoculation with rDEN1Δ30 compared to inoculation with wild-type rDEN1 (Table 16), yet sufficiently high to protect the animals against wild-type DEN1 virus challenge. Wild-type rDEN1 virus was not detected in any serum sample collected following virus challenge, indicating that monkeys were completely protected following immunization with either full-length wild-type rDEN1 or recombinant virus rDEN1Δ30. The level of attenuation specified by the Δ30 mutation was comparable in both the DEN1 and DEN4 genetic backgrounds (FIG. 5).

TABLE 16

The Δ30 mutation attenuates rDEN1 for rhesus monkeys

| Virus* | n | Mean no. days with viremia | Mean peak titer ($\log_{10}$ pfu/ml) | Mean neutralization titer | Mean peak titer of challenge virus |
|---|---|---|---|---|---|
| rDEN1 | 4 | 2.8 | 2.1 | 1230 | <0.7 |
| rDEN1Δ30 | 4 | 0.5 | 0.8 | 780 | <0.7 |

*Rhesus monkeys were inoculated subcuateously with 5.0 $\log_{10}$ PFU of virus. Serum samples were collected daily for 10 days. Serum for neutralization assay was collected on day 28. All monkeys were challenged on day 28 with 5.0 $\log_{10}$ PFU of rDEN1.

As previously reported, rDEN4 virus replicated to greater than 6.0 $\log_{10}$PFU/ml serum in SCID-HuH-7 mice, while the replication of rDEN4 virus bearing the Δ30 mutation was reduced by about 10-fold (Blaney, J. E. Jr. et al. 2002 *Virology* 300:125-139). The replication of rDEN1Δ30 was compared to that of wt rDEN1 in SCID-HuH-7 mice (Table 17). rDEN1Δ30 replicated to a level approximately 100-fold less than its wt rDEN1 parent. This result further validates the use of the SCID-HuH-7 mouse model for the evaluation of attenuated strains of DEN virus, with results correlating closely with those observed in rhesus monkeys.

TABLE 17

The Δ30 mutation attenuates rDEN1 for HuH-7-SCID mice

| Virus | No. of Mice[5] | Mean peak virus titer[6] ($\log_{10}$ pfu/ml ± SE) |
|---|---|---|
| wt rDEN1 | 9 | 7.3 ± 0.2 |
| rDEN1Δ30 | 8 | 5.0 ± 0.3 |

[5]Groups of HuH-7-SCID mice were inoculated directly into the tumor with 4.0 $\log_{10}$ pfu virus. Serum was collected on day 6 and 7, and virus titer was determined by plaque assay in Vero cells.
[6]Significant difference was found between rDEN1 and rDEN1Δ30 viruses, Tukey-Kramer test (P < 0.005).

Finally, the infectivity of rDEN1 and rDEN1Δ30 for mosquitoes was assessed, using the methods described in detail in Example 5. Previously, the Δ30 mutation was shown to decrease the ability of rDEN4 to cross the mosquito midgut barrier and establish a salivary gland infection (Troyer, J. M. et al. 2001 *Am J Trop Med Hyg* 65:414-419). However neither rDEN1 nor rDEN1Δ30 was able to infect the midgut of *Aedes aegypti* mosquitoes efficiently via an artificial bloodmeal (Table 18), so it was not possible to determine whether Δ30 might further block salivary gland infection. A previous study also showed that the Δ30 had no effect on the infectivity of rDEN4 for *Toxorhynchites splendens* mosquitoes infected via intrathoracic inoculation (Troyer, J. M. et al. 2001 *Am J Trop Med Hyg* 65:414-419), and a similar pattern was seen for rDEN1 and rDEN1Δ30 (Table 18). The genetic basis for the inability of rDEN1 to infect the mosquito midgut has not been defined at this time. However, this important property of restricted infectivity for the mosquito midgut is highly desirable in a vaccine candidate since it would serve to greatly restrict transmission of the vaccine virus from a vaccinee to a mosquito vector.

TABLE 18

DEN1 and DEN1Δ30 viruses are both highly infectious for *Toxorhynchites splendens*, but do not infect *Aedes aegypti* efficiently.

| | *Toxorhynchites splendens* (intrathoracic inoculation) | | | *Aedes aegypti* (oral infection) | | | |
|---|---|---|---|---|---|---|---|
| Virus | Dose[a] ($\log_{10}$ pfu) | No. tested | % infected[b] | Dose[c] ($\log_{10}$ pfu) | No. tested | % infected[d] Midgut | Head |
| rDEN1 | 3.5 | 7 | 100 | 4.0 | 26 | 11 | 0 |
| | 2.5 | 8 | 75 | | | | |
| | 1.5 | 7 | 71 | | | | |
| | 0.5 | 5 | 60 | | | | |
| | | | MID$_{50}$ < 0.5 | | | MID$_{50}$ ≧ 4.4 | |
| rDEN1 Δ30 | 2.7 | 8 | 100 | 3.2 | 20 | 10 | 0 |
| | 1.7 | 7 | 100 | | | | |
| | 0.7 | 6 | 83 | | | | |
| | | | MID$_{50}$ < 0.7 | | | MID$_{50}$ ≧ 3.6 | |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the MID$_{50}$ was estimated by assuming that a 10-fold more concentrated virus dose would infect 100% of the mosquitoes.

Thus, the Δ30 mutation, first described in DEN4, was successfully transferred to rDEN1. The resulting virus, rDEN1Δ30, was shown to be attenuated in monkeys and SCID-HuH-7 mice to levels similar to recombinant virus rDEN4Δ30, thereby establishing the conservation of the attenuation phenotype specified by the Δ30 mutation in a different DEN virus background. Based on the favorable results of rDEN4Δ30 in recent clinical trials (Durbin, A. P. et al. 2001 *Am J Trop Med Hyg* 65:405-13), it is predicted that rDEN1Δ30 will be suitably attenuated in humans. To complete the tetravalent vaccine, attenuated rDEN2 and rDEN3 recombinant viruses bearing the Δ30 mutation are contemplated as being prepared (See Examples 3 and 4 below). The demonstration that the Δ30 mutation specifies a phenotype that is transportable to another DEN serotype has important implications for development of the tetravalent vaccine. This indicates that the Δ30 mutation is expected to have a corresponding effect on DEN2 and DEN3 wild-type viruses.

EXAMPLE 3

Figures 6A, 6B:
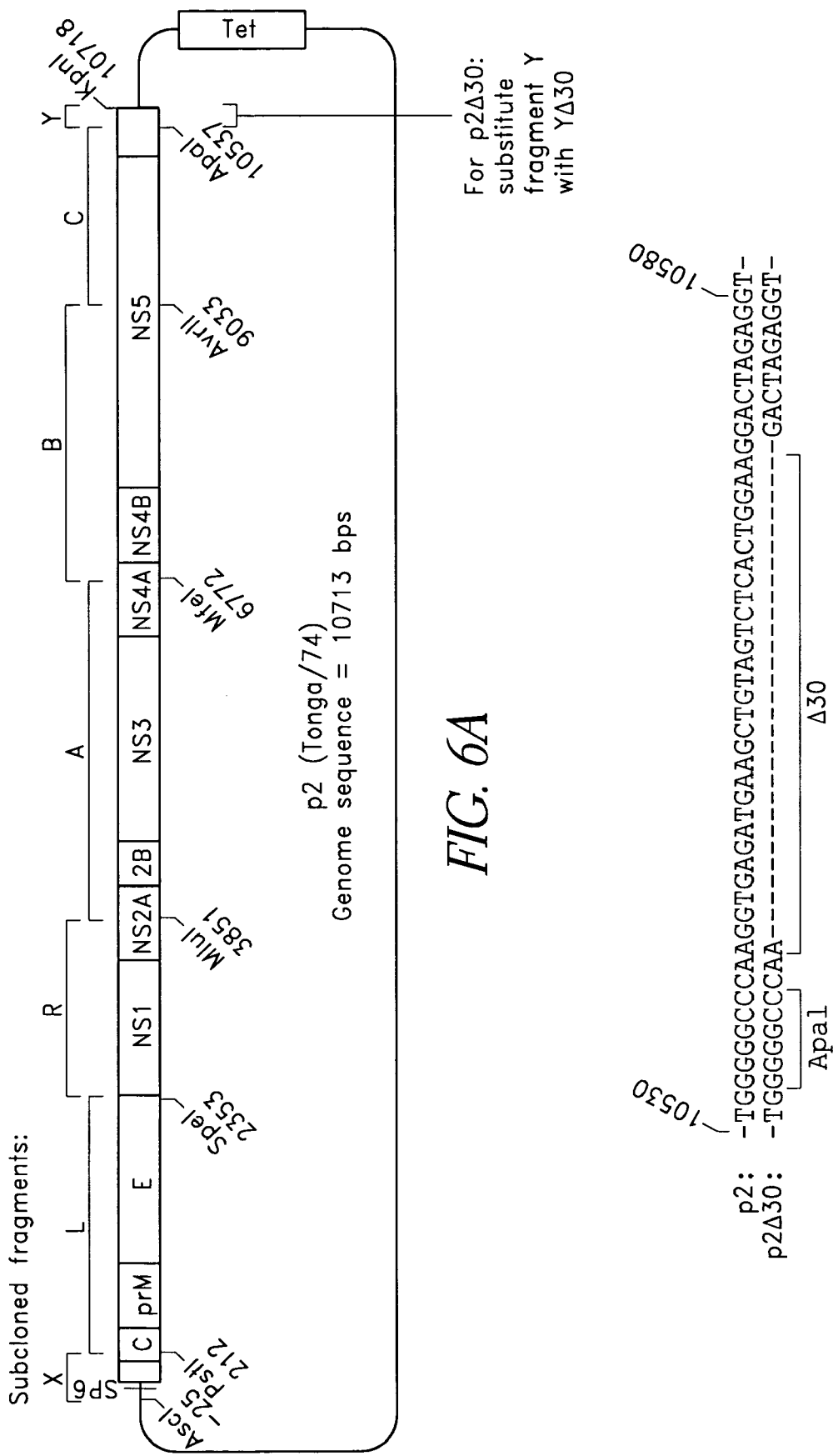
FIG. 6. A. Diagram of the p2 (Tonga/74) full-length cDNA plasmid. Regions subcloned are indicated above the plasmid. Numbering begins at the 5' end of the viral sequence. B. The Δ30 mutation removes the indicated 30 nucleotides from the 3' UTR sequence to create p2Δ30.

Generation and Characterization of a Recombinant DEN2 Virus Containing the Δ30 Mutation Evaluation of rDEN1Δ30 showed that it was satisfactorily attenuated. Based on this result, we sought to extend our technology to the creation of a DEN2 vaccine candidate. To do this, the Δ30 mutation was introduced into the cDNA of DEN2. A DEN2 virus isolate from a 1974 dengue epidemic in the Kingdom of Tonga (Tonga/74) (Gubler, D. J. et al. 1978 *Am J Trop Med Hyg* 27:581-589) was chosen to represent wt DEN2. The genome of DEN2 (Tonga/74) was sequenced in its entirety and served as consensus sequence for the construction of a full-length cDNA clone (Appendix 1). cDNA fragments of DEN2 (Tonga/74) were generated by reverse-transcription of the genome as indicated in FIG. 6A. Each fragment was subcloned into a plasmid vector and sequenced to verify that it matched the consensus sequence as determined for the virus. This yielded seven cloned cDNA fragments spanning the genome. Cloned fragments were modified as follows: Fragment X, representing the 5' end of the genome was abutted to the SP6 promoter; Fragment L was modified to contain a translationally-silent SpeI restriction site at genomic nucleotide 2353; Fragment R was modified to contain a translationally-silent SpeI restriction site also at genomic nucleotide 2353, and to stabilize the eventual full-length clone, two additional translationally-silent mutations at nucleotides 2362-2364 and 2397 were created to ensure that translation stop codons were present in all reading frames other than that used to synthesize the virus polyprotein; Fragment A was modified at nucleotide 3582 to ablate a naturally occurring SpeI restriction site and at nucleotide 4497 to ablate a naturally occurring KpnI restriction site; Fragment C was modified at nucleotide 9374 to ablate a naturally occurring KpnI restriction site; and Fragment Y, representing the 3' end of the genome was abutted to a KpnI restriction site. Each fragment was added incrementally between the AscI and KpnI restriction sites of DEN4 cDNA clone p4 (Durbin, A. P. et al. 2001 *Am J Trop Med Hyg* 65:405-13) to generate a full-length DEN2 cDNA clone (p2) with the same vector background successfully used to generate rDEN4 and rDEN4Δ30. cDNA clone p2 was sequenced to confirm that the virus genome region matched the DEN2 (Tonga/74) consensus sequence, with the exception of the translationally-silent modifications noted above. The Δ30 mutation was introduced into Fragment Y to generate Fragment YΔ30. To create p2Δ30, the Fragment Y region of p2 was replaced with Fragment YΔ30 (FIG. 6A, B).

For transcription and generation of infectious virus, cDNA (p2 and p2Δ30) was linearized with Acc65I (isoschizomer of KpnI which cleaves leaving only a single 3' nucleotide) and used as template in a transcription reaction using SP6 RNA polymerase as previously described (Blaney, J. E. et. al. 2002 *Virology* 300:125-139). Transcripts were introduced into Vero cells or C6/36 mosquito cells using liposome-mediated transfection and cell culture supernatants were harvested on day 7.

rDEN2 virus was recovered from the p2 cDNA in both Vero and C6/36 cells, while rDEN2Δ30 was recovered from the p2Δ30 cDNA clone in only C6/36 cells (Table 19). The level of infectious virus recovered in C6/36 cells was comparable for the p2 and p2Δ30 cDNA clones when assayed by plaque titration and immunostaining in Vero or C6/36 cells. As previously observed, the efficiency of transfection in C6/36 cells was higher than that in Vero cells. Two rDEN2Δ30 viruses were recovered from independent cDNA clones, #2 and #10.

TABLE 19 rDEN2 virus is recovered in Vero and C6/36 cells, but rDEN2Δ30 virus is recovered only in C6/36 cells.

| Transfection cell type | cDNA construct | Clone | Virus | Virus titer of transfection harvest (day 7) determined in the indicated cell type ($\log_{10}$ PFU/ml) | |
|---|---|---|---|---|---|
| | | | | Vero cells | C6/36 cells |
| Vero cells | p2 | #8A | rDEN2 | 3.1 | 4.3 |
| | p2Δ30 | #2 | rDEN2Δ30 | <0.7 | <0.7 |
| | p2Δ30 | #10 | rDEN2Δ30 | <0.7 | <0.7 |
| C6/36 cells | p2 | #8A | rDEN2 | 5.5 | 7.5 |
| | p2Δ30 | #2 | rDEN2Δ30 | 4.8 | 7.6 |
| | p2Δ30 | #10 | rDEN2Δ30 | 4.6 | 7.5 |

To produce working stocks of rDEN2 and rDEN2Δ30 viruses, transfection harvests were passaged and terminally diluted in Vero cells, and genomic sequences of the viruses were determined. The Vero cell transfection harvest of rDEN2 virus was terminally diluted once in Vero cells, and individual virus clones were passaged once in Vero cells. To assess whether any homologous Vero cell adaptation mutations identified in the rDEN4 NS4B 7100-7200 region were present in these virus clones, seven independent terminally diluted clones were sequenced over this region. Each of the seven rDEN2 viruses contained a single nucleotide substitution in this region at nucleotide 7169 (U>C) resulting in a Val>Ala amino acid change. This nucleotide corresponds to the 7162 mutation identified in rDEN4 (Blaney, J. E. et. al. 2002 *Virology* 300:125-139), which has a known Vero cell adaptation phenotype suggesting that this mutation may confer a replication enhancement phenotype in rDEN2 virus. One rDEN2 virus clone was completely sequenced and in addition to the 7169 mutation, a missense mutation (Glu>Ala) was found in NS5 at residue 3051 (Table 20).

TABLE 20

Missense mutations which accumulate in rDEN2 and rDEN2Δ30 viruses after transfection or passage in Vero cells.

| Virus | Gene | Nucleotide position | Nucleotide substitution | Amino acid position[a] | Amino acid change |
|---|---|---|---|---|---|
| rDEN2[b] | NS4B | 7169[c] | U > C | 2358 | Val > Ala |
| (Vero) | NS5 | 9248 | A > C | 3051 | Glu > Ala |
| rDEN2Δ30[d] | NS3 | 4946 | A > G | 1617 | Lys > Arg |
| (Vero) | NS4B | 7169[c] | U > C | 2358 | Val > Ala |

[a]Amino acid position in DEN2 polyprotein beginning with the methionine residue of the C protein (nucleotides 97–99) as position 1.
[b]Virus was recovered in Vero cells and terminally-diluted once in Vero cells. Virus stock was prepared in Vero cells.
[c]Same nucleotide position as 7162 in rDEN4.
[d]Virus was recovered in C6/36 cells and passaged three times in Vero cells. Virus was then terminally diluted and a stock was prepared in Vero cells.

Because both rDEN2 and rDEN2Δ30 viruses grown in Vero cells acquired the same mutation at nucleotide 7169, which corresponds to the Vero cell adaptation mutation previously identified in rDEN4 at nucleotide 7162, it was reasoned that this mutation is associated with growth adaptation of rDEN2 and rDEN2Δ30 in Vero cells. In anticipation that the 7169 mutation may allow rDEN2Δ30 to be recovered directly in Vero cells, the mutation was introduced into the rDEN2Δ30 cDNA plasmid to create p2Δ30-7169. Transcripts synthesized from p2Δ30-7169, as well as p2 and p2Δ30 were introduced into Vero cells or C6/36 mosquito cells using liposome-mediated transfection as described above. Virus rDEN2Δ30-7169 was recovered from the p2Δ30-7169 cDNA in both Vero and C6/36 cells, while rDEN2Δ30 was recovered from the p2Δ30 cDNA clone in only C6/36 cells (Table 21). The 7169 mutation is both necessary and sufficient for the recovery of rDEN2Δ30 in Vero cells.

TABLE 21 rDEN2Δ30-7169 virus containing the 7169 Vero cell adaptation mutation is recovered in both Vero and C6/36 cells

| Transfection cell type | cDNA construct | Clone | Virus | Virus titer of transfection harvest (day 14) determined in C6/36 cells ($\log_{10}$ PFU/ml) |
|---|---|---|---|---|
| Vero cells | p2 | #8A | rDEN2 | 6.8 |
| | p2Δ30 | #2 | rDEN2Δ30 | <0.7 |
| | p2Δ30-7169[a] | #37 | rDEN2Δ30-7169 | 5.1 |
| C6/36 cells | p2 | #8A | rDEN2 | 6.9 |
| | p2Δ30 | #2 | rDEN2Δ30 | 7.1 |
| | p2Δ30-7169 | #37 | rDEN2Δ30-7169 | 7.2 |

[a]Nucleotide 7169 in rDEN2 corresponds to nucleotide 7162 in rDEN4 which has been shown to be associated with growth adaptation in Vero cells.

To initially assess the ability of the Δ30 mutation to attenuate rDEN2 virus in an animal model, the replication of DEN2 (Tonga/74), rDEN2, and rDEN2Δ30 viruses was evaluated in SCID-HuH-7 mice. Previously, attenuation of vaccine candidates in SCID-HuH-7 mice has been demonstrated to be predictive of attenuation in the rhesus monkey model of infection (Examples 1 and 2). The recombinant viruses tested in this experiment were recovered in C6/36 cells. The DEN2 Tonga/74 virus isolate, rDEN2, and two independent rDEN2Δ30 viruses, (clones 20A and 21A) which were derived from two independent p2Δ30 cDNA clones, were terminally diluted twice in C6/36 cells prior to production of a working stock in C6/36 cells. These viruses should not contain any Vero cell adaptation mutations. DEN2 Tonga/74 virus replicated to a mean virus titer of 6.2 $\log_{10}$PFU/ml in the serum of SCID-HuH-7 mice, and rDEN2 virus replicated to a similar level, 5.6 $\log_{10}$ PFU/ml (Table 22). Both rDEN2Δ30 viruses were greater than 100-fold restricted in replication compared to rDEN2 virus. These results indicate that the Δ30 mutation has an attenuating effect on replication of rDEN2 virus similar to that observed for rDEN4 and rDEN1 viruses.

TABLE 22

The Δ30 mutation restricts rDEN2 virus replication in SCID-HuH-7 mice.

| Virus | No. of mice | Mean virus titer ± SE ($\log_{10}$ PFU/ml serum)[a] | Mean $\log_{10}$-unit reduction from value for wt[b] |
|---|---|---|---|
| DEN2 (Tonga/74) | 8 | 6.2 ± 0.3 | — |
| rDEN2 | 9 | 5.6 ± 0.2 | — |
| rDEN2Δ30 (clone 20A) | 9 | 3.1 ± 0.2 | 2.5 |
| rDEN2Δ30 (clone 21A) | 9 | 2.9 ± 0.3 | 2.7 |

[a]Groups of SCID-HuH-7 mice were inoculated directly into the tumor with $10^4$ PFU virus grown in C6/36 cells. Serum was collected on day 7 and titered in C6/36 cells.
[b]Comparison of mean virus titers of mice inoculated with mutant virus and concurrent rDEN2 control.

DEN2 virus replication in SCID-HuH-7 mice was also determined using DEN2 (Tonga/74), rDEN2, and rDEN2Δ30 which were passaged in Vero cells (see Table 20, footnotes b and d). Both rDEN2 and rDEN2Δ30 had acquired a mutation in NS4B, nucleotide 7169, corresponding to the 7162 mutation identified in rDEN4 as Vero cell adaptation mutation. In the presence of the 7169 mutation, the Δ30 mutation reduced replication of rDEN2Δ30 by 1.0 $\log_{10}$PFU/ml (Table 23). Previously, using virus grown in C6/36 cells and lacking the 7169 mutation, the Δ30 mutation reduced replication of rDEN2Δ30 by about 2.5 $\log_{10}$PFU/ml (Table 22). These results indicate that Vero cell growth adaptation in DEN2 may also confer a slight growth advantage in HuH-7 liver cells. Nevertheless, the attenuation conferred by the Δ30 mutation is still discernible in these Vero cell growth adapted viruses.

TABLE 23

The Δ30 mutation restricts Vero cell adapted rDEN2 virus replication in SCID-HuH-7 mice.

| Virus | No. of mice | Mean virus titer ± SE ($\log_{10}$ PFU/ml serum)[a] | Mean $\log_{10}$-unit reduction from value for wt[b] |
|---|---|---|---|
| DEN2 (Tonga/74) | 6 | 5.9 ± 0.3 | — |
| rDEN2 | 7 | 5.9 ± 0.2 | — |
| rDEN2Δ30 | 9 | 4.9 ± 0.3 | 1.0 |

[a]Groups of SCID-HuH-7 mice were inoculated directly into the tumor with $10^4$ PFU virus. Serum was collected on day 7 and titered in C6/36 cells.
[b]Comparison of mean virus titers of mice inoculated with rDEN2Δ30 and rDEN2 control.

Evaluation of the replication, immunogenicity, and protective efficacy of rDEN2Δ30 and wild-type parental rDEN2 virus in juvenile rhesus monkeys was performed as follows. Dengue virus-seronegative monkeys were injected subcutaneously with 5.0 $\log_{10}$PFU of virus in a 1 ml dose divided between two injections in each side of the upper shoulder area. Monkeys were observed daily and blood was collected on days 0-10 and 28 and serum was stored at −70° C. Viruses used in this experiment were passaged in Vero cells, and recombinant viruses contained the mutations shown in Table 20 (See footnotes b and d). Titer of virus in serum samples was determined by plaque assay in Vero cells as described previously (Durbin, A. P. et al. 2001 *Am J Trop Med Hyg* 65:405-13). Plaque reduction neutralization titers were determined for the day 28 serum samples as previously described (Durbin, A. P. et al. 2001 *Am J Trop Med Hyg* 65:405-13). All monkeys were challenged on day 28 with a single dose of 5.0 $\log_{10}$PFU of wt DEN2 (Tonga/74) and blood was collected for 10 days. Virus titer in post-challenge sera was determined by plaque assay in Vero cells. Monkeys inoculated with wt DEN2 (Tonga/74) or rDEN2 were viremic for 4-5 days with a mean peak titer of 2.1 or 1.9 $\log_{10}$PFU/ml, respectively.

Figure 7:
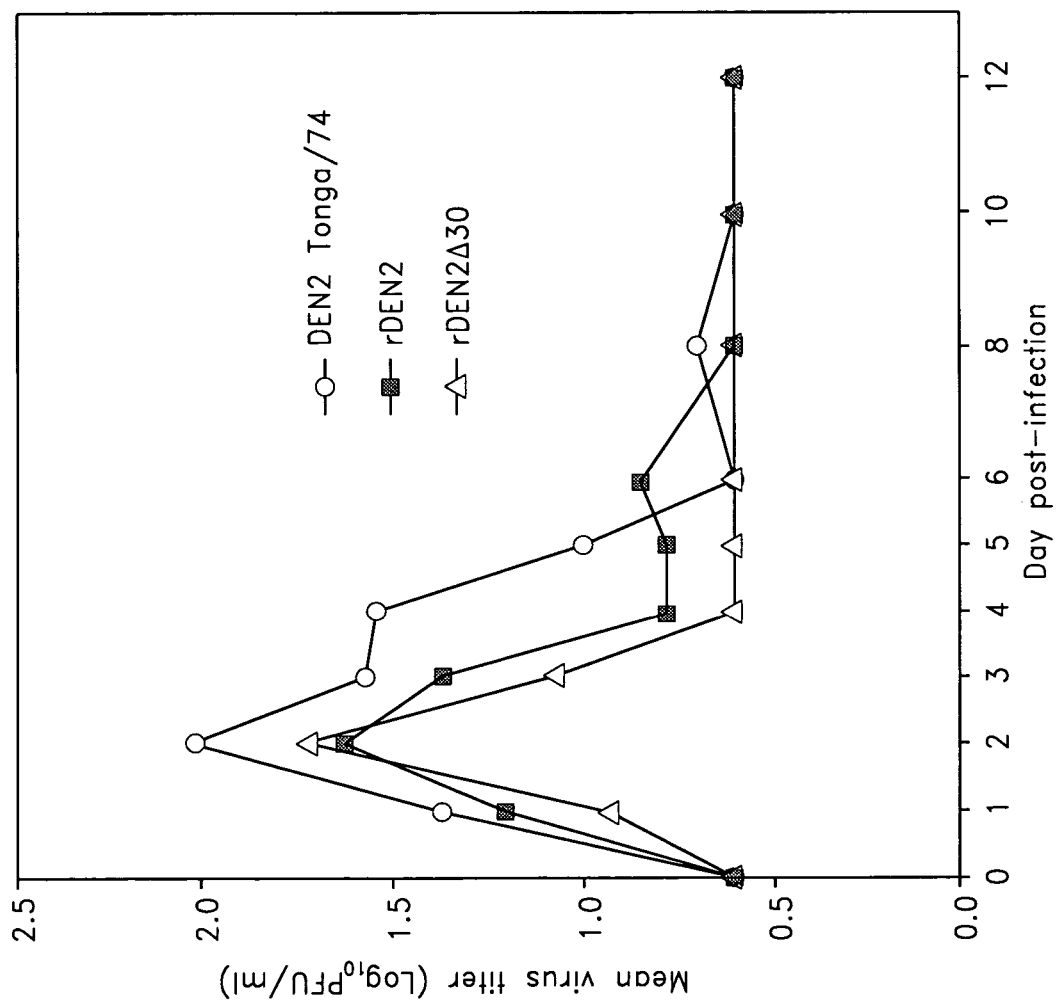
FIG. 7. Viremia levels in rhesus monkeys inoculated with DEN2 (Tonga/74), rDEN2, and rDEN2Δ30 vaccine candidate. Groups of four monkeys were inoculated with 5.0 $\log_{10}$PFU virus subcutaneously. Serum was collected daily and virus titers were determined by plaque assay in Vero cells. The limit of virus detection was 0.7 $\log_{10}$PFU/ml. Mean virus titers are indicated for each group. Viremia was not detected in any monkey after day 8.

Monkeys inoculated with rDEN2Δ30 were viremic for 2-3 days with a mean peak titer of 1.7 $\log_{10}$PFU/ml (Table 24, FIG. 7), indicating that the Δ30 mutation is capable of attenuating DEN2, although not to the same low level observed in rDEN1Δ30 (Table 16). As expected for an attenuated virus, the immune response, as measured by neutralizing antibody titer, was lower following inoculation with rDEN2Δ30 compared to inoculation with wt DEN2 (Tonga/74) or rDEN2 (Table 24), yet sufficiently high to protect the animals against wt DEN2 virus challenge (Table 25). Thus, the decreased number of days of viremia for rDEN2Δ30, the decreased mean peak titer, and the decreased serum antibody response indicate that the Δ30 mutation attenuates rDEN2 for rhesus monkeys.

indicating that DEN2 (Tonga/74) is poorly infectious for *Aedes aegypti*. As with rDEN1, the genetic basis for this lack of infectivity remains to be defined. The important property of restricted infectivity for the mosquito midgut is highly desirable in a vaccine candidate because it would serve to greatly restrict transmission of the virus from a vaccinee to a mosquito vector.

Several missense mutation identified in rDEN4 have been demonstrated to confer attenuated replication in suckling mouse brain and/or SCID-HuH-7 mice (Blaney, J. E. et al. 2002 *Virology* 300:125-139; Blaney, J. E. et al. 2001 *J Virol* 75:9731-9740). In addition, missense mutations that enhance replication of rDEN4 virus in Vero cells have been characterized. The significant sequence conservation among the DEN virus serotypes provides a strategy by which the mutations identified in rDEN4 viruses are contemplated as being used to confer similar phenotypes upon rDEN2 virus. Six mutations identified in rDEN4 virus that are at a site conserved in rDEN2 virus are being introduced into the p2 and p2Δ30 cDNA clones (Table 26). Specifically, two rDEN4 mutations, NS3 4891 and 4995, which confer Vero cell adaptation phenotypes and decreased replication in mouse brain, one mutation, NS4B 7182, which confers a Vero cell adaptation phenotype, and three mutations, NS1 2650, NS3 5097, and 3' UTR 10634 which confer decreased replication in mouse

TABLE 24 rDEN2Δ30 is slightly more attenuated for rhesus monkeys than rDEN2

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <10 | <10 |
| DEN2 (Tonga/74) | 4 | 4 | 4.5 | 2.1 ± 0.3 | <10 | 311 |
| rDEN2 (Vero) | 4 | 4 | 4.0 | 1.9 ± 0.1 | <10 | 173 |
| rDEN2Δ30 (Vero) | 4 | 4 | 2.8 | 1.7 ± 0.2 | <10 | 91 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 8.

TABLE 25 rDEN2Δ30 protects rhesus monkeys from wt DENT2 virus challenge

| Virus[a] | No. of monkeys | Mean no. of viremic days per monkey after DEN2 challenge | Mean peak virus titer ($\log_{10}$ PFU/ml ± SE) | Geometric mean serum neutralizing antibody titer (reciprocal dilution) | |
|---|---|---|---|---|---|
| | | | | Day 28 | Day 56 |
| Mock | 2 | 4.0 | 2.1 ± 0.1 | <10 | 338 |
| DEN2 (Tonga/74) | 4 | 0 | <0.7 | 311 | 334 |
| rDEN2 (Vero) | 4 | 0 | <0.7 | 173 | 318 |
| rDEN2Δ30 (Vero) | 4 | 0 | <0.7 | 91 | 267 |

[a]28 days after inoculation with the indicated viruses, monkeys were challenged subcutaneously with $10^5$ PFU DEN2 (Tonga/74) in a 1 ml dose. Serum was collected on days 28 to 34, 36, 38, and 56. Virus titer was determined by plaque assay in Vero cells.

The infectivity of DEN2 (Tonga/74), rDEN2 and rDEN2Δ30 for *Aedes aegypti* mosquitoes via an artificial bloodmeal was evaluated using the methods described in detail in Example 5. However at doses of 3.3 to 3.5 $\log_{10}$pfu ingested, none of these three viruses infected any mosquitoes, brain and SCID-HuH-7 mice are being evaluated. These mutations have been introduced into sub-cloned fragments of the p2 and p2Δ30 cDNA clones, and have been used to generate mutant full-length cDNA clones (Table 26), from which virus has been recovered in C6/36 cells (Table 27). The evaluation of these mutant rDEN2 viruses is contemplated as determining that such point mutations can be transported into a different DEN virus serotype and confer a similar useful phenotype, as has been demonstrated for the Δ30 deletion mutation.

epidemic in rural Sleman, Central Indonesia (Sleman/78) (Gubler, D. J. et al. 1981 *Am J Trop Med Hyg* 30:1094-1099) was chosen to represent wt DEN3. The genome of DEN3 (Sleman/78) was sequenced in its entirety and served as consensus sequence for the construction of a full-length cDNA

TABLE 26

Introduction of conserved point mutations characterized in rDEN4 viruses into rDEN2 Tonga/74 virus.

| Phenotype in rDEN4 virus | | | Mutation in rDEN4 virus | | | | Mutation introduced into DEN2 virus | | | |
|---|---|---|---|---|---|---|---|---|---|---|
| Vero Adaptation[a] | Mouse brain att[b] | SCID-HuH-7 att[c] | Gene/ region | Nucleotide position | Amino acid position[d] | Amino acid change | Nucleotide position | Amino acid position[d] | Amino acid change | RE site/ mutagenic region[e] |
| + | + | − | NS3 | 4891 | 1597 | Ile > Thr | 4889 | 1598 | Ile > Thr | Nar I CCAcgGGcGCCGT |
| + | + | − | NS3 | 4995 | 1632 | Ser > Pro | 4993 | 1633 | Ser > Pro | Stu I AAGGccTGGA |
| + | − | − | NS4b | 7182 | 2361 | Gly > Ser | 7189 | 2365 | Gly > Ser | Xma I TAtccCCGGGAC |
| − | + | + | NS1 | 2650 | 850 | Asn > Ser | 2648 | 851 | Asn > Ser | Sac I AGAgcTctcTC |
| − | + | + | NS3 | 5097 | 1666 | Asp > Asn | 5095 | 1667 | Asp > Asn | Xma I GaATCTCCACCCgGA |
| − | + | + | 3' UTR | 10634 | n/a[f] | n/a | 10698 | n/a | n/a | none CTGTcGAATC |

[a]Presence of the indicated mutation increases plaque size in Vero cells two-fold or greater than rDEN4 virus.
[b]Presence of the indicated mutation restricts replication in 7-day-old mouse brain greater than 100-fold compared to rDEN4 virus.
[c]Presence of the indicated mutation restricts replication in SCID-HuH-7 mice greater than 100-fold compared to rDEN4 virus.
[d]Amino acid position in DEN4 or DEN2 polyprotein beginning with the methionine residue of the C protein (nucleotides 102-104 or 97-99, respectively) as position 1.
[e]Primers were engineered which introduced (underline) translationally-silent restriction enzyme (RE) sites. Lowercase letters indicate nt changes and bold letters indicate the site of the 5-FU mutation, which in some oligonucleotides differs from the original nucleotide substitution change in order to create a unique RE site. The change preserves the codon for the amino acid substitution.
[f]Nucleotide substitution in the 3' UTR is U > C in DEN4 and DEN2 virus.

TABLE 27 rDEN2 viruses containing conserved 5-FU mutations are recovered in C6/36 cells.

| Virus (nucleotide position in rDEN2) | Nucleotide position in rDEN4 | Virus titer of transfection harvest (day 7) determined in C6/36 cells (log₁₀ PFU/ml) |
|---|---|---|
| rDEN2-4889 | 4891 | 7.6 |
| rDEN2-4993 | 4995 | 7.2 |
| rDEN2-7189 | 7182 | 3.5 |
| rDEN2-2648 | 2650 | —[a] |
| rDEN2-5095 | 5097 | —[a] |
| rDEN2-10698 | 10634 | 7.7 |

[a]Transfection has not yet been attempted.

EXAMPLE 4

Figure 8A:
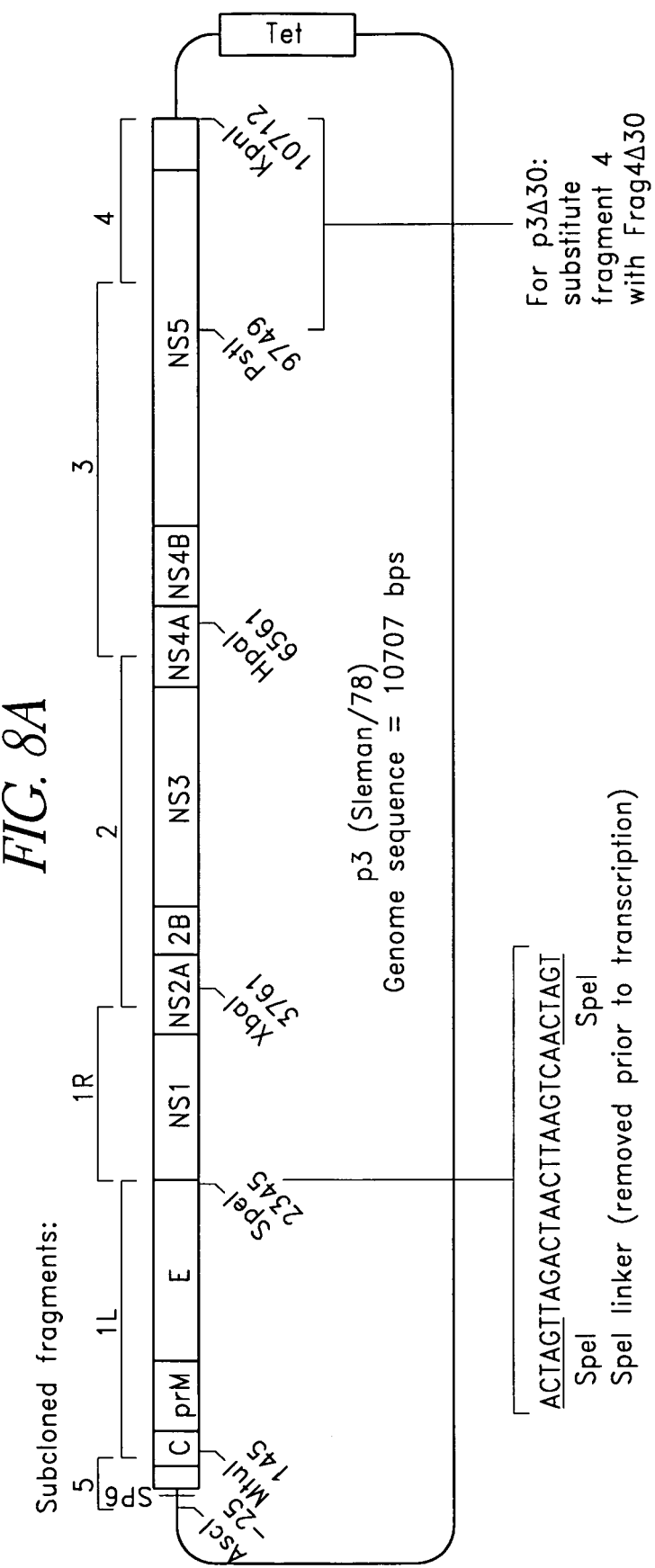
FIG. 8. A. Diagram of the p3 (Sleman/78) full-length cDNA plasmid. Regions subcloned are indicated above the plasmid. Numbering begins at the 5' end of the viral sequence. The sequence and insertion location of the SpeI linker is shown. B. The Δ30 mutation removes the indicated 31 nucleotides from the 3' UTR sequence to create p3Δ30.
Figure 8B:
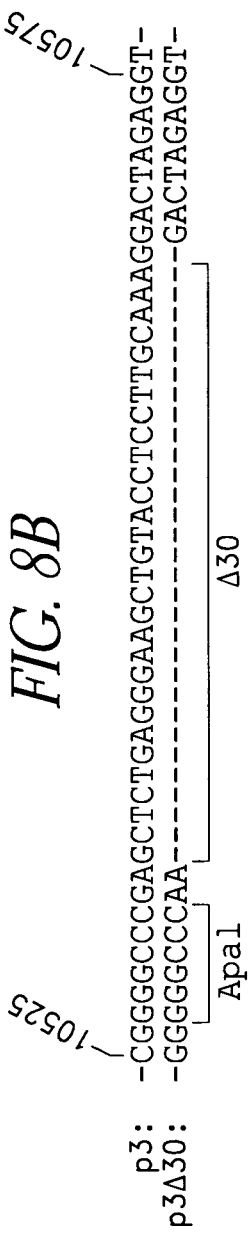

Generation and Characterization of a Recombinant DEN3 Virus Containing the Δ30 Mutation Because rDEN1Δ30 was satisfactorily attenuated, we sought to extend our technology to the creation of a DEN3 vaccine candidate. To do this, the Δ30 mutation was introduced into the cDNA of DEN3, similar to the method used to create rDEN2Δ30. A DEN3 virus isolate from a 1978 dengue clone (Appendix 2). cDNA fragments of DEN3 (Sleman/78) were generated by reverse-transcription of the genome as indicated in FIG. 8A. Each fragment was subcloned into a plasmid vector and sequenced to verify that it matched the consensus sequence as determined for the virus. This yielded six cloned cDNA fragments spanning the genome. Cloned fragments were modified as follows: Fragment 5, representing the 5' end of the genome was abutted to the SP6 promoter preceded by an AscI restriction site; Fragment 1L was modified to contain a translationally-silent SpeI restriction site at genomic nucleotide 2345; Fragment 1R was modified to contain a translationally-silent SpeI restriction site also at genomic nucleotide 2345, and to stabilize the eventual full-length clone, three additional translationally-silent mutations at nucleotides 2354-2356, 2360-2362, and 2399 were created to ensure that translation stop codons were present in all reading frames other than that used to synthesize the virus polyprotein; Fragment 3 was modified at nucleotide 9007 to ablate a naturally occurring KpnI restriction site; and Fragment 4, representing the 3' end of the genome was abutted to a KpnI restriction site. Each fragment was added incrementally between the AscI and KpnI restriction sites of DEN4 cDNA clone p4 (Durbin, A. P. et al. 2001 *Am J Trop Med Hyg* 65:405-13) to generate a full-length DEN3 cDNA clone with the same vector background successfully used to generate rDEN4 and rDEN2. However, a stable, full-length clone could not be recovered in *E. coli* when fragments 1L and 1R were combined into the same cDNA molecule. To overcome this instability, a synthetic DNA linker (FIG. 8A) containing redundant termination codons in each of the forward and reverse open reading frames was introduced into the SpeI restriction site at the same time that fragment 1L was added to complete the full-length cDNA construct. The resulting p3 clone containing the linker sequence was stable in *E. coli*, indicating that the linker sequence was sufficient to interrupt whatever deleterious element exists in this region. cDNA clone p3 was sequenced and the virus genome was found to match the DEN3 (Sleman/78) consensus sequence, with the exception of the linker sequence and translationally-silent modifications noted above (Appendix 2—shown with the linker sequence removed). The Δ30 mutation was introduced into Fragment 4 to generate Fragment 4Δ30. To create p3Δ30, the Fragment 4 region of p3 was replaced with Fragment 4Δ30 (FIG. 8A, B).

For transcription and generation of infectious virus, cDNA plasmids p3 and p3Δ30 were digested with SpeI and re-ligated to remove the linker sequence, linearized with Acc65I (isoschizomer of KpnI which cleaves leaving only a single 3' nucleotide), and used as templates in a transcription reaction using SP6 RNA polymerase as previously described (Blaney, J. E. et. al. 2002 *Virology* 300:125-139). Transcripts were introduced into Vero cells or C6/36 mosquito cells using liposome-mediated transfection and cell culture supernatants were harvested on day 14.

rDEN3 virus was recovered from the p3 cDNA in both Vero and C6/36 cells, while rDEN3Δ30 was recovered from the p3Δ30 cDNA clone in only C6/36 cells (Table 28). The level of infectious virus recovered in C6/36 cells was comparable for the p3 and p3Δ30 cDNA clones when assayed by plaque titration in Vero or C6/36 cells. As previously observed, the efficiency of transfection in C6/36 cells was higher than that in Vero cells. Two rDEN3Δ30 viruses were recovered from independent cDNA clones, #22 and #41.

TABLE 28 rDEN3 virus is recovered in Vero and C6/36 cells, but rDEN3Δ30 virus is recovered only in C6/36 cells.

| Transfection cell type | cDNA construct | Clone | Virus | Virus titer of transfection harvest (day 14) determined in the indicated cell type ($log_{10}$ PFU/ml) | |
|---|---|---|---|---|---|
| | | | | Vero cells | C6/36 cells |
| Vero cells | p3 | #50 | rDEN3 | 5.2 | 6.3 |
| | p3Δ30 | #22 | rDEN3Δ30 | <0.7 | <0.7 |
| | p3Δ30 | #41 | rDEN3Δ30 | <0.7 | <0.7 |
| C6/36 cells | p3 | #50 | rDEN3 | 5.2 | 6.0 |
| | p3Δ30 | #22 | rDEN3Δ30 | 5.9 | 6.9 |
| | p3Δ30 | #41 | rDEN3Δ30 | 5.1 | 7.2 |

To produce working stocks of viruses, transfection harvests will be passaged and terminally diluted in Vero cells, and genomic sequences of the viruses will be determined. To improve virus yield in Vero cells, the Vero cell adaptation mutation previously identified in rDEN4 at nucleotide 7162 was introduced into the homologous NS4B region of p3 and p3Δ30 to create p3-7164 and p3Δ30-7164. This mutation creates a Val to Ala substitution at amino acid position 2357. As demonstrated for rDEN2Δ30, this mutation allowed for the direct recovery of virus in Vero cells (Table 27) and is anticipated to have the same effect for rDEN3Δ30.

To initially assess the ability of the Δ30 mutation to attenuate rDEN3 virus in an animal model, the replication of DEN3 (Sleman/78), rDEN3, and rDEN3Δ30 viruses will be evaluated in SCID-HuH-7 mice and rhesus monkeys. Previously, attenuation of vaccine candidates in SCID-HuH-7 mice has been demonstrated to be predictive of attenuation in the rhesus monkey model of infection (Examples 1 and 2). The evaluation of these mutant rDEN3 viruses is contemplated as determining that the Δ30 deletion mutations can be transported into the DEN3 virus serotype and confer a similar useful phenotype, as has been demonstrated for DEN1, DEN2, and DEN4.

In summary, the strategy of introducing the Δ30 mutation into wild-type DEN viruses of each serotype to generate a suitably attenuated tetravalent vaccine formulation is a unique and attractive approach for several reasons. First, the mutation responsible for attenuation is a 30-nucleotide deletion in the 3' UTR, thus assuring that all of the structural and non-structural proteins expressed by each of the four components of the tetravalent vaccine are authentic wild-type proteins. Such wild-type proteins should elicit an antibody response that is broad based, rather than based solely on the M and E proteins that are present in chimeric dengue virus vaccine candidates (Guirakhoo, F. et al. 2001 *J Virol* 75:7290-304; Huang, C. Y. et al. 2000 *J Virol* 74:3020-8). The uniqueness of this approach derives from the fact that other live attenuated dengue virus vaccines have mutations in their structural or non-structural proteins (Butrapet, S. et al. 2000 *J Virol* 74:3011-9; Puri, B. et al. 1997 *J Gen Virol* 78:2287-91), therefore the immune response induced by these viruses will be to a mutant protein, rather than a wild-type protein. Second, deletion mutations are genetically more stable than point mutations, and reversion of the attenuation phenotype is unlikely. In humans, DEN4Δ30 present in serum of vaccinees retained its Δ30 mutation, confirming its genetic stability in vivo (Durbin, A. P. et al. 2001 *Am J Trop Med Hyg* 65:405-13). The attenuating mutations in other existing dengue live attenuated vaccine candidates are based on less stable point mutations (Butrapet, S. et al. 2000 *J Virol* 74:3011-9: Puri, B. et al. 1997 *J Gen Virol* 78:2287-91). Third, since the Δ30 mutation is common to each of the four viruses of the tetravalent vaccine, recombination between any of the four vaccine serotypes would not lead to loss of the attenuating mutation or reversion to a wild-type phenotype. Recombination between components of the trivalent polio vaccine has been observed (Guillot, S. et al. 2000 *J Virol* 74:8434-43), and naturally occurring recombinant dengue viruses have been described (Worobey, M. et al. 1999 *PNAS USA* 96:7352-7) indicating the ability of this flavivirus to exchange genetic elements between two different viruses. Clearly, gene exchange is readily achieved between different DEN virus serotypes using recombinant cDNA techniques (Bray, M. and Lai, C. J. 1991 *PNAS USA* 88:10342-6). Fourth, viruses with wild-type structural proteins appear more infectious than viruses with altered structural proteins (Huang, C. Y. et al. 2000 *J Virol* 74:3020-80). This permits the use of a low quantity of each of the four virus components in the final vaccine, contributing to the low cost of manufacture. Low-cost manufacture is an essential element in defining the ultimate utility of a dengue virus vaccine.

EXAMPLE 5

Generation and Characterization of Intertypic Chimeric DEN2 Viruses Containing the Δ30 Mutation The four serotypes of dengue virus are defined by antibody responses induced by the structural proteins of the virus, primarily by a neutralizing antibody response to the envelope (E) protein. These structural proteins include the E glycoprotein, a membrane protein (M), and a capsid (C) protein. The mature virus particle consists of a well-organized outer protein shell surrounding a lipid bilayer membrane and a less-well-defined inner nucleocapsid core (Kuhn, R. J. et al. 2002 *Cell* 108:717-25). The E glycoprotein is the major protective antigen and readily induces virus neutralizing antibodies that confer protection against dengue virus infection. An effective dengue vaccine must therefore minimally contain the E protein of all four serotypes, namely DEN1, DEN2, DEN3, and DEN4, thereby inducing broad immunity and precluding the possibility of developing the more serious illnesses DHF/DSS, which occur in humans during secondary infection with a heterotypic wild-type dengue virus. Based on a previously reported strategy (Bray, M. and Lai, C. J. 1991 *PNAS USA* 88:10342-6), a recombinant cDNA technology is being used to develop a live attenuated tetravalent dengue virus vaccine composed of a set of intertypic chimeric dengue viruses bearing the structural proteins of each serotype.

Figure 9A:
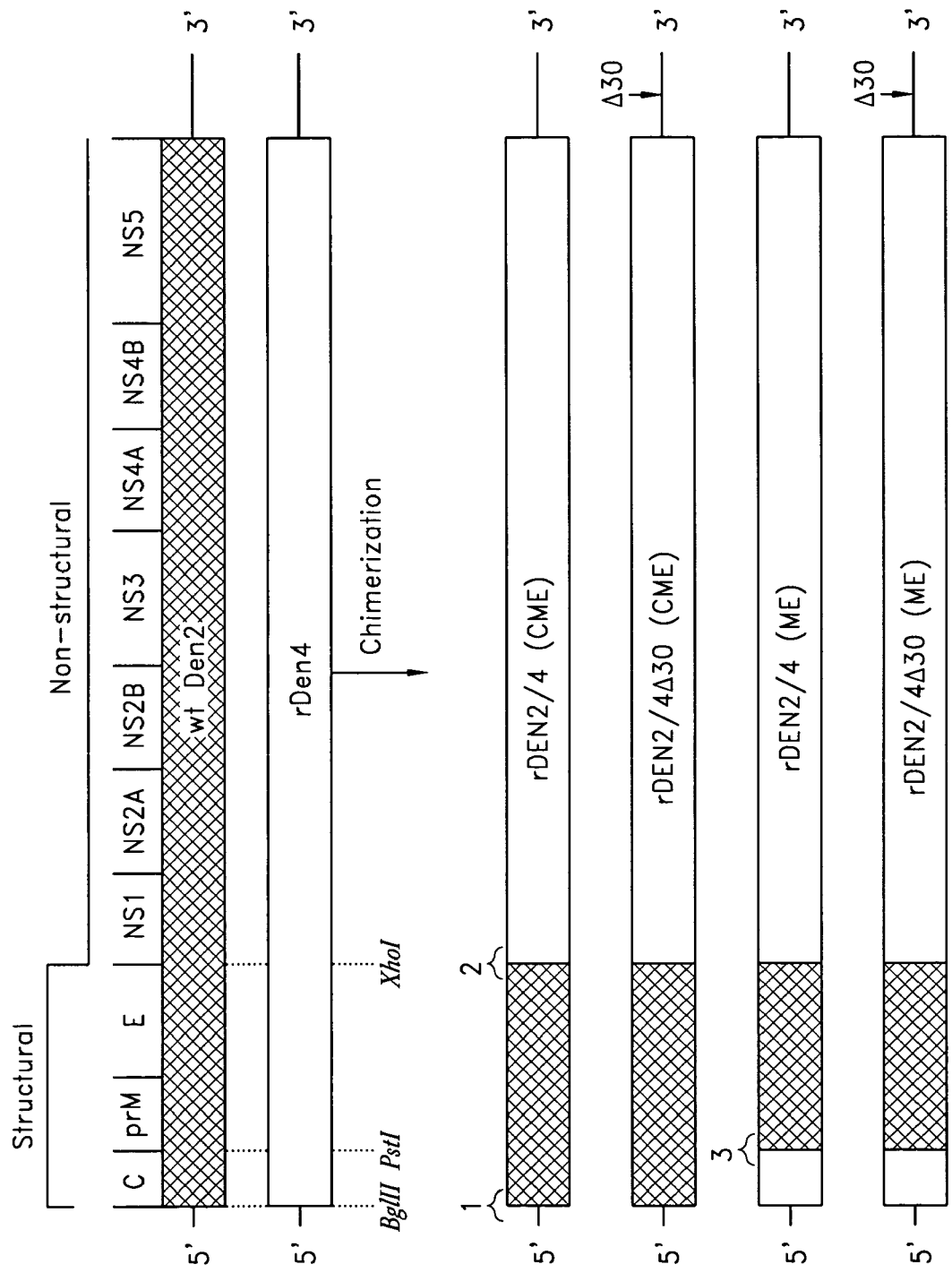
FIG. 9. A. Recombinant chimeric dengue viruses were constructed by introducing either the CME or the ME regions of DEN2 (Tonga/74) into the DEN4 genetic background. The relative location of the Δ30 mutation in the 3' UTR is indicated by an arrow and intertypic junctions 1, 2, and 3 are indicated. B. Nucleotide and amino acid sequence of the intertypic junction regions. Restriction enzyme recognition sites used in assembly of each chimeric cDNA are indicated.
Figure 9B:
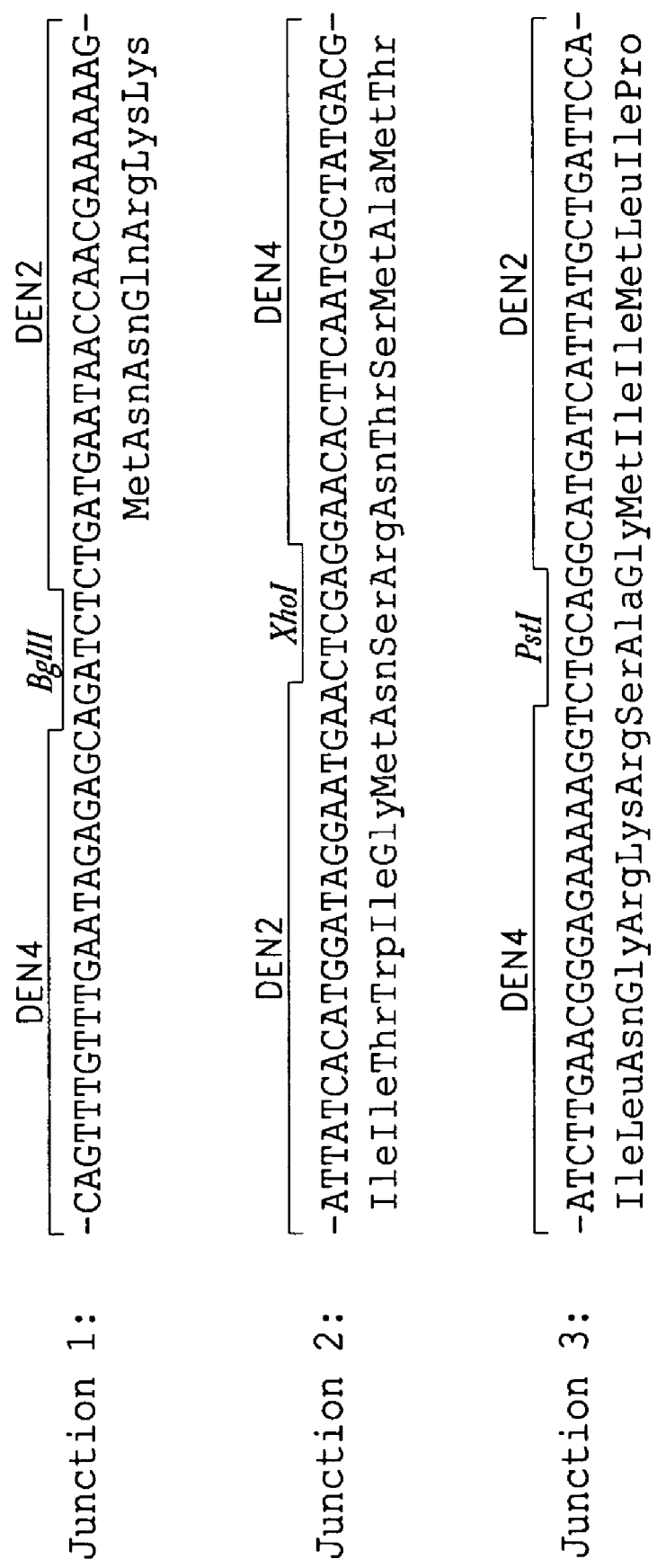

Following the identification of a suitably attenuated and immunogenic DEN4 recombinant virus, namely DEN4Δ30 (Durbin, A. P et al. 2001 *Am J Trop Med Hyg* 65:405-13), chimeric viruses based on the DEN4 cDNA have been generated in which the C-M-E (CME) or M-E (ME) genes have been replaced with the corresponding genes derived from the prototypic DEN2 New Guinea C (NGC) strain (FIG. 9A). To create the CME chimeric viruses, the BglII/XhoI region of the cDNA for either rDEN4 or rDEN4Δ30 was replaced with a similar region derived from DEN2. Likewise, to create the ME chimeric viruses, the PstI/XhoI region of the cDNA for either rDEN4 or rDEN4Δ30 was replaced with a homologous region derived from DEN2. The nucleotide and amino acid sequences of the resulting junctions are shown in FIG. 9B. The GenBank accession number for the nucleotide sequence of rDEN4Δ30 is AF326837. The GenBank accession number for DEN2 NGC is M29095, which represents the mouse neurovirulent strain of DEN2 NGC and differs from the prototypic strain used here as previously documented (Bray, M. et al. 1998 *J Virol* 72:1647-51).

For transcription and generation of virus, chimeric cDNA clones were linearized and used as template in a transcription reaction using SP6 RNA polymerase as described (Durbin, A. P et al. 2001 *Am J Trop Med Hyg* 65:405-13). Transcripts were introduced into Vero cells using liposome-mediated transfection and recombinant dengue virus was harvested on day 7. The genomes of the resulting viruses were confirmed by sequence analysis of viral RNA isolated from recovered virus as previously described (Durbin, A. P et al. 2001 *Am J Trop Med Hyg* 65:405-13). Incidental mutations arising from virus passage in tissue culture were identified in all viruses and are listed in Table 29. Notably, each virus contained a missense mutation in NS4B corresponding to a previously identified mutation from rDEN4 and associated with adaptation to replication in Vero cells (See Table 30 for correlation of nucleotide positions between rDEN4 and chimeric viruses). All viruses replicated in Vero cells to titers in excess of 6.0 $\log_{10}$ PFU/ml, indicating that the chimeric viruses, even those containing the Δ30 mutation, replicate efficiently in cell culture, a property essential for manufacture of the vaccine.

TABLE 29

Missense mutations observed among the Vero cell-grown chimeric DEN2/4 viruses

| Virus | Gene | Nucleotide position | Nucleotide change | Amino acid position | Amino acid change |
|---|---|---|---|---|---|
| rDEN2/4(CME) | NS4B | 7161[a] | A > U | 2355 | Leu > Phe |
| rDEN2/ | M | 743 | G > A | 216 | Gly > Glu |

TABLE 29-continued

Missense mutations observed among the Vero cell-grown chimeric DEN2/4 viruses

| Virus | Gene | Nucleotide position | Nucleotide change | Amino acid position | Amino acid change |
|---|---|---|---|---|---|
| 4Δ30(CME) | E | 1493 | C > U | 466 | Ser > Phe |
| | NS4B | 7544[b] | C > T | 2483 | Ala > Val |
| rDEN2/4(ME) | E | 1065 | U > C | 322 | Phe > Leu |
| | NS4B | 7163[a] | A > U | 2354 | Leu > Phe |
| rDEN2/ 4Δ30(ME) | NS4B | 7163[a] | A > C | 2354 | Leu > Phe |

[a]Same nucleotide position as 7163 in rDEN4.
[b]Same nucleotide position as 7546 in rDEN4.

TABLE 30

Nucleotide (nt) length differences for DEN chimeric viruses compared to rDEN4.

| rDEN chimeric virus | nt difference from rDEN4 (following CME region) | ORF start (nt position) | Amino acid length C | M | E |
|---|---|---|---|---|---|
| 1/4 ME | 0 | 102 | 113 | 166 | 495 |
| 1/4 CME | +3 | 102 | 114 | 166 | 495 |
| 2/4 ME | 0 | 102 | 113 | 166 | 495 |
| 2/4 CME | −2 | 97 | 114 | 166 | 495 |
| 3/4 ME | −6 | 102 | 113 | 166 | 493 |
| 3/4 CME | −3 | 102 | 114 | 166 | 493 |
| rDEN4 | — | 102 | 113 | 166 | 495 |

Results of a safety, immunogenicity, and efficacy study in monkeys are presented in Table 31. Monkeys inoculated with wild-type DEN2 were viremic for approximately 5 days with a mean peak titer of 2.1 $\log_{10}$ PFU/ml, while monkeys inoculated with any of the chimeric DEN2 viruses were viremic for 1.2 days or less and had a mean peak titer of less than 1.0 $\log_{10}$ PFU/ml. This reduction in the magnitude and duration of viremia clearly indicates that the chimeric viruses containing either the CME or ME proteins of DEN2 were more attenuated than the parental DEN2 NGC virus. Neither the animals receiving the wild-type DEN2 nor the DEN2/4 chimeric viruses were ill. The decreased replication of the attenuated viruses in monkeys is accompanied by a reduction in the immune response of inoculated monkeys. This is indicated in Table 31 by approximately a 5-fold reduction in the level of neutralizing antibody following inoculation with the chimeric viruses in comparison to titers achieved in animals inoculated with wild-type virus. Addition of the Δ30 mutation to the CME chimeric virus further attenuated the virus, such that rDEN2/4Δ30(CME) did not replicate in monkeys to a detectable level and did not induce a detectable immune response. This virus appeared over-attenuated, and if similar results were seen in humans, this virus would not be suitable for use as a vaccine. However, addition of the Δ30 mutation to the ME chimeric virus did not further attenuate this chimeric virus and the resulting rDEN2/4Δ30(ME) virus appears satisfactorily attenuated and immunogenic for use as a vaccine.

TABLE 31

Chimerization between dengue virus types 2 and 4 results in recombinant viruses which are attenuated for rhesus monkeys.

| Group* | Virus | n | Mean no. days with viremia | Mean peak virus titer ($\log_{10}$ pfu/ml) | Geometric mean neutralizing antibody titer (reciprocal) |
|---|---|---|---|---|---|
| 1 | rDEN2/4 (CME) | 6 | 1.2 | 0.9 | 50 |
| 2 | rDEN2/4Δ30 (CME) | 8 | 0 | <0.7 | <5 |
| 3 | rDEN2/4 (ME) | 4 | 1.0 | 0.8 | 76 |
| 4 | rDEN2/4Δ30 (ME) | 4 | 0.3 | 0.7 | 62 |
| 5 | DEN2 NGC | 6 | 5.5 | 2.1 | 312 |

*Rhesus monkeys were inoculated subcutaneously with 5.0 $\log_{10}$ PFU of virus. Serum samples were collected daily for 10 days. Serum for neutralization assay was collected on day 28. Serum samples obtained before virus inoculation had a neutralizing antibody titer of <5.

As described in the previous examples, SCID mice transplanted with the HuH-7 cells are a sensitive model for the evaluation of dengue virus attenuation. Each chimeric DEN2/4 virus was inoculated into groups of SCID-HuH-7 mice and levels of virus in the serum were determined (Table 32). Chimeric viruses replicated to levels between 20- and 150-fold lower than either of the parental viruses (rDEN4 and DEN2-NGC). CME chimeric viruses were slightly more attenuated than the comparable ME chimeric viruses, with the Δ30 mutation providing a 0.5 $\log_{10}$ reduction in replication. This level of attenuation by the Δ30 mutation was similar to that observed previously for rDEN4Δ30.

TABLE 32

Chimerization between dengue virus types 2 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN2-NGC | 9 | 6.1 ± 0.2 | A |
| rDEN2/4 (CME) | 7 | 4.4 ± 0.3 | B |
| rDEN2/4Δ30 (CME) | 7 | 3.9 ± 0.3 | B |
| rDEN2/4 (ME) | 6 | 4.8 ± 0.5 | B |
| rDEN2/4Δ30 (ME) | 9 | 4.3 ± 0.2 | B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

To evaluate the replication levels of each DEN2/4 chimeric virus in mosquitoes, two different genera of mosquitoes were experimentally infected. *Aedes aegypti* were infected by ingesting a virus-containing blood meal. By evaluating the presence of virus antigen in both the midgut and head tissue, infectivity could be determined for the local tissues (midgut), and the ability of virus to disseminate and replicate in tissues beyond the midgut barrier (head) could also be measured. The presence of virus in the head is limited by the ability of the ingested virus to replicate in the midgut and then disseminate to the salivary glands in the head, as well as the innate ability of the virus to replicate in the salivary glands. Intrathoracic inoculation of virus into *Toxorhynchites splendens* bypasses the mosquito midgut barrier. Parental viruses rDEN4 and DEN2-NGC readily infect *Ae. aegypti* and *T. splendens* (Table 33), with DEN2-NGC appearing to be much more infectious in *T. splendens*. Each of the rDEN2/4 chimeric viruses was also tested in both mosquito types. In many cases it was not possible to inoculate *Ae. aegypti* with an undiluted virus stock of sufficient titer to achieve a detectable infection due to the very low infectivity of several of the viruses. Nevertheless, it is clear that the rDEN2/4 chimeric viruses are less infectious for the midgut and head. Parental viruses rDEN4 and DEN2-NGC, administered at a maximum dose of approximately 4.0 $\log_{10}$PFU, were detectable in 74% and 94% of midgut preparations, and 32% and 71% of head preparations, respectively. Among the chimeric viruses, the highest level of infectivity, as observed for rDEN2/4Δ30 (CME), resulted in only 26% infected midgut samples and 6% head samples. In the more permissive *T. splendens*, the rDEN2/4 chimeric viruses were generally less infectious than either parental virus, with CME chimeric viruses being less infectious than ME viruses. It has previously been reported for DEN4 that the Δ30 mutation does not have a discernable effect on virus infectivity in *T. splendens* similar to that observed here for the rDEN2/4 chimeric viruses (Troyer, J. M. et al. 2001 *Am J Trop Med Hyg* 65:414-419).

TABLE 33

Dengue 2/4 chimeric viruses are less infectious compared to either parental virus strain in mosquitoes

| | *Toxorhynchites splendens* (intrathoracic inoculation) | | | *Aedes aegypti* (oral infection) | | | |
|---|---|---|---|---|---|---|---|
| Virus | Dose[a] $\log_{10}$ pfu | No. tested | % infected[b] | Dose[c] $\log_{10}$ pfu | No. tested | % infected[d] Midgut | Head |
| rDEN4 | 3.3 | 6 | 83 | 3.8 | 38 | 74 | 32 |
| | 2.3 | 7 | 57 | 2.8 | 15 | 26 | 6 |
| | 1.3 | 6 | 0 | 1.8 | 20 | 10 | 5 |
| | | | $MID_{50} = 2.2$ | | | $MID_{50} = 3.4$ | $MID_{50} \geq 4.1$ |

TABLE 33-continued

Dengue 2/4 chimeric viruses are less infectious compared to either parental virus strain in mosquitoes

| Virus | Toxorhynchites splendens (intrathoracic inoculation) | | | Aedes aegypti (oral infection) | | | |
|---|---|---|---|---|---|---|---|
| | Dose[a] | No. | % | Dose[c] | No. | % infected[d] | |
| | $\log_{10}$ pfu | tested | infected[b] | $\log_{10}$ pfu | tested | Midgut | Head |
| DEN2-NGC | 2.5 | 5 | 100 | 4.0 | 17 | 94 | 71 |
| | 1.2 | 15 | 93 | 3.0 | 25 | 36 | 16 |
| | 0.2 | 4 | 75 | 2.0 | 30 | 0 | 0 |
| | 0.02 | 8 | 38 | | | $MID_{50} = 3.2$ | $MID_{50} = 3.6$ |
| | | | $MID_{50} = 0.5$ | | | | |
| rDEN2/4 (CME) | 3.9 | 9 | 11 | 4.4 | 11 | 9 | 0 |
| | 2.9 | 5 | 0 | 3.4 | 10 | 0 | 0 |
| | | | $MID_{50} \geq 4.3$ | | | $MID_{50} \geq 4.9$ | Nc[e] |
| rDEN2/4Δ30 | 3.5 | 6 | 17 | 4.0 | 15 | 26 | 6 |
| (CME) | 2.5 | 6 | 17 | 3.0 | 10 | 0 | 0 |
| | | | $MID_{50} \geq 3.9$ | | | $MID_{50} \geq 4.3$ | $MID_{50} \geq 4.5$ |
| rDEN2/4 (ME) | 3.4 | 6 | 100 | 3.9 | 23 | 4 | 0 |
| | 2.4 | 5 | 20 | | | $MID_{50} \geq 4.4$ | Nc |
| | 1.4 | 5 | 0 | | | | |
| | | | $MID_{50} = 2.8$ | | | | |
| rDEN2/4Δ30 | 2.6 | 11 | 9 | 3.1 | 30 | 0 | 0 |
| (ME) | | | $MID_{50} \geq 3.0$ | | | nc | Nc |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the $MID_{50}$ was estimated by assuming that a 10-fold more concentrated virus dose would infect 100% of the mosquitoes.
[e]nc = not calculated, since virus antigen was not detected.

Chimerization of the DEN2 structural genes with rDEN4Δ30 virus resulted in a virus, rDEN2/4Δ30(CME), that had decreased replication in Vero cells compared to either parent virus. To evaluate Vero cell adaptation mutations (Blaney, J. E. et al. 2002 *Virology* 300:125-139) as a means of increasing the virus yield of a DEN vaccine candidate in Vero cells, selected mutations were introduced into this chimeric virus. Accordingly, rDEN2/4Δ30(CME) viruses bearing adaptation mutations were recovered, terminally diluted, and propagated in C6/36 cells to determine if the virus yield in Vero cells could be increased.

rDEN2/4Δ30(CME) viruses bearing Vero cell adaptation mutations were generated as follows. DNA fragments were excised from rDEN4 cDNA constructs encompassing single or double DEN4 Vero cell adaptation mutations and introduced into the cDNA clone of rDEN2/4Δ30(CME). The presence of the Vero cell adaptation mutation was confirmed by sequence analysis, and RNA transcripts derived from the mutant cDNA clones were transfected, terminally diluted, and propagated in C6/36 cells.

For evaluation of growth kinetics, Vero cells were infected with the indicated viruses at a multiplicity of infection (MOI) of 0.01. Confluent cell monolayers in duplicate 25-cm² tissue culture flasks were washed and overlaid with a 1 ml inoculum containing the indicated virus. After a two hour incubation at 37° C., cells were washed three times in MEM and 5 ml of MEM supplemented with 2% FBS was added. A 1 ml aliquot of tissue culture medium was removed, replaced with fresh medium, and designated the day 0 time-point. At the indicated time points post-infection, 1 ml samples of tissue culture medium were removed, clarified by centrifugation, and frozen at −80° C. The level of virus replication was assayed by plaque titration in C6/36 cells and visualized by immunoperoxidase staining. The limit of detection was <0.7 $\log_{10}$PFU/ml.

Figure 10:
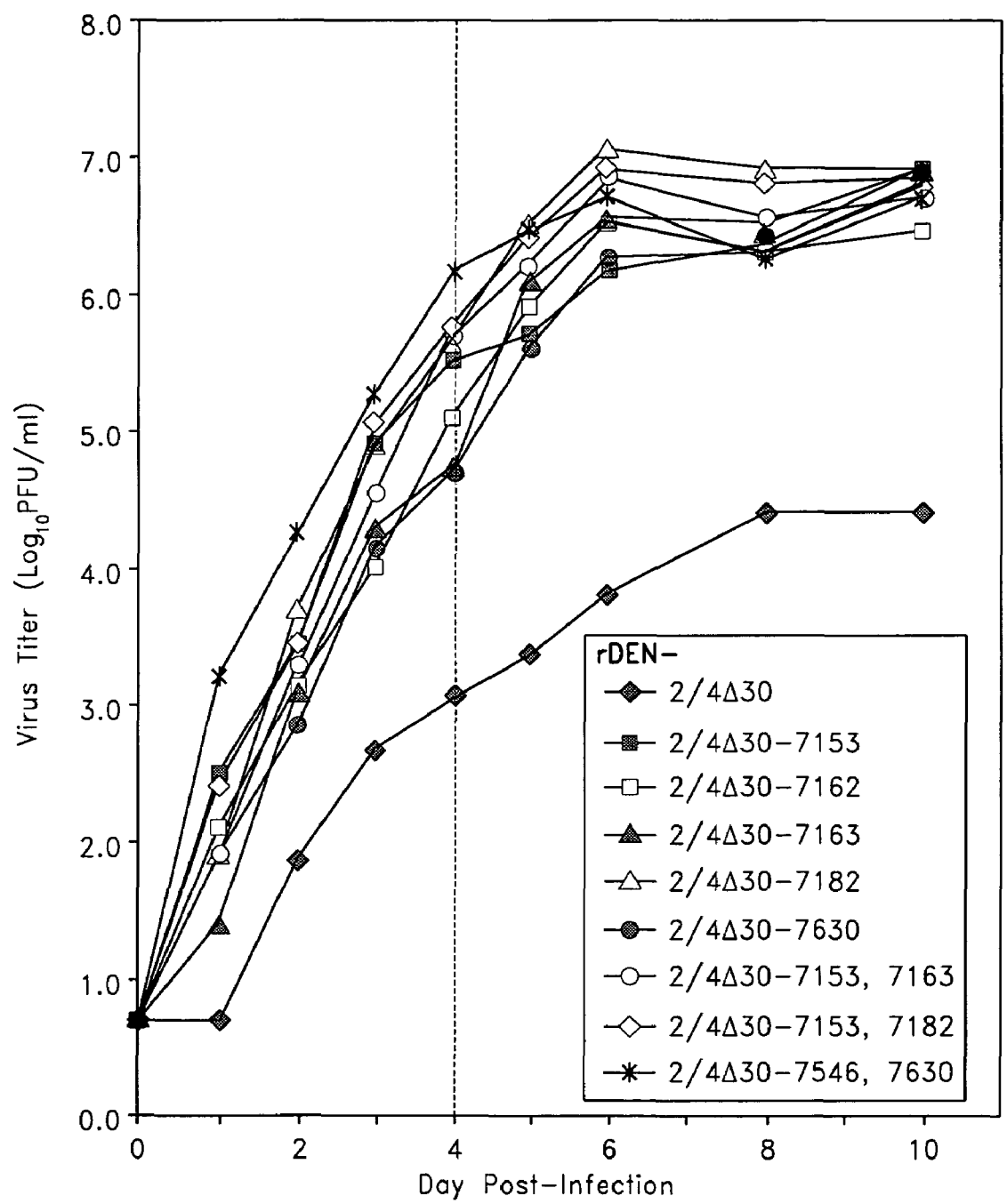
FIG. 10. Growth kinetics in Vero cells of chimeric rDEN2/4Δ30 viruses encoding single or combined Vero cell adaptation mutations. Vero cells were infected with the indicated viruses at an MOI of 0.01. At the indicated time points post-infection, 1 ml samples of tissue culture medium were removed, clarified by centrifugation, and frozen at −80° C. The level of virus replication was assayed by plaque titration in C6/36 cells. Lower limit of detection was 0.7 $\log_{10}$PFU/ml. Replication levels on day 4 post-infection are indicated by the dashed line.

The growth properties of rDEN2/4Δ30(CME) viruses bearing single Vero cell adaptation mutations at NS4B-7153, -7162, -7163, -7182, NS5-7630 or three combinations of mutations were compared in Vero cells with rDEN2/4Δ30 (CME) virus (FIG. 10). Without an introduced Vero cell adaptation mutation, rDEN2/4Δ30(CME) virus yield peaked at 4.4 $\log_{10}$PFU/ml. Each individual adaptation mutation and the combined mutations conferred a substantial increase in replication. Specifically, rDEN2/4Δ30(CME)-7182 grew to the highest titer of 7.1 $\log_{10}$PFU/ml, which was a 500-fold increase in yield. rDEN2/4Δ30(CME)-7162 had the lowest yield but still was increased 125-fold over the level of replication by rDEN2/4Δ30(CME) virus. Introduction of two adaptation mutations into rDEN2/4Δ30(CME) virus did not significantly increase virus yield over that of viruses bearing single Vero cell adaptation mutations. The observed increase of up to 500-fold in virus yield by the introduction of a Vero cell adaptation mutation into this chimeric vaccine candidate demonstrates the value of identifying and characterizing specific replication-promoting sequences in DEN viruses.

These results have particular significance for the development of a live attenuated dengue virus vaccine. First, it is clear that chimerization leads to attenuation of the resulting virus, as indicated by studies in rhesus monkeys, HuH7-SCID mice and mosquitoes. Although this conclusion was not made in the previous study with DEN2/DEN4 or DEN1/DEN4 chimeric viruses (Bray, M. et al. 1996 *J Virol* 70:4162-6), careful examination of the data would suggest that the chimeric viruses are more attenuated in monkeys compared to the wild-type parent viruses. Second, the Δ30 mutation can further augment this attenuation in a chimeric-dependent manner. Specifically, in this example, chimeric viruses bearing the CME region of DEN2 were over-attenuated by the addition of Δ30, whereas the attenuation phenotype of chimeric viruses bearing just the ME region of DEN2 was unaltered by the addition of the Δ30 mutation. This unexpected finding indicates that in a tetravalent vaccine comprised of individual component viruses bearing a shared attenuating mutation, such as the Δ30 mutation, only ME chimeric viruses can be utilized since CME chimeric viruses bearing the Δ30 mutation can be over-attenuated in rhesus monkeys and might provide only limited immunogenicity in humans.

EXAMPLE 6

Figure 11A:
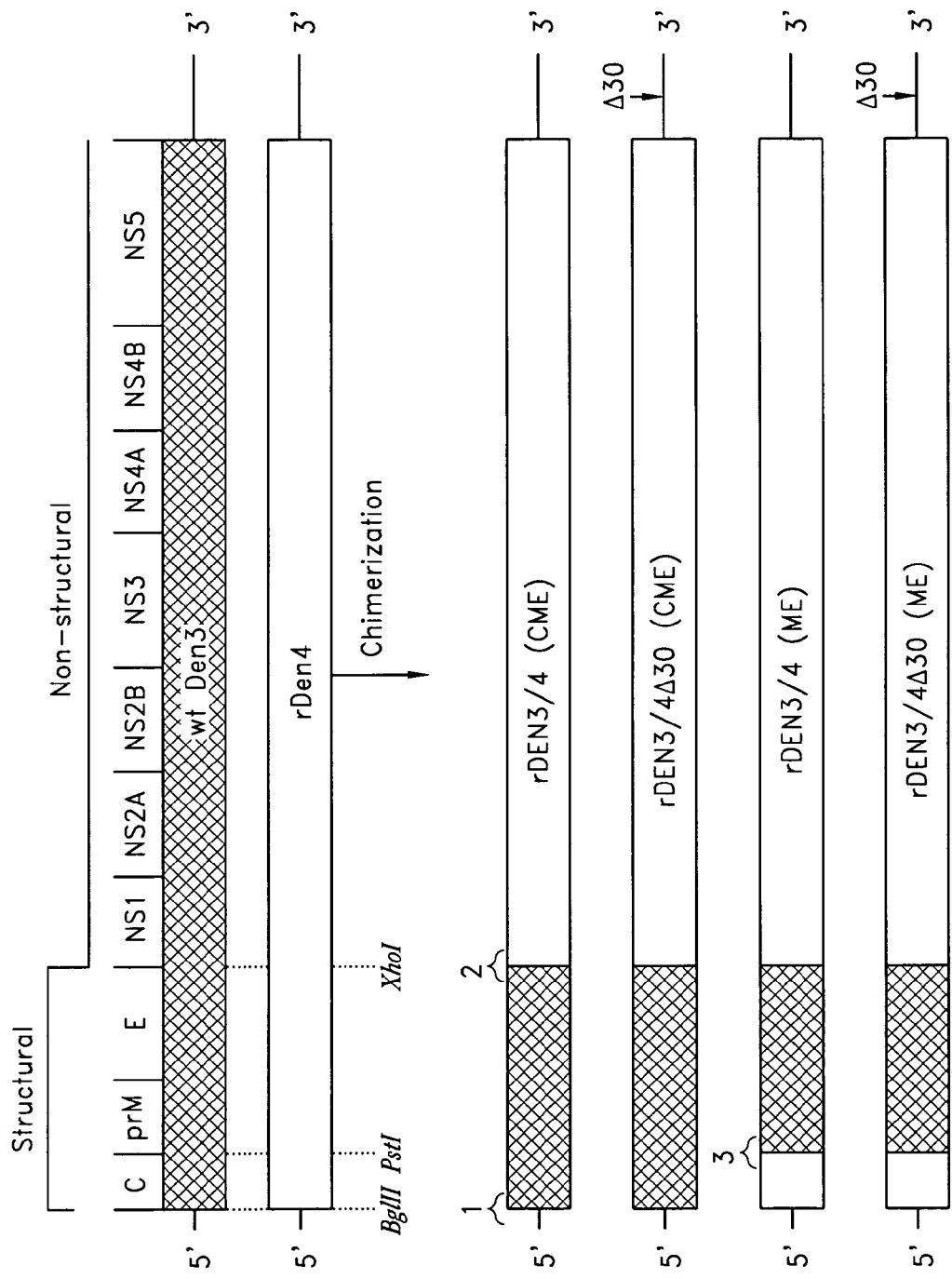
FIG. 11. A. Recombinant chimeric dengue viruses were constructed by introducing either the CME or the ME regions of DEN3 (Sleman/78) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. B. Nucleotide and amino acid sequence of the intertypic junction regions. Restriction enzyme recognition sites used in assembly of each chimeric cDNA are indicated.
Figure 11B:
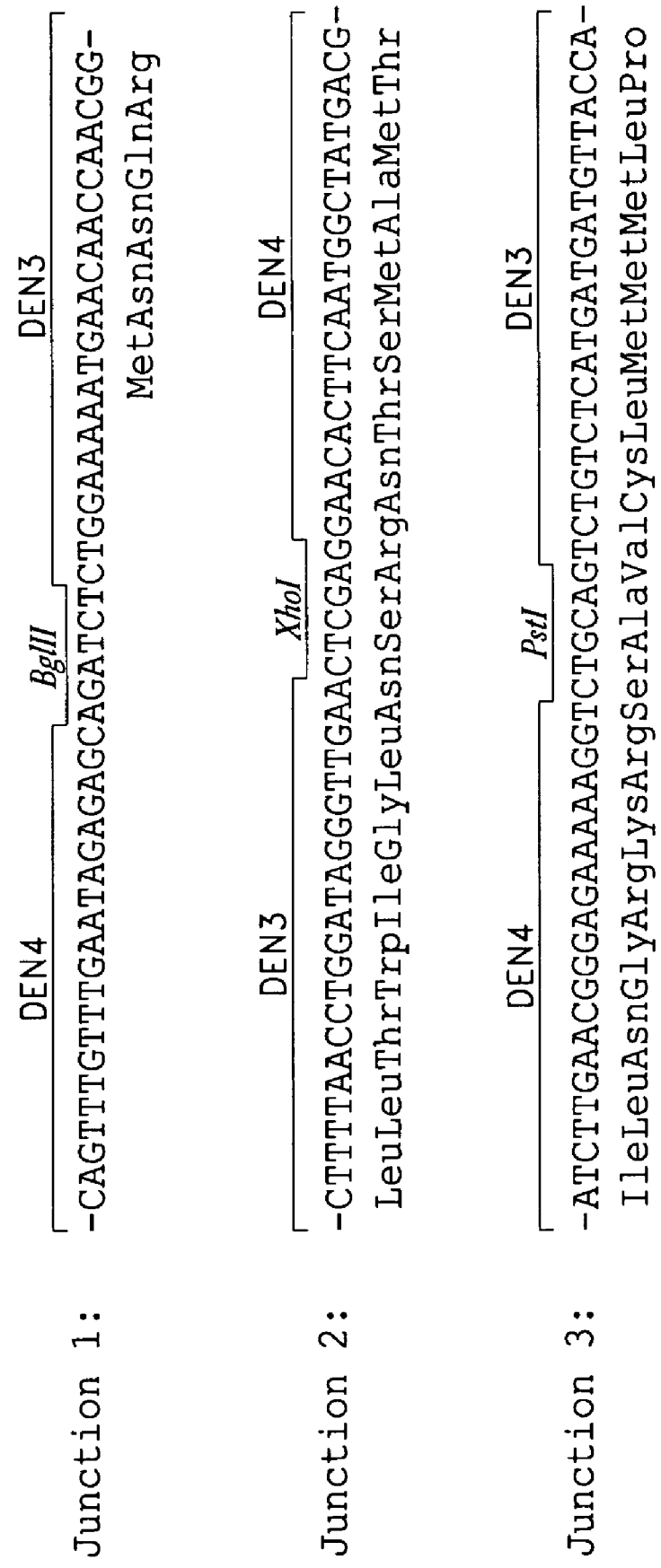

Generation and Characterization of Intertypic Chimeric DEN3 Viruses Containing the Δ30 Mutation Chimeric viruses based on the DEN4 cDNA have been generated in which the CME or ME genes have been replaced with the corresponding genes derived from DEN3 (Sleman/78), a virus isolate from the 1978 dengue outbreak in the Sleman region of Indonesia (Gubler, D. J. et al. 1981 *Am J Trop Med Hyg* 30:1094-1099) (Appendix 2). As described in Example 5 for the DEN2 chimeric viruses, CME chimeric viruses for DEN3 were generated by replacing the BglII/XhoI region of the cDNA for either rDEN4 or rDEN4Δ30 with a similar region derived from DEN3 (Sleman/78) (FIG. 11A). Likewise, to create the ME chimeric viruses, the PstI/XhoI region of the cDNA for either rDEN4 or rDEN4Δ30 was replaced with a similar region derived from DEN3 (Sleman/78). The nucleotide and amino acid sequences of the resulting junctions are shown in FIG. 11B. The genomes of the resulting viruses were confirmed by sequence analysis of viral RNA isolated from recovered virus as previously described (Durbin, A. P et al. 2001 *Am J Trop Med Hyg* 65:405-13). Incidental mutations arising from virus passage in tissue culture were identified in all viruses and are listed in Table 34. Notably, each virus contained a missense mutation in NS4B corresponding to a previously identified mutation from rDEN4 and associated with adaptation to growth in Vero cells (See Table 30 for correlation of nucleotide positions between rDEN4 and chimeric viruses). All viruses replicated in Vero cells to titers in excess of 5.7 $\log_{10}$PFU/ml, indicating that the chimeric viruses, even those containing the Δ30 mutation, replicate efficiently in cell culture, a property essential for manufacture of the vaccine.

TABLE 34

Missense mutations observed among Vero cell-grown chimeric DEN3/4 viruses

| Virus | Gene | Nucleotide position | Nucleotide change | Amino acid position | Amino acid change |
|---|---|---|---|---|---|
| rDEN3/ 4Δ30(CME) | M | 825 | T > C | 242 | Phe > Leu |
|  | E | 1641 | C > T | 514 | Leu > Phe |
|  | E | 2113 | A > G | 671 | Lys > Arg |
|  | NS4B | 7159[a] | T > C | 2353 | Leu > Ser |
| rDEN3/4(ME) | M | 460 | A > G | 120 | Asp > Gly |
|  | NS4B | 7177[b] | G > U | 2359 | Gly > Val |
|  | NS5 | 7702 | C > U | 2534 | Ser > Phe |
| rDEN3/ 4Δ30(ME) | E | 1432 | A > U | 444 | Gln > Leu |
|  | NS4B | 7156[a] | U > C | 2352 | Leu > Ser |
|  | NS5 | 8692 | A > C | 2864 | Asn > His |

[a]Same nucleotide position as 7162 in rDEN4.
[b]Same nucleotide position as 7183 in rDEN4.

As described in the previous examples, SCID mice transplanted with HuH-7 cells are a sensitive model for the evaluation of dengue virus attenuation. Each chimeric DEN3/4 virus was inoculated into groups of SCID-HuH-7 mice and levels of virus in the serum were determined (Table 35). While chimeric virus rDEN3/4 (CME) was not attenuated, the remaining chimeric viruses replicated to levels between 40- and 400-fold lower than either of the parental viruses (rDEN4 and DEN3-Sleman/78). In the CME chimeric virus, the Δ30 mutation providing a remarkable 2.7 $\log_{10}$ reduction in replication. This level of attenuation conferred by the Δ30 mutation in the CME chimeric virus was much greater than that observed previously for rDEN4Δ30. The rDEN3/4 (ME) virus was 100-fold reduced in replication compared to either parent virus indicating that the ME chimerization was attenuating per se. Addition of the Δ30 mutation to rDEN3/4 (ME) did not result in additional attenuation.

TABLE 35

Chimerization between dengue virus types 3 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN3-Sleman/78 | 23 | 6.4 ± 0.2 | A |
| rDEN3/4 (CME) | 7 | 6.4 ± 0.6 | A |
| rDEN3/4Δ30 (CME) | 5 | 3.7 ± 0.4 | B |
| rDEN3/4 (ME) | 6 | 4.2 ± 0.7 | B |
| rDEN3/4Δ30 (ME) | 7 | 4.7 ± 0.4 | A, B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

Evaluation of the replication and immunogenicity of the DEN3 chimeric recombinant viruses and wild-type DEN3 virus in monkeys was performed as described in Example 5. Results of this safety and immunogenicity study in monkeys are presented in Table 36. Monkeys inoculated with rDEN3/4(CME) and wild-type DEN (Sleman/78) were viremic for approximately 2 days with a mean peak titer of between 1.6 and 1.8 $\log_{10}$PFU/ml, respectively, indicating that chimerization of the CME structural genes of DEN3 did not lead to attenuation of virus replication, a different pattern than that observed for DEN2 chimerization (Table 31). However, chimerization of the ME structural genes resulted in attenuated viruses with undetectable viremia in monkeys, although all monkeys seroconverted with a greater than 10-fold increase in serum antibody levels. As expected for an attenuated virus, the immune response, as measured by neutralizing antibody titer, was lower following inoculation with any of the chimeric viruses compared to inoculation with wt DEN3 (Sleman/78), yet sufficiently high to protect the animals against wt DEN3 virus challenge (Table 37). It is clear that addition of the Δ30 mutation to rDEN3/4(CME) was capable of further attenuating the resulting virus rDEN3/4Δ30(CME).

TABLE 36

The Δ30 mutation further attenuates rDEN3/4(CME) for rhesus monkeys

| Virus[a] | No. of monkeys | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|
| DEN3 (Sleman/78) | 4 | 2.3 | 1.8 | <5 | 707 |
| rDEN3/4 (CME) | 4 | 2.0 | 1.6 | <5 | 211 |
| rDEN3/4Δ30 (CME) | 4 | 0 | <1.0 | <5 | 53 |
| rDEN3/4 (ME) | 4 | 0 | <1.0 | <5 | 70 |
| rDEN3/4Δ30 (ME) | 4 | 0 | <1.0 | <5 | 58 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

TABLE 37 rDEN3/4 chimeric viruses protect rhesus monkeys from wt DEN3 virus challenge

| Virus[a] | No. of monkeys | Mean no. of viremic days per monkey after rDEN3 challenge | Mean peak virus titer ($\log_{10}$ PFU/ml ± SE) | Geometric mean serum neutralizing antibody titer (reciprocal dilution) Day 28 | Day 56 |
|---|---|---|---|---|---|
| Mock | 2 | 5.0 | 2.5 ± 0.4 | <5 | 372 |
| DEN3 (Sleman/78) | 4 | 0 | <1.0 | 707 | 779 |
| rDEN3/4 (CME) | 4 | 0 | <1.0 | 211 | 695 |
| rDEN3/4Δ30 (CME) | 4 | 0.8 | 1.1 ± 0.2 | 53 | 364 |
| rDEN3/4 (ME) | 4 | 0 | <1.0 | 70 | 678 |
| rDEN3/4Δ30 (ME) | 4 | 0 | <1.0 | 58 | 694 |

[a]28 days after primary inoculation with the indicated viruses, rhesus monkeys were challenged subcutaneously with $10^5$ PFU DEN3 (Sleman/78) virus in a 1 ml dose. Serum was collected on days 28 to 34, 36, 38, and 56. Virus titer was determined by plaque assay in Vero cells.

To evaluate the replication levels of each DEN3/4 chimeric virus in mosquitoes, *Aedes aegypti* were infected by ingesting a virus-containing blood meal (Table 38). Parental viruses rDEN4 and DEN3 (Sleman/78) readily infect *Ae. aegypti*. Each of the rDEN3/4 chimeric viruses was also tested. In many cases it was not possible to infect *Ae. aegypti* with an undiluted virus stock of sufficient titer to achieve a detectable infection due to the very low infectivity of several of the viruses. At a dose of approximately 2.8-2.9 $\log_{10}$PFU, rDEN4, DEN3 (Sleman/78), and rDEN3/4(CME) were equally infectious and disseminated to the head with equal efficiency. For the remaining chimeric viruses, infection was not detectable even at a dose of 3.4 $\log_{10}$PFU, indicating that replication of rDEN3/4(ME) and rDEN3/4Δ30(CME) is restricted in *Ae. aegypti*. By comparing infectivity of rDEN3/4(CME) and rDEN3/4Δ30(CME), it is clear that the Δ30 mutation is capable of further attenuating the chimeric virus for mosquitoes.

TABLE 38

Ability of DEN3/4 chimeric viruses to infect *Aedes aegypti* fed an infectious bloodmeal.

| Virus Tested | Dose Ingested ($\log_{10}$ pfu)[a] | No. Mosquitoes Tested | No. (%) Midgut Infections[b,c,d] | No. (%) Disseminated Infections[e] |
|---|---|---|---|---|
| rDEN4 | 3.8 | 18 | 14 (77%) | 2 (14%) |
|  | 2.8 | 20 | 7 (34%) | 2 (10%) |
|  | 1.8 | 18 | 0 | 0 |
|  |  |  | $MID_{50} = 3.4$ | $MID_{50} \geq 4.4$ |
| DEN3 (Sleman) | 2.9 | 16 | 3 (18%) | 2 (12%) |
|  | 1.9 | 10 | 1 (10%) | 0 |
|  |  |  | $MID_{50} \geq 3.5$ | $MID_{50} \geq 3.5$ |
| rDEN3/4 (CME) | 3.9 | 20 | 6 (30%) | 2 (10%) |
|  | 2.9 | 18 | 4 (22%) | 0 |
|  | 1.9 | 13 | 1 (7%) | 0 |
|  |  |  | $MID_{50} \geq 4.2$ | $MID_{50} \geq 4.5$ |
| DEN3/4Δ30 (CME) | 3.3 | 20 | 0 | 0 |
|  |  |  | $MID_{50} \geq 4.3$ | $MID_{50} \geq 4.3$ |
| DEN3/4 (ME) | 3.4 | 15 | 0 | 0 |
|  |  |  | $MID_{50} \geq 4.4$ | $MID_{50} \geq 4.4$ |

[a]Amount of virus ingested, assuming a 2μ bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the $MID_{50}$ was estimated by assuming that a 10-fold more concentrated virus dose would infect 100% of the mosquitoes.
[d]When no infection was detected, the $MID_{50}$ was assumed to be greater than a 10-fold higher dose of virus than the one used.
[e]Number (percentage) of mosquitoes with detectable dengue virus antigen in both midgut and head tissue.

EXAMPLE 7

Figure 12A:
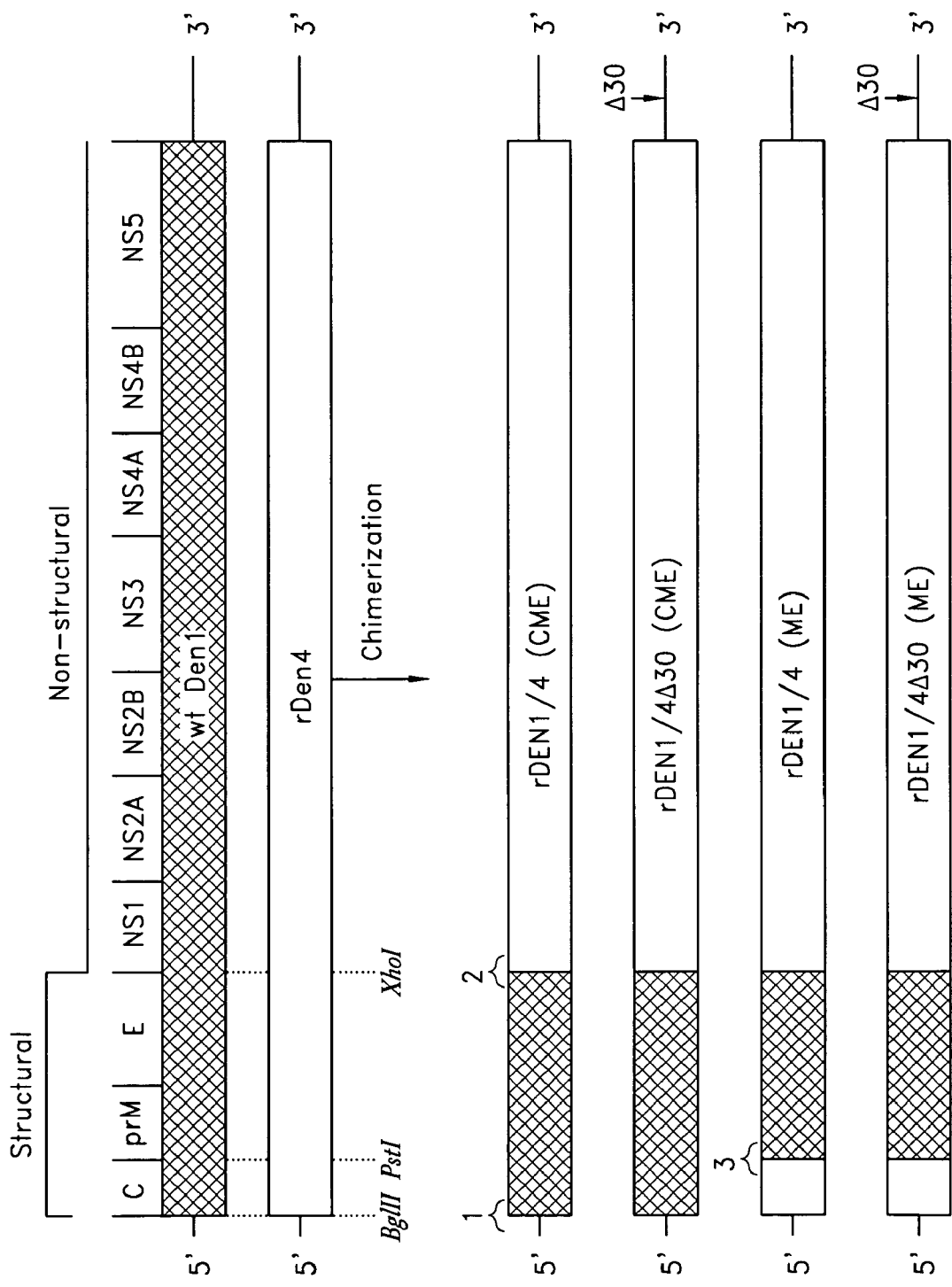
FIG. 12. A. Recombinant chimeric dengue viruses were constructed by introducing either the CME or the ME regions of DEN1 (Puerto Rico/94) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. B. Nucleotide and amino acid sequence of the intertypic junction regions. Restriction enzyme recognition sites used in assembly of each chimeric cDNA are indicated.

Generation and Characterization of Intertypic Chimeric DEN1 Viruses Containing the Δ30 Mutation Chimeric viruses based on the DEN4 cDNA have been generated in which the CME or ME genes have been replaced with the corresponding genes derived from DEN1 (Puerto Rico/94), a virus isolate from a 1994 dengue outbreak in Puerto Rico (Appendices 3 and 4). As described in Example 4 for the DEN2 chimeric viruses, CME chimeric viruses for DEN1 were generated by replacing the BglII/XhoI region of the cDNA for either rDEN4 or rDEN4Δ30 with a similar region derived from DEN1 (Puerto Rico/94) (FIG. 12A). Likewise, to create the ME chimeric viruses, the PstI/XhoI region of the cDNA for either rDEN4 or rDEN4Δ30 was replaced with a similar region derived from DEN1 (Puerto Rico/94). The nucleotide and amino acid sequences of the resulting junctions are shown in FIG. 12B.

For transcription and generation of virus, chimeric cDNA clones were linearized and used as template in a transcription reaction using SP6 RNA polymerase as described. Transcripts were introduced into C6/36 mosquito cells using liposome-mediated transfection and recombinant dengue virus was harvested between day 7 and 14. Viruses were subsequently grown in Vero cells and biologically cloned by terminal dilution in Vero cells. All viruses replicated in Vero cells to titers in excess of 6.0 $\log_{10}$PFU/ml, indicating that the chimeric viruses, even those containing the Δ30 mutation, replicate efficiently in cell culture. Genomic sequence analysis is currently underway to identify incidental mutations arising from virus passage in tissue culture.

To evaluate the replication levels of DEN1/4(CME) and rDEN1/4Δ30(CME) chimeric virus in mosquitoes, *Aedes aegypti* were infected by ingesting a virus-containing blood meal (Table 39). Parental virus rDEN4 infects *Ae. aegypti* with an MID50 of 4.0 $\log_{10}$PFU. However, parental virus DEN1(Puerto Rico/94), is unable to infect *Ae. aegypti* at a dose of up to 3.4 $\log_{10}$PFU. Thus CME chimeric viruses DEN1/4 and rDEN1/4Δ30 share this inability to infect *Ae. aegypti*. Therefore, it is unnecessary in *Ae. aegypti* to evaluate the effect of the Δ30 mutation on the infectivity of the DEN1/4 chimeric viruses, in a manner similar to that used for the DEN2/4 and DEN3/4 chimeric viruses.

TABLE 39

Inability of DEN1/4 chimeric viruses to infect *Aedes aegypti* fed an infectious bloodmeal.

| Virus tested | Dose ingested ($\log_{10}$ pfu)[a] | No. Mosquitoes Tested | No. (%) Midgut Infections[b,c,d] | No. (%) Disseminated Infections[e] |
|---|---|---|---|---|
| rDEN4 | 4.3 | 21 | 18 (85%) | 8 (44%) |
|  | 3.3 | 15 | 3 (20%) | 0 |
|  | 2.3 | 20 | 0 | 0 |
|  |  |  | MID$_{50}$ = 4.0 | MID$_{50}$ ≧ 4.3 |
| DEN1 (Puerto Rico/94) | 3.4 | 21 | 0 MID$_{50}$ ≧ 4.4 | 0 MID$_{50}$ ≧ 4.4 |
| rDEN 1/4 (CME) | 3.8 | 20 | 0 MID$_{50}$ ≧ 4.8 | 0 MID$_{50}$ ≧ 4.8 |
| rDEN1/4Δ30 (CME) | 2.8 | 20 | 0 MID$_{50}$ ≧ 3.8 | 0 MID$_{50}$ ≧ 3.8 |

[a]Amount of virus ingested, assuming a 2 μl bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the MID$_{50}$ was estimated by assuming that a 10-fold more concentrated virus dose would infect 100% of the mosquitoes.
[d]When no infection was detected, the MID$_{50}$ was assumed to be greater than a 10-fold higher dose of virus than the one used.
[e]Number (percentage) of mosquitoes with detectable dengue virus antigen in both midgut and head tissue.

As described in the previous examples, SCID mice transplanted with the HuH-7 cells are a sensitive model for the evaluation of dengue virus attenuation. Each chimeric DEN1/4 virus was inoculated into groups of SCID-HuH-7 mice and levels of virus in the serum were determined (Table 40). Chimeric viruses replicated to levels between 15- and 250-fold lower than either of the parental viruses, rDEN4 and DEN1 (Puerto Rico/94). CME chimeric viruses were more attenuated than the comparable ME chimeric viruses, with the Δ30 mutation providing a 0.8 $\log_{10}$ reduction in replication. This level of attenuation exerted by the Δ30 mutation in the CME chimeric viruses was similar to that observed previously for rDEN4Δ30. However, the attenuating effect of the Δ30 mutation in the ME chimeric viruses is indiscernible.

TABLE 40

Chimerization between dengue virus types 1 and 4 results in recombinant viruses which are attenuated for HuH-7-SCID mice.

| Virus[a] | No. of mice | Mean peak virus titer ($\log_{10}$ pfu/ml ± SE) | Statistical group[b] |
|---|---|---|---|
| rDEN4 | 32 | 6.3 ± 0.2 | A |
| DEN1 (Puerto Rico/94) | 4 | 6.4 ± 0.2 | A |
| rDEN1/4 (CME) | 8 | 4.7 ± 0.2 | B, C |
| rDEN1/4Δ30 (CME) | 6 | 3.9 ± 0.4 | C |
| rDEN1/4 (ME) | 6 | 5.0 ± 0.2 | B |
| rDEN1/4Δ30 (ME) | 6 | 5.1 ± 0.3 | B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

APPENDIX 1

Nucleotide and amino acid sequence of DEN2 (Tonga/74) cDNA plasmid p2

Bases 1 to 10713: DEN2 virus genome cDNA

Bases 97 to 10269: DEN2 polyprotein ORF

Bases 97 to 438: C protein ORF

Bases 439 to 936: prM protein ORF

Bases 937 to 2421: E protein ORF

Bases 2422 to 3477: NS1 protein ORF

Bases 3478 to 4131: NS2A protein ORF

Bases 4132 to 4521: NS2B protein ORF

Bases 4522 to 6375: NS3 protein ORF

Bases 6376 to 6756: NS4A protein ORF

Bases 6757 to 6825: 2K protein ORF

Bases 6826 to 7569: NS4B protein ORF

Bases 7570 to 10269: NS5 protein ORF 10 20 30 40 50 60 70 80 90
100
AGTTGTTAGTCTACGTGGACCGACAAAGACAGATTCTTTGAGGGAGCTAAGCTCAACGTAGTTCTAACTGTTTTTTGATTAGAGAGCAGATCTCTGATGA Met>

110 120 130 140 150 160 170 180 190
200
ATAACCAACGGAAAAAGGCGAGAAACACGCCTTTCAATATGCTGAAACGCGAGAGAAACCGCGTGTCAACTGTACAACAGTTGACAAAGAGATTCTCACT

AsnAsnGlnArgLysLysAlaArgAsnThrProPheAsnMetLeuLysArgGluArgAsnArgValSerThrValGlnGlnLeuThrLysArgPheSerLeu>

210 220 230 240 250 260 270 280 290
300
TGGAATGCTGCAGGGACGAGGACCACTAAAATTGTTCATGGCCCTGGTGGCATTCCTTCGTTTCCTAACAATCCCACCAACAGCAGGGATATTAAAAAGA

GlyMetLeuGlnGlyArgGlyProLeuLysLeuPheMetAlaLeuValAlaPheLeuArgPheLeuThrIleProProThrAlaGlyIleLeuLysArg>

310 320 330 340 350 360 370 380 390
400
TGGGGAACAATTAAAAAATCAAAGGCTATTAATGTTCTGAGAGGCTTCAGGAAGAGATTTGGAAGGATGCTGAATATCTTAAACAGGAGACGTAGAACTG

TrpGlyThrIleLysLysSerLysAlaIleAsnValLeuArgGlyPheArgLysGluIleGlyArgMetLeuAsnIleLeuAsnArgARgArgArgThr>

410 420 430 440 450 460 470 480 490
500
TAGGCATGATCATCATGCTGACTCCAACAGTGATGGCGTTTCATCTGACCACACGCAACGGAGAACCACACATGATTGTCAGTAGACAAGAAAAAGGGAA

ValGlyMetIleIleMetLeuThrProThrValMetAlaPheHisLeuThrThrArgAsnGlyGluProHisMetIleValSerArgGlnGluLysGlyLys>

510 520 530 540 550 560 570 580 590
600
AAGCCTTCTGTTCAAGACAAAGGATGGCACGAACATGTGTACCCTCATGGCCATGGACCTTGGTGAGTTGTGTGAAGACACAATCACGTATAAATGTCCT

SerLeuLeuPheLysThrLysAspGlyThrAsnMetCysThrLeuMetAlaMetAspLeuGlyGluLeuCysGluAspThrIleThrTyrLysCysPro>

610 620 630 640 650 660 670 680 690
700
TTTCTCAAGCAGAACGAACCAGAAGACATAGATTGTTGGTGCAACTCCACGTCCACATGGGTAACTTATGGGACATGTACCACCACAGGAGAGCACAGAA

PheLeuLysGlnAsnGluProGluAspIleAspCysTrpCysAsnSerThrSerThrTrpValThrTyrGlyThrCysThrThrThrGlyGluHisArg>

710 720 730 740 750 760 770 780 790
800
GAGAAAAAAGATCAGTGGCGCTTGTTCCACACGTGGGAATGGGATTGGAGACACGAACTGAAACATGGATCTCATCAGAAGGGGCCTGGAAACATGCCCA

ArgGluLysArgSerValAlaLeuValProHisValGlyMetGlyLeuGluThrArgThrGluThrTrpMetSerSerGluGlyAlaTrpLysHisAlaGln>

APPENDIX 1-continued

Nucleotide and amino acid sequence of DEN2 (Tonga/74) cDNA plasmid p2

```
         810       820       830       840       850       860       870       880       890
900
GAGAATTGAAACTTGGATTCTGAGACATCCAGGCTTTACCATAATGGCCGCAATCCTGGCATACACCATAGGGACGACGCATTTCCAAAGAGTCCTGATA

ArgIleGluThrTrpIleLeuArgHisProGlyPheThrIleMetAlaAlaIleLeuAlaTyrThrIleGlyThrThrHisPheGlnArgValLeuIle>

910       920       930       940       950       960       970       980       990
1000
TTCATCCTACTGACAGCCATCGCTCCTTCAATGACAATGCGCTGCATAGGAATATCAAATAGGGACTTTGTGGAAGGAGTGTCAGGAGGGAGTTGGGTTG

PheIleLeuLeuThrAlaIleAlaProSerMetThrMetArgCysIleGlyIleSerAsnArgAspPheValGluGlyValSerGlyGlySerTrpVal>

1010      1020      1030      1040      1050      1060      1070      1080      1090
1100
ACATAGTTTTAGAACATGGAAGTTGTGTGACGACGATGGCAAAAAACAAACCAACACTGGACTTTGAACTGATAAAAACAGAAGCCAAACAACCTGCCAC

AspIleValLeuGluHisGlySerCysValThrThrMetAlaLysAsnLysProThrLeuAspPheGluLeuIleLysThrGluAlaLysGlnProAlaThr>

1110      1120      1130      1140      1150      1160      1170      1180      1190
1200
CTTAAGGAAGTACTGTATAGAGGCCAAACTGACCAACACGACAACAGACTCGCGCTGCCCAACACAAGGGGAACCCACCCTGAATGAAGAGCAGGACAAA

LeuArgLysTyrCysIleGluAlaLysLeuThrAsnThrThrThrAspSerArgCysProThrGlnGlyGluProThrLeuAsnGluGluGlnAspLys>

1210      1220      1230      1240      1250      1260      1270      1280      1290
1300
AGGTTTGTCTGCAAACATTCCATGGTAGACAGAGGATGGGGAAATGGATGTGGATTGTTTGGAAAAGGAGGCATCGTGACCTGTGCTATGTTCACATGCA

ArgPheValCysLysHisSerMetValAspArgGlyTrpGlyAsnGlyCysGlyLeuPheGlyLysGlyGlyIleValThrCysAlaMetPheThrCys>

1310      1320      1330      1340      1350      1360      1370      1380      1390
1400
AAAAGAACATGGAAGGAAAAATTGTTCAGCCAGAAAACCTGGAATACACTGTCGTGATAACACCTCATTCAGGGGAAGAACATGCAGTGGGAAATGACAC

LysLysAsnMetGluGlyLysIleValGlnProGluAsnLeuGluTyrThrValValIleThrProHisSerGlyGluGluHisAlaValGlyAsnAspThr>

1410      1420      1430      1440      1450      1460      1470      1480      1490
1500
AGGAAAACATGGTAAAGAAGTCAAGATAACACCACAGAGCTCCATCACAGAGGCGGAACTGACAGGCTATGGCACTGTTACGATGGAGTGCTCTCCAAGA

GlyLysHisGlyLysGluValLysIleThrProGlnSerSerIleThrGluAlaGluLeuThrGlyTyrGlyThrValThrMetGluCysSerProArg>

1510      1520      1530      1540      1550      1560      1570      1580      1590
1600
ACGGGCCTCGACTTCAATGAGATGGTGTTGCTGCAAATGGAAGACAAAGCCTGGCTGGTGCACAGACAATGGTTCCTAGACCTACCGTTGCCATGGCTGC

ThrGlyLeuAspPheAsnGluMetValLeuLeuGlnMetGluAspLysAlaTrpLeuValHisArgGlnTrpPheLeuAspLeuProLeuProTrpLeu>

1610      1620      1630      1640      1650      1660      1670      1680      1690
1700
CCGGAGCAGACACACAAGGATCAAATTGGATACAGAAAGAAACACTGGTCACCTTCAAAAATCCCCATGCGAAAAAACAGGATGTTGTTGTCTTAGGATC

ProGlyAlaAspThrGlnGlySerAsnTrpIleGlnLysGluThrLeuValThrPheLysAsnProHisAlaLysLysGlnAspValValValLeuGlySer>

1710      1720      1730      1740      1750      1760      1770      1780      1790
1800
CCAAGAGGGGGCCATGCATACAGCACTCACAGGGGCTACGGAAATCCAGATGTCATCAGGAAACCTGCTGTTCACAGGACATCTCAAGTGCAGGCTGAGA

GlnGluGlyAlaMetHisThrAlaLeuThrGlyAlaThrGluIleGlnMetSerSerGlyAsnLeuLeuPheThrGlyHisLeuLysCysArgLeuArg>

1810      1820      1830      1840      1850      1860      1870      1880      1890
1900
ATGGACAAATTACAACTTAAAGGGATGTCATACTCCATGTGCACAGGAAAGTTTAAAATTGTGAAGGAAATAGCAGAAACACAACATGGAACAATAGTCA

MetAspLysLeuGlnLeuLysGlyMetSerTyrSerMetCysThrGlyLysPheLysIleValLysGluIleAlaGluThrGlnHisGlyThrIleVal>

1910      1920      1930      1940      1950      1960      1970      1980      1990
2000
TTAGAGTACAATATGAAGGAGACGGCTCTCCATGCAAGATCCCCTTTGAGATAATGGATCTGGAAAAAAGACATGTTTTGGGCCGCCTGATCACAGTCAA

IleArgValGlnTyrGluGlyAspGlySerProCysLysIleProPheGluIleMetAspLeuGluLysArgHisValLeuGlyArgLeuIleThrValAsn>

2010      2020      2030      2040      2050      2060      2070      2080      2090
2100
CCCAATTGTAACAGAAAAGGACAGTCCAGTCAACATAGAAGCAGAACCTCCATTCGGAGACAGCTACATCATCATAGGAGTGGAACCAGGACAATTGAAG

ProIleValThrGluLysAspSerProValAsnIleGluAlaGluProProPheGlyAspSerTyrIleIleIleGlyValGluProGlyGlnLeuLys>
```

APPENDIX 1-continued

Nucleotide and amino acid sequence of DEN2 (Tonga/74) cDNA plasmid p2

2110 2120 2130 2140 2150 2160 2170 2180 2190 2200

CTGGACTGGTTCAAGAAAGGAAGTTCCATCGGCCAAATGTTTGAGACAACAATGAGGGGAGCGAAAAGAATGGCCATTTTGGGTGACACAGCCTGGGATT

LeuAspTrpPheLysLysGlySerSerIleGlyGlnMetPheGluThrThrMetArgGlyAlaLysArgMetAlaIleLeuGlyAspThrAlaTrpAsp>

2210 2220 2230 2240 2250 2260 2270 2280 2290 2300

TTGGATCTCTGGGAGGAGTGTTCACATCAATAGGAAAGGCTCTCCACCAGGTTTTTGGAGCAATCTACGGGGCTGCTTTCAGTGGGGTCTCATGGACTAT

PheGlySerLeuGlyGlyValPheThrSerIleGlyLysAlaLeuHisGlnValPheGlyAlaIleTyrGlyAlaAlaPheSerGlyValSerTrpThrMet>

2310 2320 2330 2340 2350 2360 2370 2380 2390 2400

GAAGATCCTCATAGGAGTTATCATCACATGGATAGGAATGAACTCACGTAGCACTAGTCTGAGCGTGTCACTGGTGTTAGTGGGAATCGTGACACTTTAC

LysIleLeuIleGlyValIleIleThrTrpIleGlyMetAsnSerArgSerThrSerLeuSerValSerLeuValLeuValGlyIleValThrLeuTyr>

2410 2420 2430 2440 2450 2460 2470 2480 2490 2500

TTGGGAGTTATGGTGCAGGCCGATAGTGGTTGCGTTGTGAGCTGGAAGAACAAAGAACTAAAATGTGGCAGTGGAATATTCGTCACAGATAACGTGCATA

LeuGlyValMetValGlnAlaAspSerGlyCysValValSerTrpLysAsnLysGluLeuLysCysGlySerGlyIlePheValThrAspAsnValHis>

2510 2520 2530 2540 2550 2560 2570 2580 2590 2600

CATGGACAGAACAATACAAGTTCCAACCAGAATCCCCTTCAAAACTGGCCTCAGCCATCCAGAAAGCGCATGAAGAGGGCATCTGTGGAATCCGCTCAGT

ThrTrpThrGluGlnTyrLysPheGlnProGluSerProSerLysLeuAlaSerAlaIleGlnLysAlaHisGluGluGlyIleCysGlyIleArgSerVal>

2610 2620 2630 2640 2650 2660 2670 2680 2690 2700

AACAAGACTGGAAAATCTTATGTGGAAACAGATAACATCAGAATTGAATCATATTCTATCAGAAAATGAAGTGAAACTGACCATCATGACAGGAGACATC

ThrArgLeuGluAsnLeuMetTrpLysGlnIleThrSerGluLeuAsnHisIleLeuSerGluAsnGluValLysLeuThrIleMetThrGlyAspIle>

2710 2720 2730 2740 2750 2760 2770 2780 2790 2800

AAAGGAATCATGCAGGTAGGAAAACGATCTTTGCGGCCTCAACCCACTGAGTTGAGGTATTCATGGAAAACATGGGGTAAAGCGAAAATGCTCTCCACAG

LysGlyIleMetGlnValGlyLysArgSerLeuArgProGlnProThrGluLeuArgTyrserTrpLysThrTrpGlyLysAlaLysMetLeuSerThr>

2810 2820 2830 2840 2850 2860 2870 2880 2890 2900

AACTCCACAATCAGACCTTCCTCATTGATGGTCCCGAAACAGCAGAATGCCCCAACACAAACAGAGCTTGGAATTCACTGGAAGTTGAGGACTACGGCTT

GluLeuHisAsnGlnThrPheLeuIleAspGlyProGluThrAlaGluCysproAsnThrAsnArgAlaTrpAsnSerLeuGluValGluAspTyrGlyPhe>

2910 2920 2930 2940 2950 2960 2970 2980 2990 3000

TGGAGTATTCACTACCAATATATGGCTAAGATTGAGAGAAAAGCAGGATGTATTTTGTGACTCAAACTCATGTGCAGCGGCCATAAAGGACAACAGAGCC

GlyValPheThrThrAsnIleTrpLeuArgLeuArgGluLysGlnAspValPheCysAspSerLysLeuMetSreAlaAlaIleLysAspAsnArgAla>

3010 3020 3030 3040 3050 3060 3070 3080 3090 3100

GTCCATGCTGATATGGGTTATTGGATAGAAAGCGCACTCAATGATACATGGAAGATAGAGAAAGCTTCTTTCATTGAAGTCAAAAGTTGCCACTGGCCAA

ValHisAlaAspMetGlyTryTrpIleGluSerAlaLeuAsnAspThrTrpLysIleGluLysAlaSerPheIleGluValLysSerCysHisTrpPro>

3110 3120 3130 3140 3150 3160 3170 3180 3190 3200

AGTCACACACCCTATGGAGTAATGGAGTGCTAGAAAGCGAGATGGTCATTCCAAAGAATTTCGCTGGACCAGTGTCACAACATAATAACAGACCAGGCTA

LysSerHisThrLeuTrpSerAsnGlyValLeuGluSerGluMetValIleProLysAsnPheAlaGlyProValSerGlnHisAsnAsnArgProGlyTyr>

3210 3220 3230 3240 3250 3260 3270 3280 3290 3300

TTACACACAAACAGCAGGACCTTGGCATCTAGGCAAGCTTGAGATGGACTTTGATTTCTGCGAAGGGACTACAGTGGTGGTAACCGAGAACTGTGGAAAC

TyrThrGlnThrAlaGlyProTrpHisLeuGlyLysLeuGluMetAspPheAspPheCysGluGlyThrThrValValValThrGluAsnCysGlyAsn>

3310 3320 3330 3340 3350 3360 3370 3380 3390 3400

AGAGGGCCCTCTTTAAGAACAACCACTGCCTCAGGAAAACTCATAACGGAATGGTGTTGTCGATCTTGCACACTACCACCACTAAGATACAGAGGTGAGG

ArgGlyProSerLeuArgThrThrThrAlaSerGlyLysLeuIleThrGluTrpCysCysArgSerCysThrLeuProProLeuArgTyrArgGlyGlu>

APPENDIX 1-continued

Nucleotide and amino acid sequence of DEN2 (Tonga/74) cDNA plasmid p2

```
          3410      3420      3430      3440      3450      3460      3470      3480      3490
3500
ATGGATGTTGGTACGGGATGGAAATCAGACCATTGAAAGAGAAAGAAGAAAATCTGGTCAGTTCTCTGGTTACAGCCGGACATGGGCAGATTGACAATTT

AspGlyCysTrpTyrGlyMetGluIleArgProLeuLysGluLysGluGluAsnLeuValSerSerLeuValThrAlaGlyHisGlyGlnIleAspAsnPhe>

3510      3520      3530      3540      3550      3560      3570      3580      3590
3600
CTCATTAGGAATCTTGGGAATGGCACTGTTCCTTGAAGAAATGCTCAGGACTCGAGTAGGAACAAAACATGCAATATTACTCGTCGCAGTTTCTTTCGTG

SerLeuGlyIleLeuGlyMetAlaLeuPheLeuGluGluMetLeuArgThrArgValGlyThrLysHisAlaIleLeuLeuValAlaValSerPheVal>

3610      3620      3630      3640      3650      3660      3670      3680      3690
3700
ACGCTAATCACAGGGAACATGTCTTTTAGAGACCTGGGAAGAGTGATGGTTATGGTGGGTGCCACCATGACAGATGACATAGGCATGGGTGTGACTTATC

ThrLeuIleThrGlyAsnMetSerPheArgAspLeuGlyArgValMetValMetValGlyAlaThrMetThrAspAspIleGlyMetGlyValThrTyr>

3710      3720      3730      3740      3750      3760      3770      3780      3790
3800
TCGCTCTACTAGCAGCTTTTAGAGTCAGACCAACCTTTGCAGCTGGACTGCTCTTGAGAAAACTGACCTCCAAGGAATTAATGATGACTACCATAGGAAT

LeuAlaLeuLeuAlaAlaPheArgValArgProThrPheAlaAlaGlyLeuLeuLeuArgLysLeuThrSerLysGluLeuMetMetThrThrIleGlyIle>

3810      3820      3830      3840      3850      3860      3870      3880      3890
3900
CGTTCTTCTCTCCCAGAGTAGCATACCAGAGACCATTCTTGAACTGACCGACGCGTTAGCTCTAGGCATGATGGTCCTCAAGATGGTGAGAAACATGGAA

ValLeuLeuSerGlnSerSerIleProGluThrIleLeuGluLeuThrAspAlaLeuAlaLeuGlyMetMetValLeuLysMetValArgAsnMetGlu>

3910      3920      3930      3940      3950      3960      3970      3980      3990
4000
AAATATCAGCTGGCAGTGACCATCATGGCTATTTTGTGCGTCCCAAATGCTGTGATATTACAGAACGCATGGAAAGTGAGTTGCACAATATTGGCAGTGG

LysTyrGlnLeuAlaValThrIleMetAlaIleLeuCysValProAsnAlaValIleLeuGlnAsnAlaTrpLysValSerCysThrIleLeuAlaVal>

4010      4020      4030      4040      4050      4060      4070      4080      4090
4100
TGTCTGTTTCCCCCCTGCTCTTAACATCCTCACAACAGAAAGCGGACTGGATACCATTAGCGTTGACGATCAAAGGTCTTAATCCAACAGCCATTTTTCT

ValSerValSerProLeuLeuLeuThrSerSerGlnGlnLysAlaAspTrpIleProLeuAlaLeuThrIleLysGlyLeuAsnProThrAlaIlePheLeu>

4110      4120      4130      4140      4150      4160      4170      4180      4190
4200
AACAACCCTCTCAAGAACCAACAAGAAAAGGAGCTGGCCTTTAAATGAGGCCATCATGGCGGTTGGGATGGTGAGTATCTTGGCCAGCTCTCTCTTAAAG

ThrThrLeuSerArgThrAsnLysLysArgSerTrpProLeuAsnGluAlaIleMetAlaValGlyMetValSerIleLeuAlaSerSerLeuLeuLys>

4210      4220      4230      4240      4250      4260      4270      4280      4290
4300
AATGACATCCCCATGACAGGACCATTAGTGGCTGGAGGGCTCCTTACTGTGTGCTACGTGCTAACTGGGCGGTCAGCCGATCTGGAATTAGAGAGAGCTA

AsnAspIleProMetThrGlyProLeuValAlaGlyGlyLeuLeuThrValCysTyrValLeuThrGlyArgSerAlaAspLeuGluLeuGluArgAla>

4310      4320      4330      4340      4350      4360      4370      4380      4390
4400
CCGATGTCAAATGGGATGACCAGGCAGAGATATCAGGTAGCAGTCCAATCCTGTCAAGAACAATATCAGAAGATGGCAGCATGTCAATAAAGAATGAAGA

ThrAspValLysTrpAspAspGlnAlaGluIleSerGlySerSerProIleLeuSerIleThrIleSerGluAspGlySerMetSerIleLysAsnGluGlu>

4410      4420      4430      4440      4450      4460      4470      4480      4490
4500
GGAAGAGCAAACACTGACTATACTCATTAGAACAGGATTGCTTGTGATCTCAGGACTCTTTCCGGTATCAATACCAATTACAGCAGCAGCATGGTATCTG

GluGluGlnThrLeuThrIleLeuIleArgThrGlyLeuLeuValIleSerGlyLeuPheProValSerIleProIleThrAlaAlaAlaTrpTyrLeu>

4510      4520      4530      4540      4550      4560      4570      4580      4590
4600
TGGGAAGTAAAGAAACAACGGGCTGGAGTGCTGTGGGATGTCCCCTCACCACCACCCGTGGGAAAAGCTGAATTGGAAGATGGAGCCTACAGAATCAAGC

TrpGluValLysLysGlnArgAlaGlyValLeuTrpAspValProSerProProProValGlyLysAlaGluLeuGluAspGlyAlaTyrArgIleLys>

4610      4620      4630      4640      4650      4660      4670      4680      4690
4700
AAAAAGGAATCCTTGGATATTCCCAGATCGGAGCTGGAGTTTACAAAGAAGGAACATTTCACACAATGTGGCACGTCACACGTGGCGCTGTCCTAATGCA

GlnLysGlyIleLeuGlyTyrSerGlnIleGlyAlaGlyValTyrLysGluGlyThrPheHisThrMetTrpHisValThrArgGlyAlaValLeuMetHis>
```

APPENDIX 1-continued

Nucleotide and amino acid sequence of DEN2 (Tonga/74) cDNA plasmid p2

```
                   4710      4720      4730      4740      4750      4760      4770      4780      4790
4800
TAAGGGGAAGAGGATTGAACCATCATGGGCGGACGTCAAGAAAGACTTAATATCATATGGAGGAGGTTGGAAGCTAGAAGGAGAATGGAAAGAAGGAGAA

LysGlyLysArgIleGluProSerTrpAlaAspValLysLysAspLeuIleSerTyrGlyGlyGlyTrpLysLeuGluGlyGluTrpLysGluGlyGlu>

4810      4820      4830      4840      4850      4860      4870      4880      4890
4900
GAAGTCCAGGTCTTGGCATTGGAGCCAGGGAAAAATCCAAGAGCCGTCCAAACAAAGCCTGGCCTTTTTAGAACCAACACTGGAACCATAGGTGCCGTAT

GluValGlnValLeuAlaLeuGluProGlyLysAsnProArgAlaValGlnThrLysProGlyLeuPheArgThrAsnThrGlyThrIleGlyAlaVal>

4910      4920      4930      4940      4950      4960      4970      4980      4990
5000
CTCTGGACTTTTCCCCTGGGACGTCAGGATCTCCAATCGTCGACAAAAAAGGAAAAGTTGTAGGTCTCTATGGCAATGGTGTCGTTACAAGGAGTGGAGC

SerLeuAspPheSerProGlyThrSerGlySerProIleValAspLysLysGlyLysValValGlyLeuTyrGlyAsnGlyValValThrArgSerGlyAla>

5010      5020      5030      5040      5050      5060      5070      5080      5090
5100
ATATGTGAGTGCCATAGCTCAGACTGAAAAAAGCATTGAAGACAATCCAGAGATTGAAGATGACATCTTTCGAAAGAGAAGATTGACTATCATGGATCTC

TyrValSerAlaIleAlaGlnThrGluLysSerIleGluAspAsnProGluIleGluAspAspIlePheArgLysArgArgLeuThrIleMetAspLeu>

5110      5120      5130      5140      5150      5160      5170      5180      5190
5200
CACCCAGGAGCAGGAAAGACAAAGAGATACCTCCCGGCCATAGTCAGAGAGGCCATAAAAAGAGGCTTGAGAACACTAATCCTAGCCCCCACTAGAGTCG

HisProGlyAlaGlyLysThrLysArgTyrLeuProAlaIleValArgGluAlaIleLysArgGlyLeuArgThrLeuIleLeuAlaProThrArgVal>

5210      5220      5230      5240      5250      5260      5270      5280      5290
5300
TGGCAGCTGAAATGGAGGAAGCCCTTAGAGGACTTCCAATAAGATACCAAACTCCAGCTATCAGGGCTGAGCACACCGGGCGGGAGATTGTAGACTTAAT

ValAlaAlaGluMetGluGluAlaLeuArgGlyLeuProIleArgTyrGlnThrProAlaIleArgAlaGluHisThrGlyArgGluIleValAspLeuMet>

5310      5320      5330      5340      5350      5360      5370      5380      5390
5400
GTGTCATGCCACATTTACCATGAGGCTGCTATCACCAATCAGGGTGCCAAATTACAACCTGATCATCATGGACGAAGCCCATTTTACAGATCCAGCAAGC

CysHisAlaThrPheThrMetArgLeuLeuSerProIleArgValProAsnTyrAsnLeuIleIleMetAspGluAlaHisPheThrAspProAlaSer>

5410      5420      5430      5440      5450      5460      5470      5480      5490
5500
ATAGCAGCTAGGGGATACATCTCAACTCGAGTGGAGATGGGGGAGGCAGCTGGAATTTTTATGACAGCCACTCCTCCGGGTAGTAGAGATCCATTTCCTC

IleAlaAlaArgGlyTyrIleSerThrArgValGluMetGlyGluAlaAlaGlyIlePheMetThrAlaThrProProGlySerArgAspProPhePro>

5510      5520      5530      5540      5550      5560      5570      5580      5590
5600
AGAGCAATGCACCAATTATGGACGAAGAAAGAGAAATTCCGGAACGTTCATGGAACTCTGGGCACGAGTGGGTCACGGATTTTAAAGGAAAGACTGTCTG

GlnSerAsnAlaProIleMetAspGluGluArgGluIleProGluArgSerTrpAsnSerGlyHisGluTrpValThrAspPheLysGlyLysThrValTrp>

5610      5620      5630      5640      5650      5660      5670      5680      5690
5700
GTTTGTTCCAAGCATAAAAACCGGAAATGACATAGCAGCCTGCCTGAGAAAGAATGGAAAGAGGGTGATACAACTCAGTAGGAAGACCTTTGATTCTGAA

PheValProSerIleLysThrGlyAsnAspIleAlaAlaCysLeuArgLysAsnGlyLysArgValIleGlnLeuSerArgLysThrPheAspSerGlu>

5710      5720      5730      5740      5750      5760      5770      5780      5790
5800
TATGTCAAGACTAGAACCAATGACTGGGATTTCGTGGTTACAACTGACATCTCGGAAATGGGCGCCAACTTTAAAGCTGAGAGGGTCATAGACCCCAGAC

TyrValLysThrArgThrAsnAspTrpAspPheValValThrThrAspIleSerGluMetGlyAlaAsnPheLysAlaGluArgValIleAspProArg>

5810      5820      5830      5840      5850      5860      5870      5880      5890
5900
GCTGCATGAAACCAGTTATATTGACAGACGGCGAAGAGCGGGTGATTCTGGCAGGACCCATGCCAGTGACCCACTCTAGTGCAGCACAAAGAAGAGGGAG

ArgCysMetLysProValIleLeuThrAspGlyGluGluArgValIleLeuAlaGluProMetProValThrHisSerSerAlaAlaGlnArgArgGlyArg>

5910      5920      5930      5940      5950      5960      5970      5980      5990
6000
AATAGGAAGGAATCCAAGGAATGAAAATGATCAATATATATATATGGGGGAACCACTGGAAAATGATGAAGACTGTGCGCACTGGAAGGAAGCTAAGATG

IleGlyArgAsnProArgAsnGluAsnAspGlnTyrIleTyrMetGlyGluProLeuGluAsnAspGluAspCysAlaHisTrpLysGluAlaLysMet>
```

APPENDIX 1-continued

Nucleotide and amino acid sequence of DEN2 (Tonga/74) cDNA pl

APPENDIX 1-continued

Nucleotide and amino acid sequence of DEN2 (Tonga/74) cDNA plasmid p2

7310 7320 7330 7340 7350 7360 7370 7380 7390 7400
CCTATGATCCAAAGTTTGAAAAGCAGTTGGGACAAGTAATGCTCCTAGTCCTCTGCGTGACCCAAGTGCTGATGATGAGGACTACGTGGGCTTTGTGTGA

ProTyrAspProLysPheGluLysGlnLeuGlyGlnValMetLeuLeuValLeuCysValThrGlnValLeuMetMetArgThrThrTrpAlaLeuCysGlu>

7410 7420 7430 7440 7450 7460 7470 7480 7490 7500
AGCCTTAACTCTAGCAACTGGACCCGTGTCCACATTGTGGGAAGGAAATCCAGGGAGATTCTGGAACACAACCATTGCAGTGTCAATGGCAAACATCTTT

AlaLeuThrLeuAlaThrGlyProValSerThrLeuTrpGluGlyAsnProGlyArgPheTrpAsnThrThrIleAlaValSerMetAlaAsnIlePhe>

7510 7520 7530 7540 7550 7560 7570 7580 7590 7600
AGAGGGAGTTACCTGGCTGGAGCTGGACTTCTCTTTTCTATCATGAAGAACACAACCAGCACGAGAAGAGGAACTGGCAATATAGGAGAAACGTTAGGAG

ArgGlySerTyrLeuAlaGlyAlaGlyLeuLeuPheSerIleMetLysAsnThrThrSerThrArgArgGlyThrGlyAsnIleGlyGluThrLeuGly>

7610 7620 7630 7640 7650 7660 7670 7680 7690 7700
AGAAATGGAAAAGCAGACTGAACGCATTGGGGAAAAGTGAATTCCAGATCTACAAAAAAAGTGGAATTCAAGAAGTGGACAGAACCTTAGCAAAAGAAGG

GluLysTrpLysSerArgLeuAsnAlaLeuGlyLysSerGluPheGlnIleTyrLysLysSerGlyIleGlnGluValAspArgThrLeuAlaLysGluGly>

7710 7720 7730 7740 7750 7760 7770 7780 7790 7800
CATTAAAAGAGGAGAAACGGATCATCACGCTGTGTCGCGAGGCTCAGCAAAACTGAGATGGTTCGTTGAAAGGAATTTGGTCACACCAGAAGGGAAAGTA

IleLysArgGlyGluThrAspHisHisAlaValSerArgGlySerAlaLysLeuArgTrpPheValGluArgAsnLeuValThrProGluGlyLysVal>

7810 7820 7830 7840 7850 7860 7870 7880 7890 7900
GTGGACCTTGGTTGTGGCAGAGGGGGCTGGTCATACTATTGTGGAGGATTAAAGAATGTAAGAGAAGTTAAAGGCTTAACAAAAGGAGGACCAGGACACG

ValAspLeuGlyCysGlyArgGlyGlyTrpSerTyrTyrCysGlyGlyLeuLysAsnValArgGluValLysGlyLeuThrLysGlyGlyProGlyHis>

7910 7920 7930 7940 7950 7960 7970 7980 7990 8000
AAGAACCTATCCCTATGTCAACATATGGGTGGAATCTAGTACGCTTACAGAGCGGAGTTGATGTTTTTTTGTTCCACCAGAGAAGTGTGACACATTGTT

GluGluProIleProMetSerThrTyrGlyTrpAsnLeuValArgLeuGlnSerGlyValAspValPhePheValProProGluLysCysAspThrLeuLeu>

8010 8020 8030 8040 8050 8060 8070 8080 8090 8100
GTGTGACATAGGGGAATCATCACCAAATCCCACGGTAGAAGCGGGACGAACACTCAGAGTCCTCAACCTAGTGGAAAATTGGCTGAACAATAACACCCAA

CysAspIleGlyGluSerSerProAsnProThrValGluAlaGlyArgThrLeuArgValLeuAsnLeuValGluAsnTrpLeuAsnAsnAsnThrGln>

8110 8120 8130 8140 8150 8160 8170 8180 8190 8200
TTTTGCGTAAAGGTTCTTAACCCGTACATGCCCTCAGTCATTGAAAGAATGGAAACCTTACAACGGAAATACGGAGGAGCCTTGGTGAGAAATCCACTCT

PheCysValLysValLeuAsnProTyrMetProSerValIleGluArgMetGluThrLeuGlnArgLysTyrGlyGlyAlaLeuValArgAsnProLeu>

8210 8220 8230 8240 8250 8260 8270 8280 8290 8300
CACGGAATTCCACACATGAGATGTACTGGGTGTCCAATGCTTCCGGGAACATAGTGTCATCAGTGAACATGATTTCAAGAATGCTGATCAACAGATTCAC

SerArgAsnSerThrHisGluMetTyrTrpValSerAsnAlaSerGlyAsnIleValSerSerValAsnMetIleSerArgMetLeuIleAsnArgPheThr>

8310 8320 8330 8340 8350 8360 8370 8380 8390 8400
TATGAGACACAAGAAGGCCACCTATGAGCCAGATGTCGACCTCGGAAGCGGAACCCGCAATATTGGAATTGAAAGTGAGACACCGAACCTAGACATAATT

MetArgHisLysLysAlaThrTyrGluProAspValAspLeuGlySerGlyThrArgAsnIleGlyIleGluSerGluThrProAsnLeuAspIleIle>

8410 8420 8430 8440 8450 8460 8470 8480 8490 8500
GGGAAAAGAATAGAAAAAATAAAACAAGAGCATGAAACGTCATGGCACTATGATCAAGACCACCCATACAAAACATGGGCTTACCATGGCAGCTATGAAA

GlyLysArgIleGluLysIleLysGlnGluHisGluThrSerTrpHisTyrAspGlnAspHisProTyrLysThrTrpAlaTyrHisGlySerTyrGlu>

8510 8520 8530 8540 8550 8560 8570 8580 8590 8600
CAAAACAGACTGGATCAGCATCATCCATGGTGAACGGAGTAGTCAGATTGCTGACAAAACCCTGGGACGTTGTTCCAATGGTGACACAGATGGCAATGAC

ThrLysGlnThrGlySerAlaSerSerMetValAsnGlyValValArgLeuLeuThrLysProTrpAspValValProMetValThrGlnMetAlaMetThr>

APPENDIX 1-continued

Nucleotide and amino acid sequence of DEN2 (Tonga/74) cDNA plasmid p2

```
           8610      8620      8630      8640      8650      8660      8670      8680      8690
8700
AGACACAACTCCTTTTGGACAACAGCGCGTCTTCAAAGAGAAGGTGGATACGAGAACCCAAGAACCAAAAGAAGGCACAAAAAAACTAATGAAAATCACG

AspThrThrProPheGlyGlnGlnArgValPheLysGluLysValAspThrArgThrGlnGluProLysGluGlyThrLysLysLeuMetLysIleThr>

8710      8720      8730      8740      8750      8760      8770      8780      8790
8800
GCAGAGTGGCTCTGGAAAGAACTAGGAAAGAAAAAGACACCTAGAATGTGTACCAGAGAAGAATTCACAAAAAAGGTGAGAAGCAATGCAGCCTTGGGGG

AlaGluTrpLeuTrpLysGluLeuGlyLysLysLysThrProArgMetCysThrArgGluGluPheThrLysLysValArgSerAsnAlaAlaLeuGly>

8810      8820      8830      8840      8850      8860      8870      8880      8890
8900
CCATATTCACCGATGAGAACAAGTGGAAATCGGCGCGTGAAGCCGTTGAAGATAGTAGGTTTTGGGAGCTGGTTGACAAGGAAAGGAACCTCCATCTTGA

AlaIlePheThrAspGluAsnLysTrpLysSerAlaArgGluAlaValGluAspSerArgPheTrpGluLeuValAspLySGluArgAsnLeuHisLeuGlu>

8910      8920      8930      8940      8950      8960      8970      8980      8990
9000
AGGGAAATGTGAAACATGTGTATACAACATGATGGGGAAAAGAGAGAAAAAACTAGGAGAGTTTGGTAAAGCAAAAGGCAGCAGAGCCATATGGTACATG

GlyLysCysGluThrCysValTyrAsnMetMetGlyLysArgGluLysLysLeuGlyGluPheGlyLysAlaLysGlySerArgAlaIleTrpTyrMet>

9010      9020      9030      9040      9050      9060      9070      9080      9090
9100
TGGCTCGGAGCACGCTTCTTAGAGTTTGAAGCCCTAGGATTTTTGAATGAAGACCATTGGTTCTCCAGAGAGAACTCCCTGAGTGGAGTGGAAGGAGAAG

TrpLeuGlyAlaArgPheLeuGluPheGluAlaLeuGlyPheLeuAsnGluAspHisTrpPheSerArgGluAsnSerLeuSerGlyValGluGlyGlu>

9110      9120      9130      9140      9150      9160      9170      9180      9190
9200
GGCTGCATAAGCTAGGTTACATCTTAAGAGAGGTGAGCAAGAAAGAAGGAGGAGCAATGTATGCCGATGACACCGCAGGCTGGGACACAAGAATCACAAT

GlyLeuHisLysLeuGlyTyrIleLeuArgGluValSerLysLysGluGlyGlyAlaMetTyrAlaAspAspThrAlaGlyTrpAspThrArgIleThrIle>

9210      9220      9230      9240      9250      9260      9270      9280      9290
9300
AGAGGATTTGAAAAATGAAGAAATGATAACGAACCACATGGCAGGAGAACACAAGAAACTTGCCGAGGCCATTTTTAAATTGACGTACCAAAACAAGGTG

GluAspLeuLysAsnGluGluMetIleThrAsnHisMetAlaGlyGluHisLysLysLeuAlaGluAlaIlePheLysLeuThrTyrGlnAsnLysVal>

9310      9320      9330      9340      9350      9360      9370      9380      9390
9400
GTGCGTGTGCAAAGACCAACACCAAGAGGCACAGTAATGGACATCATATCGAGAAGAGACCAAAGGGGTAGTGGACAAGTTGGCACCTATGGCCTCAACA

ValArgValGlnArgProThrProArgGlyThrValMetAspIleIleSerArgArgAspGlnArgGlySerGlyGlnValGlyThrTyrGlyLeuAsn>

9410      9420      9430      9440      9450      9460      9470      9480      9490
9500
CTTTCACCAACATGGAAGCACAACTAATTAGGCAAATGGAGGGGGAAGGAATCTTCAAAAGCATCCAGCACTTGACAGCCTCAGAAGAAATCGCTGTGCA

ThrPheThrAsnMetGluAlaGlnLeuIleArgGlnMetGluGlyGluGlyIlePheLysSerIleGlnHisLeuThrAlaSerGluGluIleAlaValGln>

9510      9520      9530      9540      9550      9560      9570      9580      9590
9600
AGATTGGCTAGTAAGAGTAGGGCGTGAAAGGTTGTCAAGAATGGCCATCAGTGGAGATGATTGTGTTGTGAAACCTTTAGATGATAGATTTGCAAGAGCT

AspTrpLeuValArgValGlyArgGluArgLeuSerArgMetAlaIleSerGlyAspAspCysValValLysProLeuAspAspArgPheAlaArgAla>

9610      9620      9630      9640      9650      9660      9670      9680      9690
9700
CTAACAGCTCTAAATGACATGGGAAAGGTTAGGAAGGACATACAGCAATGGGAGCCCTCAAGAGGATGGAACGACTGGACGCAGGTGCCCTTCTGTTCAC

LeuThrAlaLeuAsnAspMetGlyLysValArgLysAspIleGlnGlnTrpGluProSerArgGlyTrpAsnAspTrpThrGlnValProPheCysSer>

9710      9720      9730      9740      9750      9760      9770      9780      9790
9800
ACCATTTTCACGAGTTAATTATGAAAGATGGTCGCACACTCGTAGTTCCATGCAGAAACCAAGATGAATTGATCGGCAGAGCCCGAATTTCCCAGGGAGC

HisHisPheHisGluLeuIleMetLysAspGlyArgThrLeuValValProCysArgAsnGlnAspGluLeuIleGlyArgAlaArgIleSerGlnGlyAla>

9810      9820      9830      9840      9850      9860      9870      9880      9890
9900
TGGGTGGTCTTTACGGGAGACGGCCTGTTTGGGAAGTCTTACGCCCAAATGTGGAGCTTGATGTACTTCCACAGACGTGATCTCAGGCTAGCGGCAAAT

GlyTrpSerLeuArgGluThrAlaCysLeuGlyLysSerTyrAlaGlnMetTrpSerLeuMetTyrPheHisArgArgAspLeuArgLeuAlaAlaAsn>
```

APPENDIX 1-continued

Nucleotide and amino acid sequence of DEN2 (Tonga/74) cDNA plasmid p2

```
                 9910      9920      9930      9940      9950      9960      9970      9980      9990
10000
GCCATCTGCTCGGCAGTCCCATCACACTGGATTCCAACAAGCCGGACAACCTGGTCCATACACGCCAGCCATGAATGGATGACGACGGAAGACATGTTGA

AlaIleCysSerAlaValProSerHisTrpIleProThrSerArgThrThrTrpSerIleHisAlaSerHisGluTrpMetThrThrGluAspMetLeu>

10010     10020     10030     10040     10050     10060     10070     10080     10090
10100
CAGTTTGGAACAGAGTGTGGATCCTAGAAAATCCATGGATGGAAGACAAAACTCCAGTGGAATCATGGGAGGAAATCCCATACCTGGGAAAAAGAGAAGA

ThrValTrpAsnArgValTrpIleLeuGluAsnProTrpMetGluAspLysThrProValGluSerTrpGluGluIleProTyrLeuGlyLysArgGluAsp>

10110     10120     10130     10140     10150     10160     10170     10180     10190
10200
CCAATGGTGCGGCTCGCTGATTGGGCTGACAAGCAGAGCCACCTGGGCGAAGAATATCCAGACAGCAATAAACCAAGTCAGATCCCTCATTGGCAATGAG

GlnTrpCysGlySerLeuIleGlyLeuThrSerArgAlaThrTrpAlaLysAsnIleGlnThrAlaIleAsnGlnValArgSerLeuIleGlyAsnGlu>

10210     10220     10230     10240     10250     10260     10270     10280     10290
10300
GAATACACAGATTACATGCCATCCATGAAAAGATTCAGAAGAGAAGAGGAAGAGGCAGGAGTTTTGTGGTAGAAAAACATGAAACAAAACAGAAGTCAGG

GluTyrThrAspTyrMetProSerMetLysArgPheArgArgGluGluGluGluAlaGlyValLeuTrp***>

10310     10320     10330     10340     10350     10360     10370     10380     10390
10400
TCGGATTAAGCCATAGTACGGGAAAAACTATGCTACCTGTGAGCCCCGTCCAAGGACGTTAAAAGAAGTCAGGCCATTTTGATGCCATAGCTTGAGCAAA 10410     10420     10430     10440     10450     10460     10470     10480     10490
10500
CTGTGCAGCCTGTAGCTCCACCTGAGAAGGTGTAAAAAATCCGGGAGGCCACAAACCATGGAAGCTGTACGCATGGCGTAGTGGACTAGCGGTTAGAGGA 10510     10520     10530     10540     10550     10560     10570     10580     10590
10600
GACCCCTCCCTTACAGATCGCAGCAACAATGGGGGCCCAAGGTGAGATGAAGCTGTAGTCTCACTGGAAGGACTAGAGGTTAGAGGAGACCCCCCCAAAA 10610     10620     10630     10640     10650     10660     10670     10680     10690
10700
CAAAAAACAGCATATTGACGCTGGGAAAGACCAGAGATCCTGCTGTCTCCTCAGCATCATTCCAGGCACAGGACGCCAGAAAATGGAATGGTGCTGTTGA 10710     10720     10730     10740     10750     10760     10770     10780     10790
10800
ATCAACAGGTTCTGGTACCGGTAGGCATCGTGGTGTCACGCTCGTCGTTTGGTATGGCTTCATTCAGCTCCGGTTCCCAACGATCAAGGCGAGTTACATG 10810     10820     10830     10840     10850     10860     10870     10880     10890
10900
ATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCA 10910     10920     10930     10940     10950     10960     10970     10980     10990
11000
CTGCATAATTCTCTTACTGTCATGCCATCCGTAAGATGCTTTTCTGTGACTGGTGAGTACTCAACCAAGTCATTCTGAGAATAGTGTATGCGGCGACCGA 11010     11020     11030     11040     11050     11060     11070     11080     11090
11100
GTTGCTCTTGCCCGGCGTCAACACGGGATAATACCGCGCCACATAGCAGAACTTTAAAAGTGCTCATCATTGGAAAACGTTCTTCGGGGCGAAAACTCTC 11110     11120     11130     11140     11150     11160     11170     11180     11190
11200
AAGGATCTTACCGCTGTTGAGATCCAGTTCGATGTAACCCACTCGTGCACCCAACTGATCTTCAGCATCTTTTACTTTCACCAGCGTTTCTGGGTGAGCA 11210     11220     11230     11240     11250     11260     11270     11280     11290
11300
AAAACAGGAAGGCAAAATGCCGCAAAAAAGGGAATAAGGGCGACACGGAAATGTTGAATACTCATACTCTTCCTTTTTCAATATTATTGAAGCATTTATC 11310     11320     11330     11340     11350     11360     11370     11380     11390
11400
AGGGTTATTGTCTCATGAGCGGATACATATTTGAATGTATTTAGAAAAATAAACAAATAGGGGTTCCGCGCACATTTCCCCGAAAAGTGCCACCTGACGT 11410     11420     11430     11440     11450     11460     11470     11480     11490
11500
CTAAGAAACCATTATTATCATGACATTAACCTATAAAAATAGGCGTATCACGAGGCCCTTTCGTCTTCAAGAATTCTCATGTTTGACAGCTTATCATCGA 11510     11520     11530     11540     11550     11560     11570     11580     11590
11600
TAAGCTTTAATGCGGTAGTTTATCACAGTTAAATTGCTAACGCAGTCAGGCACCGTGTATGAAATCTAACAATGCGCTCATCGTCATCCTCGGCACCGTC
```

APPENDIX 1-continued

Nucleotide and amino acid sequence of DEN2 (Tonga/74) cDNA plasmid p2

```
                11610     11620     11630     11640     11650     11660     11670     11680     11690
11700
ACCCTGGATGCTGTAGGCATAGGCTTGGTTATGCCGGTACTGCCGGGCCTCTTGCGGGATATCGTCCATTCCGACAGCATCGCCAGTCACTATGGCGTGC 11710     11720     11730     11740     11750     11760     11770     11780     11790
11800
TGCTGGCGCTATATGCGTTGATGCAATTTCTATGCGCACCCGTTCTCGGAGCACTGTCCGACCGCTTTGGCCGCCGCCCAGTCCTGCTCGCTTCGCTACT 11810     11820     11830     11840     11850     11860     11870     11880     11890
11900
TGGAGCCACTATCGACTACGCGATCATGGCGACCACACCCGTCCTGTGGATCCTCTACGCCGGACGCATCGTGGCCGGCATCACCGGCGCCACAGGTGCG 11910     11920     11930     11940     11950     11960     11970     11980     11990
12000
GTTGCTGGCGCCTATATCGCCGACATCACCGATGGGGAAGATCGGGCTCGCCACTTCGGGCTCATGAGCGCTTGTTTCGGCGTGGGTATGGTGGCAGGCC 12010     12020     12030     12040     12050     12060     12070     12080     12090
12100
CCGTGGCCGGGGGACTGTTGGGCGCCATCTCCTTGCATGCACCATTCCTTGCGGCGGCGGTGCTCAACGGCCTCAACCTACTACTGGGCTGCTTCCTAAT 12110     12120     12130     12140     12150     12160     12170     12180     12190
12200
GCAGGAGTCGCATAAGGGAGAGCGTCGACCGATGCCCTTGAGAGCCTTCAACCCAGTCAGCTCCTTCCGGTGGGCGCGGGGCATGACTATCGTCGCCGCA 12210     12220     12230     12240     12250     12260     12270     12280     12290
12300
CTTATGACTGTCTTCTTTATCATGCAACTCGTAGGACAGGTGCCGGCAGCGCTCTGGGTCATTTTCGGCGAGGACCGCTTTCGCTGGAGCGCGACGATGA 12310     12320     12330     12340     12350     12360     12370     12380     12390
12400
TCGGCCTGTCGCTTGCGGTATTCGGAATCTTGCACGCCCTCGCTCAAGCCTTCGTCACTGGTCCCGCCACCAAACGTTTCGGCGAGAAGCAGGCCATTAT 12410     12420     12430     12440     12450     12460     12470     12480     12490
12500
CGCCGGCATGGCGGCCGACGCGCTGGGCTACGTCTTGCTGGCGTTCGCGACGCGAGGCTGGATGGCCTTCCCCATTATGATTCTTCTCGCTTCCGGCGGC 12510     12520     12530     12540     12550     12560     12570     12580     12590
12600
ATCGGGATGCCCGCGTTGCAGGCCATGCTGTCCAGGCAGGTAGATGACGACCATCAGGGACAGCTTCAAGGATCGCTCGCGGCTCTTACCAGCCTAACTT 12610     12620     12630     12640     12650     12660     12670     12680     12690
12700
CGATCACTGGACCGCTGATCGTCACGGCGATTTATGCCGCCTCGGCGAGCACATGGAACGGGTTGGCATGGATTGTAGGCGCCGCCCTATACCTTGTCTG 12710     12720     12730     12740     12750     12760     12770     12780     12790
12800
CCTCCCCGCGTTGCGTCGCGGTGCATGGAGCCGGGCCACCTCGACCTGAATGGAAGCCGGCGGCACCTCGCTAACGGATTCACCACTCCAAGAATTGGAG 12810     12820     12830     12840     12850     12860     12870     12880     12890
12900
CCAATCAATTCTTGCGGAGAACTGTGAATGCGCAAACCAACCCTTGGCAGAACATATCCATCGCGTCCGCCATCTCCAGCAGCCGCACGCGGCGCATCTC 12910     12920     12930     12940     12950     12960     12970     12980     12990
13000
GGGCAGCGTTGGGTCCTGGCCACGGGTGCGCATGATCGTGCTCCTGTCGTTGAGGACCCGGCTAGGCTGGCGGGGTTGCCTTACTGGTTAGCAGAATGAA 13010     13020     13030     13040     13050     13060     13070     13080     13090
13100
TCACCGATACGCGAGCGAACGTGAAGCGACTGCTGCTGCAAAACGTCTGCGACCTGAGCAACAACATGAATGGTCTTCGGTTTCCGTGTTTCGTAAAGTC 13110     13120     13130     13140     13150     13160     13170     13180     13190
13200
TGGAAACGCGGAAGTCAGCGCCCTGCACCATTATGTTCCGGATCTGCATCGCAGGATGCTGCTGGCTACCCTGTGGAACACCTACATCTGTATTAACGAA 13210     13220     13230     13240     13250     13260     13270     13280     13290
13300
GCGCTGGCATTGACCCTGAGTGATTTTTCTCTGGTCCCGCCGCATCCATACCGCCAGTTGTTTACCCTCACAACGTTCCAGTAACCGGGCATGTTCATCA 13310     13320     13330     13340     13350     13360     13370     13380     13390
13400
TCAGTAACCCGTATCGTGAGCATCCTCTCTCGTTTCATCGGTATCATTACCCCCATGAACAGAAATCCCCCTTACACGGAGGCATCAGTGACCAAACAGG 13410     13420     13430     13440     13450     13460     13470     13480     13490
13500
AAAAAACCGCCCTTAACATGGCCCGCTTTATCAGAAGCCAGACATTAACGCTTCTGGAGAAACTCAACGAGCTGGACGCGGATGAACAGGCAGACATCTG
```

APPENDIX 1-continued

Nucleotide and amino acid sequence of DEN2 (Tonga/74) cDNA plasmid p2

```
          13510     13520     13530     13540     13550     13560     13570     13580     13590
13600
TGAATCGCTTCACGACCACGCTGATGAGCTTTACCGCAGCTGCCTCGCGCGTTTCGGTGATGACGGTGAAAACCTCTGACACATGCAGCTCCCGGAGACG 13610     13620     13630     13640     13650     13660     13670     13680     13690
13700
GTCACAGCTTGTCTGTAAGCGGATGCCGGGAGCAGACAAGCCCGTCAGGGCGCGTCAGCGGGTGTTGGCGGGTGTCGGGGCGCAGCCATGACCCAGTCAC 13710     13720     13730     13740     13750     13760     13770     13780     13790
13800
GTAGCGATAGCGGAGTGTATACTGGCTTAACTATGCGGCATCAGAGCAGATTGTACTGAGAGTGCACCATATGCGGTGTGAAATACCGCACAGATGCGTA 13810     13820     13830     13840     13850     13860     13870     13880     13890
13900
AGGAGAAAATACCGCATCAGGCGCTCTTCCGCTTCCTCGCTCACTGACTCGCTGCGCTCGGTCGTTCGGCTGCGGCGAGCGGTATCAGCTCACTCAAAGG 13910     13920     13930     13940     13950     13960     13970     13980     13990
14000
CGGTAATACGGTTATCCACAGAATCAGGGGATAACGCAGGAAAGAACATGTGAGCAAAAGGCCAGCAAAAGGCCAGGAACCGTAAAAAGGCCGCGTTGCT 14010     14020     14030     14040     14050     14060     14070     14080     14090
14100
GGCGTTTTTCCATAGGCTCCGCCCCCCTGACGAGCATCACAAAAATCGACGCTCAAGTCAGAGGTGGCGAAACCCGACAGGACTATAAAGATACCAGGCG 14110     14120     14130     14140     14150     14160     14170     14180     14190
14200
TTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTC 14210     14220     14230     14240     14250     14260     14270     14280     14290
14300
ATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATC 14310     14320     14330     14340     14350     14360     14370     14380     14390
14400
CGGTAACTATCGTCTTGAGTCCAACCCGGTAAGACACGACTTATCGCCACTGGCAGCAGCCACTGGTAACAGGATTAGCAGAGCGAGGTATGTAGGCGGT 14410     14420     14430     14440     14450     14460     14470     14480     14490
14500
GCTACAGAGTTCTTGAAGTGGTGGCCTAACTACGGCTACACTAGAAGGACAGTATTTGGTATCTGCGCTCTGCTGAATCCAGTTACCTTCGGAAAAAGAG 14510     14520     14530     14540     14550     14560     14570     14580     14590
14600
TTGGTAGCTCTTGATCCGGCAAACAAACCACCGCTGGTAGCGGTGGTTTTTTGTTTGCAAGCAGCAGATTACGCGCAGAAAAAAAGGATCTCAAGAAGA 14610     14620     14630     14640     14650     14660     14670     14680     14690
14700
TCCTTTGATCTTTTCTACGGGGTCTGACGCTCAGTGGAACGAAAACTCACGTTAAGGGATTTTGGTCATGAGATTATCAAAAGGATCTTCACCTAGATC 14710     14720     14730     14740     14750     14760     14770     14780     14790
14800
CTTTTAAATTAAAAATGAAGTTTTAAATCAATCTAAAGTATATATGAGTAAACTTGGTCTGACAGTTACCAATGCTTAATCAGTGAGGCACCTATCTCAG 14810     14820     14830     14840     14850     14860     14870     14880     14890
14900
CGATCTGTCTATTTCGTTCATCCATAGTTGCCTGACTCCCCGTCGTGTAGATAACTACGATACGGGAGGGCTTACCATCTGGCCCCAGTGCTGCAATGAT 14910     14920     14930     14940     14950     14960     14970     14980     14990
15000
ACCGCGAGACCCACGCTCACCGGCTCCAGATTTATCAGCAATAAACCAGCCAGCCGGAAGGGCCGAGCGCAGAAGTGGTCCTGCAACTTTATCCGCCTCC 15010     15020     15030     15040     15050     15060     15070     15080     15090
15100
ATCCAGTCTATTAATTGTTGCCGGGAAGCTAGAGTAAGTAGTTCGCCAGTTAATAGTTTGCGCAACGTTGTTGCCATTGCTGCAAGATCTGGCTAGCGAT 15110     15120     15130     15140     15150
          GACCCTGCTGATTGGTTCGCTGACCATTTCCGGGCGCGCCGATTTAGGTGACACTATAG
```

APPENDIX 2

Nucleotide and amino acid sequence of DEN3
(Sleman/78) cDNA plasmid p3

Bases 1 to 10707: DEN3 virus genome cDNA

Bases 95 to 10264: DEN3 polyprotein ORF

Bases 95 to 436: C protein ORF

Bases 437 to 934: prM protein ORF

Bases 935 to 2413: E protein ORF

Bases 2414 to 3469: NS1 protein ORF

Bases 3470 to 4123: NS2A protein ORF

Bases 4124 to 4513: NS2B protein ORF

Bases 4514 to 6370: NS3 protein ORF

Bases 6371 to 6751: NS4A protein ORF

Bases 6752 to 6820: 2K protein ORF

Bases 6821 to 7564: NS4B protein ORF

Bases 7575 to 10264: NS5 protein ORF 10 20 30 40 50 60 70 80 90 100
AGTTGTTAGTCTACGTGGACCGACAAGAACAGTTTCGACTCGGAAGCTTGCTTAACGTAGTACTGACAGTTTTTTATTAGAGAGCAGATCTCTGATGAACMet
Asn>

110 120 130 140 150 160 170 180 190 200
AACCAACGGAAAAAGACGGGAAAACCGTCTATCAATATGCTGAAACGCGTGAGAAACCGTGTGTCAACTGGATCACAGTTGGCGAAGAGATTCTCAAGAG
AsnGlnArgLysLysThrGlyLysProSerIleAsnMetLeuLysArgValArgAsnArgValSerThrGlySerGlnLeuAlaLysArgPheSerArg>

210 220 230 240 250 260 270 280 290 300
GACTGCTGAACGGCCAAGGACCAATGAAATTGGTTATGGCGTTCATAGCTTTCCTCAGATTTCTAGCCATTCCACCGACAGCAGGAGTCTTGGCTAGATG
GlyLeuLeuAsnGlyGlnGlyProMetLysLeuValMetAlaPheIleAlaPheLeuArgPheLeuAlaIleProProThrAlaGlyValLeuAlaArgTrp>

310 320 330 340 350 360 370 380 390 400
GGGAACCTTTAAGAAGTCGGGGGCTATTAAGGTCCTGAGAGGCTTCAAGAAGGAGATCTCAAACATGCTGAGCATTATCAACAGACGGAAAAAGACATCG
GlyThrPheLysLysSerGlyAlaIleLysValLeuArgGlyPheLysLysGluIleSerAsnMetLeuSerIleIleAsnArgArgLysLysThrSer>

410 420 430 440 450 460 470 480 490 500
CTCTGTCTCATGATGATGTTACCAGCAACACTTGCTTTCCACTTGACTTCACGAGATGGAAGCCGCGCATGATTGTGGGGAAGAATGAAAGAGGAAAAT
LeuCysLeuMetMetLeuProAlaThrLeuAlaPheHisLeuThrSerArgAspGlyGluProArgMetIleValGlyLysAsnGluArgGlyLys>

510 520 530 540 550 560 570 580 590 600
CCCTACTTTTTAAGACAGCCTCTGGAATCAACATGTGCACACTCATAGCCATGGATTTGGGAGAGATGTGTGATGACACGGTCACCTACAAATGCCCCCT
SerLeuLeuPheLysThrAlaSerGlyIleAsnMetCysThrLeuIleAlaMetAspLeuGlyGluMetCysAspAspThrValThrTyrLysCysProLeu>

610 620 630 640 650 660 670 680 690 700
CATTACTGAAGTGGAGCCTGAAGACATTGACTGCTGGTGCAACCTTACATCGACATGGGTGACCTACGGAACGTGCAATCAAGCTGGAGAGCACAGACGC
IleThrGluValGluProGluAspIleAspCysTrpCysAsnLeuThrSerThrTrpValThrTyrGlyThrCysAsnGlnAlaGlyGluHisArgArg>

710 720 730 740 750 760 770 780 790 800
GACAAAAGATCGGTGGCGTTAGCTCCCCATGTCGGCATGGGACTGGACACACGCACCCAAACCTGGATGTCGGCTGAAGGAGCTTGGAGACAGGTCGAGA
AspLysArgSerValAlaLeuAlaProHisValGlyMetGlyLeuAspThrArgThrGlnThrTrpMetSerAlaGluGlyAlaTrpArgGlnValGlu>

810 820 830 840 850 860 870 880 890 900
AGGTAGAGACATGGGCCTTTAGGCACCCAGGGTTCACAATACTAGCCCTATTTCTTGCCCATTACATAGGCACTTCCTTGACCCAGAAAGTGGTTATTTT
LysValGluThrTrpAlaPheArgHisProGlyPheThrIleLeuAlaLeuPheLeuAlaHisTyrIleGlyThrSerLeuThrGlnLysValValIlePhe>

910 920 930 940 950 960 970 980 990 1000
CATACTACTAATGCTGGTCACCCCATCCATGACAATGAGATGCGTGGGAGTAGGAAACAGAGATTTTGTGGAAGGCCTATCAGGAGCTACGTGGGTTGAC
IleLeuLeuMetLeuValThrProSerMetThrMetArgCysValGlyValGlyAsnArgAspPheValGluGlyLeuSerGlyAlaThrTrpValAsp>

1010 1020 1030 1040 1050 1060 1070 1080 1090 1100
GTGGTGCTCGAGCACGGTGGGTGTGTGACTACCATGGCTAAGAACAAGCCCACGCTGGATATAGAGCTCCAGAAGACCGAGGCCACCCAACTGGCGACCC
ValValLeuGluHisGlyGlyCysValThrThrMetAlaLysAsnLysProThrLeuAspIleGluLeuGlnLysThrGluAlaThrGlnLeuAlaThr>

1110 1120 1130 1140 1150 1160 1170 1180 1190 1200
TAAGGAAACTATGTATTGAGGGAAAAATTACCAACGTAACAACCGACTCAAGGTGCCCCACCCAAGGGGAAGCGATTTTACCTGAGGAGCAGGACCAGAA
LeuArgLysLeuCysIleGluGlyLysIleThrAsnValThrThrAspSerArgCysProThrGlnGlyGluAlaIleLeuProGluGluGlnAspGlnAsn>

APPENDIX 2-continued

Nucleotide and amino acid sequence of DEN3
(Sleman/78) cDNA plasmid p3

```
1210    1220    1230    1240    1250    1260    1270    1280    1290    1300
CCACGTGTGCAAGCACACATACGTGGACAGAGGCTGGGGAAACGGTTGTGGTTTGTTTGGCAAGGGAAGCCTGGTAACATGCGCGAAATTTCAATGTTTG
HisValCysLysHisThrTyrValAspArgGlyTrpGlyAsnGlyCysGlyLeuPheGlyLysGlySerLeuValThrCysAlaLysPheGlnCysLeu>

1310    1320    1330    1340    1350    1360    1370    1380    1390    1400
GAATCAATAGAGGGAAAAGTGGTGCAGCATGAGAACCTCAAATACACCGTCATCATCACAGTGCACACAGGAGATCAACACCAGGTGGGAAATGAAACGC
GluSerIleGluGlyLysValValGlnHisGluAsnLeuLysTyrThrValIleIleThrValHisThrGlyAspGlnHisGlnValGlyAsnGluThr>

1410    1420    1430    1440    1450    1460    1470    1480    1490    1500
AGGGAGTCACGGCTGAGATAACACCCCAGGCATCAACCGTTGAAGCCATCTTACCTGAATATGGAACCCTTGGGCTAGAATGCTCACCACGGACAGGTTT
GlnGlyValThrAlaGluIleThrProGlnAlaSerThrValGluAlaIleLeuProGluTyrGlyThrLeuGlyLeuGluCysSerProArgThrGlyLeu>

1510    1520    1530    1540    1550    1560    1570    1580    1590    1600
AGATTTCAATGAAATGATTTTGTTGACAATGAAGAACAAAGCATGGATGGTACATAGACAATGGTTTTTGACCTACCTTTACCATGGACATCAGGAGCT
AspPheAsnGluMetIleLeuLeuThrMetLysAsnLysAlaTrpMetValHisArgGlnTrpPhePheAspLeuProLeuProTrpThrSerGlyAla>

1610    1620    1630    1640    1650    1660    1670    1680    1690    1700
ACAACAGAAACACCAACCTGGAATAAGAAAGAGCTTCTTGTGACATTCAAAAACGCACATGCAAAAAAGCAAGAAGTAGTAGTCCTTGGATCGCAAGAGG
ThrThrGluThrProThrTrpAsnLysLysGluLeuLeuValThrPheLysAsnAlaHisAlaLysLysGlnGluValValValLeuGlySerGlnGlu>

1710    1720    1730    1740    1750    1760    1770    1780    1790    1800
GAGCAATGCACACAGCACTGACAGGAGCTACAGAGATCCAAACCTCAGGAGGCACAAGTATTTTTGCGGGGCACTTAAAATGTAGACTCAAGATGGACAA
GlyAlaMetHisThrAlaLeuThrGlyAlaThrGluIleGlnThrSerGlyGlyThrSerIlePheAlaGlyHisLeuLysCysArgLeuLysMetAspLys>

1810    1820    1830    1840    1850    1860    1870    1880    1890    1900
ATTGGAACTCAAGGGGATGAGCTATGCAATGTGCTTGAATGCCTTTGTGTTGAAGAAAGAAGTCTCCGAAACGCAACATGGGACAATACTCATCAAGGTT
LeuGluLeuLysGlyMetSerTyrAlaMetCysLeuAsnAlaPheValLeuLysLysGluValSerGluThrGlnHisGlyThrIleLeuIleLysVal>

1910    1920    1930    1940    1950    1960    1970    1980    1990    2000
GAGTACAAAGGGGAAGATGCACCTTGCAAGATTCCTTTCTCCACGGAGGATGGACAAGGGAAAGCCCACAATGGCAGACTGATCACAGCTAACCCAGTGG
GluTyrLysGlyGluAspAlaProCysLysIleProPheSerThrGluAspGlyGlnGlyLysAlaHisAsnGlyArgLeuIleThrAlaAsnProVal>

2010    2020    2030    2040    2050    2060    2070    2080    2090    2100
TGACCAAGAAGGAGGAGCCTGTCAATATTGAGGCAGAACCTCCTTTTGGGGAAAGCAATATAGTAATTGGAATTGGAGACAAAGCCTTGAAAATCAACTG
ValThrLysLysGluGluProValAsnIleGluAlaGluProProPheGlyGluSerAsnIleValIleGlyIleGlyAspLysAlaLeuLysIleAsnTrp>

2110    2120    2130    2140    2150    2160    2170    2180    2190    2200
GTACAAGAAGGGAAGCTCGATTGGGAAGATGTTCGAGGCCACTGCCAGAGGTGCAAGGCGCATGGCCATCTTGGGAGACACAGCCTGGGACTTTGGATCA
TyrLysLysGlySerSerIleGlyLysMetPheGluAlaThrAlaArgGlyAlaArgArgMetAlaIleLeuGlyAspThrAlaTrpAspPheGlySer>

2210    2220    2230    2240    2250    2260    2270    2280    2290    2300
GTAGGTGGTGTTTTAAATTCATTAGGAAAAATGGTGCACCAAATATTTGGAAGTGCTTACACAGCCCTATTTAGTGGAGTCTCCTGGATAATGAAAATTG
ValGlyGlyValLeuAsnSerLeuGlyLysMetValHisGlnIlePheGlySerAlaTyrThrAlaLeuPheSerGlyValSerTrpIleMetLysIle>

2310    2320    2330    2340    2350    2360    2370    2380    2390    2400
GAATAGGTGTCCTTTTAACCTGGATAGGGTTGAATTCAAAAAACACTAGTATGAGCTTTAGCTGCATTGTGATAGGAATCATTACACTCTATCTGGGAGC
GlyIleGlyValLeuLeuThrTrpIleGlyLeuAsnSerLysAsnThrSerMetSerPheSerCysIleValIleGlyIleIleThrLeuTyrLeuGlyAla>

2410    2420    2430    2440    2450    2460    2470    2480    2490    2500
CGTGGTGCAAGCTGACATGGGGTGTGTCATAAACTGGAAAGGCAAAGAACTCAAATGTGGAAGTGGAATTTTCGTCACTAATGAGGTCCACACCTGGACA
ValValGlnAlaAspMetGlyCysValIleAsnTrpLysGlyLysGluLeuLysCysGlySerGlyIlePheValThrAsnGluValHisThrTrpThr>

2510    2520    2530    2540    2550    2560    2570    2580    2590    2600
GAGCAATACAAATTTCAAGCAGACTCCCCCAAAAGACTGGCGACAGCCATTGCAGGCGCTTGGGAGAATGGAGTGTGCGGAATCAGGTCGACAACCAGAA
GluGlnTyrLysPheGlnAlaAspSerProLysArgLeuAlaThrAlaIleAlaGlyAlaTrpGluAsnGlyValCysGlyIleArgSerThrThrArg>

2610    2620    2630    2640    2650    2660    2670    2680    2690    2700
TGGAGAACCTCTTGTGGAAGCAAATAGCCAATGAACTGAACTACATATTATGGGAAAACAACATCAAATTAACGGTAGTTGTGGGTGATATAATTGGGGT
MetGluAsnLeuLeuTrpLysGlnIleAlaAsnGluLeuAsnTyrIleLeuTrpGluAsnAsnIleLysLeuThrValValValGlyAspIleIleGlyVal>

2710    2720    2730    2740    2750    2760    2770    2780    2790    2800
CTTAGAGCAAGGGAAAAGAACACTAACACCACAACCCATGGAACTAAAATATTCATGGAAAACATGGGGAAAGGCGAAGATAGTGACAGCTGAAACACAA
LeuGluGlnGlyLysArgThrLeuThrProGlnProMetGluLeuLysTyrSerTrpLysThrTrpGlyLysAlaLysIleValThrAlaGluThrGln>

2810    2820    2830    2840    2850    2860    2870    2880    2890    2900
AATTCCTCTTTCATAATAGATGGGCCAAACACACCAGAGTGTCCAAGTGCCTCAAGAGCATGGAATGTGTGGGAGGTGGAAGATTACGGGTTCGGAGTCT
AsnSerSerPheIleIleAspGlyProAsnThrProGluCysProSerAlaSerArgAlaTrpAsnValTrpGluValGluAspTyrGlyPheGlyVal>

2910    2920    2930    2940    2950    2960    2970    2980    2990    3000
TCACAACTAACATATGGCTGAAACTCCGAGAGATGTACACCCAACTATGTGACCACAGGCTAATGTCGGCAGCCGTTAAGGATGAGAGGGCCGTACACGC
PheThrThrAsnIleTrpLeuLysLeuArgGluMetTyrThrGlnLeuCysAspHisArgLeuMetSerAlaAlaValLysAspGluArgAlaValHisAla>

3010    3020    3030    3040    3050    3060    3070    3080    3090    3100
CGACATGGGCTATTGGATAGAAAGCCAAAAGAATGGAAGTTGGAAGCTAGAAAAGGCATCCCTCATAGAGGTAAAAACCTGCACATGGCCAAAATCACAC
AspMetGlyTyrTrpIleGluSerGlnLysAsnGlySerTrpLysLeuGluLysAlaSerLeuIleGluValLysThrCysThrTrpProLysSerHis>
```

APPENDIX 2-continued

Nucleotide and amino acid sequence of DEN3
(Sleman/78) cDNA plasmid p3

3110 3120 3130 3140 3150 3160 3170 3180 3190 3200
ACTCTTTGGAGCAATGGTGTGCTAGAGAGTGACATGATCATCCCAAAGAGTCTGGCTGGTCCCATTTCGCAACACAACTACAGGCCCGGATACCACACCC
ThrLeuTrpSerAsnGlyValLeuGluSerAspMetIleIleProLysSerLeuAlaGlyProIleSerGlnHisAsnTyrArgProGlyTyrHisThr>

3210 3220 3230 3240 3250 3260 3270 3280 3290 3300
AAACGGCAGGACCCTGGCACTTAGGAAAATTGGAGCTGGACTTCAACTATTGTGAAGGAACAACAGTTGTCATCACAGAAAATTGTGGGACAAGAGGCCC
GlnThrAlaGlyProTrpHisLeuGlyLysLeuGluLeuAspPheAsnTyrCysGluGlyThrThrValValIleThrGluAsnCysGlyThrArgGlyPro>

3310 3320 3330 3340 3350 3360 3370 3380 3390 3400
ATCACTGAGAACAACAACAGTGTCAGGGAAGTTGATACACGAATGGTGTTGCCGCTCGTGTACACTTCCTCCCCTGCGATACATGGGAGAAGACGGCTGC
SerLeuArgThrThrThrValSerGlyLysLeuIleHisGluTrpCysCysArgSerCysThrLeuProProLeuArgTyrMetGlyGluAspGlyCys>

3410 3420 3430 3440 3450 3460 3470 3480 3490 3500
TrpTyrGlyMetGluIleArgProIleAsnGluLysGluGluAsnMetValLysSerLeuValSerAlaGlySerGlyLysValAspAsnPheThrMet>
TGGTATGGCATGGAAATTAGACCCATTAATGAGAAAGAAGAGAACATGGTAAAGTCTTTAGTCTCAGCAGGGAGTGGAAAGGTGGATAACTTCACAATGG 3510 3520 3530 3540 3550 3560 3570 3580 3590 3600
GTGTCTTGTGTTTGGCAATCCTTTTTGAAGAGGTGATGAGAGGAAAATTTGGGAAAAAGCACATGATTGCAGGGGTTCTCTTCACGTTTGTACTCCTCT
GlyValLeuCysLeuAlaIleLeuPheGluGluValMetArgGlyLysPheGlyLysLysHisMetIleAlaGlyValLeuPheThrPheValLeuLeuLeu>

3610 3620 3630 3640 3650 3660 3670 3680 3690 3700
CTCAGGGCAAATAACATGGAGAGACATGGCGCACACACTCATAATGATTGGGTCCAACGCCTCTGACAGAATGGGAATGGGCGTCACTTACCTAGCATTG
SerGlyGlnIleThrTrpArgAspMetAlaHisThrLeuIleMetIleGlySerAsnAlaSerAspArgMetGlyMetGlyValThrTyrLeuAlaLeu>

3710 3720 3730 3740 3750 3760 3770 3780 3790 3800
ATTGCAACATTTAAAATTCAGCCATTTTTGGCTTTGGGATTCTTCCTGAGGAAACTGACATCTAGAGAAAATTTATTGTTGGGAGTTGGGTTGGCCATGG
IleAlaThrPheLysIleGlnProPheLeuAlaLeuGlyPhePheLeuArgLysLeuThrSerArgGluAsnLeuLeuLeuGlyValGlyLeuAlaMet>

3810 3820 3830 3840 3850 3860 3870 3880 3890 3900
CAACAACGTTACAACTGCCAGAGGACATTGAACAAATGGCGAATGGAATAGCTTTAGGGCTCATGGCTCTTAAATTAATAACACAATTTGAAACATACCA
AlaThrThrLeuGlnLeuProGluAspIleGluGlnMetAlaAsnGlyIleAlaLeuGlyLeuMetAlaLeuLysLeuIleThrGlnPheGluThrTyrGln>

3910 3920 3930 3940 3950 3960 3970 3980 3990 4000
ACATGGACGGCATTAGTCTCCCTAATGTGTTCAAATACAATTTTCACGTTGACTGTTGCCTGGAGAACAGCCACCCTGATTTTGGCCGGAATTTCTCTT
LeuTrpThrAlaLeuValSerLeuMetCysSerAsnThrIlePheThrLeuThrValAlaTrpArgThrAlaThrLeuIleLeuAlaGlyIleSerLeu>

4010 4020 4030 4040 4050 4060 4070 4080 4090 4100
TTGCCAGTGTGCCAGTCTTCGAGCATGAGGAAAACAGATTGGCTCCCAATGGCTGTGGCAGCTATGGGAGTTCCACCCCTACCACTTTTTATTTTCAGTT
LeuProValCysGlnSerSerSerMetArgLysThrAspTrpLeuProMetAlaValAlaAlaMetGlyValProProLeuProLeuPheIlePheSer>

4110 4120 4130 4140 4150 4160 4170 4180 4190 4200
TGAAAGATACGCTCAAAAGGAGAAGCTGGCCACTGAATGAGGGGGTGATGGCTGTTGGACTTGTGAGTATTCTAGCTAGTTCTCTCCTTAGGAATGACGT
LeuLysAspThrLeuLysArgArgSerTrpProLeuAsnGluGlyValMetAlaValGlyLeuValSerIleLeuAlaSerSerLeuLeuArgAsnAspVal>

4210 4220 4230 4240 4250 4260 4270 4280 4290 4300
GCCCATGGCTGGACCATTAGTGGCTGGGGGCTTGCTGATAGCGTGCTACGTCATAACTGGCACGTCAGCAGACCTCACTGTAGAAAAAGCAGCAGATGTC
ProMetAlaGlyProLeuValAlaGlyGlyLeuLeuIleAlaCysTyrValIleThrGlyThrSerAlaAspLeuThrValGluLysAlaAlaAspVal>

4310 4320 4330 4340 4350 4360 4370 4380 4390 4400
ACATGGGAGGAAGAGGCTGAGCAAACAGGAGTGTCCCACAATTTAATGATCACAGTTGATGACGATGGAACAATGAGAATAAAAGATGATGAGACTGAGA
ThrTrpGluGluGluAlaGluGlnThrGlyValSerHisAsnLeuMetIleThrValAspAspAspGlyThrMetArgIleLysAspAspGluThrGlu>

4410 4420 4430 4440 4450 4460 4470 4480 4490 4500
ACATCTTAACAGTGCTTTTGAAAACAGCATTACTAATAGTGTCAGGCATTTTTCCATACTCCATACCCGCAACACTGTTGGTCTGGCACACTTGGCAAAA
AsnIleLeuThrValLeuLeuLysThrAlaLeuLeuIleValSerGlyIlePheProTyrSerIleProAlaThrLeuLeuValTrpHisThrTrpGlnLys>

4510 4520 4530 4540 4550 4560 4570 4580 4590 4600
GCAAACCCAAAGATCCGGTGTCCTATGGGACGTTCCCAGCCCCCCAGAGACACAGAAAGCAGAACTGGAAGAAGGGGTTTATAGGATCAAGCAGCAAGGA
GlnThrGlnArgSerGlyValLeuTrpAspValProSerProProGluThrGlnLysAlaGluLeuGluGluGlyValTyrArgIleLysGlnGlnGly>

4610 4620 4630 4640 4650 4660 4670 4680 4690 4700
ATTTTTGGGAAAACCCAAGTGGGGGTTGGAGTACAAAAAGAAGGAGTTTTCCACACCATGTGGCACGTCACAAGAGGAGCAGTGTTGACACACAATGGGA
IlePheGlyLysThrGlnValGlyValGlyValGlnLysGluGlyValPheHisThrMetTrpHisValThrArgGlyAlaValLeuThrHisAsnGly>

4710 4720 4730 4740 4750 4760 4770 4780 4790 4800
AAAGACTGGAACCAAACTGGGCTAGCGTGAAAAAAGATCTGATTTCATACGGAGGAGGATGGAAATTGAGTGCACAATGGCAAAAAGGAGAGGAGGTGCA
LysArgLeuGluProAsnTrpAlaSerValLysLysAspLeuIleSerTyrGlyGlyGlyTrpLysLeuSerAlaGlnTrpGlnLysGlyGluGluValGln>

4810 4820 4830 4840 4850 4860 4870 4880 4890 4900
GGTTATTGCCGTAGAGCCTGGGAAGAACCCAAAGAACTTTCAAACCATGCCAGGCATTTTCCAGACAACAACAGGGGGAGATAGGAGCGATTGCACTGGAC
ValIleAlaValGluProGlyLysAsnProLysAsnPheGlnThrMetProGlyIlePheGlnThrThrThrGlyGluIleGlyAlaIleAlaLeuAsp>

4910 4920 4930 4940 4950 4960 4970 4980 4990 5000
TTCAAGCCTGGAACTTCAGGATCTCCCATCATAAACAGAGAGGGAAAGGTACTGGGATTGTATGGCAATGGAGTGGTCACAAAGAATGGTGGCTATGTCA
PheLysProGlyThrSerGlySrProIleIleAsnArgGluGlyLysValLeuGlyLeuTyrGlyAsnGlyValValThrLysAsnGlyGlyTyrVal>

APPENDIX 2-continued

Nucleotide and amino acid sequence of DEN3
(Sleman/78) cDNA plasmid p3

```
     5010      5020      5030      5040      5050      5060      5070      5080      5090      5100
GTGGAATAGCACAAACAAATGCAGAACCAGACGGACCGACACCAGAGTTGGAAGAAGAGATGTTCAAAAAGCGAAATCTAACCATAATGGATCTCCATCC
SerGlyIleAlaGlnThrAsnAlaGluProAspGlyProThrProGluLeuGluGluGluMetPheLysLysArgAsnLeuThrIleMetAspLeuHisPro>

5110      5120      5130      5140      5150      5160      5170      5180      5190      5200
CGGGTCAGGAAAGACGCGGAAATATCTTCCAGCTATTGTTAGAGAGGCAATCAAGAGACGCTTAAGGACTCTAATTTTGGCACCAACAAGGGTAGTTGCA
GlySerGlyLysThrArgLysTyrLeuProAlaIleValArgGluAlaIleLysArgArgLeuArgThrLeuIleLeuAlaProThrArgValValAla>

5210      5220      5230      5240      5250      5260      5270      5280      5290      5300
GCTGAGATGGAAGAAGCATTGAAAGGGCTCCCAATAAGGTATCAAACAACTGCAACAAAATCTGAACACACAGGGAGAGAGATTGTTGATCTAATGTGCC
AlaGluyMetGluGluAlaLeuLysGlyLeuProIleArgTyrGlnThrThrAlaThrLysSerGluHisThrGlyArgGluIleValAspLeuMetCys>

5310      5320      5330      5340      5350      5360      5370      5380      5390      5400
ACGCAACGTTCACAATGCGTTTGCTGTCACCAGTCAGGGTTCCAAACTACAACTTGATAATAATGGATGAGGCTCATTTCACAGACCCAGCCAGTATAGC
HisAlaThrPheThrMetArgLeuLeuSerProValArgValProAsnTyrAsnLeuIleIleMetAspGluAlaHisPheThrAspProAlaSerIleAla>

5410      5420      5430      5440      5450      5460      5470      5480      5490      5500
GGCTAGAGGGTACATATCAACTCGTGTAGGAATGGGAGAGGCAGCCGCAATTTTCATGACAGCCACACCCCCTGGAACAGCTGATGCCTTTCCTCAGAGC
AlaArgGlyTyrIleSerThrArgValGlyMetGlyGluAlaAlaAlaIlePheMetThrAlaThrProProGlyThrAlaAspAlaPheProGlnSer>

5510      5520      5530      5540      5550      5560      5570      5580      5590      5600
AACGCTCCAATTCAAGATGAAGAAAGAGACATACCAGAACGCTCATGGAATTCAGGCAATGAATGGATTACCGACTTTGCCGGGAAGACGGTGTGGTTTG
AsnAlaProIleGlnAspGluGluArgAspIleProGluArgSerTrpAsnSerGlyAsnGluTrpIleThrAspPheAlaGlyLysThrValTrpPhe>

5610      5620      5630      5640      5650      5660      5670      5680      5690      5700
TCCCTAGCATCAAAGCTGGAAATGACATAGCAAACTGCTTGCGGAAAAATGGAAAAAAGGTCATTCAACTTAGTAGGAAGACTTTTGACACAGAATATCA
ValProSerIleLysAlaGlyAsnAspIleAlaAsnCysLeuArgLysAsnGlyLysLysValIleGlnLeuSerArgLysThrPheAspThrGluTyrGln>

5710      5720      5730      5740      5750      5760      5770      5780      5790      5800
AAAGACTAAACTAAATGATTGGGACTTTGTGGTGACAACAGACATTTCAGAAATGGGAGCCAATTTCAAAGCAGACAGAGTGATCGACCCAAGAAGATGT
LysThrLysLeuAsnAspTrpAspPheValValThrThrAspIleSerGluMetGlyAlaAsnPheLysAlaAspArgValIleAspProArgArgCys>

5810      5820      5830      5840      5850      5860      5870      5880      5890      5900
CTCAAGCCAGTGATTTTGACAGACGGACCCGAGCGCGTGATCCTGGCGGGACCAATGCCAGTCACCGTAGCGAGCGCTGCGCAAAGGAGAGGGAGAGTTG
LeuLysProValIleLeuThrAspGlyProGluArgValIleLeuAlaGlyProMetProValThrValAlaSerAlaAlaGlnArgArgGlyArgVal>

5910      5920      5930      5940      5950      5960      5970      5980      5990      6000
GCAGGAACCCACAAAAAGAAAATGACCAATACATATTCATGGGCCAGCCCCTCAATAATGATGAAGACCATGCTCACTGGACAGAAGCAAAATGCTGCT
GlyArgAsnProGlnLysGluAsnAspGlnTyrIlePheMetGlyGlnProLeuAsnAsnAspGluAspHisAlaHisTrpThrGluAlaLysMetLeuLeu>

6010      6020      6030      6040      6050      6060      6070      6080      6090      6100
AGACAACATCAACACACCAGAAGGGATCATACCAGCTCTCTTTGAACCAGAAAGGGAGAAGTCAGCCGCCATAGACGGCGAATACCGCCTGAAGGGTGAG
AspAsnIleAsnThrProGluGlyIleIleProAlaLeuPheGluProGluArgGluLysSerAlaAlaIleAspGlyGluTyrArgLeuLysGlyGlu>

6110      6120      6130      6140      6150      6160      6170      6180      6190      6200
TCCAGGAAGACCTTCGTGGAACTCATGAGGAGGGGTGACCTCCCAGTTTGGCTAGCCCATAAAGTAGCATCAGAAGGGATCAAATATACAGATAGAAAGT
SerArgLysThrPheValGluLeuMetArgArgGlyAspLeuProValTrpLeuAlaHisLysValAlaSerGluGlyIleLysTyrThrAspArgLys>

6210      6220      6230      6240      6250      6260      6270      6280      6290      6300
GGTGTTTTGATGGAGAACGCAACAATCAAATTTTAGAGGAGAATATGGATGTGGAAATCTGGACAAAGGAAGGAGAAAAGAAAAAATTGAGACCTAGGTG
TrpCysPheAspGlyGluArgAsnAsnGlnIleLeuGluGluAsnMetAspValGluIleTrpThrLysGluGlyGluLysLysLysLeuArgProArgTrp>

6310      6320      6330      6340      6350      6360      6370      6380      6390      6400
GCTTGATGCCCGCACTTATTCAGATCCCTTAGCGCTCAAGGAATTCAAGGACTTTGCGGCTGGTAGAAAGTCAATTGCCCTTGATCTTGTGACAGAAATA
LeuAspAlaArgThrTyrSerAspProLeuAlaLeuLysGluPheLysAspPheAlaAlaGlyArgLysSerIleAlaLeuAspLeuValThrGluIle>

6410      6420      6430      6440      6450      6460      6470      6480      6490      6500
GGAAGAGTGCCTTCACACTTAGCTCACAGAACGAGAAACGCCCTGGACAATCTGGTGATGTTGCACACGTCAGAACATGGCGGGAGGGCCTACAGGCATG
GlyArgValProSerHisLeuAlaHisArgThrArgAsnAAlaLeuAspAsnLeuValMetLeuHisThrSerGluHisGlyGlyArgAlaTyrArgHis>

6510      6520      6530      6540      6550      6560      6570      6580      6590      6600
CAGTGGAGGAACTACCAGAAACAATGGAAACACTCTTACTCCTGGGACTCATGATCCTGTTAACAGGTGGAGCAATGCTTTTCTTGATATCAGGTAAAGG
AlaValGluGluLeuProGluThrMetGluThrLeuLeuLeuLeuGlyLeuMetIleLeuLeuThrGlyGlyAlaMetLeuPheLeuIleSerGlyLysGly>

6610      6620      6630      6640      6650      6660      6670      6680      6690      6700
GATTGGAAAGACTTCAATAGGACTCATTTGTGTAGCTGCTTCCAGCGGTATGTTATGGATGGCTGATGTCCCACTCCAATGGATCGCGTCTGCCATAGTC
IleGlyLysThrSerIleGlyLeuIleCysValAlaAlaSerSerGlyMetLeuTrpMetAlaAspValProLeuGlnTrpIleAlaSerAlaIleVal>

6710      6720      6730      6740      6750      6760      6770      6780      6790      6800
CTGGAGTTTTTTATGATGGTGTTACTTATACCAGAACCAGAAAAGCAGAGAACTCCCCAAGACAATCAACTCGCATATGTCGTGATAGGCATACTCACAC
LeuGluPhePheMetMetValLeuLeuIleProGluProGluLysGlnArgThrProGlnAspAsnGlnLeuAlaTyrValValIleGlyIleLeuThr>

6810      6820      6830      6840      6850      6860      6870      6880      6890      6900
TGGCTGCAATAGTAGCAGCCAATGAAATGGGACTGTTGGAAACCACAAAGAGAGATTTAGGAATGTCCAAGGAACCAGGTGTTGTTTCTCCAACCAGCTA
LeuAlaAlaIleValAlaAlaAsnGluMetGlyLeuLeuGluThrThrLysArgAspLeuGlyMetSerLysGluProGlyValValSerProThrSerTyr>
```

APPENDIX 2-continued

Nucleotide and amino acid sequence of DEN3
(Sleman/78) cDNA plasmid p3

```

APPENDIX 2-continued

Nucleotide and amino acid sequence of DEN3
(Sleman/78) cDNA plasmid p3

8810 8820 8830 8840 8850 8860 8870 8880 8890 8900
ACAGAGGAGAACCAATGGGACAGTGCTAGAGCTGCTGTTGAGGATGAAGAATTCTGGAAACTCGTGGACAGAGAACGTGAACTCCACAAATTGGGCAAGT
ThrGluGluAsnGlnTrpAspSerAlaArgAlaAlaValGluAspGluGluPheTrpLysLeuValAspArgGluArgGluLeuHisLysLeuGlyLys 8910 8920 8930 8940 8950 8960 8970 8980 8990 9000
GTGGAAGCTGCGTTTACAACATGATGGGCAAGAGAGAGAAGAAACTTGGAGAGTTTGGCAAAGCAAAAGGCAGTAGAGCCATATGGTACATGTGGTTGGG
CysGlySerCysValTyrAsnMetMetGlyLysArgGluLysLysLeuGlyGluPheGlyLysAlaLysGlySerArgAlaIleTrpTyrMetTrpLeuGly>

9010 9020 9030 9040 9050 9060 9070 9080 9090 9100
AGCCAGATACCTTGAGTTCGAAGCACTCGGATTCTTAAATGAAGACCATTGGTTCTCGCGTGAAAACTCTTACAGTGGAGTAGAAGGAGAAGGACTGCAC
AlaArgTyrLeuGluPheGluAlaLeuGlyPheLeuAsnGluAspHisTrpPheSerArgGluAsnSerTyrSerGlyValGluGlyGluGlyLeuHis>

9110 9120 9130 9140 9150 9160 9170 9180 9190 9200
AAGCTGGGATACATCTTAAGAGACATTTCCAGATACCCGGAGGAGCTATGTATGCTGATGACACAGCTGGTTGGGACACAAGAATTAACAGAAGATGACC
LysLeuGlyTyrIleLeuArgAspIleSerLysIleProGlyGlyAlaMetTyrAlaAspAspThrAlaGlyTrpAspThrArgIleThrGluAspAsp>

9210 9220 9230 9240 9250 9260 9270 9280 9290 9300
TGCACAATGAGGAAAAAATCACACAGCAAATGGACCCTGAACACAGGCAGTTAGCAAACGCTATATTCAAGCTCACATACCAAAACAAAGTGGTCAAAGT
LeuHisAsnGluGluLysIleThrGlnGlnMetAspProGluHisArgGlnLeuAlaAsnAlaIlePheLysLeuThrTyrGlnAsnLysValValLysVal>

9310 9320 9330 9340 9350 9360 9370 9380 9390 9400
TCAACGACCAACTCCAAAGGGCACGGTAATGGACATCATATCTAGGAAAGACCAAAGAGGCAGTGGACAGGTGGGAACTTATGGTCTGAATACATTCACC
GlnArgProThrProLysGlyThrValMetAspIleIleSerArgLysAspGlnArgGlySerGlyGlnValGlyThrTyrGlyLeuAsnThrPheThr>

9410 9420 9430 9440 9450 9460 9470 9480 9490 9500
AACATGGAAGCCCAGTTAATCAGACAAATGGAAGGAGAAGGTGTGTTGTCGAAGGCAGACCTCGAGAACCCTCATCTGCTAGAGAAGAAAGTTACACAAT
AsnMetGluAlaGlnLeuIleArgGlnMetGluGlyGluGlyValLeuSerLysAlaAspLeuGluAsnProHisLeuLeuGluLysLysValThrGln>

9510 9520 9530 9540 9550 9560 9570 9580 9590 9600
GGTTGGAAACAAAAGGAGTGGAGAGGTTAAAAAGAATGGCCATCAGCGGGGATGATTGCGTGGTGAAACCAATTGATGACAGGTTCGCCAATGCCCTGCT
TrpLeuGluThrLysGlyValGluArgLeuLysArgMetAlaIleSerGlyAspAspCysValValLysProIleAspAspArgPheAlaAsnAlaLeuLeu>

9610 9620 9630 9640 9650 9660 9670 9680 9690 9700
TGCCCTGAATGACATGGGAAAAGTTAGGAAGGACATACCTCAATGGCAGCCATCAAAGGGATGGCATGATTGGCAACAGGTCCCTTTCTGCTCCCACCAC
AlaLeuAsnAspMetGlyLysValArgLysAspIleProGlnTrpGlnProSerLysGlyTrpHisAspTrpGLnGlnValProPheCysSerHisHis>

9710 9720 9730 9740 9750 9760 9770 9780 9790 9800
TTTCATGAATTGATCATGAAAGATGGAAGAAAGTTGGTAGTTCCCTGCAGACCTCAGGATGAATTAATCGGGAGAGCGAGAATCTCTCAAGGAGCAGGAT
PheHisGluLeuIleMetLysAspGlyArgLysLeuValValProCysArgProGlnAspGluLeuIleGlyArgAlaArgIleSerGlnGlyAlaGly>

9810 9820 9830 9840 9850 9860 9870 9880 9890 9900
GGAGCCTTAGAGAAACTGCATGCCTAGGGAAAGCCTACGCCCAAATGTGGACTCTCATGTACTTTCACAGAAGAGATCTTAGACTAGCATCCAACGCCAT
TrpSerLeuArgGluThrAlaCysLeuGlyLysAlaTyrAlaGlnMetTrpThrLeuMetTyrPheHisArgArgAspLeuArgLeuAlaSerAsnAlaIle>

9910 9920 9930 9940 9950 9960 9970 9980 9990 10000
ATGTTCAGCAGTACCAGTCCATTGGGTCCCCACAAGCAGAACGACGTGGTCTATTCATGCTCACCATCAGTGGATGACTACAGAAGACATGCTTACTGTT
CysSerAlaValProValHisTrpValProThrSerArgThrThrTrpSerIleHisAlaHisHisGlnTrpMetThrThrGluAspMetLeuThrVal>

10010 10020 10030 10040 10050 10060 10070 10080 10090 10100
TGGAACAGGGTGTGGATAGAGGATAATCCATGGATGGAAGACAAAACTCCAGTCAAAACCTGGGAAGATGTTCCATATCTAGGGAAGAGAGAAGACCAAT
TrpAsnArgValTrpIleGluAspAsnProTrpMetGluAspLysThrProValLysThrTrpGluAspValProTyrLeuGlyLysArgGluAspGln>

10110 10120 10130 10140 10150 10160 10170 10180 10190 10200
GGTGCGGATCACTCATTGGTCTCACTTCCAGAGCAACCTGGGCCCAGAACATACTTACGGCAATCCAACAGGTGAGAAGCCTTATAGGCAATGAAGAGTT
TrpCysGlySerLeuIleGlyLeuThrSerArgAlaThrTrpAlaGlnAsnIleLeuThrAlaIleGlnGlnValArgSerLeuIleGlyAsnGluGluPhe>

10210 10220 10230 10240 10250 10260 10270 10280 10290 10300
TCTGGACTACATGCCTTCGATGAAGAGATTCAGGAAGGAGGAGGAGTCAGAGGGAGCCATTTGGTAAACGTAGGAAGTGAAAAAGAGGCAAACTGTCAGG
LeuAspTyrMetProSerMetLysArgPheArgLysGluGluGluSerGluGlyAlaIleTrp***>

10310 10320 10330 10340 10350 10360 10370 10380 10390 10400
CCACCTTAAGCCACAGTACGGAAGAAGCTGTGCAGCCTGTGAGCCCCGTCCAAGGACGTTAAAAGAAGAAGTCAGGCCCAAAAGCCACGGTTTGAGCAAA 10410 10420 10430 10440 10450 10460 10470 10480 10490 10500
CCGTGCTGCCTGTGGCTCCGTCGTGGGGACGTAAAACCTGGGAGGCTGCAAACTGTGGAAGCTGTACGCACGGTGTAGCAGACTAGCGGTTAGAGGAGAC 10510 10520 10530 10540 10550 10560 10570 10580 10590 10600
CCCTCCCATGACACAACGCAGCAGCGGGGCCCGAGCTCTGAGGGAAGCTGTACCTCCTTGCAAAGGACTAGAGGTTAGAGGAGACCCCCCGCAAATAAAA 10610 10620 10630 10640 10650 10660 10670 10680 10690 10700
ACAGCATATTGACGCTGGGAGAGACCAGAGATCCTGCTGTCTCCTCAGCATCATTCCAGGCACAGAACGCCAGAAAATGGAATGGTGCTGTTGAATCAAC 10710 10720 10730 10740 10750 10760 10770 10780 10790 10800
AGGTTCTGGTACCGGTAGGCATCGTGGTGTCACGCTCGTCGTTTGGTATGGCTTCATTCAGCTCCGGTTCCCAACGATCAAGGCGAGTTACATGATCCCC

APPENDIX 2-continued

Nucleotide and amino acid sequence of DEN3
(Sleman/78) cDNA plasmid p3

```
10810     10820     10830     10840     10850     10860     10870     10880     10890     10900
CATGTTGTGCAAAAAAGCGGTTAGCTCCTTCGGTCCTCCGATCGTTGTCAGAAGTAAGTTGGCCGCAGTGTTATCACTCATGGTTATGGCAGCACTGCAT 10910     10920     10930     10940     10950     10960     10970     10980     10990     11000
AATTCTCTTACTGTCATGCCATCCGTAAGATGCTTTTCTGTGACTGGTGAGTACTCAACCAAGTCATTCTGAGAATAGTGTATGCGGCGACCGAGTTGCT 11010     11020     11030     11040     11050     11060     11070     11080     11090     11100
CTTGCCCGGCGTCAACACGGGATAATACCGCGCCACATAGCAGAACTTTAAAAGTGCTCATCATTGGAAAACGTTCTTCGGGGCGAAAACTCTCAAGGAT 11110     11120     11130     11140     11150     11160     11170     11180     11190     11200
CTTACCGCTGTTGAGATCCAGTTCGATGTAACCCACTCGTGCACCCAACTGATCTTCAGCATCTTTTACTTTCACCAGCGTTTCTGGGTGAGCAAAAACA 11210     11220     11230     11240     11250     11260     11270     11280     11290     11300
GGAAGGCAAAATGCCGCAAAAAAGGGAATAAGGGCGACACGGAAATGTTGAATACTCATACTCTTCCTTTTTCAATATTATTGAAGCATTTATCAGGGTT 11310     11320     11330     11340     11350     11360     11370     11380     11390     11400
ATTGTCTCATGAGCGGATACATATTTGAATGTATTTAGAAAAATAAACAAATAGGGGTTCCGCGCACATTTCCCCGAAAAGTGCCACCTGACGTCTAAGA 11410     11420     11430     11440     11450     11460     11470     11480     11490     11500
AACCATTATTATCATGACATTAACCTATAAAAATAGGCGTATCACGAGGCCCTTTCGTCTTCAAGAATTCTCATGTTTGACAGCTTATCATCGATAAGCT 11510     11520     11530     11540     11550     11560     11570     11580     11590     11600
TTAATGCGGTAGTTTATCACAGTTAAATTGCTAACGCAGTCAGGCACCGTGTATGAAATCTAACAATGCGCTCATCGTCATCCTCGGCACCGTCACCCTG 11610     11620     11630     11640     11650     11660     11670     11680     11690     11700
GATGCTGTAGGCATAGGCTTGGTTATGCCGGTACTGCCGGGCCTCTTGCGGGATATCGTCCATTCCGACAGCATCGCCAGTCACTATGGCGTGCTGCTGG 11710     11720     11730     11740     11750     11760     11770     11780     11790     11800
CGCTATATGCGTTGATGCAATTTCTATGCGCACCCGTTCTCGGAGCACTGTCCGACCGCTTTGGCCGCCGCCCAGTCCTGCTCGCTTCGCTACTTGGAGC 11810     11820     11830     11840     11850     11860     11870     11880     11890     11900
CACTATCGACTACGCGATCATGGCGACCACACCCGTCCTGTGGATCCTCTACGCCGGACGCATCGTGGCCGGCATCACCGGCGCCACAGGTGCGGTTGCT 11910     11920     11930     11940     11950     11960     11970     11980     11990     12000
GGCGCCTATATCGCGACATCACCGATGGGGAAGATCGGGCTCGCCACTTCGGGCTCATGAGCGCTTGTTTCGGCGTGGGTATGGTTGGCAGGCCCCGTGG 12010     12020     12030     12040     12050     12060     12070     12080     12090     12100
CCGGGGGACTGTTGGGCGCCATCTCCTTGCATGCACCATTCCTTGCGGCGGCGGTGCTCAACGGCCTCAACCTACTACTGGGCTGCTTCCTAATGCAGGA 12110     12120     12130     12140     12150     12160     12170     12180     12190     12200
GTCGCATAAGGGAGAGCGTCGACCGATGCCCTTGAGAGCCTTCAACCCAGTCAGCTCCTTCCGGTGGGCGCGGGCATGACTATCGTCGCCGCACTTATG 12210     12220     12230     12240     12250     12260     12270     12280     12290     12300
ACTGTCTTCTTTATCATGCAACTCGTAGGACAGGTGCCGGCAGCGCTCTGGGTCATTTTCGGCGAGGACCGCTTTCGCTGGAGCGCGACGATGATCGGCC 12310     12320     12330     12340     12350     12360     12370     12380     12390     12400
TGTCGCTTGCGGTATTCGGAATCTTGCACGCCCTCGCTCAAGCCTTCGTCACTGGTCCCGCCACCAAACGTTCGGCGAGAAGCAGGCCATTATCGCCGG 12410     12420     12430     12440     12450     12460     12470     12480     12490     12500
CATGGCGGCCGACGCGCTGGGCTACGTCTTGCTGGCGTTCGCGACGCGAGGCTGGATGGCCTTCCCCATTATGATTCTTCTCGCTTCCGGCGGCATCGGG 12510     12520     12530     12540     12550     12560     12570     12580     12590     12600
ATGCCCGCGTTGCAGGCCATGCTGTCCAGGCAGGTAGATGACGACCATCAGGGACAGCTTCAAGGATCGCTCGCGGCTCTTACCAGCCTAACTTCGATCA 12610     12620     12630     12640     12650     12660     12670     12680     12690     12700
CTGGACCGCTGATCGTCACGGCGATTTATGCCGCCTCGGCGAGCACATGGAACGGGTTGGCATGGATTGTAGGCGCCGCCCTATACCTTGTCTGCCTCCC 12710     12720     12730     12740     12750     12760     12770     12780     12790     12800
CGCGTTGCGTCGCGGTGCATGGAGCCGGGCCACCTCGACCTGAATGGAAGCCGGCGGCACCTCGCTAACGGATTCACCACTCCAAGAATTGGAGCCAATC 12810     12820     12830     12840     12850     12860     12870     12880     12890     12900
AATTCTTGCGGAGAACTGTGAATGCGCAAACCAACCCTTGGCAGAACATATCCATCGCGTCCGCCATCTCCAGCAGCCGCACGCGGCGCATCTCGGGCAG 12910     12920     12930     12940     12950     12960     12970     12980     12990     13000
CGTTGGGTCCTGGCCACGGGTGCGCATGATCGTGCTCCTGTCGTTGAGGACCCGGCTAGGCTGGCGGGGTTGCCTTACTGGTTAGCAGAATGAATCACCG 13010     13020     13030     13040     13050     13060     13070     13080     13090     13100
ATACGCGAGCGAACGTGAAGCGACTGCTGCTGCAAAACGTCTGCGACCTGAGCAACAACATGAATGGTCTTCGGTTTCCGTGTTTCGTAAAGTCTGGAAA 13110     13120     13130     13140     13150     13160     13170     13180     13190     13200
CGCGGAAGTCAGCGCCCTGCACCATTATGTTCCGGATCTGCATCGCAGGATGCTGCTGGCTACCCTGTGGAACACCTACATCTGTATTAACGAAGCGCTG 13210     13220     13230     13240     13250     13260     13270     13280     13290     13300
GCATTGACCCTGAGTGATTTTTCTCTGGTCCCGCCGCATCCATACCGCCAGTTGTTTACCCTCACAACGTTCCAGTAACCGGGCATGTTCATCATCAGTA
```

APPENDIX 2-continued

Nucleotide and amino acid sequence of DEN3 (Sleman/78) cDNA plasmid p3

APPENDIX 3-continued

Nucleotide and amino acid sequence of DEN1 (Puerto Rico/94) CME chimeric region

```
         110       120       130       140       150       160       170       180       190       200
AATGAACAACCAACGGAAAAAGACGGGTCGACCGTCTTTCAATATGCTGAAACGCGCGAGAAACCGCGTGTCAACTGGTTCACAGTTGGCGAAGAGATTC
MetAsnAsnGlnArgLysLysThrGlyArgProSerPheAsnMetLeuLysArgAlaArgAsnArgValSerThrGlySerGlnLeuAlaLysArgPhe>

210       220       230       240       250       260       270       280       290       300
TCAAAAGGATTGCTTTCAGGCCAAGGACCCATGAAATTGGTGATGGCTTTCATAGCATTTCTAAGATTTCTAGCCATACCCCCAACAGCAGGAATTTGG
SerLysGlyLeuLeuSerGlyGlnGlyProMetLysLeuValMetAlaPheIleAlaPheLeuArgPheLeuAlaIleProProThrAlaGlyIleLeu>

310       320       330       340       350       360       370       380       390       400
CTAGATGGAGCTCATTCAAGAAGAATGGAGCGATCAAAGTGTTACGGGGTTTCAAAAAGAGATCTCAAGCATGTTGAACATTATGAACAGGAGGAAAAA
AlaArgTrpSerSerPheLysLysAsnGlyAlaIleLysValLeuArgGlyPheLysLysGluIleSerSerMetLeuAsnIleMetAsnArgArgLysLys>

410       420       430       440       450       460       470       480       490       500
ATCTGTGACCATGCTCCTCATGCTGCTGCCCACAGCCCTGGCGTTCCATTTGACCACACGAGGGGGAGAGCCACACATGATAGTTAGTAAGCAGGAAAGA
SerValThrMetLeuLeuMetLeuLeuProThrAlaLeuAlaPheHisLeuThrThrArgGlyGlyGluProHisMetIleValSerLysGlnGluArg>

510       520       530       540       550       560       570       580       590       600
GGAAAGTCACTGTTGTTTAAGACCTCTGCAGGCATCAATATGTGCACTCTCATTGCGATGGATTTGGGAGAGTTATGCGAGGACACAATGACCTACAAAT
GlyLysSerLeuLeuPheLysThrSerAlaGlyIleAsnMetCysThrLeuIleAlaMetAspLeuGlyGluLeuCysGluAspThrMetThrTyrLys>

610       620       630       640       650       660       670       680       690       700
GCCCCCCGGATCACTGAGGCGGAACCAGATGACGTTGACTGCTGGTGCAATGCCACAGACACATGGGTGACCTATGGGACGTGTTCTCAAACCGGCGAACA
CysProArgIleThrGluAlaGluProAspAspValAspCysTrpCysAsnAlaThrAspThrTrpValThrTyrGlyThrCysSerGlnThrGlyGluHis>

710       720       730       740       750       760       770       780       790       800
CCGACGAGACAAACGTTCCGTGGCACTGGCCCCACACGTGGGACTTGGTCTAGAAACAAGAACCGAAACATGGATGTCCTCTGAAGGTGCCTGGAAACAA
ArgArgAspLysArgSerValAlaLeuAlaProHisValGlyLeuGlyLeuGluThrArgThrGluThrTrpMetSerSerGluGlyAlaTrpLysGln>

810       820       830       840       850       860       870       880       890       900
GTACAAAAAGTGGAGACTTGGGCTTTGAGACACCCAGGATTCACGGTGACAGCCCTTTTTTTAGCACATGCCATAGGAACATCCATTACTCAGAAAGGGA
ValGlnLysValGluThrTrpAlaLeuArgHisProGlyPheThrValThrAlaLeuPheLeuAlaHisAlaIleGlyThrSerIleThrGlnLysGly>

910       920       930       940       950       960       970       980       990      1000
TCATTTTCATTCTGCTGATGCTAGTAACACCATCAATGGCCATGCGATGTGTGGGAATAGGCAACAGAGACTTCGTTGAAGGACTGTCAGGAGCAACGTG
IleIlePheIleLeuLeuMetLeuValThrProSerMetAlaMetArgCysValGlyIleGlyAsnArgAspPheValGluGlyLeuSerGlyAlaThrTrp>

1010      1020      1030      1040      1050      1060      1070      1080      1090      1100
GGTGGACGTGGTATTGGAGCATGGAAGCTGCGTCACCACCATGGCAAAAGATAAACCAACATTGGACATTGAACTCTTGAAGACGGAGGTCACAAACCCT
ValAspValValLeuGluHisGlySerCysValThrThrMetAlaLysAspLysProThrLeuAspIleGluLeuLeuLysThrGluValThrAsnPro>

1110      1120      1130      1140      1150      1160      1170      1180      1190      1200
GCCGTCTTGCGCAAACTGTGCATTGAAGCTAAAATATCAAACACCACCACCGATTCAAGGTGTCCAACACAAGGAGAGGCTACACTGGTGGAAGAACAGG
AlaValLeuArgLysLeuCysIleGluAlaLysIleSerAsnThrThrThrAspSerArgCysProThrGlnGlyGluAlaThrLeuValGluGluGln>

1210      1220      1230      1240      1250      1260      1270      1280      1290      1300
ACTCGAACTTTGTGTGTCGACGAACGTTTGTGGACAGAGGCTGGGGTAATGGCTGCGGACTATTTGGAAAAGGAAGCCTACTGACGTGTGCTAAGTTCAA
AspSerAsnPheValCysArgArgThrPheValAspArgGlyTrpGlyAsnGlyCysGlyLeuPheGlyLysGlySerLeuLeuThrCysAlaLysPheLys>

1310      1320      1330      1340      1350      1360      1370      1380      1390      1400
GTGTGTGACAAAACTAGAAGGAAAGATAGTTCAATATGAAAACTTAAAATATTCAGTGATAGTCACTGTCCACACTGGGGACCAGCACCAGGTGGGAAAC
CysValThrLysLeuGluGlyLysIleValGlnTyrGluAsnLeuLysTyrSerValIleValThrValHisThrGlyAspGlnHisGlnValGlyAsn>

1410      1420      1430      1440      1450      1460      1470      1480      1490      1500
GAGACTACAGAACATGGAACAATTGCAACCATAACACCTCAAGCTCCTACGTCGGAAATACAGCTGACTGACTACGGAGCCCTCACATTGGACTGCTCGC
GluThrThrGluHisGlyThrIleAlaThrIleThrProGlnAlaProThrSerGluIleGlnLeuThrAspTyrGlyAlaLeuThrLeuAspCysSer>

1510      1520      1530      1540      1550      1560      1570      1580      1590      1600
CTAGAACAGGGCTGGACTTTAATGAGATGGTTCTATTGACAATGAAAGAAAAATCATGGCTTGTCCACAAACAATGGTTTCTAGACTTACCACTGCCTTG
ProArgThrGlyLeuAspPheAsnGluMetValLeuLeuThrMetLysGluLysSerTrpLeuValHisLysGlnTrpPheLeuAspLeuProLeuPro>

1610      1620      1630      1640      1650      1660      1670      1680      1690      1700
GACTTCAGGAGCTTCAACATCTCAAGAGACTTGGAACAGACAAGATTTGCTGGTCACATTCAAGACAGCTCATGCAAAGAAACAGGAAGTAGTCGTACTG
ThrSerGlyAlaSerThrSerGlnGluThrTrpAsnArgGlnAspLeuLeuValThrPheLysThrAlaHisAlaLysLysGlnGluValValValLeu>

1710      1720      1730      1740      1750      1760      1770      1780      1790      1800
GGATCACAGGAAGGAGCAATGCACACTGCGTTGACTGGGGCGACAGAAATCCAGACGTCAGGAACGACAACAATCTTTGCAGGACACCTGAAATGCAGAC
GlySerGlnGluGlyAlaMetHisThrAlaLeuThrGlyAlaThrGluIleGlnThrSerGlyThrThrThrIlePheAlaGlyHisLeuLysCysArg>

1810      1820      1830      1840      1850      1860      1870      1880      1890      1900
TAAAAATGGATAAACTGACTTTAAAAGGGAGTCATATGTAATGTGCACAGGCTCATTTAAGCTAGAAGGAAGTGGCTGAGACCCAGCATGGAACTGT
LeuLysMetAspLysLeuThrLeuLysGlyMetSerTyrValMetCysThrGlySerPheLysLeuGluLysGluValAlaGluThrGlnHisGlyThrVal>

1910      1920      1930      1940      1950      1960      1970      1980      1990      2000
TTTAGTGCAGGTTAAATACGAAGGAACAGATGCGCCATGCAAGATCCCTTTTTCGGCCCAAGATGAGAAAGGAGTGACCCAGAATGGGAGATTGATAACA
LeuValGlnValLysTyrGluGlyThrAspAlaProCysLysIleProPheSerAlaGlnAspGluLysGlyValThrGlnAsnGlyArgLeuIleThr>
```

APPENDIX 3-continued

Nucleotide and amino acid sequence of DEN1 (Puerto Rico/94) CME chimeric region

```
        2010      2020      2030      2040      2050      2060      2070      2080      2090      2100
GCCAACCCCATAGTCACTGACAAAGAAAAACCAGTCAACATTGAGACAGAACCACCTTTTGGTGAGAGCTACATCGTGGTAGGGCAGGTGAAAAAGCTT
AlaAsnProIleValThrAspLysGluLysProValAsnIleGluThrGluProProPheGlyGluSerTyrIleValValGlyAlaGlyGluLysAla>

2110      2120      2130      2140      2150      2160      2170      2180      2190      2200
TGAAACTGAGCTGGTTCAAGAAAGGGAGCAGCATAGGGAAAATGTTCGAAGCAACTGCCCGAGGAGCGCGAAGGATGGCTATCCTGGGAGACACCGCATG
LeuLysLeuSerTrpPheLysLysGlySerSerIleGlyLysMetPheGluAlaThrAlaArgGlyAlaArgArgMetAlaIleLeuGlyAspThrAlaTrp>

2210      2220      2230      2240      2250      2260      2270      2280      2290      2300
GGACTTTGGCTCTATAGGAGGAGTGTTCACATCAGTGGGAAAATTGGTACACCAGGTTTTTGGAGCCGCATATGGGGTTCTGTTCAGCGGTGTTTCTTGG
AspPheGlySerIleGlyGlyValPheThrSerValGlyLysLeuValHisGlnValPheGlyAlaAlaTyrGlyValLeuPheSerGlyValSerTyr>

2310      2320      2330      2340      2350      2360      2370      2380      2390      2400
ACCATGAAAATAGGAATAGGGATTCTGCTGACATGGCTAGGATTAAACTCGAGGAACACTTCAATGGCTATGACGTGCATAGCTGTTGGAGGAATCACTC
ThrMetLysIleGlyIleGlyIleLeuLeuThrTrpLeuGlyLeuAsnSerArgAsnThrSerMetAlaMetThrCysIleAlaValGlyGlyIleThr>

2410      2420
TGTTTCTGGGCTTCACAGTTCAAGCA
LeuPheLeuGlyPheThrValGlnAla>
```

APPENDIX 4

Nucleotide and amino acid sequence of DEN1 (Puerto Rico/94) ME chimeric region

Bases 1 to 404 (PstI): DEN4
Bases 405 (PstI) to 2345 (XhoI): DEN1
Bases 2346 (XhoI) to 2423: DEN4
Bases 102 to 440: C protein ORF
Bases 441 to 938: prM protein ORF
Bases 939 to 2423: E protein ORF

```
         10        20        30        40        50        60        70        80        90       100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA 110       120       130       140       150       160       170       180       190       200
AATGAACCAACGAAAAAAGGTGGTTAGACCACCTTTCAATATGCTGAAACGCGAGAGAAACCGCGTATCAACCCCTCAAGGGTTGGTGAAGAGATTCTCA
MetAsnGlnArgLysLysValValArgProProPheAsnMetLeuLysArgGluArgAsnArgValSerThrProGlnGlyLeuValLysArgPheSer>

210       220       230       240       250       260       270       280       290       300
ACCGGACTTTTTTTCTGGGAAAGGACCCTTACGGATGGTGCTAGCATTCATCACGTTTTTGCGAGTCCTTTCCATCCCACCAACAGCAGGGATTCTGAAGA
ThrGlyLeuPheSerGlyLysGlyProLeuArgMetValLeuAlaPheIleThrPheLeuArgValLeuSerIleProProThrAlaGlyIleLeuLys>

310       320       330       340       350       360       370       380       390       400
GATGGGGACAGTTGAAGAAAAATAAGGCCATCAAGATACTGATTGGATTCAGGAAGGAGATAGGCCGCATGCTGAACATCTTGAACGGGAGAAAAAGGTC
ArgTrpGlyGlnLeuLysLysAsnLysAlaIleLysIleLeuIleGlyPheArgLysGluIleGlyArgMetLeuAsnIleLeuAsnGlyArgLysArgSer>

410       420       430       440       450       460       470       480       490       500
TGCAGCCATGCTCCTCATGCTGCTGCCCACAGCCCTGGCGTTCCATTTGACCACACGAGGGGGAGAGCCACACATGATAGTTAGTAAGCAGGAAAGAGGA
AlaAlaMetLeuLeuMetLeuLeuProThrAlaLeuAlaPheHisLeuThrThrArgGlyGlyGluProHisMetIleValSerLysGlnGluArgGly>

510       520       530       540       550       560       570       580       590       600
AAGTCACTGTTGTTTAAGACCTCTGCAGGCATCAATATGTGCACTCTCATTGCGATGGATTTGGGAGAGTTATGCGAGGACACAATGACCTACAAATGCC
LysSerLeuLeuPheLysThrSerAlaGlyIleAsnMetCysThrLeuIleAlaMetAspLeuGlyGluLeuCysGluAspThrMetThrTyrLysCys>

610       620       630       640       650       660       670       680       690       700
CCCGGATCACTGAGGCGGAACCAGATGACGTTGACTGCTGGTGCAATGCCACAGACACATGGGTGACCTATGGGACGTGTTCTCAAACCGGCGAACACCG
ProArgIleThrGluAlaGluProAspAspValAspCysTrpCysAsnAlaThrAspThrTrpValThrTyrGlyThrCysSerGlnThrGlyGluHisArg>

710       720       730       740       750       760       770       780       790       800
ACGAGACAAACGTTCCGTGGCACTGGCCCCACACGTGGGACTTGGTCTAGAAACAAGAACCGAAACGTGGATGTCCTCTGAAGGTGCCTGGAAACAAGTA
ArgAspLysArgSerValAlaLeuAlaProHisValGlyLeuGlyLeuGluThrArgThrGluThrTrpMetSerSerGluGlyAlaTrpLysGlnVal>

810       820       830       840       850       860       870       880       890       900
CAAAAAGTGGAGACTTGGGCTTTGAGACACCCAGGATTCACGGTGACAGCCCTTTTTTTAGCACATGCCATAGGAACATCCATTACTCAGAAAGGGATCA
GlnLysValGluThrTrpAlaLeuArgHisProGlyPheThrValThrAlaLeuPheLeuAlaHisAlaIleGlyThrSerIleThrGlnLysGlyIle>

910       920       930       940       950       960       970       980       990      1000
TTTTCATTCTGCTGATGCTAGTAACACCATCAATGGCCATGCGATGTGTGGGAATAGGCAACAGAGACTTCGTTGAAGGACTGTCAGGAGCAACGTGGGT
IlePheIleLeuLeuMetLeuValThrProSerMetAlaMetArgCysValGlyIleGlyAsnArgAspPheValGluGlyLeuSerGlyAlaThrTrpVal>

1010      1020      1030      1040      1050      1060      1070      1080      1090      1100
GGACGTGGTATTGGAGCATGGAAGCTGCGTCACCACCATGGCAAAAGATAAACCAACATTGGACATTGAACTCTTGAAGACGGAGGTCACAAACCCTGCC
AspValValLeuGluHisGlySerCysValThrThrMetAlaLysAspLysProThrLeuAspIleGluLeuLeuLysThrGluValThrAsnProAla>
```

APPENDIX 4-continued

Nucleotide and amino acid sequence of DEN1 (Puerto Rico/94) ME chimeric region

```
      1110       1120       1130       1140       1150       1160       1170       1180       1190       1200
GTCTTGCGCAAACTGTGCATTGAAGCTAAAATATCAAACACCACCACCGATTCAAGGTGTCCAACACAAGGAGAGGCTACACTGGTGGAAGAACAGGACT
ValLeuArgLysLeuCysIleGluAlaLysIleSerAsnThrThrThrAspSerArgCysProThrGlnGlyGluAlaThrLeuValGluGluGlnAsp>

1210       1220       1230       1240       1250       1260       1270       1280       1290       1300
CGAACTTTGTGTGTCGACGAACGTTTGTGGACAGAGGCTGGGGTAATGGCTGCGGACTATTTGGAAAAGGAAGCCTACTGACGTGTGCTAAGTTCAAGTG
SerAsnPheValCysArgArgThrPheValAspArgGlyTrpGlyAsnGlyCysGlyLeuPheGlyLysGlySerLeuLeuThrCysAlaLysPheLysCys>

1310       1320       1330       1340       1350       1360       1370       1380       1390       1400
TGTGACAAAACTAGAAGGAAAGATAGTTCAATATGAAAACTTAAAATATTCAGTGATAGTCACTGTCCACACTGGGGACCAGCACCAGGTGGGAAACGAG
ValThrLysLeuGluGlyLysIleValGlnTyrGluAsnLeuLysTyrSerValIleValThrValHisThrGlyAspGlnHisGlnValGlyAsnGlu>

1410       1420       1430       1440       1450       1460       1470       1480       1490       1500
ACTACAGAACATGGAACAATTGCAACCATAACACCTCAAGCTCCTACGTCGGAAATACAGCTGACTGACTACGGAGCCCTCACATTGGACTGCTCGCCTA
ThrThrGluHisGlyThrIleAlaThrIleThrProGlnAlaProThrSerGluIleGlnLeuThrAspTyrGlyAlaLeuThrLeuAspCysSerPro>

1510       1520       1530       1540       1550       1560       1570       1580       1590       1600
GAACAGGGCTGGACTTTAATGAGATGGTTCTATTGACAATGAAAGAAAAATCATGGCTTGTCCACAAACAATGGTTTCTAGACTTACCACTGCCTTGGAC
ArgThrGlyLeuAspPheAsnGluMetValLeuLeuThrMetLysGluLysSerTrpLeuValHisLysGlnTrpPheLeuAspLeuProLeuProTrpThr>

1610       1620       1630       1640       1650       1660       1670       1680       1690       1700
TTCAGGAGCTTCAACATCTCAAGAGACTTGGAACAGACAAGATTTGCTGGTCACATTCAAGACAGCTCATGCAAAGAAACAGGAAGTAGTCGTACTGGGA
SerGlyAlaSerThrSerGlnGluThrTrpAsnArgGlnAspLeuLeuValThrPheLysThrAlaHisAlaLysLysGlnGluValValValLeuGly>

1710       1720       1730       1740       1750       1760       1770       1780       1790       1800
TCACAGGAAGGAGCAATGCACACTGCGTTGACTGGGGCGACAGAAATCCAGACGTCAGGAACGACAACAATCTTTGCAGGACACCTGAAATGCAGACTAA
SerGlnGluGlyAlaMetHisThrAlaLeuThrGlyAlaThrGluIleGlnThrSerGlyThrThrThrIlePheAlaGlyHisLeuLysCysArgLeu>

1810       1820       1830       1840       1850       1860       1870       1880       1890       1900
AAATGGATAAACTGACTTTAAAAGGGATGTCATATGTAATGTGCACAGGCTCATTTAAGCTAGAGAAGGAAGTGGCTGAGACCCAGCATGGAACTGTTTT
LysMetAspLysLeuThrLeuLysGlyMetSerTyrValMetCysThrGlySerPheLysLeuGluLysGluValAlaGluThrGlnHisGlyThrValLeu>

1910       1920       1930       1940       1950       1960       1970       1980       1990       2000
AGTGCAGGTTAAATACGAAGGAACAGATGCGCCATGCAAGATCCCTTTTTCGGCCCAAGATGAGAAAGGAGTGACCCAGAATGGGAGATTGATAACAGCC
ValGlnValLysTyrGluGlyThrAspAlaProCysLysIleProPheSerAlaGlnAspGluLysGlyValThrGlnAsnGlyArgLeuIleThrAla>

2010       2020       2030       2040       2050       2060       2070       2080       2090       2100
AACCCCATAGTCACTGACAAAGAAAAACCAGTCAACATTGAGACAGAACCACCTTTTGGTGAGAGCTACATCGTGGTAGGGGCAGGTGAAAAAGCTTTGA
AsnProIleValThrAspLysGluLysProValAsnIleGluThrGluProProPheGlyGluSerTyrIleValValGlyAlaGlyGluLysAlaLeu>

2110       2120       2130       2140       2150       2160       2170       2180       2190       2200
AACTGAGCTGGTTCAAGAAAGGGAGCAGCATAGGGAAAATGTTCGAAGCAACTGCCCGAGGAGCGCGAAGGATGGCTATCCTGGGAGACACCGCATGGGA
LysLeuSerTrpPheLysLysGlySerSerIleGlyLysMetPheGluAlaThrAlaArgGlyAlaArgArgMetAlaIleLeuGlyAspThrAlaTrpAsp>

2210       2220       2230       2240       2250       2260       2270       2280       2290       2300
CTTTGGCTCTATAGGAGGAGTGTTCACATCAGTGGGAAAATTGGTACACCAGGTTTTTGGAGCCGCATATGGGGTTCTGTTCAGCGGTGTTTCTTGGACC
PheGlySerIleGlyGlyValPheThrSerValGlyLysLeuValHisGlnValPheGlyAlaAlaTyrGlyValLeuPheSerGlyValSerTrpThr>

2310       2320       2330       2340       2350       2360       2370       2380       2390       2400
ATGAAAATAGGAATAGGGATTCTGCTGACATGGCTAGGATTAAACTCGAGGAACACTTCAATGGCTATGACGTGCATAGCTGTTGGAGGAATCACTCTGT
MetLysIleGlyIleGlyIleLeuLeuThrTrpLeuGlyLeuAsnSerArgAsnThrSerMetAlaMetThrCysIleAlaValGlyGlyIleThrLeu>

2410       2420
TTCTGGGCTTCACAGTTCAAGCA
PheLeuGlyPheThrValGlnAla
```

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

SEQUENCE LISTING

<160> NUMBER OF SEQ ID NOS: 53

<210> SEQ ID NO 1
<211> LENGTH: 82
<212> TYPE: RNA
<213> ORGANISM: Dengue 1 virus -continued

```
<400> SEQUENCE: 1
gcagcagcgg ggcccaacac caggggaagc uguacccugg ugguaaggac uagagguuag    60
aggagacccc ccgcaacaac aa                                             82

<210> SEQ ID NO 2
<211> LENGTH: 84
<212> TYPE: RNA
<213> ORGANISM: Dengue 2 virus

<400> SEQUENCE: 2
agcaacaaug ggggcccaag gugagaugaa gcuguagucu cacuggaagg acuagagguu    60
agaggagacc cccccaaaac aaaa                                           84

<210> SEQ ID NO 3
<211> LENGTH: 83
<212> TYPE: RNA
<213> ORGANISM: Dengue 3 virus

<400> SEQUENCE: 3
gcagcagcgg ggcccgagcu cugagggaag cuguaccucc uugcaaagga cuagagguua    60
gaggagaccc cccgcaaaua aaa                                            83

<210> SEQ ID NO 4
<211> LENGTH: 83
<212> TYPE: RNA
<213> ORGANISM: Dengue 4 virus

<400> SEQUENCE: 4
agcaaaaggg ggcccgaagc caggaggaag cuguacuccu gguggaagga cuagagguua    60
gaggagaccc ccccaacaca aaa                                            83

<210> SEQ ID NO 5
<211> LENGTH: 16
<212> TYPE: RNA
<213> ORGANISM: Artificial Sequence
<220> FEATURE:
<223> OTHER INFORMATION: Dengue 1 delta 30

<400> SEQUENCE: 5
ggggcccaag acuaga                                                    16

<210> SEQ ID NO 6
<211> LENGTH: 16
<212> TYPE: RNA
<213> ORGANISM: Artificial Sequence
<220> FEATURE:
<223> OTHER INFORMATION: Dengue 2 delta 30

<400> SEQUENCE: 6
ggggcccaag acuaga                                                    16

<210> SEQ ID NO 7
<211> LENGTH: 16
<212> TYPE: RNA
<213> ORGANISM: Artificial Sequence
<220> FEATURE:
<223> OTHER INFORMATION: Dengue 3 delta 30

<400> SEQUENCE: 7
ggggcccaag acuaga                                                    16
```

```
<210> SEQ ID NO 8
<211> LENGTH: 16
<212> TYPE: RNA
<213> ORGANISM: Artificial Sequence
<220> FEATURE:
<223> OTHER INFORMATION: Dengue 4 delta 30

<400> SEQUENCE: 8
ggggcccaag acuaga                                                   16

<210> SEQ ID NO 9
<211> LENGTH: 51
<212> TYPE: DNA
<213> ORGANISM: Artificial Sequence
<220> FEATURE:
<223> OTHER INFORMATION: TL2 region of p2 plasmid

<400> SEQUENCE: 9
tgggggccca aggtgagatg aagctgtagt ctcactggaa ggactagagg t            51

<210> SEQ ID NO 10
<211> LENGTH: 21
<212> TYPE: DNA
<213> ORGANISM: Artificial Sequence
<220> FEATURE:
<223> OTHER INFORMATION: TL2 region of p2 delta 30

<400> SEQUENCE: 10
tgggggccca agactagagg t                                             21

<210> SEQ ID NO 11
<211> LENGTH: 51
<212> TYPE: DNA
<213> ORGANISM: Artificial Sequence
<220> FEATURE:
<223> OTHER INFORMATION: TL2 region of p3 plasmid

<400> SEQUENCE: 11
cggggcccga gctctgaggg aagctgtacc tccttgcaaa ggactagagg t            51

<210> SEQ ID NO 12
<211> LENGTH: 20
<212> TYPE: DNA
<213> ORGANISM: Artificial Sequence
<220> FEATURE:
<223> OTHER INFORMATION: TL2 region of p3 delta 30

<400> SEQUENCE: 12 ggggcccaa gactagaggt                                                20

<210> SEQ ID NO 13
<211> LENGTH: 29
<212> TYPE: DNA
<213> ORGANISM: Artificial Sequence
<220> FEATURE:
<223> OTHER INFORMATION: SpeI linker in p3

<400> SEQUENCE: 13
actagttaga ctaacttaag tcaactagt                                     29

<210> SEQ ID NO 14
<211> LENGTH: 51
<212> TYPE: DNA
<213> ORGANISM: Artificial Sequence
<220> FEATURE:
<223> OTHER INFORMATION: rDEN2/4 junction 1
```

-continued

<400> SEQUENCE: 14
cagtttgttt gaatagagag cagatctctg atgaataacc aacgaaaaaa g 51

<210> SEQ ID NO 15
<211> LENGTH: 7
<212> TYPE: PRT
<213> ORGANISM: Artificial Sequence
<220> FEATURE:
<223> OTHER INFORMATION: rDEN2/4 junction 1

<400> SEQUENCE: 15

Met Asn Asn Gln Arg Lys Lys
1 5

<210> SEQ ID NO 16
<211> LENGTH: 51
<212> TYPE: DNA
<213> ORGANISM: Artificial Sequence
<220> FEATURE:
<223> OTHER INFORMATION: rDEN2/4 junction 2

<400> SEQUENCE: 16
attatcacat ggataggaat gaactcgagg aacacttcaa tggctatgac g 51

<210> SEQ ID NO 17
<211> LENGTH: 17
<212> TYPE: PRT
<213> ORGANISM: Artificial Sequence
<220> FEATURE:
<223> OTHER INFORMATION: rDEN2/4 junction 2

<400> SEQUENCE: 17

Ile Ile Thr Trp Ile Gly Met Asn Ser Arg Asn Thr Ser Met Ala Met
1 5 10 15

Thr

<210> SEQ ID NO 18
<211> LENGTH: 51
<212> TYPE: DNA
<213> ORGANISM: Artificial Sequence
<220> FEATURE:
<223> OTHER INFORMATION: rDEN2/4 junction 3

<400> SEQUENCE: 18
atcttgaacg ggagaaaaag gtctgcaggc atgatcatta tgctgattcc a 51

<210> SEQ ID NO 19
<211> LENGTH: 17
<212> TYPE: PRT
<213> ORGANISM: Artificial Sequence
<220> FEATURE:
<223> OTHER INFORMATION: rDEN2/4 junction 3

<400> SEQUENCE: 19

Ile Leu Asn Gly Arg Lys Arg Ser Ala Gly Met Ile Ile Met Leu Ile
1 5 10 15

Pro

<210> SEQ ID NO 20
<211> LENGTH: 50
<212> TYPE: DNA
<213> ORGANISM: Artificial Sequence
<220> FEATURE:
<223> OTHER INFORMATION: rDEN3/4 junction 1

```
<400> SEQUENCE: 20
cagtttgttt gaatagagag cagatctctg gaaaaatgaa caaccaacgg         50

<210> SEQ ID NO 21
<211> LENGTH: 5
<212> TYPE: PRT
<213> ORGANISM: Artificial Sequence
<220> FEATURE:
<223> OTHER INFORMATION: rDEN3/4 junction 1

<400> SEQUENCE: 21

Met Asn Asn Gln Arg
 1               5

<210> SEQ ID NO 22
<211> LENGTH: 51
<212> TYPE: DNA
<213> ORGANISM: Artificial Sequence
<220> FEATURE:
<223> OTHER INFORMATION: rDEN3/4 junction 2

<400> SEQUENCE: 22
cttttaacct ggatagggtt gaactcgagg aacacttcaa tggctatgac g        51

<210> SEQ ID NO 23
<211> LENGTH: 17
<212> TYPE: PRT
<213> ORGANISM: Artificial Sequence
<220> FEATURE:
<223> OTHER INFORMATION: rDEN3/4 junction 2

<400> SEQUENCE: 23

Leu Leu Thr Trp Ile Gly Leu Asn Ser Arg Asn Thr Ser Met Ala Met
 1               5                  10                  15

Thr

<210> SEQ ID NO 24
<211> LENGTH: 51
<212> TYPE: DNA
<213> ORGANISM: Artificial Sequence
<220> FEATURE:
<223> OTHER INFORMATION: rDEN3/4 junction 3

<400> SEQUENCE: 24
atcttgaacg ggagaaaaag gtctgcagtc tgtctcatga tgatgttacc a        51

<210> SEQ ID NO 25
<211> LENGTH: 17
<212> TYPE: PRT
<213> ORGANISM: Artificial Sequence
<220> FEATURE:
<223> OTHER INFORMATION: rDEN3/4 junction 3

<400> SEQUENCE: 25

Ile Leu Asn Gly Arg Lys Arg Ser Ala Val Cys Leu Met Met Met Leu
 1               5                  10                  15

Pro

<210> SEQ ID NO 26
<211> LENGTH: 50
<212> TYPE: DNA
<213> ORGANISM: Artificial Sequence
<220> FEATURE:
<223> OTHER INFORMATION: rDEN1/4 junction 1
```

<400> SEQUENCE: 26
cagtttgttt gaatagagag cagatctctg gaaaaatgaa caaccaacgg          50

<210> SEQ ID NO 27
<211> LENGTH: 5
<212> TYPE: PRT
<213> ORGANISM: Artificial Sequence
<220> FEATURE:
<223> OTHER INFORMATION: rDEN1/4 junction 1

<400> SEQUENCE: 27

Met Asn Asn Gln Arg
1               5

<210> SEQ ID NO 28
<211> LENGTH: 51
<212> TYPE: DNA
<213> ORGANISM: Artificial Sequence
<220> FEATURE:
<223> OTHER INFORMATION: rDEN1/4 junction 2

<400> SEQUENCE: 28
ctgctgacat ggctaggatt aaactcgagg aacacttcaa tggctatgac g         51

<210> SEQ ID NO 29
<211> LENGTH: 17
<212> TYPE: PRT
<213> ORGANISM: Artificial Sequence
<220> FEATURE:
<223> OTHER INFORMATION: rDEN1/4 junction 2

<400> SEQUENCE: 29

Leu Leu Thr Trp Leu Gly Leu Asn Ser Arg Asn Thr Ser Met Ala Met
1               5                   10                  15

Thr

<210> SEQ ID NO 30
<211> LENGTH: 51
<212> TYPE: DNA
<213> ORGANISM: Artificial Sequence
<220> FEATURE:
<223> OTHER INFORMATION: rDEN1/4 junction 3

<400> SEQUENCE: 30
atcttgaacg ggagaaaaag gtctgcagcc atgctcctca tgctgctgcc c         51

<210> SEQ ID NO 31
<211> LENGTH: 17
<212> TYPE: PRT
<213> ORGANISM: Artificial Sequence
<220> FEATURE:
<223> OTHER INFORMATION: rDEN1/4 junction 3

<400> SEQUENCE: 31

Ile Leu Asn Gly Arg Lys Arg Ser Ala Ala Met Leu Leu Met Leu Leu
1               5                   10                  15

Pro

<210> SEQ ID NO 32
<211> LENGTH: 60
<212> TYPE: RNA
<213> ORGANISM: Dengue 4 virus

```
<400> SEQUENCE: 32
ccaacaaccu ugacagcauc cuuagucaug cuuuuaguccc auuaugcaau aauaggccca    60

<210> SEQ ID NO 33
<211> LENGTH: 20
<212> TYPE: PRT
<213> ORGANISM: Dengue 4 virus

<400> SEQUENCE: 33

Pro Thr Thr Leu Thr Ala Ser Leu Val Met Leu Leu Val His Thr Ala
 1               5                  10                  15

Ile Ile Gly Pro
            20

<210> SEQ ID NO 34
<211> LENGTH: 60
<212> TYPE: RNA
<213> ORGANISM: Dengue 1 virus

<400> SEQUENCE: 34
ccgcugacgc ugacagcggc gguauuuaug cuaguggcuc auuaugccau aauuggaccc    60

<210> SEQ ID NO 35
<211> LENGTH: 20
<212> TYPE: PRT
<213> ORGANISM: Dengue 1 virus

<400> SEQUENCE: 35

Pro Leu Thr Leu Thr Ala Ala Val Pro Met Leu Val Ala His Thr Ala
 1               5                  10                  15

Ile Ile Gly Pro
            20

<210> SEQ ID NO 36
<211> LENGTH: 60
<212> TYPE: RNA
<213> ORGANISM: Dengue 2 virus

<400> SEQUENCE: 36
ccuauaaccc ucacagcggc ucuucuuuua uugguagcac auuaugccau cauaggaccg    60

<210> SEQ ID NO 37
<211> LENGTH: 20
<212> TYPE: PRT
<213> ORGANISM: Dengue 2 virus

<400> SEQUENCE: 37

Pro Ile Thr Leu Thr Ala Ala Leu Leu Leu Leu Val Ala His Thr Ala
 1               5                  10                  15

Ile Ile Gly Pro
            20

<210> SEQ ID NO 38
<211> LENGTH: 60
<212> TYPE: RNA
<213> ORGANISM: Dengue 3 virus

<400> SEQUENCE: 38
ccacuaacuc ucacagcggc aguucuccug cuagucacgc auuaugcuau uauaggucca    60
```

```
<210> SEQ ID NO 39
<211> LENGTH: 20
<212> TYPE: PRT
<213> ORGANISM: Dengue 3 virus

<400> SEQUENCE: 39

Pro Leu Thr Leu Thr Ala Ala Val Leu Leu Val Thr His Thr Ala
1               5                   10                  15

Ile Ile Gly Pro
            20

<210> SEQ ID NO 40
<211> LENGTH: 13
<212> TYPE: DNA
<213> ORGANISM: Artificial Sequence
<220> FEATURE:
<223> OTHER INFORMATION: primer

<400> SEQUENCE: 40
ccacgggcgc cgt                                                              13

<210> SEQ ID NO 41
<211> LENGTH: 10
<212> TYPE: DNA
<213> ORGANISM: Artificial Sequence
<220> FEATURE:
<223> OTHER INFORMATION: primer

<400> SEQUENCE: 41
aaggcctgga                                                                  10

<210> SEQ ID NO 42
<211> LENGTH: 12
<212> TYPE: DNA
<213> ORGANISM: Artificial Sequence
<220> FEATURE:
<223> OTHER INFORMATION: primer

<400> SEQUENCE: 42
tatccccggg ac                                                               12

<210> SEQ ID NO 43
<211> LENGTH: 11
<212> TYPE: DNA
<213> ORGANISM: Artificial Sequence
<220> FEATURE:
<223> OTHER INFORMATION: primer

<400> SEQUENCE: 43
agagctctct c                                                                11

<210> SEQ ID NO 44
<211> LENGTH: 15
<212> TYPE: DNA
<213> ORGANISM: Artificial Sequence
<220> FEATURE:
<223> OTHER INFORMATION: primer

<400> SEQUENCE: 44
gaatctccac ccgga                                                            15

<210> SEQ ID NO 45
<211> LENGTH: 10
<212> TYPE: DNA
<213> ORGANISM: Artificial Sequence
```

```
<220> FEATURE:
<223> OTHER INFORMATION: primer

<400> SEQUENCE: 45
ctgtcgaatc                                                            10

<210> SEQ ID NO 46
<211> LENGTH: 15159
<212> TYPE: DNA
<213> ORGANISM: Artificial Sequence
<220> FEATURE:
<223> OTHER INFORMATION: Dengue 2 plasmid p2

<400> SEQUENCE: 46
agttgttagt ctacgtggac cgacaaagac agattctttg agggagctaa gctcaacgta      60
gttctaactg ttttttgatt agagagcaga tctctgatga ataaccaacg gaaaaaggcg     120
agaaacacgc ctttcaatat gctgaaacgc gagagaaacc gcgtgtcaac tgtacaacag     180
ttgacaaaga gattctcact tggaatgctg cagggacgag gaccactaaa attgttcatg     240
gccctggtgg cattccttcg tttcctaaca atcccaccaa cagcaggat attaaaaga      300 tggggaacaa ttaaaaaatc aaaggctatt aatgttctga gaggcttcag gaaagagatt     360
ggaaggatgc tgaatatctt aaacaggaga cgtagaactg taggcatgat catcatgctg     420
actccaacag tgatggcgtt tcatctgacc acacgcaacg gagaaccaca catgattgtc     480
agtagacaag aaaaagggaa aagccttctg ttcaagacaa aggatggcac gaacatgtgt     540
accctcatgg ccatgacct tggtgagttg tgtgaagaca caatcacgta taatgtcct    600 tttctcaagc agaacgaacc agaagacata gattgttggt gcaactccac gtccacatgg     660
gtaacttatg gacatgtac caccacagga gagcacagaa gagaaaaaag atcagtggcg     720
cttgttccac acgtgggaat gggattggag acacgaactg aaacatggat gtcatcagaa     780
ggggcctgga acatgccca gagaattgaa acttggattc tgagacatcc aggctttacc     840
ataatggccg caatcctggc atacaccata gggacgacgc atttccaaag agtcctgata     900
ttcatcctac tgcagccat cgctccttca atgacaatgc gctgcatagg aatatcaaat     960
agggactttg tggaaggagt gtcaggaggg agttgggttg acatagtttt agaacatgga    1020
agttgtgtga cgacgatggc aaaaaacaaa ccaacactgg actttgaact gataaaaaca    1080
gaagccaaac aacctgccac cttaaggaag tactgtatag aggccaaact gaccaacacg    1140
acaacagact cgcgctgccc aacacaaggg gaacccaccc tgaatgaaga gcaggacaaa    1200
aggtttgtct gcaaacattc catggtagac agaggatggg gaaatggatg tggattgttt    1260
ggaaaaggag gcatcgtgac ctgtgctatg ttcacatgca aaaagaacat ggaaggaaaa    1320
attgtgcagc cagaaaacct ggaatacact gtcgtgataa cacctcattc aggggaagaa    1380
catgcagtgg gaaatgacac aggaaaacat ggtaaagaag tcaagataac accacagagc    1440
tccatcacag aggcggaact gacaggctat ggcactgtta cgatggagtg ctctccaaga    1500
acgggcctcg acttcaatga gatggtgttg ctgcaaatgg aagacaaagc ctggctggtg    1560
cacagacaat ggttcctaga cctaccgttg ccatggctgc ccggagcaga cacacaagga    1620
tcaaattgga tacagaaaga aacactggtc accttcaaaa atccccatgc gaaaaaacag    1680
gatgttgttg tcttaggatc ccaagagggg gccatgcata gcagcactcac aggggctacg    1740 gaaatccaga tgtcatcagg aaacctgctg ttcacaggac atctcaagtg caggctgaga    1800
atggacaaat acaacttaa agggatgtca tactccatgt gcacaggaaa gtttaaaatt    1860
```

-continued

```
gtgaaggaaa tagcagaaac acaacatgga acaatagtca ttagagtaca atatgaagga    1920
gacggctctc catgcaagat ccccttgag ataatggatc tggaaaaaag acatgttttg    1980
ggccgcctga tcacagtcaa cccaattgta acagaaaagg acagtccagt caacatagaa    2040
gcagaacctc cattcggaga cagctacatc atcataggag tggaaccagg acaattgaag    2100
ctggactggt tcaagaaagg aagttccatc ggccaaatgt ttgagacaac aatgagggga    2160
gcgaaaagaa tggccatttt gggtgacaca gcctgggatt ttggatctct gggaggagtg    2220
ttcacatcaa taggaaaggc tctccaccag gttttggag caatctacgg ggctgctttc    2280 agtgggtct catggactat gaagatcctc ataggagtta tcatcacatg gataggaatg    2340
aactcacgta gcactagtct gagcgtgtca ctggtgttag tgggaatcgt gacactttac    2400
ttgggagtta tggtgcaggc cgatagtggt tgcgttgtga gctggaagaa caaagaacta    2460
aaatgtggca gtggaatatt cgtcacagat aacgtgcata catggacaga acaatacaag    2520
ttccaaccag aatcccctc aaaactggcc tcagccatcc agaaagcgca tgaagagggc    2580
atctgtggaa tccgctcagt aacaagactg gaaaatctta tgtggaaaca gataacatca    2640
gaattgaatc atattctatc agaaaatgaa gtgaaactga ccatcatgac aggagacatc    2700
aaaggaatca tgcaggtagg aaaacgatct ttgcggcctc aacccactga gttgaggtat    2760
tcatggaaaa catgggtaa agcgaaaatg ctctccacag aactccacaa tcagaccttc    2820
ctcattgatg gtcccgaaac agcagaatgc cccaacacaa acagagcttg gaattcactg    2880
gaagttgagg actacggctt tggagtattc actaccaata tatggctaag attgagagaa    2940
aagcaggatg tattttgtga ctcaaaactc atgtcagcgg ccataaagga caacagagcc    3000
gtccatgctg atatgggtta ttggatagaa agcgcactca atgatacatg gaagatagag    3060
aaagcttctt tcattgaagt caaaagttgc cactggccaa agtcacacac cctatggagt    3120
aatggagtgc tagaaagcga gatggtcatt ccaagaatt tcgctggacc agtgtcacaa    3180
cataataaca gaccaggcta ttacacacaa acagcaggac cttggcatct aggcaagctt    3240
gagatggact tgatttctg cgaagggact acagtggtgg taaccgagaa ctgtggaaac    3300
agagggccct ctttaagaac aaccactgcc tcaggaaaac tcataacgga atggtgttgt    3360
cgatcttgca cactaccacc actaagatac agaggtgagg atggatgttg gtacgggatg    3420
gaaatcagac cattgaaaga gaagaagaa aatctggtca gttctctggt tacagccgga    3480
catgggcaga ttgacaattt ctcattagga atcttgggaa tggcactgtt ccttgaagaa    3540
atgctcagga ctcgagtagg aacaaaacat gcaatattac tcgtcgcagt ttctttcgtg    3600
acgctaatca cagggaacat gtcttttaga gacctgggaa gagtgatggt tatggtgggt    3660
gccaccatga cagatgacat aggcatgggt gtgacttatc tcgctctact agcagctttt    3720
agagtcagac caacctttgc agctggactg ctcttgagaa aactgaccte caaggaatta    3780 atgatgacta ccataggaat cgttcttctc tcccagtta gcataccaga gaccattctt    3840
gaactgaccg acgcgttagc tctaggcatg atggtcctca gatggtgag aaacatggaa    3900 aaatatcagc tggcagtgac catcatggct attttgtgcg tcccaaatgc tgtgatatta    3960
cagaacgcat ggaaagtgag ttgcacaata ttggcagtgg tgtctgtttc cccctgctc    4020 ttaacatcct cacaacagaa agcggactgg ataccattag cgttgacgat caaaggtctt    4080
aatccaacag ccatttttct aacaaccctc tcaagaacca acaagaaaag gagctggcct    4140
ttaaatgagg ccatcatggc ggttgggatg gtgagtatct tggccagctc tctcttaaag    4200
aatgacatcc ccatgacagg accattagtg gctggagggc tccttactgt gtgctacgtg    4260
```

```
ctaactgggc ggtcagccga tctggaatta gagagagcta ccgatgtcaa atgggatgac    4320
caggcagaga tatcaggtag cagtccaatc ctgtcaataa caatatcaga agatggcagc    4380
atgtcaataa agaatgaaga ggaagagcaa acactgacta tactcattag aacaggattg    4440
cttgtgatct caggactctt tccggtatca ataccaatta cagcagcagc atggtatctg    4500
tgggaagtaa agaaacaacg ggctggagtg ctgtgggatg tcccctcacc accacccgtg    4560
ggaaaagctg aattggaaga tggagcctac agaatcaagc aaaaaggaat ccttggatat    4620
tcccagatcg gagctggagt ttacaaagaa ggaacatttc acacaatgtg gcacgtcaca    4680
cgtggcgctg tcctaatgca taaggggaag aggattgaac catcatgggc ggacgtcaag    4740
aaagacttaa tatcatatgg aggaggttgg aagctagaag agaatggaa  agaaggagaa    4800 gaagtccagg tcttggcatt ggagccaggg aaaaatccaa gagccgtcca aacaaagcct    4860
ggccttttta gaaccaacac tggaaccata ggtgccgtat ctctggactt ttcccctggg    4920
acgtcaggat ctccaatcgt cgacaaaaaa ggaaaagttg taggtctcta tggcaatggt    4980
gtcgttacaa ggagtggagc atatgtgagt gccatagctc agactgaaaa aagcattgaa    5040
gacaatccag agattgaaga tgacatcttt cgaaagagaa gattgactat catggatctc    5100
cacccaggag caggaaagac aaagagatac ctcccggcca tagtcagaga ggccataaaa    5160
agaggcttga acactaat  cctagccccc actagagtcg tggcagctga atgaggaa     5220 gcccttagag gacttccaat aagataccaa actccagcta tcagggctga gcacaccggg    5280
cgggagattg tagacttaat gtgtcatgcc acatttacca tgaggctgct atcaccaatc    5340
agggtgccaa attacaacct gatcatcatg gacgaagccc attttacaga tccagcaagc    5400
atagcagcta ggggatacat ctcaactcga gtggagatgg gggaggcagc tggaattttt    5460
atgacagcca ctcctccggg tagtagagat ccatttcctc agagcaatgc accaattatg    5520
gacgaagaaa gagaaattcc ggaacgttca tggaactctg gcacgagtg  ggtcacggat    5580 tttaaggaa  agactgtctg gtttgttcca agcataaaaa ccggaaatga catagcagcc    5640
tgcctgagaa agaatggaaa gagggtgata caactcagta ggaagacctt tgattctgaa    5700
tatgtcaaga ctagaaccaa tgactgggat ttcgtggtta caactgacat ctcggaaatg    5760
ggcgccaact ttaaagctga gagggtcata daccccagac gctgcatgaa accagttata    5820
ttgacagacg gcgaagagcg ggtgattctg gcaggaccca tgccagtgac ccactctagt    5880
gcagcacaaa aagagggag  aataggaagg aatccaagga atgaaaatga tcaatatata    5940
tatatggggg aaccactgga aaatgatgaa actgtgcgc  actggaagga agctaagatg    6000
ctcctagata tatcaacac  acctgaagga atcattccca gcttgttcga gccagagcgt    6060
gaaaaggtgg atgccattga cggtgaatat cgcttgagag gagaagcacg gaaaactttt    6120
gtggacctaa tgagaagagg agacctacca gtctggttgg cttataaagt ggcagctgaa    6180
ggtatcaact acgcagacag aagatggtgt tttgacggaa ccagaacaa  tcaaatcttg    6240 gaagaaaatg tggaagtgga aatctggaca aaggaagggg aaaggaaaaa attgaaacct    6300
agatggttag atgctaggat ctactccgac ccactggcgc taaaagagtt caaggaattt    6360
gcagccggaa gaaagtccct aaccctgaac ctaattacag atgggcag  actcccaact    6420 tttatgactc agaaggccag agatgcacta gacaacttgg cggtgctgca cacggctgaa    6480
gcgggtggaa aggcatacaa tcatgctctc agtgaattac cggagaccct ggagacattg    6540
cttttgctga cactgttggc cacagtcacg ggaggaatct tcctattcct gatgagcgga    6600
aggggtatgg ggaagatgac cctgggaatg tgctgcataa tcacggccag catcctctta    6660
```

```
tggtatgcac aaatacagcc acattggata gcagcctcaa taatattgga gttctttctc    6720
atagtcttgc tcattccaga accagaaaag cagaggacac ctcaggataa tcaattgact    6780
tatgtcatca tagccatcct cacagtggtg gccgcaacca tggcaaacga aatgggtttt    6840
ctggaaaaaa caaagaaaga cctcggactg ggaaacattg caactcagca acctgagagc    6900
aacattctgg acatagatct acgtcctgca tcagcatgga cgttgtatgc cgtggctaca    6960
acatttatca caccaatgtt gagacatagc attgaaaatt cctcagtaaa tgtgtcccta    7020
acagccatag ctaaccaagc cacagtgcta atgggtctcg aaaaggatg gccattgtca    7080
aagatggaca ttggagttcc cctccttgct attgggtgtt actcacaagt caaccctata    7140
accctcacag cggctcttct tttattggta gcacattatg ccatcatagg accgggactt    7200
caagccaaag caactagaga agctcagaaa agagcagcag cgggcatcat gaaaaaccca    7260
actgtggatg gaataacagt gatagatcta gatccaatac cctatgatcc aaagtttgaa    7320
aagcagttgg gacaagtaat gctcctagtc tctgcgtga cccaagtgct gatgatgagg    7380
actacgtggg cttttgtgtga agccttaact ctagcaactg gacccgtgtc cacattgtgg    7440
gaaggaaatc cagggagatt ctggaacaca accattgcag tgtcaatggc aaacatcttt    7500
agagggagtt acctggctgg agctggactt ctcttttcta tcatgaagaa cacaaccagc    7560
acgagaagag gaactggcaa tataggagaa acgttaggag agaaatggaa aagcagactg    7620
aacgcattgg ggaaaagtga attccagatc tacaaaaaaa gtggaattca agaagtggac    7680
agaaccttag caaagaagg cattaaaaga ggagaaacgg atcatcacgc tgtgtcgcga    7740
ggctcagcaa aactgagatg gttcgttgaa aggaatttgg tcacaccaga agggaaagta    7800
gtggaccttg gttgtggcag aggggctgg tcatactatt gtggaggatt aaagaatgta    7860
agagaagtta aaggcttaac aaaaggagga ccaggacacg aagaacctat ccctatgtca    7920
acatatgggt ggaatctagt acgcttacag agcggagttg atgttttttt tgttccacca    7980
gagaagtgtg acacattgtt gtgtgacata ggggaatcat caccaaatcc cacggtagaa    8040
gcgggacgaa cactcagagt cctcaaccta gtggaaaatt ggctgaacaa taacacccaa    8100
ttttgcgtaa aggttcttaa cccgtacatg ccctcagtca ttgaaagaat ggaaccctta    8160
caacggaaat acgaggagc cttggtgaga aatccactct cacggaattc cacacatgag    8220
atgtactggg tgtccaatgc ttccgggaac atagtgtcat cagtgaacat gatttcaaga    8280
atgctgatca acagattcac tatgagacac aagaaggcca cctatgagcc agatgtcgac    8340
ctcggaagcg gaacccgcaa tattggaatt gaaagtgaga caccgaacct agacataatt    8400
gggaaaagaa tagaaaaaat aaaacaagag catgaaacgt catggcacta tgatcaagac    8460
cacccataca aaacatgggc ttaccatggc agctatgaaa caaaacagac tggatcagca    8520
tcatccatgg tgaacggagt agtcagattg ctgacaaaac cctgggacgt tgttccaatg    8580
gtgacacaga tggcaatgac agacacaact ccttttggac aacagcgcgt cttcaaagag    8640
aaggtggata cgagaaccca agaaccaaaa gaaggcacaa aaaactaat gaaaatcacg    8700
gcagagtggc tctggaaaga actaggaaag aaaaagacac ctagaatgtg taccagaaa    8760
gaattcacaa aaaggtgag aagcaatgca gccttggggg ccatattcac cgatgagaac    8820
aagtggaaat cggcgcgtga agccgttgaa gatagtaggg tttgggagct ggttgacaag    8880
gaaaggaacc tccatcttga agggaaatgt gaaacatgtg tatacaacat gatggggaaa    8940
agagagaaaa aactaggaga gtttggtaaa gcaaaaggca gcagagccat atggtacatg    9000
tggctcggag cacgcttctt agagtttgaa gccctaggat ttttgaatga agaccattgg    9060
```

```
ttctccagag agaactccct gagtggagtg gaaggagaag ggctgcataa gctaggttac    9120
atcttaagag aggtgagcaa gaaagaagga ggagcaatgt atgccgatga caccgcaggc    9180
tgggacacaa gaatcacaat agaggatttg aaaaatgaag aaatgataac gaaccacatg    9240
gcaggagaac acaagaaact tgccgaggcc attttaaat tgacgtacca aaacaaggtg     9300
gtgcgtgtgc aaagaccaac accaagaggc acagtaatgg acatcatatc gagaagagac    9360
caaaggggta gtggacaagt tggcacctat ggcctcaaca ctttcaccaa catggaagca    9420
caactaatta ggcaaatgga gggggaagga atcttcaaaa gcatccagca cttgacagcc    9480
tcagaagaaa tcgctgtgca agattggcta gtaagagtag ggcgtgaaag gttgtcaaga    9540
atggccatca gtggagatga ttgtgttgtg aaacctttag atgatagatt tgcaagagct    9600
ctaacagctc taaatgacat gggaaaggtt aggaaggaca tacagcaatg ggagccctca    9660
agaggatgga acgactggac gcaggtgccc ttctgttcac accattttca cgagttaatt    9720
atgaaagatg gtcgcacact cgtagttcca tgcagaaacc aagatgaatt gatcggcaga    9780
gcccgaattt cccagggagc tgggtggtct ttacgggaga cggcctgttt ggggaagtct    9840
tacgcccaaa tgtggagctt gatgtacttc cacagacgtg atctcaggct agcggcaaat    9900
gccatctgct cggcagtccc atcacactgg attccaacaa gccggacaac ctggtccata    9960
cacgccagcc atgaatggat gacgacggaa gacatgttga cagtttggaa cagagtgtgg   10020
atcctagaaa atccatggat ggaagacaaa actccagtgg aatcatggga ggaaatccca   10080
tacctggaa aaagaagaa ccaatggtgc ggctcgctga ttgggctgac aagcagagcc      10140
acctgggcga agaatatcca gacagcaata aaccaagtca gatccctcat tggcaatgag   10200
gaatacacag attacatgcc atccatgaaa agattcagaa gagaagagga agaggcagga   10260
gttttgtggt agaaaaacat gaaacaaaac agaagtcagg tcggattaag ccatagtacg   10320
ggaaaaacta tgctacctgt gagccccgtc caaggacgtt aaaagaagtc aggccatttt   10380
gatgccatag cttgagcaaa ctgtgcagcc tgtagctcca cctgagaagg tgtaaaaaat   10440
ccgggaggcc acaaaccatg gaagctgtac gcatggcgta gtggactagc ggttagagga   10500
gacccctccc ttacagatcg cagcaacaat gggggcccaa ggtgagatga agctgtagtc   10560
tcactggaag gactagaggt tagaggagac ccccccaaaa caaaaaacag catattgacg   10620
ctgggaaaga ccagagatcc tgctgtctcc tcagcatcat tccaggcaca ggacgccaga   10680
aaatggaatg gtgctgttga atcaacaggt tctggtaccg gtaggcatcg tggtgtcacg   10740
ctcgtcgttt ggtatggctt cattcagctc cggttcccaa cgatcaaggc gagttacatg   10800
atcccccatg ttgtgcaaaa aagcggttag ctccttcggt cctccgatcg ttgtcagaag   10860
taagttggcc gcagtgttat cactcatggt tatggcagca ctgcataatt ctcttactgt   10920
catgccatcc gtaagatgct tttctgtgac tggtgagtac tcaaccaagt cattctgaga   10980
atagtgtatg cggcgaccga gttgctcttg cccggcgtca acgggata taccgcgcc     11040
acatagcaga actttaaaag tgctcatcat tggaaaacgt tcttcggggc gaaaactctc    11100
aaggatctta ccgctgttga gatccagttc gatgtaaccc actcgtgcac ccaactgatc   11160
ttcagcatct tttactttca ccagcgtttc tgggtgagca aaaacaggaa ggcaaaatgc   11220
cgcaaaaaag gaataaggg cgacacgaa atgttgaata ctcatactct ccttttca     11280
atattattga agcatttatc agggttattg tctcatgagc ggatacatat ttgaatgtat   11340
ttagaaaaat aaacaaatag gggttccgcg cacatttccc cgaaaagtgc cacctgacgt   11400
ctaagaaacc attattatca tgacattaac ctataaaaat aggcgtatca cgaggccctt   11460
```

```
tcgtcttcaa gaattctcat gtttgacagc ttatcatcga taagctttaa tgcggtagtt    11520
tatcacagtt aaattgctaa cgcagtcagg caccgtgtat gaaatctaac aatgcgctca    11580
tcgtcatcct cggcaccgtc accctggatg ctgtaggcat aggcttggtt atgccggtac    11640
tgccgggcct cttgcgggat atcgtccatt ccgacagcat cgccagtcac tatggcgtgc    11700
tgctggcgct atatgcgttg atgcaatttc tatgcgcacc cgttctcgga gcactgtccg    11760
accgctttgg ccgccgccca gtcctgctcg cttcgctact tggagccact atcgactacg    11820
cgatcatggc gaccacaccc gtcctgtgga tcctctacgc cggacgcatc gtggccggca    11880
tcaccggcgc cacaggtgcg gttgctggcg cctatatcgc cgacatcacc gatggggaag    11940
atcgggctcg ccacttcggg ctcatgagcg cttgtttcgg cgtgggtatg gtggcaggcc    12000
ccgtggccgg gggactgttg ggcgccatct ccttgcatgc accattcctt gcggcggcg    12060 tgctcaacgg cctcaaccta ctactgggct gcttcctaat gcaggagtcg cataagggag    12120
agcgtcgacc gatgcccttg agagccttca acccagtcag ctccttccgg tgggcgcggg    12180
gcatgactat cgtcgccgca cttatgactg tcttctttat catgcaactc gtaggacagg    12240
tgccggcagc gctctgggtc atttttcggcg aggaccgctt cgctggagc gcgacgatga    12300 tcggcctgtc gcttgcggta ttcggaatct tgcacgccct cgctcaagcc ttcgtcactg    12360
gtcccgccac caaacgtttc ggcgagaagc aggccattat cgccggcatg gcggccgacg    12420
cgctgggcta cgtcttgctg gcgttcgcga cgcgaggctg gatggccttc cccattatga    12480
ttcttctcgc ttccggcggc atcgggatgc ccgcgttgca ggccatgctg tccaggcagg    12540
tagatgacga ccatcaggga cagcttcaag gatcgctcgc ggctcttacc agcctaactt    12600
cgatcactgg accgctgatc gtcacggcga tttatgccgc ctcggcgagc acatggaacg    12660
ggttggcatg gattgtaggc gccgccctat accttgtctg cctccccgcg ttgcgtcgcg    12720
gtgcatggag ccgggccacc tcgacctgaa tggaagccgg cggcacctcg ctaacggatt    12780
caccactcca agaattggag ccaatcaatt cttgcggaga actgtgaatg cgcaaaccaa    12840
cccttggcag aacatatcca tcgcgtccgc catctccagc agccgcacgc ggcgcatctc    12900
gggcagcgtt gggtcctggc cacgggtgcg catgatcgtg ctcctgtcgt tgaggacccg    12960
gctaggctgg cggggttgcc ttactggtta gcagaatgaa tcaccgatac gcgagcgaac    13020
gtgaagcgac tgctgctgca aaacgtctgc gacctgagca acaacatgaa tggtcttcgg    13080
tttccgtgtt tcgtaaagtc tggaaacgcg gaagtcagcg ccctgcacca ttatgttccg    13140
gatctgcatc gcaggatgct gctggctacc ctgtggaaca cctacatctg tattaacgaa    13200
gcgctggcat tgaccctgag tgattttct ctggtcccgc cgcatccata ccgccagttg    13260
tttaccctca caacgttcca gtaaccgggc atgttcatca tcagtaaccc gtatcgtgag    13320
catcctctct cgtttcatcg gtatcattac ccccatgaac agaaatcccc cttacacgga    13380
ggcatcagtg accaaacagg aaaaaaccgc ccttaacatg gcccgcttta tcagaagcca    13440
gacattaacg cttctggaga aactcaacga gctggacgcg gatgaacagg cagacatctg    13500
tgaatcgctt cacgaccacg ctgatgagct ttaccgcagc tgcctcgcgc gtttcggtga    13560
tgacggtgaa aacctctgac acatgcagct cccggagacg gtcacagctt gtctgtaagc    13620
ggatgccggg agcagacaag cccgtcaggg cgcgtcagcg ggtgttggcg ggtgtcgggg    13680
cgcagccatg acccagtcac gtagcgatag cggagtgtat actggcttaa ctatgcggca    13740
tcagagcaga ttgtactgag agtgcaccat atgcggtgtg aaataccgca cagatgcgta    13800
aggagaaaat accgcatcag gcgctcttcc gcttcctcgc tcactgactc gctgcgctcg    13860
```

-continued gtcgttcggc tgcggcgagc ggtatcagct cactcaaagg cggtaatacg gttatccaca 13920
gaatcagggg ataacgcagg aaagaacatg tgagcaaaag gccagcaaaa ggccaggaac 13980
cgtaaaaagg ccgcgttgct ggcgtttttc cataggctcc gcccccctga cgagcatcac 14040
aaaaatcgac gctcaagtca gaggtggcga aacccgacag gactataaag ataccaggcg 14100
tttccccctg gaagctccct cgtgcgctct cctgttccga ccctgccgct taccggatac 14160
ctgtccgcct ttctcccttc gggaagcgtg gcgctttctc atagctcacg ctgtaggtat 14220
ctcagttcgg tgtaggtcgt tcgctccaag ctgggctgtg tgcacgaacc ccccgttcag 14280
cccgaccgct gcgccttatc cggtaactat cgtcttgagt ccaacccggt aagacacgac 14340
ttatcgccac tggcagcagc cactggtaac aggattagca gagcgaggta tgtaggcggt 14400
gctacagagt tcttgaagtg gtggcctaac tacggctaca ctagaaggac agtatttggt 14460
atctgcgctc tgctgaagcc agttaccttc ggaaaaagag ttggtagctc ttgatccggc 14520
aaacaaacca ccgctggtag cggtggtttt tttgtttgca agcagcagat tacgcgcaga 14580
aaaaaaggat ctcaagaaga tcctttgatc ttttctacgg ggtctgacgc tcagtggaac 14640
gaaaactcac gttaagggat tttggtcatg agattatcaa aaaggatctt cacctagatc 14700
cttttaaatt aaaaatgaag ttttaaatca atctaaagta tatatgagta aacttggtct 14760
gacagttacc aatgcttaat cagtgaggca cctatctcag cgatctgtct atttcgttca 14820
tccatagttg cctgactccc cgtcgtgtag ataactacga tacgggaggg cttaccatct 14880
ggccccagtg ctgcaatgat accgcgagac ccacgctcac cggctccaga tttatcagca 14940
ataaaccagc cagccggaag ggccgagcgc agaagtggtc ctgcaacttt atccgcctcc 15000
atccagtcta ttaattgttg ccgggaagct agagtaagta gttcgccagt taatagtttg 15060
cgcaacgttg ttgccattgc tgcaagatct ggctagcgat gaccctgctg attggttcgc 15120
tgaccatttc cgggcgcgcc gatttaggtg acactatag 15159

<210> SEQ ID NO 47
<211> LENGTH: 3391
<212> TYPE: PRT
<213> ORGANISM: Dengue 2 virus (Tonga/74)

<400> SEQUENCE: 47

Met Asn Asn Gln Arg Lys Lys Ala Arg Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Thr Val Gly Met Ile Ile Met Leu Thr Pro Thr Val
100 105 110

Met Ala Phe His Leu Thr Thr Arg Asn Gly Glu Pro His Met Ile Val
115 120 125

Ser Arg Gln Glu Lys Gly Lys Ser Leu Leu Phe Lys Thr Lys Asp Gly
130 135 140

```
Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
            165                 170                 175

Asp Ile Asp Cys Trp Cys Asn Ser Thr Ser Thr Trp Val Thr Tyr Gly
        180                 185                 190

Thr Cys Thr Thr Thr Gly Glu His Arg Arg Glu Lys Arg Ser Val Ala
    195                 200                 205

Leu Val Pro His Val Gly Met Gly Leu Glu Thr Arg Thr Glu Thr Trp
210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
            245                 250                 255

Thr Ile Gly Thr Thr His Phe Gln Arg Val Leu Ile Phe Ile Leu Leu
        260                 265                 270

Thr Ala Ile Ala Pro Ser Met Thr Met Arg Cys Ile Gly Ile Ser Asn
    275                 280                 285

Arg Asp Phe Val Glu Gly Val Ser Gly Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
            325                 330                 335

Arg Lys Tyr Cys Ile Glu Ala Lys Leu Thr Asn Thr Thr Thr Asp Ser
        340                 345                 350

Arg Cys Pro Thr Gln Gly Glu Pro Thr Leu Asn Glu Glu Gln Asp Lys
    355                 360                 365

Arg Phe Val Cys Lys His Ser Met Val Asp Arg Gly Trp Gly Asn Gly
370                 375                 380

Cys Gly Leu Phe Gly Lys Gly Ile Val Thr Cys Ala Met Phe Thr
385                 390                 395                 400

Cys Lys Lys Asn Met Glu Gly Lys Ile Val Gln Pro Glu Asn Leu Glu
            405                 410                 415

Tyr Thr Val Val Ile Thr Pro His Ser Gly Glu Glu His Ala Val Gly
        420                 425                 430

Asn Asp Thr Gly Lys His Gly Lys Glu Val Lys Ile Thr Pro Gln Ser
    435                 440                 445

Ser Ile Thr Glu Ala Glu Leu Thr Gly Tyr Gly Thr Val Thr Met Glu
450                 455                 460

Cys Ser Pro Arg Thr Gly Leu Asp Phe Asn Glu Met Val Leu Leu Gln
465                 470                 475                 480

Met Glu Asp Lys Ala Trp Leu Val His Arg Gln Trp Phe Leu Asp Leu
            485                 490                 495

Pro Leu Pro Trp Leu Pro Gly Ala Asp Thr Gln Gly Ser Asn Trp Ile
        500                 505                 510

Gln Lys Glu Thr Leu Val Thr Phe Lys Asn Pro His Ala Lys Lys Gln
    515                 520                 525

Asp Val Val Val Leu Gly Ser Gln Glu Gly Ala Met His Thr Ala Leu
530                 535                 540

Thr Gly Ala Thr Glu Ile Gln Met Ser Ser Gly Asn Leu Leu Phe Thr
545                 550                 555                 560
```

-continued

```
Gly His Leu Lys Cys Arg Leu Arg Met Asp Lys Leu Gln Leu Lys Gly
                565                 570                 575

Met Ser Tyr Ser Met Cys Thr Gly Lys Phe Lys Ile Val Lys Glu Ile
        580                 585                 590

Ala Glu Thr Gln His Gly Thr Ile Val Ile Arg Val Gln Tyr Glu Gly
    595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asp Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
                740                 745                 750

Thr Ser Leu Ser Val Ser Leu Val Leu Val Gly Ile Val Thr Leu Tyr
            755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Ser
    835                 840                 845

Glu Leu Asn His Ile Leu Ser Glu Asn Glu Val Lys Leu Thr Ile Met
850                 855                 860

Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
                885                 890                 895

Lys Met Leu Ser Thr Glu Leu His Asn Gln Thr Phe Leu Ile Asp Gly
            900                 905                 910

Pro Glu Thr Ala Glu Cys Pro Asn Thr Asn Arg Ala Trp Asn Ser Leu
    915                 920                 925

Glu Val Glu Asp Tyr Gly Phe Gly Val Phe Thr Thr Asn Ile Trp Leu
    930                 935                 940

Arg Leu Arg Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975
```

```
Ile Glu Ser Ala Leu Asn Asp Thr Trp Lys Ile Glu Lys Ala Ser Phe
            980                 985                 990

Ile Glu Val Lys Ser Cys His Trp Pro Lys Ser His Thr Leu Trp Ser
            995                 1000                1005

Asn Gly Val Leu Glu Ser Glu Met Val Ile Pro Lys Asn Phe Ala Gly
            1010                1015                1020

Pro Val Ser Gln His Asn Asn Arg Pro Gly Tyr Tyr Thr Gln Thr Ala
1025                1030                1035                1040

Gly Pro Trp His Leu Gly Lys Leu Glu Met Asp Phe Asp Phe Cys Glu
            1045                1050                1055

Gly Thr Thr Val Val Thr Glu Asn Cys Gly Asn Arg Gly Pro Ser
            1060                1065                1070

Leu Arg Thr Thr Thr Ala Ser Gly Lys Leu Ile Thr Glu Trp Cys Cys
            1075                1080                1085

Arg Ser Cys Thr Leu Pro Pro Leu Arg Tyr Arg Gly Glu Asp Gly Cys
1090                1095                1100

Trp Tyr Gly Met Glu Ile Arg Pro Leu Lys Glu Lys Glu Glu Asn Leu
1105                1110                1115                1120

Val Ser Ser Leu Val Thr Ala Gly His Gly Gln Ile Asp Asn Phe Ser
            1125                1130                1135

Leu Gly Ile Leu Gly Met Ala Leu Phe Leu Glu Glu Met Leu Arg Thr
            1140                1145                1150

Arg Val Gly Thr Lys His Ala Ile Leu Leu Val Ala Val Ser Phe Val
            1155                1160                1165

Thr Leu Ile Thr Gly Asn Met Ser Phe Arg Asp Leu Gly Arg Val Met
            1170                1175                1180

Val Met Val Gly Ala Thr Met Thr Asp Asp Ile Gly Met Gly Val Thr
1185                1190                1195                1200

Tyr Leu Ala Leu Leu Ala Ala Phe Arg Val Arg Pro Thr Phe Ala Ala
            1205                1210                1215

Gly Leu Leu Leu Arg Lys Leu Thr Ser Lys Glu Leu Met Met Thr Thr
            1220                1225                1230

Ile Gly Ile Val Leu Leu Ser Gln Ser Ser Ile Pro Glu Thr Ile Leu
            1235                1240                1245

Glu Leu Thr Asp Ala Leu Ala Leu Gly Met Met Val Leu Lys Met Val
1250                1255                1260

Arg Asn Met Glu Lys Tyr Gln Leu Ala Val Thr Ile Met Ala Ile Leu
1265                1270                1275                1280

Cys Val Pro Asn Ala Val Ile Leu Gln Asn Ala Trp Lys Val Ser Cys
            1285                1290                1295

Thr Ile Leu Ala Val Val Ser Val Ser Pro Leu Leu Leu Thr Ser Ser
            1300                1305                1310

Gln Gln Lys Ala Asp Trp Ile Pro Leu Ala Leu Thr Ile Lys Gly Leu
            1315                1320                1325

Asn Pro Thr Ala Ile Phe Leu Thr Thr Leu Ser Arg Thr Asn Lys Lys
            1330                1335                1340

Arg Ser Trp Pro Leu Asn Glu Ala Ile Met Ala Val Gly Met Val Ser
1345                1350                1355                1360

Ile Leu Ala Ser Ser Leu Leu Lys Asn Asp Ile Pro Met Thr Gly Pro
            1365                1370                1375

Leu Val Ala Gly Gly Leu Leu Thr Val Cys Tyr Val Leu Thr Gly Arg
            1380                1385                1390
```

-continued

```
Ser Ala Asp Leu Glu Leu Glu Arg Ala Thr Asp Val Lys Trp Asp Asp
        1395                1400                1405

Gln Ala Glu Ile Ser Gly Ser Ser Pro Ile Leu Ser Ile Thr Ile Ser
    1410                1415                1420

Glu Asp Gly Ser Met Ser Ile Lys Asn Glu Glu Glu Gln Thr Leu
1425                1430                1435                1440

Thr Ile Leu Ile Arg Thr Gly Leu Leu Val Ile Ser Gly Leu Phe Pro
                1445                1450                1455

Val Ser Ile Pro Ile Thr Ala Ala Trp Tyr Leu Trp Glu Val Lys
            1460                1465                1470

Lys Gln Arg Ala Gly Val Leu Trp Asp Val Pro Ser Pro Pro Val
        1475                1480                1485

Gly Lys Ala Glu Leu Glu Asp Gly Ala Tyr Arg Ile Lys Gln Lys Gly
    1490                1495                1500

Ile Leu Gly Tyr Ser Gln Ile Gly Ala Gly Val Tyr Lys Glu Gly Thr
1505                1510                1515                1520

Phe His Thr Met Trp His Val Thr Arg Gly Ala Val Leu Met His Lys
                1525                1530                1535

Gly Lys Arg Ile Glu Pro Ser Trp Ala Asp Val Lys Lys Asp Leu Ile
            1540                1545                1550

Ser Tyr Gly Gly Gly Trp Lys Leu Glu Gly Glu Trp Lys Glu Gly Glu
        1555                1560                1565

Glu Val Gln Val Leu Ala Leu Glu Pro Gly Lys Asn Pro Arg Ala Val
    1570                1575                1580

Gln Thr Lys Pro Gly Leu Phe Arg Thr Asn Thr Gly Thr Ile Gly Ala
1585                1590                1595                1600

Val Ser Leu Asp Phe Ser Pro Gly Thr Ser Gly Ser Pro Ile Val Asp
                1605                1610                1615

Lys Lys Gly Lys Val Val Gly Leu Tyr Gly Asn Gly Val Val Thr Arg
            1620                1625                1630

Ser Gly Ala Tyr Val Ser Ala Ile Ala Gln Thr Glu Lys Ser Ile Glu
        1635                1640                1645

Asp Asn Pro Glu Ile Glu Asp Asp Ile Phe Arg Lys Arg Arg Leu Thr
    1650                1655                1660

Ile Met Asp Leu His Pro Gly Ala Gly Lys Thr Lys Arg Tyr Leu Pro
1665                1670                1675                1680

Ala Ile Val Arg Glu Ala Ile Lys Arg Gly Leu Arg Thr Leu Ile Leu
                1685                1690                1695

Ala Pro Thr Arg Val Val Ala Ala Glu Met Glu Glu Ala Leu Arg Gly
            1700                1705                1710

Leu Pro Ile Arg Tyr Gln Thr Pro Ala Ile Arg Ala Glu His Thr Gly
        1715                1720                1725

Arg Glu Ile Val Asp Leu Met Cys His Ala Thr Phe Thr Met Arg Leu
    1730                1735                1740

Leu Ser Pro Ile Arg Val Pro Asn Tyr Asn Leu Ile Ile Met Asp Glu
1745                1750                1755                1760

Ala His Phe Thr Asp Pro Ala Ser Ile Ala Ala Arg Gly Tyr Ile Ser
                1765                1770                1775

Thr Arg Val Glu Met Gly Glu Ala Ala Gly Ile Phe Met Thr Ala Thr
            1780                1785                1790

Pro Pro Gly Ser Arg Asp Pro Phe Pro Gln Ser Asn Ala Pro Ile Met
        1795                1800                1805
```

-continued

```
Asp Glu Glu Arg Glu Ile Pro Glu Arg Ser Trp Asn Ser Gly His Glu
    1810                1815                1820
Trp Val Thr Asp Phe Lys Gly Lys Thr Val Trp Phe Val Pro Ser Ile
1825                1830                1835                1840
Lys Thr Gly Asn Asp Ile Ala Ala Cys Leu Arg Lys Asn Gly Lys Arg
                1845                1850                1855
Val Ile Gln Leu Ser Arg Lys Thr Phe Asp Ser Glu Tyr Val Lys Thr
            1860                1865                1870
Arg Thr Asn Asp Trp Asp Phe Val Val Thr Thr Asp Ile Ser Glu Met
        1875                1880                1885
Gly Ala Asn Phe Lys Ala Glu Arg Val Ile Asp Pro Arg Arg Cys Met
    1890                1895                1900
Lys Pro Val Ile Leu Thr Asp Gly Glu Glu Arg Val Ile Leu Ala Gly
1905                1910                1915                1920
Pro Met Pro Val Thr His Ser Ser Ala Ala Gln Arg Arg Gly Arg Ile
                1925                1930                1935
Gly Arg Asn Pro Arg Asn Glu Asn Asp Gln Tyr Ile Tyr Met Gly Glu
            1940                1945                1950
Pro Leu Glu Asn Asp Glu Asp Cys Ala His Trp Lys Glu Ala Lys Met
        1955                1960                1965
Leu Leu Asp Asn Ile Asn Thr Pro Glu Gly Ile Ile Pro Ser Leu Phe
    1970                1975                1980
Glu Pro Glu Arg Glu Lys Val Asp Ala Ile Asp Gly Glu Tyr Arg Leu
1985                1990                1995                2000
Arg Gly Glu Ala Arg Lys Thr Phe Val Asp Leu Met Arg Arg Gly Asp
                2005                2010                2015
Leu Pro Val Trp Leu Ala Tyr Lys Val Ala Ala Glu Gly Ile Asn Tyr
            2020                2025                2030
Ala Asp Arg Arg Trp Cys Phe Asp Gly Thr Arg Asn Asn Gln Ile Leu
        2035                2040                2045
Glu Glu Asn Val Glu Val Glu Ile Trp Thr Lys Glu Gly Glu Arg Lys
    2050                2055                2060
Lys Leu Lys Pro Arg Trp Leu Asp Ala Arg Ile Tyr Ser Asp Pro Leu
2065                2070                2075                2080
Ala Leu Lys Glu Phe Lys Glu Phe Ala Ala Gly Arg Lys Ser Leu Thr
                2085                2090                2095
Leu Asn Leu Ile Thr Glu Met Gly Arg Leu Pro Thr Phe Met Thr Gln
            2100                2105                2110
Lys Ala Arg Asp Ala Leu Asp Asn Leu Ala Val Leu His Thr Ala Glu
        2115                2120                2125
Ala Gly Gly Lys Ala Tyr Asn His Ala Leu Ser Glu Leu Pro Glu Thr
    2130                2135                2140
Leu Glu Thr Leu Leu Leu Leu Thr Leu Leu Ala Thr Val Thr Gly Gly
2145                2150                2155                2160
Ile Phe Leu Phe Leu Met Ser Gly Arg Gly Met Gly Lys Met Thr Leu
                2165                2170                2175
Gly Met Cys Cys Ile Ile Thr Ala Ser Ile Leu Leu Trp Tyr Ala Gln
            2180                2185                2190
Ile Gln Pro His Trp Ile Ala Ala Ser Ile Ile Leu Glu Phe Phe Leu
        2195                2200                2205
Ile Val Leu Leu Ile Pro Glu Pro Glu Lys Gln Arg Thr Pro Gln Asp
    2210                2215                2220
```

```
Asn Gln Leu Thr Tyr Val Ile Ala Ile Leu Thr Val Val Ala Ala
2225                2230                2235                2240

Thr Met Ala Asn Glu Met Gly Phe Leu Glu Lys Thr Lys Lys Asp Leu
        2245                2250                2255

Gly Leu Gly Asn Ile Ala Thr Gln Gln Pro Glu Ser Asn Ile Leu Asp
        2260                2265                2270

Ile Asp Leu Arg Pro Ala Ser Ala Trp Thr Leu Tyr Ala Val Ala Thr
        2275                2280                2285

Thr Phe Ile Thr Pro Met Leu Arg His Ser Ile Glu Asn Ser Ser Val
        2290                2295                2300

Asn Val Ser Leu Thr Ala Ile Ala Asn Gln Ala Thr Val Leu Met Gly
2305                2310                2315                2320

Leu Gly Lys Gly Trp Pro Leu Ser Lys Met Asp Ile Gly Val Pro Leu
                2325                2330                2335

Leu Ala Ile Gly Cys Tyr Ser Gln Val Asn Pro Ile Thr Leu Thr Ala
                2340                2345                2350

Ala Leu Leu Leu Leu Val Ala His Tyr Ala Ile Ile Gly Pro Gly Leu
                2355                2360                2365

Gln Ala Lys Ala Thr Arg Glu Ala Gln Lys Arg Ala Ala Ala Gly Ile
        2370                2375                2380

Met Lys Asn Pro Thr Val Asp Gly Ile Thr Val Ile Asp Leu Asp Pro
2385                2390                2395                2400

Ile Pro Tyr Asp Pro Lys Phe Glu Lys Gln Leu Gly Gln Val Met Leu
                2405                2410                2415

Leu Val Leu Cys Val Thr Gln Val Leu Met Met Arg Thr Thr Trp Ala
                2420                2425                2430

Leu Cys Glu Ala Leu Thr Leu Ala Thr Gly Pro Val Ser Thr Leu Trp
                2435                2440                2445

Glu Gly Asn Pro Gly Arg Phe Trp Asn Thr Thr Ile Ala Val Ser Met
2450                2455                2460

Ala Asn Ile Phe Arg Gly Ser Tyr Leu Ala Gly Ala Gly Leu Leu Phe
2465                2470                2475                2480

Ser Ile Met Lys Asn Thr Thr Ser Thr Arg Arg Gly Thr Gly Asn Ile
                2485                2490                2495

Gly Glu Thr Leu Gly Glu Lys Trp Lys Ser Arg Leu Asn Ala Leu Gly
                2500                2505                2510

Lys Ser Glu Phe Gln Ile Tyr Lys Lys Ser Gly Ile Gln Glu Val Asp
                2515                2520                2525

Arg Thr Leu Ala Lys Glu Gly Ile Lys Arg Gly Glu Thr Asp His His
        2530                2535                2540

Ala Val Ser Arg Gly Ser Ala Lys Leu Arg Trp Phe Val Glu Arg Asn
2545                2550                2555                2560

Leu Val Thr Pro Glu Gly Lys Val Val Asp Leu Gly Cys Gly Arg Gly
                2565                2570                2575

Gly Trp Ser Tyr Tyr Cys Gly Gly Leu Lys Asn Val Arg Glu Val Lys
                2580                2585                2590

Gly Leu Thr Lys Gly Gly Pro Gly His Glu Glu Pro Ile Pro Met Ser
                2595                2600                2605

Thr Tyr Gly Trp Asn Leu Val Arg Leu Gln Ser Gly Val Asp Val Phe
        2610                2615                2620

Phe Val Pro Pro Glu Lys Cys Asp Thr Leu Leu Cys Asp Ile Gly Glu
2625                2630                2635                2640
```

-continued

```
Ser Ser Pro Asn Pro Thr Val Glu Ala Gly Arg Thr Leu Arg Val Leu
            2645                2650                2655

Asn Leu Val Glu Asn Trp Leu Asn Asn Thr Gln Phe Cys Val Lys
            2660                2665                2670

Val Leu Asn Pro Tyr Met Pro Ser Val Ile Glu Arg Met Glu Thr Leu
            2675                2680                2685

Gln Arg Lys Tyr Gly Gly Ala Leu Val Arg Asn Pro Leu Ser Arg Asn
            2690                2695                2700

Ser Thr His Glu Met Tyr Trp Val Ser Asn Ala Ser Gly Asn Ile Val
2705                2710                2715                2720

Ser Ser Val Asn Met Ile Ser Arg Met Leu Ile Asn Arg Phe Thr Met
            2725                2730                2735

Arg His Lys Lys Ala Thr Tyr Glu Pro Asp Val Asp Leu Gly Ser Gly
            2740                2745                2750

Thr Arg Asn Ile Gly Ile Glu Ser Glu Thr Pro Asn Leu Asp Ile Ile
            2755                2760                2765

Gly Lys Arg Ile Glu Lys Ile Lys Gln Glu His Glu Thr Ser Trp His
            2770                2775                2780

Tyr Asp Gln Asp His Pro Tyr Lys Thr Trp Ala Tyr His Gly Ser Tyr
2785                2790                2795                2800

Glu Thr Lys Gln Thr Gly Ser Ala Ser Ser Met Val Asn Gly Val Val
            2805                2810                2815

Arg Leu Leu Thr Lys Pro Trp Asp Val Val Pro Met Val Thr Gln Met
            2820                2825                2830

Ala Met Thr Asp Thr Thr Pro Phe Gly Gln Gln Arg Val Phe Lys Glu
            2835                2840                2845

Lys Val Asp Thr Arg Thr Gln Glu Pro Lys Glu Gly Thr Lys Lys Leu
            2850                2855                2860

Met Lys Ile Thr Ala Glu Trp Leu Trp Lys Glu Leu Gly Lys Lys Lys
2865                2870                2875                2880

Thr Pro Arg Met Cys Thr Arg Glu Glu Phe Thr Lys Lys Val Arg Ser
            2885                2890                2895

Asn Ala Ala Leu Gly Ala Ile Phe Thr Asp Glu Asn Lys Trp Lys Ser
            2900                2905                2910

Ala Arg Glu Ala Val Glu Asp Ser Arg Phe Trp Glu Leu Val Asp Lys
            2915                2920                2925

Glu Arg Asn Leu His Leu Glu Gly Lys Cys Glu Thr Cys Val Tyr Asn
            2930                2935                2940

Met Met Gly Lys Arg Glu Lys Lys Leu Gly Glu Phe Gly Lys Ala Lys
2945                2950                2955                2960

Gly Ser Arg Ala Ile Trp Tyr Met Trp Leu Gly Ala Arg Phe Leu Glu
            2965                2970                2975

Phe Glu Ala Leu Gly Phe Leu Asn Glu Asp His Trp Phe Ser Arg Glu
            2980                2985                2990

Asn Ser Leu Ser Gly Val Glu Gly Glu Gly Leu His Lys Leu Gly Tyr
            2995                3000                3005

Ile Leu Arg Glu Val Ser Lys Lys Glu Gly Gly Ala Met Tyr Ala Asp
            3010                3015                3020

Asp Thr Ala Gly Trp Asp Thr Arg Ile Thr Ile Glu Asp Leu Lys Asn
3025                3030                3035                3040

Glu Glu Met Ile Thr Asn His Met Ala Gly Glu His Lys Lys Leu Ala
            3045                3050                3055
```

-continued

```
Glu Ala Ile Phe Lys Leu Thr Tyr Gln Asn Lys Val Val Arg Val Gln
            3060                3065                3070

Arg Pro Thr Pro Arg Gly Thr Val Met Asp Ile Ile Ser Arg Arg Asp
        3075                3080                3085

Gln Arg Gly Ser Gly Gln Val Gly Thr Tyr Gly Leu Asn Thr Phe Thr
    3090                3095                3100

Asn Met Glu Ala Gln Leu Ile Arg Gln Met Glu Gly Glu Gly Ile Phe
3105                3110                3115                3120

Lys Ser Ile Gln His Leu Thr Ala Ser Glu Glu Ile Ala Val Gln Asp
                3125                3130                3135

Trp Leu Val Arg Val Gly Arg Glu Arg Leu Ser Arg Met Ala Ile Ser
            3140                3145                3150

Gly Asp Asp Cys Val Val Lys Pro Leu Asp Asp Arg Phe Ala Arg Ala
        3155                3160                3165

Leu Thr Ala Leu Asn Asp Met Gly Lys Val Arg Lys Asp Ile Gln Gln
    3170                3175                3180

Trp Glu Pro Ser Arg Gly Trp Asn Asp Trp Thr Gln Val Pro Phe Cys
3185                3190                3195                3200

Ser His His Phe His Glu Leu Ile Met Lys Asp Gly Arg Thr Leu Val
                3205                3210                3215

Val Pro Cys Arg Asn Gln Asp Glu Leu Ile Gly Arg Ala Arg Ile Ser
            3220                3225                3230

Gln Gly Ala Gly Trp Ser Leu Arg Glu Thr Ala Cys Leu Gly Lys Ser
        3235                3240                3245

Tyr Ala Gln Met Trp Ser Leu Met Tyr Phe His Arg Arg Asp Leu Arg
    3250                3255                3260

Leu Ala Ala Asn Ala Ile Cys Ser Ala Val Pro Ser His Trp Ile Pro
3265                3270                3275                3280

Thr Ser Arg Thr Thr Trp Ser Ile His Ala Ser His Glu Trp Met Thr
                3285                3290                3295

Thr Glu Asp Met Leu Thr Val Trp Asn Arg Val Trp Ile Leu Glu Asn
            3300                3305                3310

Pro Trp Met Glu Asp Lys Thr Pro Val Glu Ser Trp Glu Glu Ile Pro
        3315                3320                3325

Tyr Leu Gly Lys Arg Glu Asp Gln Trp Cys Gly Ser Leu Ile Gly Leu
    3330                3335                3340

Thr Ser Arg Ala Thr Trp Ala Lys Asn Ile Gln Thr Ala Ile Asn Gln
3345                3350                3355                3360

Val Arg Ser Leu Ile Gly Asn Glu Glu Tyr Thr Asp Tyr Met Pro Ser
                3365                3370                3375

Met Lys Arg Phe Arg Arg Glu Glu Glu Glu Ala Gly Val Leu Trp
            3380                3385                3390
```

<210> SEQ ID NO 48
<211> LENGTH: 15153
<212> TYPE: DNA
<213> ORGANISM: Artificial Sequence
<220> FEATURE:
<223> OTHER INFORMATION: Dengue 3 plasmid p3

<400> SEQUENCE: 48

```
agttgttagt ctacgtggac cgacaagaac agtttcgact cggaagcttg cttaacgtag      60
tactgacagt tttttattag agagcagatc tctgatgaac aaccaacgga aaaagacggg     120
aaaaccgtct atcaatatgc tgaaacgcgt gagaaaccgt gtgtcaactg gatcacagtt     180
```

```
ggcgaagaga ttctcaagag gactgctgaa cggccaagga ccaatgaaat tggttatggc    240
gttcatagct ttcctcagat ttctagccat tccaccgaca gcaggagtct tggctagatg    300 gggaacctt aagaagtcgg gggctattaa ggtcctgaga ggcttcaaga aggagatctc    360
aaacatgctg agcattatca acagacggaa aaagacatcg ctctgtctca tgatgatgtt    420
accagcaaca cttgctttcc acttgacttc acgagatgga gagccgcgca tgattgtggg    480
gaagaatgaa agaggaaaat ccctactttt taagacagcc tctggaatca acatgtgcac    540
actcatagcc atggatttgg gagagatgtg tgatgacacg gtcacctaca aatgcccct    600 cattactgaa gtggagcctg aagacattga ctgctggtgc aaccttacat cgacatgggt    660
gacctacgga acgtgcaatc aagctggaga gcacagacgc gacaaaagat cggtggcgtt    720
agctccccat gtcggcatgg gactggacac acgcacccaa acctggatgt cggctgaagg    780
agcttggaga caggtcgaga aggtagagac atgggccttt aggcacccag ggttcacaat    840
actagcccta tttcttgccc attacatagg cacttccttg acccagaaag tggttatttt    900
catactacta atgctggtca ccccatccat gacaatgaga tgcgtgggag taggaaacag    960
agattttgtg gaaggcctat caggagctac gtgggttgac gtggtgctcg agcacggtgg    1020
gtgtgtgact accatggcta agaacaagcc cacgctggat atagagctcc agaagaccga    1080
ggccacccaa ctggcgaccc taaggaaact atgtattgag ggaaaaatta ccaacgtaac    1140
aaccgactca aggtgcccca cccaagggga agcgatttta cctgaggagc aggaccagaa    1200
ccacgtgtgc aagcacacat acgtggacag aggctgggga aacggttgtg gtttgtttgg    1260
caagggaagc ctggtaacat gcgcgaaatt tcaatgtttg gaatcaatag agggaaaagt    1320
ggtgcagcat gagaacctca aatacaccgt catcatcaca gtgcacacag agatcaaca    1380 ccaggtggga aatgaaacgc agggagtcac ggctgagata cacccccagg catcaaccgt    1440
tgaagccatc ttacctgaat atggaacct tgggctagaa tgctcaccac ggacaggttt    1500
agattccaat gaaatgattt tgttgacaat gaagaacaaa gcatggatgg tacatagaca    1560 atggttttt gacctacctt taccatggac atcaggagct acaacagaaa caccaacctg    1620
gaataagaaa gagcttcttg tgacattcaa aaacgcacat gcaaaaaagc aagaagtagt    1680
agtccttgga tcgcaagagg gagcaatgca cacagcactg acaggagcta cagagatcca    1740
aacctcagga ggcacaagta tttttgcggg gcacttaaaa tgtagactca agatggacaa    1800
attggaactc aagggggatga gctatgcaat gtgcttgaat gcctttgtgt tgaagaaaga    1860
agtctccgaa acgcaacatg gacaatact catcaaggt gagtacaaag gggaagatgc    1920
accttgcaag attcctttct ccacggagga tggacaaggg aaagcccaca atggcagact    1980
gatcacagct aacccagtgg tgaccaagaa ggaggagcct gtcaatattg aggcagaacc    2040
tccttttggg gaaagcaata tagtaattgg aattggagac aaagccttga aaatcaactg    2100
gtacaagaag ggaagctcga ttgggaagat gttcgaggcc actgccagag gtgcaaggcg    2160
catggccatc ttgggagaca cagcctggga ctttggatca gtaggtggtg ttttaaattc    2220
attaggaaaa atggtgcacc aaatatttgg aagtgcttac acagccctat ttagtggagt    2280
ctcctggata atgaaaattg gataggtgt ccttttaacc tggataggt gaattcaaa    2340 aaacactagt atgagctta gctgcattgt gataggaatc attacactct atctgggagc    2400
cgtggtgcaa gctgacatgg ggtgtgtcat aaactggaaa ggcaaagaac tcaaatgtgg    2460
aagtggaatt tcgtcacta atgaggtcca cacctggaca gagcaataca aatttcaagc    2520
agactccccc aaaagactgg cgacagccat tgcaggcgct tgggagaatg gagtgtgcgg    2580
```

```
aatcaggtcg acaaccagaa tggagaacct cttgtggaag caaatagcca atgaactgaa    2640
ctacatatta tgggaaaaca acatcaaatt aacggtagtt gtgggtgata taattgggt    2700
cttagagcaa gggaaaagaa cactaacacc acaacccatg gaactaaaat attcatggaa    2760
aacatgggga aaggcgaaga tagtgacagc tgaaacacaa aattcctctt tcataataga    2820
tgggccaaac acaccagagt gtccaagtgc ctcaagagca tggaatgtgt gggaggtgga    2880
agattacggg ttcggagtct tcacaactaa catatggctg aaactccgag agatgtacac    2940
ccaactatgt gaccacaggc taatgtcggc agccgttaag gatgagaggg ccgtacacgc    3000
cgacatgggc tattggatag aaagccaaaa gaatggaagt tggaagctag aaaaggcatc    3060
cctcatagag gtaaaaacct gcacatggcc aaaatcacac actctttgga gcaatggtgt    3120
gctagagagt gacatgatca tcccaaagag tctggctggt cccatttcgc aacacaacta    3180
caggcccgga taccacaccc aaacggcagg accctggcac ttaggaaaat tggagctgga    3240
cttcaactat tgtgaaggaa caacagttgt catcacagaa aattgtggga caagaggccc    3300
atcactgaga acaacaacag tgtcaggaaa gttgatacac aatggtgtt gccgctcgtg    3360
tacacttcct cccctgcgat acatgggaga agacggctgc tggtatgcca tggaaattag    3420
acccattaat gagaaagaag agaacatggt aaagtcttta gtctcagcag ggagtggaaa    3480
ggtggataac ttcacaatgg gtgtcttgtg tttggcaatc cttttgaag aggtgatgag    3540
aggaaaattt gggaaaaagc acatgattgc aggggttctc ttcacgtttg tactccttct    3600
ctcagggcaa ataacatgga gagacatggc gcacacactc ataatgattg ggtccaacgc    3660
ctctgacaga atgggaatgg gcgtcactta cctagcattg attgcaacat ttaaaattca    3720
gccattttg gctttgggat tcttcctgag gaaactgaca tctagagaaa atttattgtt    3780
gggagttggg ttggccatgg caacaacgtt acaactgcca gaggacattg aacaaatggc    3840
gaatggaata gctttagggc tcatggctct taaattaata acacaatttg aaacatacca    3900
actatggacg gcattagtct ccctaatgtg ttcaaataca attttcacgt tgactgttgc    3960
ctggagaaca gccaccctga ttttggccgg aatttctctt ttgccagtgt gccagtcttc    4020
gagcatgagg aaaacagatt ggctcccaat ggctgtggca gctatgggag ttccacccct    4080
accacttttt attttcagtt tgaaagatac gctcaaaagg agaagctggc cactgaatga    4140
gggggtgatg gctgttggac ttgtgagtat tctagctagt tctctcctta ggaatgacgt    4200
gcccatggct ggaccattag tggctggggg ccttctgata gcgtgctacg tcataactgg    4260
cacgtcagca gacctcactg tagaaaaagc agcagatgtg acatgggagg aagaggctga    4320
gcaaacagga gtgtcccaca atttaatgat cacagttgat gacgatgaa caatgagaat    4380
aaaagatgat gagactgaga acatcttaac agtgcttttg aaaacagcat tactaatagt    4440
gtcaggcatt tttccatact ccataccgc aacactgttg gtctggcaca cttggcaaaa    4500
gcaaacccaa agatccggtg tcctatggga cgttcccagc cccccagaga cacagaaagc    4560
agaactggaa gagggggtt ataggatcaa gcagcaagga ttttttggga aacccaagt    4620
ggggggttgga gtacaaaaag aaggagtttt ccacaccatg tggcacgtca agagagagc    4680
agtgttgaca cacaatgggga aaagactgga accaaactgg gctagcgtga aaaagatct    4740
gatttcatac ggaggaggat ggaaattgag tgcacaatgg caaaaggag aggaggtgca    4800
ggttattgcc gtagagcctg gaagaaccc aaagaacttt caaaccatgc caggcatttt    4860
ccagacaaca acaggggaga taggagcgat tgcactggac ttcaagcctg aacttcagg    4920
atctcccatc ataaacagag agggaaaggt actgggattg tatggcaatg gagtggtcac    4980
```

```
aaagaatggt ggctatgtca gtggaatagc acaaacaaat gcagaaccag acggaccgac   5040
accagagttg gaagaagaga tgttcaaaaa gcgaaatcta accataatgg atctccatcc   5100
cgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggagaga   5280 gattgttgat ctaatgtgcc acgcaacgtt cacaatgcgt ttgctgtcac cagtcagggt   5340
tccaaactac aacttgataa taatggatga ggctcatttc acagaccag ccagtatagc    5400 ggctagaggg tacatatcaa ctcgtgtagg aatgggagag gcagccgcaa ttttcatgac   5460
agccacaccc cctggaacag ctgatgcctt tcctcagagc aacgctccaa ttcaagatga   5520
agaaagagac ataccagaac gctcatggaa ttcaggcaat gaatggatta ccgactttgc   5580
cgggaagacg gtgtggtttg tccctagcat caaagctgga aatgacatag caaactgctt   5640
gcggaaaaat ggaaaaaagg tcattcaact tagtaggaag acttttgaca cagaatatca   5700
aaagactaaa ctaaatgatt gggactttgt ggtgacaaca gacatttcag aaatgggagc   5760
caatttcaaa gcagacagag tgatcgaccc aagaagatgt ctcaagccag tgattttgac   5820
agacggaccc gagcgcgtga tcctggcggg accaatgcca gtcaccgtag cgagcgctgc   5880 gcaaggaga gggagagttg gcaggaaccc acaaaaagaa aatgaccaat acatattcat    5940
gggccagccc ctcaataatg atgaagacca tgctcactgg acagaagcaa aaatgctgct   6000
agacaacatc aacacaccag aagggatcat accagctctc tttgaaccag aaagggagaa   6060
gtcagccgcc atagacggcg aataccgcct gaagggtgag tccaggaaga ccttcgtgga   6120
actcatgagg aggggtgacc tcccagtttg gctagcccat aaagtagcat cagaagggat   6180
caaatataca gatagaaagt ggtgttttga tggagaacgc aacaatcaaa ttttagagga   6240
gaatatggat gtgaaatct ggacaaagga aggagaaaag aaaaaattga gacctagtg     6300 gcttgatgcc cgcacttatt cagatccctt agcgctcaag gaattcaagg actttgcggc   6360
tggtagaaag tcaattgccc ttgatcttgt gacagaaata ggaagagtgc cttcacactt   6420
agctcacaga acgagaaacg ccctggacaa tctggtgatg ttgcacacgt cagaacatgg   6480 cgggaggggcc tacaggcatg cagtggagga actaccagaa acaatggaaa cactcttact   6540
cctgggactc atgatcctgt aacaggtgg agcaatgctt ttcttgatat caggtaaagg   6600
gattggaaag acttcaatag gactcatttg tgtagctgct tccagcggta tgttatggat   6660
ggctgatgtc ccactccaat ggatcgcgtc tgccatagtc ctggagtttt ttatgatggt   6720
gttacttata ccagaaccag aaaagcagag aactccccaa gacaatcaac tcgcatatgt   6780
cgtgataggc atactcacac tggctgcaat agtagcagcc aatgaaatgg gactgttgga   6840
aaccacaaag agagatttag gaatgtccaa agaaccaggt gttgtttctc caaccagcta   6900
tttggatgtg gacttgcacc cagcatcagc ctggacattg tacgctgtgg ccacaacagt   6960
aataacacca atgttgagac ataccataga gaattccaca gcaaatgtgt ccctggcagc   7020
tatagccaac caggcagtgg tcctgatggg tttagacaaa ggatggccga tatcgaaaat   7080
ggacttaggc gtgccactat ggcactgggt tgttattca caagtgaacc cactaactct    7140
cacagcggca gttctcctgc tagtcacgca ttatgctatt ataggtccag gattgcaggc   7200
aaaagccact cgtgaagctc aaaaaaggac agctgctgga ataatgaaga atccaacggt   7260
ggatgggata atgacaatag accctagatcc tgtaatatac gattcaaaat ttgaaaagca   7320
actaggacag gttatgctcc tggttctgtg tgcagttcaa cttttgttaa tgagaacatc   7380
```

```
atgggctttt tgtgaagctc taaccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg aacaggaaa    7560 gagagggaca gggtcacagg gtgaaacctt gggagaaaag tggaaaaaga aattgaatca   7620 attacccgg  aaagagtttg acctttacaa gaaatccgga atcactgaag tggatagaac   7680
agaagccaaa gaagggttga aaagaggaga ataacacac  catgccgtgt ccagaggcag   7740
cgcaaaactt caatggttcg tggagagaaa catggtcatc cccgaaggaa gagtcataga   7800
cttaggctgt ggaagaggag gctggtcata ttattgtgca ggactgaaaa aagttacaga   7860
agtgcgagga tacacaaaag gcggcccagg acatgaagaa ccagtaccta tgtctacata   7920
cggatggaac atagtcaagt taatgagtgg aaaggatgtg ttttatcttc cacctgaaaa   7980
gtgtgatact ctattgtgtg acattggaga atcttcacca agcccaacag tggaagaaag   8040
cagaaccata agagtcttga agatggttga accatggcta aaaataaccc agttttgcat   8100
taaagtattg aacccttaca tgccaactgt gattgagcac ctagaaagac tacaaaggaa   8160
acatggagga atgcttgtga gaaatccact ctcacgaaac tccacgcacg aaatgtactg   8220
gatatctaat ggcacaggca atatcgtttc ttcagtcaac atggtatcca gattgctact   8280
taacagattc acaatgacac ataggagacc caccatagag aaagatgtgg atttaggagc   8340
ggggacccga catgtcaatg cggaaccaga acacccaac  atggatgtca ttggggaaag   8400
aataagaagg atcaaggagg agcatagttc aacatggcac tatgatgatg aaaatcctta   8460
taaaacgtgg gcttaccatg gatcctatga agttaaggcc acaggctcag cctcctccat   8520
gataaatgga gtcgtgaaac tcctcacgaa accatgggg  tggtgccca tggtgacaca   8580 gatggcaatg acggatacaa ccccattcgg ccagcaaagg gtttttaaag agaaagtgga   8640
caccaggaca cccagaccta tgccaggaac aagaaaggtt atggagatca cagcggaatg   8700
gctttggaga acctgggaa  ggaacaaaag acccagatta tgtacgagag aggagttcac   8760 aaaaaggtc  agaaccaacg cagctatggg cgccgttttt acagaggaga accaatggga   8820
cagtgctaga gctgctgttg aggatgaaga attctggaaa ctcgtggaca gagaacgtga   8880
actccacaaa ttgggcaagt gtggaagctg cgtttacaac atgatgggca agagagagaa   8940
gaaacttgga gagtttggca aagcaaaagg cagtagagcc atatggtaca tgtggttggg   9000
agccagatac cttgagttcg aagcactcgg attcttaaat gaagaccatt ggttctcgcg   9060
tgaaaactct tacagtggag tagaaggaga aggactgcac aagctgggat acatcttaag   9120
agacatttcc aagatacccg gaggagctat gtatgctgat gacacagctg gttgggacac   9180
aagaataaca gaagatgacc tgcacaatga ggaaaaaatc acacagcaaa tggacctga   9240 acacaggcag ttagcaaacg ctatattcaa gctcacatac caaaacaaag tggtcaaagt   9300
tcaacgacca actccaaagg gcacggtaat ggacatcata tctaggaaag accaagagg   9360 cagtggacag gtgggaactt atggtctgaa tacattcacc aacatggaag cccagttaat   9420
cagacaaatg gaaggagaag gtgtgttgtc gaaggcagac tcgagaacc  ctcatctgct   9480 agagaagaaa gttacacaat ggttggaaac aaaaggagtg gagaggttaa aagaatggc    9540 catcagcggg gatgattgcg tggtgaaacc aattgatgac aggttcgcca atgccctgct   9600
tgccctgaat gacatgggaa agttaggaa  ggacatacct caatggcagc catcaaaggg   9660
atggcatgat tggcaacagg tcccttctg  ctcccaccac tttcatgaat tgatcatgaa   9720
agatggaaga aagttggtag ttcctgcag  acctcaggat gaattaatcg ggagagcgag   9780
```

```
aatctctcaa ggagcaggat ggagccttag agaaactgca tgcctaggga aagcctacgc    9840
ccaaatgtgg actctcatgt actttcacag aagagatctt agactagcat ccaacgccat    9900
atgttcagca gtaccagtcc attgggtccc cacaagcaga acgacgtggt ctattcatgc    9960
tcaccatcag tggatgacta cagaagacat gcttactgtt tggaacaggg tgtggataga   10020
ggataatcca tggatggaag acaaaactcc agtcaaaacc tgggaagatg ttccatatct   10080
agggaagaga gaagaccaat ggtgcggatc actcattggt ctcacttcca gagcaacctg   10140
ggcccagaac atacttacgg caatccaaca ggtgagaagc cttataggca atgaagagtt   10200
tctggactac atgccttcga tgaagagatt caggaaggag gaggagtcag agggagccat   10260
ttggtaaacg taggaagtga aaagaggca aactgtcagg ccaccttaag ccacagtacg   10320
gaagaagctg tgcagcctgt gagccccgtc caaggacgtt aaaagaagaa gtcaggccca   10380
aaagccacgg tttgagcaaa ccgtgctgcc tgtggctccg tcgtgggac gtaaaacctg   10440 ggaggctgca aactgtggaa gctgtacgca cggtgtagca gactagcggt tagaggagac   10500
ccctcccatg acacaacgca gcagcggggc ccgagctctg agggaagctg tacctccttg   10560
caaaggacta gaggttagag gagaccccc gcaaataaaa acagcatatt gacgctggga   10620
gagaccagag atcctgctgt ctcctcagca tcattccagg cacagaacgc cagaaaatgg   10680
aatggtgctg ttgaatcaac aggttctggt accggtaggc atcgtggtgt cacgctcgtc   10740
gtttggtatg gcttcattca gctccggttc ccaacgatca aggcgagtta catgatcccc   10800
catgttgtgc aaaaaagcgg ttagctcctt cggtcctccg atcgttgtca gaagtaagtt   10860
ggccgcagtg ttatcactca tggttatggc agcactgcat aattctctta ctgtcatgcc   10920
atccgtaaga tgcttttctg tgactggtga gtactcaacc aagtcattct gagaatagtg   10980
tatgcggcga ccgagttgct cttgcccggc gtcaacacgg ataataccg cgccacatag   11040 cagaacttta aaagtgctca tcattggaaa acgttcttcg gggcgaaaac tctcaaggat   11100
cttaccgctg ttgagatcca gttcgatgta acccactcgt gcacccaact gatcttcagc   11160
atcttttact ttcaccagcg tttctgggtg agcaaaaaca ggaaggcaaa atgccgcaaa   11220
aaagggaata agggcgacac ggaaatgttg aatactcata ctcttccttt ttcaatatta   11280
ttgaagcatt tatcagggtt attgtctcat gagcggatac atatttgaat gtatttagaa   11340
aaataaacaa atagggggttc cgcgcacatt tccccgaaaa gtgccacctg acgtctaaga   11400
aaccattatt atcatgacat taacctataa aaataggcgt atcacgaggc cctttcgtct   11460
tcaagaattc tcatgtttga cagcttatca tcgataagct ttaatgcggt agtttatcac   11520
agttaaattg ctaacgcagt caggcaccgt gtatgaaatc taacaatgcg ctcatcgtca   11580
tcctcggcac cgtcaccctg gatgctgtag gcataggctt ggttatgccg gtactgccgg   11640
gcctcttgcg ggatatcgtc cattccgaca gcatcgccag tcactatggc gtgctgctgg   11700
cgctatatgc gttgatgcaa tttctatgcg cacccgttct cggagcactg tccgaccgct   11760
ttggccgccg cccagtcctg ctcgcttcgc tacttggagc cactatcgac tacgcgatca   11820
tggcgaccac accgtcctg tggatcctct acgccggacg catcgtggcc ggcatcaccg   11880
gcgccacagg tgcggttgct ggcgcctata tcgccgacat caccgatggg gaagatcggg   11940
ctcgccactt cgggctcatg agcgcttgtt tcggcgtggg tatggtggca ggccccgtgg   12000 ccggggact gttgggcgcc atctccttgc atgcaccatt ccttgcggcg gcggtgctca   12060
acggcctcaa cctactactg ggctgcttcc taatgcagga gtcgcataag ggagagcgtc   12120
gaccgatgcc cttgagagcc ttcaacccag tcagctcctt ccggtgggcg cggggcatga   12180
```

```
ctatcgtcgc cgcacttatg actgtcttct ttatcatgca actcgtagga caggtgccgg    12240
cagcgctctg ggtcattttc ggcgaggacc gctttcgctg gagcgcgacg atgatcggcc    12300
tgtcgcttgc ggtattcgga atcttgcacg ccctcgctca agccttcgtc actggtcccg    12360
ccaccaaacg tttcggcgag aagcaggcca ttatcgccgg catggcggcc gacgcgctgg    12420
gctacgtctt gctggcgttc gcgacgcgag gctggatggc cttccccatt atgattcttc    12480
tcgcttccgg cggcatcggg atgcccgcgt tgcaggccat gctgtccagg caggtagatg    12540
acgaccatca gggacagctt caaggatcgc tcgcggctct taccagccta acttcgatca    12600
ctggaccgct gatcgtcacg gcgatttatg ccgcctcggc gagcacatgg aacgggttgg    12660
catggattgt aggcgccgcc ctataccttg tctgcctccc cgcgttgcgt cgcggtgcat    12720
ggagccgggc cacctcgacc tgaatggaag ccggcggcac ctcgctaacg gattcaccac    12780
tccaagaatt ggagccaatc aattcttgcg gagaactgtg aatgcgcaaa ccaacccttg    12840
gcagaacata tccatcgcgt ccgccatctc cagcagccgc acgcggcgca tctcgggcag    12900
cgttgggtcc tggccacggg tgcgcatgat cgtgctcctg tcgttgagga cccggctagg    12960
ctggcggggt tgccttactg gttagcagaa tgaatcaccg atacgcgagc gaacgtgaag    13020
cgactgctgc tgcaaaacgt ctgcgacctg agcaacaaca tgaatggtct tcggtttccg    13080
tgtttcgtaa agtctggaaa cgcggaagtc agcgccctgc accattatgt tccggatctg    13140
catcgcagga tgctgctggc taccctgtgg aacacctaca tctgtattaa cgaagcgctg    13200
gcattgaccc tgagtgattt ttctctggtc ccgccgcatc cataccgcca gttgtttacc    13260
ctcacaacgt tccagtaacc gggcatgttc atcatcagta acccgtatcg tgagcatcct    13320
ctctcgtttc atcggtatca ttaccccccat gaacagaaat ccccccttaca cggaggcatc    13380
agtgaccaaa caggaaaaaa ccgcccttaa catggcccgc tttatcagaa gccagacatt    13440
aacgcttctg gagaaactca acgagctgga cgcggatgaa caggcagaca tctgtgaatc    13500
gcttcacgac cacgctgatg agctttaccg cagctgcctc gcgcgtttcg gtgatgacgg    13560
tgaaaacctc tgcacacatg cagctcccgga gacggtcaca gcttgtctgt aagcggatgc    13620
cgggagcaga caagcccgtc agggcgcgtc agcgggtgtt ggcgggtgtc ggggcgcagc    13680
catgacccag tcacgtagcg atagcggagt gtatactggc ttaactatgc ggcatcagag    13740
cagattgtac tgagagtgca ccatatgcgg tgtgaaatac cgcacagatg cgtaaggaga    13800
aaataccgca tcaggcgctc ttccgcttcc tcgctcactg actcgctgcg ctcggtcgtt    13860
cggctgcggc gagcggtatc agctcactca aaggcggtaa tacggttatc cacagaatca    13920
ggggataacg caggaaagaa catgtgagca aaaggccagc aaaaggccag gaaccgtaaa    13980
aaggccgcgt tgctggcgtt tttccatagg ctccgccccc ctgacgagca tcacaaaaat    14040
cgacgctcaa gtcagaggtg gcgaaacccg acaggactat aaagatacca ggcgtttccc    14100
cctggaagct ccctcgtgcg ctctcctgtt ccgaccctgc cgcttaccgg atacctgtcc    14160
gcctttctcc cttcgggaag cgtggcgctt tctcatagct cacgctgtag gtatctcagt    14220
tcggtgtagg tcgttcgctc caagctgggc tgtgtgcacg aaccccccgt tcagcccgac    14280
cgctgcgcct tatccggtaa ctatcgtctt gagtccaacc cggtaagaca cgacttatcg    14340
ccactggcag cagccactgg taacaggatt agcagagcga gtatgtagg cggtgctaca    14400
gagttcttga agtggtggcc taactacggc tacactagaa ggacagtatt tggtatctgc    14460
gctctgctga agccagttac cttcggaaaa agagttggta gctcttgatc cggcaaacaa    14520
accaccgctg gtagcggtgg ttttttttgtt tgcaagcagc agattacgcg cagaaaaaaa    14580
```

-continued

```
ggatctcaag aagatccttt gatcttttct acggggtctg acgctcagtg gaacgaaaac  14640
tcacgttaag ggattttggt catgagatta tcaaaaagga tcttcaccta gatcctttta  14700
aattaaaaat gaagttttaa atcaatctaa agtatatatg agtaaacttg gtctgacagt  14760
taccaatgct taatcagtga ggcacctatc tcagcgatct gtctatttcg ttcatccata  14820
gttgcctgac tccccgtcgt gtagataact acgatacggg agggcttacc atctggcccc  14880
agtgctgcaa tgataccgcg agacccacgc tcaccggctc cagatttatc agcaataaac  14940
cagccagccg gaagggccga gcgcagaagt ggtcctgcaa ctttatccgc ctccatccag  15000
tctattaatt gttgccggga agctagagta agtagttcgc cagttaatag tttgcgcaac  15060
gttgttgcca ttgctgcaag atctggctag cgatgaccct gctgattggt tcgctgacca  15120
tttccgggcg cgccgattta ggtgacacta tag                                15153
```

```

<210> SEQ ID NO 49
<211> LENGTH: 3390
<212> TYPE: PRT
<213> ORGANISM: Dengue 3 (Sleman/78) virus

<400> SEQUENCE: 49

Met Asn Asn Gln Arg Lys Lys Thr Gly Lys Pro Ser Ile Asn Met Leu
 1               5                  10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Arg Gly Phe Lys Lys Glu Ile Ser Asn Met Leu Ser Ile Ile Asn
                85                  90                  95

Arg Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro Leu Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Phe Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270
```

```
Met Leu Val Thr Pro Ser Met Thr Met Arg Cys Val Gly Val Gly Asn
            275                 280                 285

Arg Asp Phe Val Glu Gly Leu Ser Gly Ala Thr Trp Val Asp Val Val
        290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Val Thr Thr Asp Ser
            340                 345                 350

Arg Cys Pro Thr Gln Gly Glu Ala Ile Leu Pro Glu Glu Gln Asp Gln
        355                 360                 365

Asn His Val Cys Lys His Thr Tyr Val Asp Arg Gly Trp Gly Asn Gly
370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Val Glu Ala Ile Leu Pro Glu Tyr Gly Thr Leu Gly Leu Glu Cys Ser
450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Thr Glu Thr Pro Thr Trp Asn Lys Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Asn Ala Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685
```

-continued

```
Arg Met Ala Ile Leu Gly Asp Thr Ala Trp Asp Phe Gly Ser Val Gly
    690                 695                 700
Gly Val Leu Asn Ser Leu Gly Lys Met Val His Gln Ile Phe Gly Ser
705                 710                 715                 720
Ala Tyr Thr Ala Leu Phe Ser Gly Val Ser Trp Ile Met Lys Ile Gly
                725                 730                 735
Ile Gly Val Leu Leu Thr Trp Ile Gly Leu Asn Ser Lys Asn Thr Ser
            740                 745                 750
Met Ser Phe Ser Cys Ile Val Ile Gly Ile Ile Thr Leu Tyr Leu Gly
        755                 760                 765
Ala Val Val Gln Ala Asp Met Gly Cys Val Ile Asn Trp Lys Gly Lys
770                 775                 780
Glu Leu Lys Cys Gly Ser Gly Ile Phe Val Thr Asn Glu Val His Thr
785                 790                 795                 800
Trp Thr Glu Gln Tyr Lys Phe Gln Ala Asp Ser Pro Lys Arg Leu Ala
                805                 810                 815
Thr Ala Ile Ala Gly Ala Trp Glu Asn Gly Val Cys Gly Ile Arg Ser
            820                 825                 830
Thr Thr Arg Met Glu Asn Leu Leu Trp Lys Gln Ile Ala Asn Glu Leu
        835                 840                 845
Asn Tyr Ile Leu Trp Glu Asn Asn Ile Lys Leu Thr Val Val Val Gly
850                 855                 860
Asp Ile Ile Gly Val Leu Glu Gln Gly Lys Arg Thr Leu Thr Pro Gln
865                 870                 875                 880
Pro Met Glu Leu Lys Tyr Ser Trp Lys Thr Trp Gly Lys Ala Lys Ile
                885                 890                 895
Val Thr Ala Glu Thr Gln Asn Ser Ser Phe Ile Ile Asp Gly Pro Asn
            900                 905                 910
Thr Pro Glu Cys Pro Ser Ala Ser Arg Ala Trp Asn Val Trp Glu Val
        915                 920                 925
Glu Asp Tyr Gly Phe Gly Val Phe Thr Thr Asn Ile Trp Leu Lys Leu
930                 935                 940
Arg Glu Met Tyr Thr Gln Leu Cys Asp His Arg Leu Met Ser Ala Ala
945                 950                 955                 960
Val Lys Asp Glu Arg Ala Val His Ala Asp Met Gly Tyr Trp Ile Glu
                965                 970                 975
Ser Gln Lys Asn Gly Ser Trp Lys Leu Glu Lys Ala Ser Leu Ile Glu
            980                 985                 990
Val Lys Thr Cys Thr Trp Pro Lys Ser His Thr Leu Trp Ser Asn Gly
        995                 1000                1005
Val Leu Glu Ser Asp Met Ile Ile Pro Lys Ser Leu Ala Gly Pro Ile
    1010                1015                1020
Ser Gln His Asn Tyr Arg Pro Gly Tyr His Thr Gln Thr Ala Gly Pro
1025                1030                1035                1040
Trp His Leu Gly Lys Leu Glu Leu Asp Phe Asn Tyr Cys Glu Gly Thr
                1045                1050                1055
Thr Val Val Ile Thr Glu Asn Cys Gly Thr Arg Gly Pro Ser Leu Arg
            1060                1065                1070
Thr Thr Thr Val Ser Gly Lys Leu Ile His Glu Trp Cys Cys Arg Ser
        1075                1080                1085
Cys Thr Leu Pro Pro Leu Arg Tyr Met Gly Glu Asp Gly Cys Trp Tyr
    1090                1095                1100
```

```
Gly Met Glu Ile Arg Pro Ile Asn Glu Lys Glu Asn Met Val Lys
1105                1110                1115                1120

Ser Leu Val Ser Ala Gly Ser Lys Val Asp Asn Phe Thr Met Gly
        1125                1130                1135

Val Leu Cys Leu Ala Ile Leu Phe Glu Glu Val Met Arg Gly Lys Phe
    1140                1145                1150

Gly Lys Lys His Met Ile Ala Gly Val Leu Phe Thr Phe Val Leu Leu
        1155                1160                1165

Leu Ser Gly Gln Ile Thr Trp Arg Asp Met Ala His Thr Leu Ile Met
    1170                1175                1180

Ile Gly Ser Asn Ala Ser Asp Arg Met Gly Met Gly Val Thr Tyr Leu
1185                1190                1195                1200

Ala Leu Ile Ala Thr Phe Lys Ile Gln Pro Phe Leu Ala Leu Gly Phe
        1205                1210                1215

Phe Leu Arg Lys Leu Thr Ser Arg Glu Asn Leu Leu Leu Gly Val Gly
        1220                1225                1230

Leu Ala Met Ala Thr Thr Leu Gln Leu Pro Glu Asp Ile Glu Gln Met
        1235                1240                1245

Ala Asn Gly Ile Ala Leu Gly Leu Met Ala Leu Lys Leu Ile Thr Gln
        1250                1255                1260

Phe Glu Thr Tyr Gln Leu Trp Thr Ala Leu Val Ser Leu Met Cys Ser
1265                1270                1275                1280

Asn Thr Ile Phe Thr Leu Thr Val Ala Trp Arg Thr Ala Thr Leu Ile
                1285                1290                1295

Leu Ala Gly Ile Ser Leu Leu Pro Val Cys Gln Ser Ser Met Arg
        1300                1305                1310

Lys Thr Asp Trp Leu Pro Met Ala Val Ala Ala Met Gly Val Pro Pro
        1315                1320                1325

Leu Pro Leu Phe Ile Phe Ser Leu Lys Asp Thr Leu Lys Arg Arg Ser
        1330                1335                1340

Trp Pro Leu Asn Glu Gly Val Met Ala Val Gly Leu Val Ser Ile Leu
1345                1350                1355                1360

Ala Ser Ser Leu Leu Arg Asn Asp Val Pro Met Ala Gly Pro Leu Val
                1365                1370                1375

Ala Gly Gly Leu Leu Ile Ala Cys Tyr Val Ile Thr Gly Thr Ser Ala
                1380                1385                1390

Asp Leu Thr Val Glu Lys Ala Ala Asp Val Thr Trp Glu Glu Glu Ala
                1395                1400                1405

Glu Gln Thr Gly Val Ser His Asn Leu Met Ile Thr Val Asp Asp Asp
        1410                1415                1420

Gly Thr Met Arg Ile Lys Asp Asp Glu Thr Glu Asn Ile Leu Thr Val
1425                1430                1435                1440

Leu Leu Lys Thr Ala Leu Leu Ile Val Ser Gly Ile Phe Pro Tyr Ser
                1445                1450                1455

Ile Pro Ala Thr Leu Leu Val Trp His Thr Trp Gln Lys Gln Thr Gln
                1460                1465                1470

Arg Ser Gly Val Leu Trp Asp Val Pro Ser Pro Glu Thr Gln Lys
        1475                1480                1485

Ala Glu Leu Glu Glu Gly Val Tyr Arg Ile Lys Gln Gln Gly Ile Phe
        1490                1495                1500

Gly Lys Thr Gln Val Gly Val Gly Val Gln Lys Glu Gly Val Phe His
1505                1510                1515                1520
```

```
Thr Met Trp His Val Thr Arg Gly Ala Val Leu Thr His Asn Gly Lys
            1525                1530                1535

Arg Leu Glu Pro Asn Trp Ala Ser Val Lys Lys Asp Leu Ile Ser Tyr
            1540                1545                1550

Gly Gly Gly Trp Lys Leu Ser Ala Gln Trp Gln Lys Gly Glu Val
        1555                1560                1565

Gln Val Ile Ala Val Glu Pro Gly Lys Asn Pro Lys Asn Phe Gln Thr
        1570                1575                1580

Met Pro Gly Ile Phe Gln Thr Thr Gly Glu Ile Gly Ala Ile Ala
1585                1590                1595                1600

Leu Asp Phe Lys Pro Gly Thr Ser Gly Ser Pro Ile Ile Asn Arg Glu
            1605                1610                1615

Gly Lys Val Leu Gly Leu Tyr Gly Asn Gly Val Val Thr Lys Asn Gly
        1620                1625                1630

Gly Tyr Val Ser Gly Ile Ala Gln Thr Asn Ala Glu Pro Asp Gly Pro
        1635                1640                1645

Thr Pro Glu Leu Glu Glu Glu Met Phe Lys Lys Arg Asn Leu Thr Ile
        1650                1655                1660

Met Asp Leu His Pro Gly Ser Gly Lys Thr Arg Lys Tyr Leu Pro Ala
1665                1670                1675                1680

Ile Val Arg Glu Ala Ile Lys Arg Arg Leu Arg Thr Leu Ile Leu Ala
            1685                1690                1695

Pro Thr Arg Val Val Ala Ala Glu Met Glu Glu Ala Leu Lys Gly Leu
        1700                1705                1710

Pro Ile Arg Tyr Gln Thr Thr Ala Thr Lys Ser Glu His Thr Gly Arg
        1715                1720                1725

Glu Ile Val Asp Leu Met Cys His Ala Thr Phe Thr Met Arg Leu Leu
        1730                1735                1740

Ser Pro Val Arg Val Pro Asn Tyr Asn Leu Ile Ile Met Asp Glu Ala
1745                1750                1755                1760

His Phe Thr Asp Pro Ala Ser Ile Ala Ala Arg Gly Tyr Ile Ser Thr
            1765                1770                1775

Arg Val Gly Met Gly Glu Ala Ala Ala Ile Phe Met Thr Ala Thr Pro
        1780                1785                1790

Pro Gly Thr Ala Asp Ala Phe Pro Gln Ser Asn Ala Pro Ile Gln Asp
        1795                1800                1805

Glu Glu Arg Asp Ile Pro Glu Arg Ser Trp Asn Ser Gly Asn Glu Trp
        1810                1815                1820

Ile Thr Asp Phe Ala Gly Lys Thr Val Trp Phe Val Pro Ser Ile Lys
1825                1830                1835                1840

Ala Gly Asn Asp Ile Ala Asn Cys Leu Arg Lys Asn Gly Lys Lys Val
            1845                1850                1855

Ile Gln Leu Ser Arg Lys Thr Phe Asp Thr Glu Tyr Gln Lys Thr Lys
        1860                1865                1870

Leu Asn Asp Trp Asp Phe Val Val Thr Thr Asp Ile Ser Glu Met Gly
        1875                1880                1885

Ala Asn Phe Lys Ala Asp Arg Val Ile Asp Pro Arg Arg Cys Leu Lys
        1890                1895                1900

Pro Val Ile Leu Thr Asp Gly Pro Glu Arg Val Ile Leu Ala Gly Pro
1905                1910                1915                1920

Met Pro Val Thr Val Ala Ser Ala Ala Gln Arg Arg Gly Arg Val Gly
            1925                1930                1935
```

-continued

```
Arg Asn Pro Gln Lys Glu Asn Asp Gln Tyr Ile Phe Met Gly Gln Pro
            1940                1945                1950

Leu Asn Asn Asp Glu Asp His Ala His Trp Thr Glu Ala Lys Met Leu
            1955                1960                1965

Leu Asp Asn Ile Asn Thr Pro Glu Gly Ile Ile Pro Ala Leu Phe Glu
            1970                1975                1980

Pro Glu Arg Glu Lys Ser Ala Ala Ile Asp Gly Glu Tyr Arg Leu Lys
1985                1990                1995                2000

Gly Glu Ser Arg Lys Thr Phe Val Glu Leu Met Arg Arg Gly Asp Leu
            2005                2010                2015

Pro Val Trp Leu Ala His Lys Val Ala Ser Glu Gly Ile Lys Tyr Thr
            2020                2025                2030

Asp Arg Lys Trp Cys Phe Asp Gly Glu Arg Asn Asn Gln Ile Leu Glu
            2035                2040                2045

Glu Asn Met Asp Val Glu Ile Trp Thr Lys Glu Gly Glu Lys Lys Lys
            2050                2055                2060

Leu Arg Pro Arg Trp Leu Asp Ala Arg Thr Tyr Ser Asp Pro Leu Ala
2065                2070                2075                2080

Leu Lys Glu Phe Lys Asp Phe Ala Ala Gly Arg Lys Ser Ile Ala Leu
            2085                2090                2095

Asp Leu Val Thr Glu Ile Gly Arg Val Pro Ser His Leu Ala His Arg
            2100                2105                2110

Thr Arg Asn Ala Leu Asp Asn Leu Val Met Leu His Thr Ser Glu His
            2115                2120                2125

Gly Gly Arg Ala Tyr Arg His Ala Val Glu Glu Leu Pro Glu Thr Met
            2130                2135                2140

Glu Thr Leu Leu Leu Leu Gly Leu Met Ile Leu Leu Thr Gly Gly Ala
2145                2150                2155                2160

Met Leu Phe Leu Ile Ser Gly Lys Gly Ile Gly Lys Thr Ser Ile Gly
            2165                2170                2175

Leu Ile Cys Val Ala Ala Ser Ser Gly Met Leu Trp Met Ala Asp Val
            2180                2185                2190

Pro Leu Gln Trp Ile Ala Ser Ala Ile Val Leu Glu Phe Phe Met Met
            2195                2200                2205

Val Leu Leu Ile Pro Glu Pro Glu Lys Gln Arg Thr Pro Gln Asp Asn
            2210                2215                2220

Gln Leu Ala Tyr Val Val Ile Gly Ile Leu Thr Leu Ala Ala Ile Val
2225                2230                2235                2240

Ala Ala Asn Glu Met Gly Leu Leu Glu Thr Thr Lys Arg Asp Leu Gly
            2245                2250                2255

Met Ser Lys Glu Pro Gly Val Val Ser Pro Thr Ser Tyr Leu Asp Val
            2260                2265                2270

Asp Leu His Pro Ala Ser Ala Trp Thr Leu Tyr Ala Val Ala Thr Thr
            2275                2280                2285

Val Ile Thr Pro Met Leu Arg His Thr Ile Glu Asn Ser Thr Ala Asn
            2290                2295                2300

Val Ser Leu Ala Ala Ile Ala Asn Gln Ala Val Val Leu Met Gly Leu
2305                2310                2315                2320

Asp Lys Gly Trp Pro Ile Ser Lys Met Asp Leu Gly Val Pro Leu Leu
            2325                2330                2335

Ala Leu Gly Cys Tyr Ser Gln Val Asn Pro Leu Thr Leu Thr Ala Ala
            2340                2345                2350
```

```
Val Leu Leu Leu Val Thr His Tyr Ala Ile Ile Gly Pro Gly Leu Gln
            2355                2360                2365

Ala Lys Ala Thr Arg Glu Ala Gln Lys Arg Thr Ala Ala Gly Ile Met
            2370                2375                2380

Lys Asn Pro Thr Val Asp Gly Ile Met Thr Ile Asp Leu Asp Pro Val
2385                2390                2395                2400

Ile Tyr Asp Ser Lys Phe Glu Lys Gln Leu Gly Gln Val Met Leu Leu
            2405                2410                2415

Val Leu Cys Ala Val Gln Leu Leu Met Arg Thr Ser Trp Ala Phe
            2420                2425                2430

Cys Glu Ala Leu Thr Leu Ala Thr Gly Pro Ile Thr Thr Leu Trp Glu
            2435                2440                2445

Gly Ser Pro Gly Lys Phe Trp Asn Thr Thr Ile Ala Val Ser Met Ala
            2450                2455                2460

Asn Ile Phe Arg Gly Ser Tyr Leu Ala Gly Ala Gly Leu Ala Phe Ser
2465                2470                2475                2480

Ile Met Lys Ser Val Gly Thr Gly Lys Arg Gly Thr Gly Ser Gln Gly
            2485                2490                2495

Glu Thr Leu Gly Glu Lys Trp Lys Lys Lys Leu Asn Gln Leu Pro Arg
            2500                2505                2510

Lys Glu Phe Asp Leu Tyr Lys Lys Ser Gly Ile Thr Glu Val Asp Arg
            2515                2520                2525

Thr Glu Ala Lys Glu Gly Leu Lys Arg Gly Glu Ile Thr His His Ala
            2530                2535                2540

Val Ser Arg Gly Ser Ala Lys Leu Gln Trp Phe Val Glu Arg Asn Met
2545                2550                2555                2560

Val Ile Pro Glu Gly Arg Val Ile Asp Leu Gly Cys Gly Arg Gly Gly
            2565                2570                2575

Trp Ser Tyr Tyr Cys Ala Gly Leu Lys Lys Val Thr Glu Val Arg Gly
            2580                2585                2590

Tyr Thr Lys Gly Gly Pro Gly His Glu Glu Pro Val Pro Met Ser Thr
            2595                2600                2605

Tyr Gly Trp Asn Ile Val Lys Leu Met Ser Gly Lys Asp Val Phe Tyr
            2610                2615                2620

Leu Pro Pro Glu Lys Cys Asp Thr Leu Leu Cys Asp Ile Gly Glu Ser
2625                2630                2635                2640

Ser Pro Ser Pro Thr Val Glu Glu Ser Arg Thr Ile Arg Val Leu Lys
            2645                2650                2655

Met Val Glu Pro Trp Leu Lys Asn Asn Gln Phe Cys Ile Lys Val Leu
            2660                2665                2670

Asn Pro Tyr Met Pro Thr Val Ile Glu His Leu Glu Arg Leu Gln Arg
            2675                2680                2685

Lys His Gly Gly Met Leu Val Arg Asn Pro Leu Ser Arg Asn Ser Thr
            2690                2695                2700

His Glu Met Tyr Trp Ile Ser Asn Gly Thr Gly Asn Ile Val Ser Ser
2705                2710                2715                2720

Val Asn Met Val Ser Arg Leu Leu Leu Asn Arg Phe Thr Met Thr His
            2725                2730                2735

Arg Arg Pro Thr Ile Glu Lys Asp Val Asp Leu Gly Ala Gly Thr Arg
            2740                2745                2750

His Val Asn Ala Glu Pro Glu Thr Pro Asn Met Asp Val Ile Gly Glu
            2755                2760                2765
```

-continued

```
Arg Ile Arg Arg Ile Lys Glu Glu His Ser Ser Thr Trp His Tyr Asp
    2770                2775                2780

Asp Glu Asn Pro Tyr Lys Thr Trp Ala Tyr His Gly Ser Tyr Glu Val
2785                2790                2795                2800

Lys Ala Thr Gly Ser Ala Ser Ser Met Ile Asn Gly Val Val Lys Leu
                2805                2810                2815

Leu Thr Lys Pro Trp Asp Val Val Pro Met Val Thr Gln Met Ala Met
            2820                2825                2830

Thr Asp Thr Thr Pro Phe Gly Gln Gln Arg Val Phe Lys Glu Lys Val
        2835                2840                2845

Asp Thr Arg Thr Pro Arg Pro Met Pro Gly Thr Arg Lys Val Met Glu
    2850                2855                2860

Ile Thr Ala Glu Trp Leu Trp Arg Thr Leu Gly Arg Asn Lys Arg Pro
2865                2870                2875                2880

Arg Leu Cys Thr Arg Glu Glu Phe Thr Lys Lys Val Arg Thr Asn Ala
                2885                2890                2895

Ala Met Gly Ala Val Phe Thr Glu Glu Asn Gln Trp Asp Ser Ala Arg
            2900                2905                2910

Ala Ala Val Glu Asp Glu Glu Phe Trp Lys Leu Val Asp Arg Glu Arg
        2915                2920                2925

Glu Leu His Lys Leu Gly Lys Cys Gly Ser Cys Val Tyr Asn Met Met
    2930                2935                2940

Gly Lys Arg Glu Lys Lys Leu Gly Glu Phe Gly Lys Ala Lys Gly Ser
2945                2950                2955                2960

Arg Ala Ile Trp Tyr Met Trp Leu Gly Ala Arg Tyr Leu Glu Phe Glu
                2965                2970                2975

Ala Leu Gly Phe Leu Asn Glu Asp His Trp Phe Ser Arg Glu Asn Ser
            2980                2985                2990

Tyr Ser Gly Val Glu Gly Glu Gly Leu His Lys Leu Gly Tyr Ile Leu
        2995                3000                3005

Arg Asp Ile Ser Lys Ile Pro Gly Gly Ala Met Tyr Ala Asp Asp Thr
    3010                3015                3020

Ala Gly Trp Asp Thr Arg Ile Thr Glu Asp Asp Leu His Asn Glu Glu
3025                3030                3035                3040

Lys Ile Thr Gln Gln Met Asp Pro Glu His Arg Gln Leu Ala Asn Ala
                3045                3050                3055

Ile Phe Lys Leu Thr Tyr Gln Asn Lys Val Val Lys Val Gln Arg Pro
            3060                3065                3070

Thr Pro Lys Gly Thr Val Met Asp Ile Ile Ser Arg Lys Asp Gln Arg
        3075                3080                3085

Gly Ser Gly Gln Val Gly Thr Tyr Gly Leu Asn Thr Phe Thr Asn Met
    3090                3095                3100

Glu Ala Gln Leu Ile Arg Gln Met Glu Gly Glu Gly Val Leu Ser Lys
3105                3110                3115                3120

Ala Asp Leu Glu Asn Pro His Leu Leu Glu Lys Lys Val Thr Gln Trp
                3125                3130                3135

Leu Glu Thr Lys Gly Val Glu Arg Leu Lys Arg Met Ala Ile Ser Gly
            3140                3145                3150

Asp Asp Cys Val Val Lys Pro Ile Asp Asp Arg Phe Ala Asn Ala Leu
        3155                3160                3165

Leu Ala Leu Asn Asp Met Gly Lys Val Arg Lys Asp Ile Pro Gln Trp
    3170                3175                3180
```

-continued

```
Gln Pro Ser Lys Gly Trp His Asp Trp Gln Gln Val Pro Phe Cys Ser
3185                3190                3195                3200

His His Phe His Glu Leu Ile Met Lys Asp Gly Arg Lys Leu Val Val
                3205                3210                3215

Pro Cys Arg Pro Gln Asp Glu Leu Ile Gly Arg Ala Arg Ile Ser Gln
            3220                3225                3230

Gly Ala Gly Trp Ser Leu Arg Glu Thr Ala Cys Leu Gly Lys Ala Tyr
        3235                3240                3245

Ala Gln Met Trp Thr Leu Met Tyr Phe His Arg Arg Asp Leu Arg Leu
    3250                3255                3260

Ala Ser Asn Ala Ile Cys Ser Ala Val Pro Val His Trp Val Pro Thr
3265                3270                3275                3280

Ser Arg Thr Thr Trp Ser Ile His Ala His His Gln Trp Met Thr Thr
                3285                3290                3295

Glu Asp Met Leu Thr Val Trp Asn Arg Val Trp Ile Glu Asp Asn Pro
            3300                3305                3310

Trp Met Glu Asp Lys Thr Pro Val Lys Thr Trp Glu Asp Val Pro Tyr
        3315                3320                3325

Leu Gly Lys Arg Glu Asp Gln Trp Cys Gly Ser Leu Ile Gly Leu Thr
    3330                3335                3340

Ser Arg Ala Thr Trp Ala Gln Asn Ile Leu Thr Ala Ile Gln Gln Val
3345                3350                3355                3360

Arg Ser Leu Ile Gly Asn Glu Glu Phe Leu Asp Tyr Met Pro Ser Met
                3365                3370                3375

Lys Arg Phe Arg Lys Glu Glu Glu Ser Glu Gly Ala Ile Trp
            3380                3385                3390
```

<210> SEQ ID NO 50
<211> LENGTH: 2426
<212> TYPE: DNA
<213> ORGANISM: Artificial Sequence
<220> FEATURE:
<223> OTHER INFORMATION: Dengue 1 CME chimeric region

<400> SEQUENCE: 50

```
agttgttagt ctgtgtggac cgacaaggac agttccaaat cggaagcttg cttaacacag     60
ttctaacagt ttgtttgaat agagagcaga tctctggaaa aatgaacaac caacggaaaa    120
agacgggtcg accgtctttc aatatgctga aacgcgcgag aaaccgcgtg tcaactggtt    180
cacagttggc gaagagattc tcaaaaggat tgctttcagg ccaaggaccc atgaaattgg    240
tgatggcttt catagcattt ctaagatttc tagccatacc cccaacagca ggaattttgg    300
ctagatggag ctcattcaag aagaatggag cgatcaaagt gttacggggt ttcaaaaaag    360
agatctcaag catgttgaac attatgaaca ggaggaaaaa atctgtgacc atgctcctca    420
tgctgctgcc cacagccctg gcgttccatt tgaccacacg agggggagag ccacacatga    480
tagttagtaa gcaggaaaga ggaaagtcac tgttgtttaa gacctctgca ggcatcaata    540
tgtgcactct cattgcgatg gatttgggag agttatgcga ggacacaatg acctacaaat    600
gcccccggat cactgaggcg gaaccagatg acgttgactg ctggtgcaat gccacagaca    660
catgggtgac ctatgggacg tgttctcaaa ccggcgaaca ccgacgagac aaacgttccg    720
tggcactggc cccacacgtg ggacttggtc tagaaacaag aaccgaaaca tggatgtcct    780
ctgaaggtgc ctggaaacaa gtacaaaaag tggagacttg ggctttgaga cacccaggat    840
tcacggtgac agcccttttt ttagcacatg ccataggaac atccattact cagaaaggga    900
```

-continued

```
tcattttcat tctgctgatg ctagtaacac catcaatggc catgcgatgt gtgggaatag    960
gcaacagaga cttcgttgaa ggactgtcag gagcaacgtg ggtggacgtg gtattggagc   1020
atggaagctg cgtcaccacc atggcaaaag ataaaccaac attggacatt gaactcttga   1080
agacggaggt cacaaaccct gccgtcttgc gcaaactgtg cattgaagct aaaatatcaa   1140
acaccaccac cgattcaagg tgtccaacac aaggagaggc tacactggtg gaagaacagg   1200
actcgaactt tgtgtgtcga cgaacgtttg tggacagagg ctggggtaat ggctgcggac   1260
tatttggaaa aggaagccta ctgacgtgtg ctaagttcaa gtgtgtgaca aaactagaag   1320
gaaagatagt tcaatatgaa aacttaaaat attcagtgat agtcactgtc cacactgggg   1380
accagcacca ggtgggaaac gagactacag aacatggaac aattgcaacc ataacacctc   1440
aagctcctac gtcggaaata cagctgactg actacggagc cctcacattg gactgctcgc   1500
ctagaacagg gctggacttt aatgagatgg ttctattgac aatgaaagaa aaatcatggc   1560
ttgtccacaa acaatggttt ctagacttac cactgccttg gacttcagga gcttcaacat   1620
ctcaagagac ttggaacaga caagatttgc tggtcacatt caagacagct catgcaaaga   1680
aacaggaagt agtcgtactg ggatcacagg aaggagcaat gcacactgcg ttgactgggg   1740
cgacagaaat ccagacgtca ggaacgacaa caatctttgc aggacacctg aaatgcagac   1800
taaaaatgga taaactgact ttaaaaggga tgtcatatgt aatgtgcaca ggctcattta   1860
agctagagaa ggaagtggct gagacccagc atggaactgt tttagtgcag gttaaatacg   1920
aaggaacaga tgcgccatgc aagatccctt tttcggccca agatgagaaa ggagtgaccc   1980
agaatgggag attgataaca gccaacccca tagtcactga caaagaaaaa ccagtcaaca   2040
ttgagacaga accacctttt ggtgagagct acatcgtggt aggggcaggt gaaaaagctt   2100
tgaaactgag ctggttcaag aaagggagca gcatagggaa aatgttcgaa gcaactgccc   2160
gaggagcgcg aaggatggct atcctgggag acaccgcatg ggactttggc tctataggag   2220
gagtgttcac atcagtggga aaattggtac accaggtttt tggagccgca tatggggttc   2280
tgttcagcgg tgtttcttgg accatgaaaa taggaatagg gattctgctg acatggctag   2340
gattaaactc gaggaacact tcaatggcta tgacgtgcat agctgttgga ggaatcactc   2400
tgtttctggg cttcacagtt caagca                                        2426
```

<210> SEQ ID NO 51
<211> LENGTH: 775
<212> TYPE: PRT
<213> ORGANISM: Artificial Sequence
<220> FEATURE:
<223> OTHER INFORMATION: Dengue 1 CME chimeric region

<400> SEQUENCE: 51

```
Met Asn Asn Gln Arg Lys Lys Thr Gly Arg Pro Ser Phe Asn Met Leu
 1               5                  10                  15

Lys Arg Ala Arg Asn Arg Val Ser Thr Gly Ser Gln Leu Ala Lys Arg
            20                  25                  30

Phe Ser Lys Gly Leu Leu Ser Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Ile Leu Ala Arg Trp Ser Ser Phe Lys Lys Asn Gly Ala Ile Lys Val
65                  70                  75                  80

Leu Arg Gly Phe Lys Lys Glu Ile Ser Ser Met Leu Asn Ile Met Asn
                85                  90                  95
```

-continued

```
Arg Arg Lys Lys Ser Val Thr Met Leu Leu Met Leu Leu Pro Thr Ala
            100                 105                 110
Leu Ala Phe His Leu Thr Thr Arg Gly Gly Glu Pro His Met Ile Val
        115                 120                 125
Ser Lys Gln Glu Arg Gly Lys Ser Leu Leu Phe Lys Thr Ser Ala Gly
    130                 135                 140
Ile Asn Met Cys Thr Leu Ile Ala Met Asp Leu Gly Glu Leu Cys Glu
145                 150                 155                 160
Asp Thr Met Thr Tyr Lys Cys Pro Arg Ile Thr Glu Ala Glu Pro Asp
                165                 170                 175
Asp Val Asp Cys Trp Cys Asn Ala Thr Asp Thr Trp Val Thr Tyr Gly
            180                 185                 190
Thr Cys Ser Gln Thr Gly Glu His Arg Arg Asp Lys Arg Ser Val Ala
        195                 200                 205
Leu Ala Pro His Val Gly Leu Gly Leu Glu Thr Arg Thr Glu Thr Trp
    210                 215                 220
Met Ser Ser Glu Gly Ala Trp Lys Gln Val Gln Lys Val Glu Thr Trp
225                 230                 235                 240
Ala Leu Arg His Pro Gly Phe Thr Val Thr Ala Leu Phe Leu Ala His
                245                 250                 255
Ala Ile Gly Thr Ser Ile Thr Gln Lys Gly Ile Ile Phe Ile Leu Leu
            260                 265                 270
Met Leu Val Thr Pro Ser Met Ala Met Arg Cys Val Gly Ile Gly Asn
        275                 280                 285
Arg Asp Phe Val Glu Gly Leu Ser Gly Ala Thr Trp Val Asp Val Val
    290                 295                 300
Leu Glu His Gly Ser Cys Val Thr Thr Met Ala Lys Asp Lys Pro Thr
305                 310                 315                 320
Leu Asp Ile Glu Leu Leu Lys Thr Glu Val Thr Asn Pro Ala Val Leu
                325                 330                 335
Arg Lys Leu Cys Ile Glu Ala Lys Ile Ser Asn Thr Thr Thr Asp Ser
            340                 345                 350
Arg Cys Pro Thr Gln Gly Glu Ala Thr Leu Val Glu Glu Gln Asp Ser
        355                 360                 365
Asn Phe Val Cys Arg Arg Thr Phe Val Asp Arg Gly Trp Gly Asn Gly
    370                 375                 380
Cys Gly Leu Phe Gly Lys Gly Ser Leu Leu Thr Cys Ala Lys Phe Lys
385                 390                 395                 400
Cys Val Thr Lys Leu Glu Gly Lys Ile Val Gln Tyr Glu Asn Leu Lys
                405                 410                 415
Tyr Ser Val Ile Val Thr Val His Thr Gly Asp Gln His Gln Val Gly
            420                 425                 430
Asn Glu Thr Thr Glu His Gly Thr Ile Ala Thr Ile Thr Pro Gln Ala
        435                 440                 445
Pro Thr Ser Glu Ile Gln Leu Thr Asp Tyr Gly Ala Leu Thr Leu Asp
    450                 455                 460
Cys Ser Pro Arg Thr Gly Leu Asp Phe Asn Glu Met Val Leu Leu Thr
465                 470                 475                 480
Met Lys Glu Lys Ser Trp Leu Val His Lys Gln Trp Phe Leu Asp Leu
                485                 490                 495
Pro Leu Pro Trp Thr Ser Gly Ala Ser Thr Ser Gln Glu Thr Trp Asn
            500                 505                 510
```

-continued

```
Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Ala Gln Asp Glu Lys Gly
    610                 615                 620

Val Thr Gln Asn Gly Arg Leu Ile Thr Ala Asn Pro Ile Val Thr Asp
625                 630                 635                 640

Lys Glu Lys Pro Val Asn Ile Glu Thr Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Val Gly Lys Leu Val His Gln Val Phe
705                 710                 715                 720

Gly Ala Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Met Ala Met Thr Cys Ile Ala Val Gly Gly Ile Thr Leu Phe
        755                 760                 765

Leu Gly Phe Thr Val Gln Ala
    770                 775

<210> SEQ ID NO 52
<211> LENGTH: 2423
<212> TYPE: DNA
<213> ORGANISM: Artificial Sequence
<220> FEATURE:
<223> OTHER INFORMATION: Dengue 1 ME chimeric region

<400> SEQUENCE: 52
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggaccctta cggatggtgc    240
tagcattcat cacgtttttg cgagtccttt ccatccccacc aacagcaggg attctgaaga    300
gatggggaca gttgaagaaa aataaggcca tcaagatact gattggattc aggaaggaga    360
taggccgcat gctgaacatc ttgaacggga gaaaaaggtc tgcagccatg ctcctcatgc    420
tgctgcccac agccctggcg ttccatttga ccacacgagg gggagagcca cacatgatag    480
ttagtaagca ggaaagagga aagtcactgt tgtttaagac ctctgcaggc atcaatatgt    540
```

-continued

```
gcactctcat tgcgatggat ttgggagagt tatgcgagga cacaatgacc tacaaatgcc      600
cccggatcac tgaggcggaa ccagatgacg ttgactgctg gtgcaatgcc acagacacat      660
gggtgaccta tggacgtgt tctcaaaccg gcgaacaccg acgagacaaa cgttccgtgg       720
cactggcccc acacgtggga cttggtctag aaacaagaac cgaaacatgg atgtcctctg      780
aaggtgcctg gaaacaagta caaaaagtgg agacttgggc tttgagacac ccaggattca      840
cggtgacagc cctttttta gcacatgcca taggaacatc cattactcag aaagggatca      900
ttttcattct gctgatgcta gtaacaccat caatggccat gcgatgtgtg ggaataggca      960
acagagactt cgttgaagga ctgtcaggag caacgtgggt ggacgtggta ttggagcatg     1020
gaagctgcgt caccaccatg gcaaaagata accaacatt ggacattgaa ctcttgaaga      1080
cggaggtcac aaaccctgcc gtcttgcgca aactgtgcat tgaagctaaa atatcaaaca     1140
ccaccaccga ttcaaggtgt ccaacacaag gagaggctac actggtggaa gaacaggact     1200
cgaactttgt gtgtcgacga acgttttgtgg acagaggctg gggtaatggc tgcggactat    1260
ttggaaaagg aagcctactg acgtgtgcta agttcaagtg tgtgacaaaa ctagaaggaa     1320
agatagttca atatgaaaac ttaaaatatt cagtgatagt cactgtccac actggggacc     1380
agcaccaggt gggaaacgag actacagaac atggaacaat tgcaaccata cacctcaag      1440 ctcctacgtc ggaaatacag ctgactgact acggagccct cacattggac tgctcgccta     1500
gaacagggct ggactttaat gagatggttc tattgacaat gaaagaaaaa tcatggcttg     1560
tccacaaaca atggtttcta gacttaccac tgccttggac ttcaggagct tcaacatctc     1620
aagagacttg gaacagacaa gatttgctgg tcacattcaa gacagctcat gcaaagaaac     1680
aggaagtagt cgtactggga tcacaggaag gagcaatgca cactgcgttg actggggcga     1740
cagaaatcca gacgtcagga acgacaacaa tctttgcagg acacctgaaa tgcagactaa     1800
aaatggataa actgacttta aagggatgt catatgtaat gtgcacaggc tcatttaagc     1860
tagagaagga agtggctgag acccagcatg gaactgtttt agtgcaggtt aaatacgaag     1920
gaacagatgc gccatgcaag atccctttt cggcccaaga tgagaaagga gtgacccaga     1980
atgggagatt gataacagcc aaccccatag tcactgacaa agaaaaacca gtcaacattg     2040
agacagaacc acctttggt gagagctaca tcgtggtagg ggcaggtgaa aaagctttga     2100
aactgagctg gttcaagaaa gggagcagca tagggaaaat gttcgaagca actgcccgag     2160
gagcgcgaag gatggctatc ctgggagaca ccgcatggga ctttggctct ataggaggag     2220
tgttcacatc agtgggaaaa ttggtacacc aggttttgg agccgcatat ggggttctgt      2280
tcagcggtgt ttcttggacc atgaaaatag aatagggat tctgctgaca tggctaggat     2340
taaactcgag gaacacttca atggctatga cgtgcatagc tgttggagga atcactctgt     2400
ttctgggctt cacagttcaa gca                                            2423
```

<210> SEQ ID NO 53
<211> LENGTH: 774
<212> TYPE: PRT
<213> ORGANISM: Artificial Sequence
<220> FEATURE:
<223> OTHER INFORMATION: Dengue 1 ME chimeric region
<400> SEQUENCE: 53

```
Met Asn Gln Arg Lys Lys Val Val Arg Pro Pro Phe Asn Met Leu Lys
 1               5                  10                  15

Arg Glu Arg Asn Arg Val Ser Thr Pro Gln Gly Leu Val Lys Arg Phe
            20                  25                  30
```

-continued

```
Ser Thr Gly Leu Phe Ser Gly Lys Gly Pro Leu Arg Met Val Leu Ala
            35                  40                  45

Phe Ile Thr Phe Leu Arg Val Leu Ser Ile Pro Pro Thr Ala Gly Ile
 50                  55                  60

Leu Lys Arg Trp Gly Gln Leu Lys Lys Asn Lys Ala Ile Lys Ile Leu
 65                  70                  75                  80

Ile Gly Phe Arg Lys Glu Ile Gly Arg Met Leu Asn Ile Leu Asn Gly
                     85                  90                  95

Arg Lys Arg Ser Ala Ala Met Leu Leu Met Leu Leu Pro Thr Ala Leu
                100                 105                 110

Ala Phe His Leu Thr Thr Arg Gly Gly Glu Pro His Met Ile Val Ser
            115                 120                 125

Lys Gln Glu Arg Gly Lys Ser Leu Leu Phe Lys Thr Ser Ala Gly Ile
            130                 135                 140

Asn Met Cys Thr Leu Ile Ala Met Asp Leu Gly Glu Leu Cys Glu Asp
145                 150                 155                 160

Thr Met Thr Tyr Lys Cys Pro Arg Ile Thr Glu Ala Glu Pro Asp Asp
                165                 170                 175

Val Asp Cys Trp Cys Asn Ala Thr Asp Thr Trp Val Thr Tyr Gly Thr
            180                 185                 190

Cys Ser Gln Thr Gly Glu His Arg Arg Asp Lys Arg Ser Val Ala Leu
            195                 200                 205

Ala Pro His Val Gly Leu Gly Leu Glu Thr Arg Thr Glu Thr Trp Met
            210                 215                 220

Ser Ser Glu Gly Ala Trp Lys Gln Val Gln Lys Val Glu Thr Trp Ala
225                 230                 235                 240

Leu Arg His Pro Gly Phe Thr Val Thr Ala Leu Phe Leu Ala His Ala
                245                 250                 255

Ile Gly Thr Ser Ile Thr Gln Lys Gly Ile Ile Phe Ile Leu Leu Met
            260                 265                 270

Leu Val Thr Pro Ser Met Ala Met Arg Cys Val Gly Ile Gly Asn Arg
            275                 280                 285

Asp Phe Val Glu Gly Leu Ser Gly Ala Thr Trp Val Asp Val Val Leu
290                 295                 300

Glu His Gly Ser Cys Val Thr Thr Met Ala Lys Asp Lys Pro Thr Leu
305                 310                 315                 320

Asp Ile Glu Leu Leu Lys Thr Glu Val Thr Asn Pro Ala Val Leu Arg
                325                 330                 335

Lys Leu Cys Ile Glu Ala Lys Ile Ser Asn Thr Thr Thr Asp Ser Arg
            340                 345                 350

Cys Pro Thr Gln Gly Glu Ala Thr Leu Val Glu Glu Gln Asp Ser Asn
            355                 360                 365

Phe Val Cys Arg Arg Thr Phe Val Asp Arg Gly Trp Gly Asn Gly Cys
            370                 375                 380

Gly Leu Phe Gly Lys Gly Ser Leu Leu Thr Cys Ala Lys Phe Lys Cys
385                 390                 395                 400

Val Thr Lys Leu Glu Gly Lys Ile Val Gln Tyr Glu Asn Leu Lys Tyr
                405                 410                 415

Ser Val Ile Val Thr Val His Thr Gly Asp Gln His Gln Val Gly Asn
            420                 425                 430

Glu Thr Thr Glu His Gly Thr Ile Ala Thr Ile Thr Pro Gln Ala Pro
            435                 440                 445
```

-continued

```
Thr Ser Glu Ile Gln Leu Thr Asp Tyr Gly Ala Leu Thr Leu Asp Cys
    450                 455                 460
Ser Pro Arg Thr Gly Leu Asp Phe Asn Glu Met Val Leu Leu Thr Met
465                 470                 475                 480
Lys Glu Lys Ser Trp Leu Val His Lys Gln Trp Phe Leu Asp Leu Pro
                485                 490                 495
Leu Pro Trp Thr Ser Gly Ala Ser Thr Ser Gln Glu Thr Trp Asn Arg
                500                 505                 510
Gln Asp Leu Leu Val Thr Phe Lys Thr Ala His Ala Lys Lys Gln Glu
            515                 520                 525
Val Val Val Leu Gly Ser Gln Glu Gly Ala Met His Thr Ala Leu Thr
        530                 535                 540
Gly Ala Thr Glu Ile Gln Thr Ser Gly Thr Thr Thr Ile Phe Ala Gly
545                 550                 555                 560
His Leu Lys Cys Arg Leu Lys Met Asp Lys Leu Thr Leu Lys Gly Met
                565                 570                 575
Ser Tyr Val Met Cys Thr Gly Ser Phe Lys Leu Glu Lys Glu Val Ala
                580                 585                 590
Glu Thr Gln His Gly Thr Val Leu Val Gln Val Lys Tyr Glu Gly Thr
            595                 600                 605
Asp Ala Pro Cys Lys Ile Pro Phe Ser Ala Gln Asp Glu Lys Gly Val
        610                 615                 620
Thr Gln Asn Gly Arg Leu Ile Thr Ala Asn Pro Ile Val Thr Asp Lys
625                 630                 635                 640
Glu Lys Pro Val Asn Ile Glu Thr Glu Pro Pro Phe Gly Glu Ser Tyr
                645                 650                 655
Ile Val Val Gly Ala Gly Glu Lys Ala Leu Lys Leu Ser Trp Phe Lys
                660                 665                 670
Lys Gly Ser Ser Ile Gly Lys Met Phe Glu Ala Thr Ala Arg Gly Ala
            675                 680                 685
Arg Arg Met Ala Ile Leu Gly Asp Thr Ala Trp Asp Phe Gly Ser Ile
        690                 695                 700
Gly Gly Val Phe Thr Ser Val Gly Lys Leu Val His Gln Val Phe Gly
705                 710                 715                 720
Ala Ala Tyr Gly Val Leu Phe Ser Gly Val Ser Trp Thr Met Lys Ile
                725                 730                 735
Gly Ile Gly Ile Leu Leu Thr Trp Leu Gly Leu Asn Ser Arg Asn Thr
                740                 745                 750
Ser Met Ala Met Thr Cys Ile Ala Val Gly Gly Ile Thr Leu Phe Leu
            755                 760                 765
Gly Phe Thr Val Gln Ala
    770
```

What is claimed is:

1. A tetravalent immunogenic composition comprising
a) a first attenuated virus that is immunogenic against dengue serotype 1,
b) a second attenuated virus that is immunogenic against dengue serotype 2,
c) a third attenuated virus that is immunogenic against dengue serotype 3, and
d) a fourth attenuated virus that is immunogenic against dengue serotype 4,
wherein each of a), b), c) and d) comprises a nucleic acid comprising i) a first nucleotide sequence encoding at least one structural protein from a first dengue virus,
ii) a second nucleotide sequence encoding nonstructural proteins from the first dengue virus or a second dengue virus, and
iii) a 3' untranslated region, wherein the 3' untranslated region contains a deletion of about 30 nucleotides corresponding to the TL2 stem-loop structure, and wherein both the 3' untranslated region and the second nucleotide sequence encoding nonstructural proteins are from either the first dengue virus or the second dengue virus;

wherein the tetravalent immunogenic composition is not rDEN1/4Δ30, rDEN2/4Δ30, rDEN3/4Δ30, rDEN4Δ30.

2. The tetravalent immunogenic composition of claim 1, wherein the nucleic acid of at least one of a), b), c) or d) further comprises a mutation that confers a phenotype wherein the phenotype is temperature sensitivity in Vero cells or the human liver cell line HuH-7, host-cell restriction in mosquito cells or the human liver cell line HuH-7, host-cell adaptation for improved replication in Vero cells, or attenuation in mice or monkeys.

3. The composition of claim 1, wherein the first nucleotide sequence encoding at least one structural protein and the second nucleotide sequence encoding nonstructural proteins of at least one of a), b), c) and d) are from the first dengue virus.

4. The composition of claim 3, wherein the deletion of a) is a deletion of about 30 nucleotides from the 3' untranslated region of the dengue type 1 genome corresponding to the TL2 stem-loop structure between about nucleotides 10562-10591.

5. The composition of claim 3, wherein the deletion of b) is a deletion of about 30 nucleotides from the 3' untranslated region of the dengue type 2 genome corresponding to the TL2 stem-loop structure between about nucleotides 10541-10570.

6. The composition of claim 3, wherein the deletion of c) is by a deletion of about 30 nucleotides from the 3' untranslated region of the dengue type 3 genome corresponding to the TL2 stem-loop structure between about nucleotides 10535-10565.

7. The composition of claim 3, herein the deletion of d) is a deletion of about 30 nucleotides from the 3' untranslated region of the dengue type 4 genome corresponding to the TL2 stem-loop structure between about nucleotides 10478-10507.

8. The composition of claim 1, wherein the first nucleotide sequence encoding at least one structural protein of at least one of a), b), c), and d) is from the first dengue virus and the second nucleotide sequence encoding nonstructural proteins of at least one of a), b), c), and d) is from the second dengue virus, wherein the serotype of the first dengue virus and the second dengue virus are different.

9. The composition of claim 8, wherein the serotype of the second dengue virus having the deletion is type 1.

10. The composition of claim 9, wherein the serotype of the first dengue virus of b) is type 2.

11. The composition of claim 9, wherein the serotype of the first dengue virus of c) is type 3.

12. The composition of claim 9, wherein the serotype of the first dengue virus of d) is type 4.

13. The composition of claim 9, wherein the first nucleotide sequence encodes at least two structural proteins of the first dengue virus.

14. The composition of claim 13, wherein the structural proteins are prM and E proteins.

15. The composition of claim 9, wherein the deletion of a) is a deletion of about 30 nucleotides from the 3' untranslated region of the dengue type 1 genome corresponding to the TL2 stem-loop structure between about nucleotides 10562 and 10591.

16. The composition of claim 8, wherein the serotype of the second dengue virus having the deletion is type 2.

17. The composition of claim 16, wherein the serotype of the first dengue virus of a) is type 1.

18. The composition of claim 16, wherein the serotype of the first dengue virus of c) is type 3.

19. The composition of claim 16, wherein the serotype of the first dengue of d) virus is type 4.

20. The composition of claim 16, wherein the first nucleotide sequence encodes at least two structural proteins of the first dengue virus.

21. The composition of claim 20, wherein the structural proteins are prM and E proteins.

22. The composition of claim 16, wherein the deletion is a deletion of about 30 nucleotides from the 3' untranslated region of the dengue type 2 genome corresponding to the TL2 stem-loop structure between about nucleotides 10541 and 10570.

23. The composition of claim 8, wherein the serotype of the second dengue virus having the deletion is type 3.

24. The composition of claim 23, wherein the serotype of the first dengue virus of a) is type 1.

25. The composition of claim 23, wherein the serotype of the first dengue virus of b) is type 2.

26. The composition of claim 23, wherein the serotype of the first dengue virus of d) is type 4.

27. The composition of claim 23, wherein the first nucleotide sequence encodes at least two structural proteins of the first dengue virus.

28. The composition of claim 27, wherein the structural proteins are prM and E proteins.

29. The composition of claim 23, wherein the deletion is a deletion of about 30 nucleotides from the 3' untranslated region of the dengue type 3 genome corresponding to the TL2 stem-loop structure between about nucleotides 10535 and 10565.

30. The composition of claim 8, wherein the serotype of the second dengue virus having the deletion is type 4.

31. The composition of claim 30, wherein the serotype of the first dengue virus of a) is type 1.

32. The composition of claim 30, wherein the serotype of the first dengue virus of b) is type 2.

33. The composition of claim 30, wherein the serotype of the first dengue virus of c) is type 3.

34. The composition of claim 30, wherein the first nucleotide sequence encodes at least two structural proteins of the first dengue virus.

35. The composition of claim 34, wherein the structural proteins are prM and E proteins.

36. The composition of claim 30, wherein the deletion is a deletion of about 30 nucleotides from the 3' untranslated region of the dengue type 4 genome corresponding to the TL2 stem-loop structure between about nucleotides 10478 and 10507.

37. A method of inducing an immune response in a subject comprising administering an effective amount of the composition of claim 1 to the subject.

38. The method of claim 37 wherein the subject is a human.

39. A tetravalent vaccine comprising the composition of claim 1.

40. A method of preventing disease caused by dengue virus in a subject comprising administering an effective amount of the vaccine of claim 39 to the subject.

41. The method of claim 40 wherein the subject is a human.

42. The tetravalent immunogenic composition defined in claim 1, selected from the group consisting of:

(1) rDEN1Δ30, rDEN2Δ30, rDEN3Δ30, rDEN4Δ30,
(2) rDEN1Δ30, rDEN2Δ30, rDEN3Δ30, rDEN4/1Δ30,
(3) rDEN1Δ30, rDEN2Δ30, rDEN3Δ30, rDEN4/2Δ30,
(4) rDEN1Δ30, rDEN2Δ30, rDEN3Δ30, rDEN4/3Δ30,
(5) rDEN1Δ30, rDEN2Δ30, rDEN3/1Δ30, rDEN4Δ30,
(6) rDEN1Δ30, rDEN2Δ30, rDEN3/1Δ30, rDEN4/1Δ30,
(7) rDEN1Δ30, rDEN2Δ30, rDEN3/1Δ30, rDEN4/2Δ30,
(8) rDEN1Δ30, rDEN2Δ30, rDEN3/1Δ30, rDEN4/3Δ30,
(9) rDEN1Δ30, rDEN2Δ30, rDEN3/2Δ30, rDEN4Δ30,

(10) rDEN1Δ30, rDEN2Δ30, rDEN3/2Δ30, rDEN4/1Δ30,
(11) rDEN1Δ30, rDEN2Δ30, rDEN3/2Δ30, rDEN4/2Δ30,
(12) rDEN1Δ30, rDEN2Δ30, rDEN3/2Δ30, rDEN4/3Δ30,
(13) rDEN1Δ30, rDEN2Δ30, rDEN3/4Δ30, rDEN4Δ30,
(14) rDEN1Δ30, rDEN2Δ30, rDEN3/4Δ30, rDEN4/1Δ30,
(15) rDEN1Δ30, rDEN2Δ30, rDEN3/4Δ30, rDEN4/2Δ30,
(16) rDEN1Δ30, rDEN2Δ30, rDEN3/4Δ30, rDEN4/3Δ30,
(17) rDEN1Δ30, rDEN2/1Δ30, rDEN3Δ30, rDEN4Δ30,
(18) rDEN1Δ30, rDEN2/1Δ30, rDEN3Δ30, rDEN4/1Δ30,
(19) rDEN1Δ30, rDEN2/1Δ30, rDEN3Δ30, rDEN4/2Δ30,
(20) rDEN1Δ30, rDEN2/1Δ30, rDEN3Δ30, rDEN4/3Δ30,
(21) rDEN1Δ30, rDEN2/1Δ30, rDEN3/1Δ30, rDEN4Δ30,
(22) rDEN1Δ30, rDEN2/1Δ30, rDEN3/1Δ30, rDEN4/1Δ30,
(23) rDEN1Δ30, rDEN2/1Δ30, rDEN3/1Δ30, rDEN4/2Δ30,
(24) rDEN1Δ30, rDEN2/1Δ30, rDEN3/1Δ30, rDEN4/3Δ30,
(25) rDEN1Δ30, rDEN2/1Δ30, rDEN3/2Δ30, rDEN4Δ30,
(26) rDEN1Δ30, rDEN2/1Δ30, rDEN3/2Δ30, rDEN4/1Δ30,
(27) rDEN1Δ30, rDEN2/1Δ30, rDEN3/2Δ30, rDEN4/2Δ30,
(28) rDEN1Δ30, rDEN2/1Δ30, rDEN3/2Δ30, rDEN4/3Δ30,
(29) rDEN1Δ30, rDEN2/1Δ30, rDEN3/4Δ30, rDEN4Δ30,
(30) rDEN1Δ30, rDEN2/1Δ30, rDEN3/4Δ30, rDEN4/1Δ30,
(31) rDEN1Δ30, rDEN2/1Δ30, rDEN3/4Δ30, rDEN4/2Δ30,
(32) rDEN1Δ30, rDEN2/1Δ30, rDEN3/4Δ30, rDEN4/3Δ30,
(33) rDEN1Δ30, rDEN2/3Δ30, rDEN3Δ30, rDEN4Δ30,
(34) rDEN1Δ30, rDEN2/3Δ30, rDEN3Δ30, rDEN4/1Δ30,
(35) rDEN1Δ30, rDEN2/3Δ30, rDEN3Δ30, rDEN4/2Δ30,
(36) rDEN1Δ30, rDEN2/3Δ30, rDEN3Δ30, rDEN4/3Δ30,
(37) rDEN1Δ30, rDEN2/3Δ30, rDEN3/1Δ30, rDEN4Δ30,
(38) rDEN1Δ30, rDEN2/3Δ30, rDEN3/1Δ30, rDEN4/1Δ30,
(39) rDEN1Δ30, rDEN2/3Δ30, rDEN3/1Δ30, rDEN4/2Δ30,
(40) rDEN1Δ30, rDEN2/3Δ30, rDEN3/1Δ30, rDEN4/3Δ30,
(41) rDEN1Δ30, rDEN2/3Δ30, rDEN3/2Δ30, rDEN4Δ30,
(42) rDEN1Δ30, rDEN2/3Δ30, rDEN3/2Δ30, rDEN4/1Δ30,
(43) rDEN1Δ30, rDEN2/3Δ30, rDEN3/2Δ30, rDEN4/2Δ30,
(44) rDEN1Δ30, rDEN2/3Δ30, rDEN3/2Δ30, rDEN4/3Δ30,
(45) rDEN1Δ30, rDEN2/3Δ30, rDEN3/4Δ30, rDEN4Δ30,
(46) rDEN1Δ30, rDEN2/3Δ30, rDEN3/4Δ30, rDEN4/1Δ30,
(47) rDEN1Δ30, rDEN2/3Δ30, rDEN3/4Δ30, rDEN4/2Δ30,
(48) rDEN1Δ30, rDEN2/3Δ30, rDEN3/4Δ30, rDEN4/3Δ30,
(49) rDEN1Δ30, rDEN2/4Δ30, rDEN3Δ30, rDEN4Δ30,
(50) rDEN1Δ30, rDEN2/4Δ30, rDEN3Δ30, rDEN4/1Δ30,
(51) rDEN1Δ30, rDEN2/4Δ30, rDEN3Δ30, rDEN4/2Δ30,
(52) rDEN1Δ30, rDEN2/4Δ30, rDEN3Δ30, rDEN4/3Δ30,
(53) rDEN1Δ30, rDEN2/4Δ30, rDEN3/1Δ30, rDEN4Δ30,
(54) rDEN1Δ30, rDEN2/4Δ30, rDEN3/1Δ30, rDEN4/1Δ30,
(55) rDEN1Δ30, rDEN2/4Δ30, rDEN3/1Δ30, rDEN4/2Δ30,

(56) rDEN1Δ30, rDEN2/4Δ30, rDEN3/1Δ30, rDEN4/3Δ30,
(57) rDEN1Δ30, rDEN2/4Δ30, rDEN3/2Δ30, rDEN4Δ30,
(58) rDEN1Δ30, rDEN2/4Δ30, rDEN3/2Δ30, rDEN4/1Δ30,
(59) rDEN1Δ30, rDEN2/4Δ30, rDEN3/2Δ30, rDEN4/2Δ30,
(60) rDEN1Δ30, rDEN2/4Δ30, rDEN3/2Δ30, rDEN4/3Δ30,
(61) rDEN1Δ30, rDEN2/4Δ30, rDEN3/4Δ30, rDEN4Δ30,
(62) rDEN1Δ30, rDEN2/4Δ30, rDEN3/4Δ30, rDEN4/1Δ30,
(63) rDEN1Δ30, rDEN2/4Δ30, rDEN3/4Δ30, rDEN4/2Δ30,
(64) rDEN1Δ30, rDEN2/4Δ30, rDEN3/4Δ30, rDEN4/3Δ30,
(65) rDEN1/2Δ30, rDEN2Δ30, rDEN3Δ30, rDEN4Δ30,
(66) rDEN1/2Δ30, rDEN2Δ30, rDEN3Δ30, rDEN4/1Δ30,
(67) rDEN1/2Δ30, rDEN2Δ30, rDEN3Δ30, rDEN4/2Δ30,
(68) rDEN1/2Δ30, rDEN2Δ30, rDEN3Δ30, rDEN4/3Δ30,
(69) rDEN1/2Δ30, rDEN2Δ30, rDEN3/1Δ30, rDEN4Δ30,
(70) rDEN1/2Δ30, rDEN2Δ30, rDEN3/1Δ30, rDEN4/1Δ30,
(71) rDEN1/2Δ30, rDEN2Δ30, rDEN3/1Δ30, rDEN4/2Δ30,
(72) rDEN1/2Δ30, rDEN2Δ30, rDEN3/1Δ30, rDEN4/3Δ30,
(73) rDEN1/2Δ30, rDEN2Δ30, rDEN3/2Δ30, rDEN4Δ30,
(74) rDEN1/2Δ30, rDEN2Δ30, rDEN3/2Δ30, rDEN4/1Δ30,
(75) rDEN1/2Δ30, rDEN2Δ30, rDEN3/2Δ30, rDEN4/2Δ30,
(76) rDEN1/2Δ30, rDEN2Δ30, rDEN3/2Δ30, rDEN4/3Δ30,
(77) rDEN1/2Δ30, rDEN2Δ30, rDEN3/4Δ30, rDEN4Δ30,
(78) rDEN1/2Δ30, rDEN2Δ30, rDEN3/4Δ30, rDEN4/1Δ30,
(79) rDEN1/2Δ30, rDEN2Δ30, rDEN3/4Δ30, rDEN4/2Δ30,
(80) rDEN1/2Δ30, rDEN2Δ30, rDEN3/4Δ30, rDEN4/3Δ30,
(81) rDEN1/2Δ30, rDEN2/1Δ30, rDEN3Δ30, rDEN4Δ30,
(82) rDEN1/2Δ30, rDEN2/1Δ30, rDEN3Δ30, rDEN4/1Δ30,
(83) rDEN1/2Δ30, rDEN2/1Δ30, rDEN3Δ30, rDEN4/2Δ30,
(84) rDEN1/2Δ30, rDEN2/1Δ30, rDEN3Δ30, rDEN4/3Δ30,
(85) rDEN1/2Δ30, rDEN2/1Δ30, rDEN3/1Δ30, rDEN4Δ30,
(86) rDEN1/2Δ30, rDEN2/1Δ30, rDEN3/1Δ30, rDEN4/1Δ30,
(87) rDEN1/2Δ30, rDEN2/1Δ30, rDEN3/1Δ30, rDEN4/2Δ30,
(88) rDEN1/2Δ30, rDEN2/1Δ30, rDEN3/1Δ30, rDEN4/3Δ30,
(89) rDEN1/2Δ30, rDEN2/1Δ30, rDEN3/2Δ30, rDEN4Δ30,
(90) rDEN1/2Δ30, rDEN2/1Δ30, rDEN3/2Δ30, rDEN4/1Δ30,
(91) rDEN1/2Δ30, rDEN2/1Δ30, rDEN3/2Δ30, rDEN4/2Δ30,
(92) rDEN1/2Δ30, rDEN2/1Δ30, rDEN3/2Δ30, rDEN4/3Δ30,
(93) rDEN1/2Δ30, rDEN2/1Δ30, rDEN3/4Δ30, rDEN4Δ30,

(94) rDEN1/2Δ30, rDEN2/1Δ30, rDEN3/4Δ30, rDEN4/1Δ30,
(95) rDEN1/2Δ30, rDEN2/1Δ30, rDEN3/4Δ30, rDEN4/2Δ30,
(96) rDEN1/2Δ30, rDEN2/1Δ30, rDEN3/4Δ30, rDEN4/3Δ30,
(97) rDEN1/2Δ30, rDEN2/3Δ30, rDEN3Δ30, rDEN4Δ30,
(98) rDEN1/2Δ30, rDEN2/3Δ30, rDEN3Δ30, rDEN4/1Δ30,
(99) rDEN1/2Δ30, rDEN2/3Δ30, rDEN3Δ30, rDEN4/2Δ30,
(100) rDEN1/2Δ30, rDEN2/3Δ30, rDEN3Δ30, rDEN4/3Δ30,
(101) rDEN1/2Δ30, rDEN2/3Δ30, rDEN3/1Δ30, rDEN4Δ30,
(102) rDEN1/2Δ30, rDEN2/3Δ30, rDEN3/1Δ30, rDEN4/1Δ30,
(103) rDEN1/2Δ30, rDEN2/3Δ30, rDEN3/1Δ30, rDEN4/2Δ30,
(104) rDEN1/2Δ30, rDEN2/3Δ30, rDEN3/1Δ30, rDEN4/3Δ30,
(105) rDEN1/2Δ30, rDEN2/3Δ30, rDEN3/2Δ30, rDEN4Δ30,
(106) rDEN1/2Δ30, rDEN2/3Δ30, rDEN3/2Δ30, rDEN4/1Δ30,
(107) rDEN1/2Δ30, rDEN2/3Δ30, rDEN3/2Δ30, rDEN4/2Δ30,
(108) rDEN1/2Δ30, rDEN2/3Δ30, rDEN3/2Δ30, rDEN4/3Δ30,
(109) rDEN1/2Δ30, rDEN2/3Δ30, rDEN3/4Δ30, rDEN4Δ30,
(110) rDEN1/2Δ30, rDEN2/3Δ30, rDEN3/4Δ30, rDEN4/1Δ30,
(111) rDEN1/2Δ30, rDEN2/3Δ30, rDEN3/4Δ30, rDEN4/2Δ30,
(112) rDEN1/2Δ30, rDEN2/3Δ30, rDEN3/4Δ30, rDEN4/3Δ30,
(113) rDEN1/2Δ30, rDEN2/4Δ30, rDEN3Δ30, rDEN4Δ30,
(114) rDEN1/2Δ30, rDEN2/4Δ30, rDEN3Δ30, rDEN4/1Δ30,
(115) rDEN1/2Δ30, rDEN2/4Δ30, rDEN3Δ30, rDEN4/2Δ30,
(116) rDEN1/2Δ30, rDEN2/4Δ30, rDEN3Δ30, rDEN4/3Δ30,
(117) rDEN1/2Δ30, rDEN2/4Δ30, rDEN3/1Δ30, rDEN4Δ30,
(118) rDEN1/2Δ30, rDEN2/4Δ30, rDEN3/1Δ30, rDEN4/1Δ30,
(119) rDEN1/2Δ30, rDEN2/4Δ30, rDEN3/1Δ30, rDEN4/2Δ30,
(120) rDEN1/2Δ30, rDEN2/4Δ30, rDEN3/1Δ30, rDEN4/3Δ30,
(121) rDEN1/2Δ30, rDEN2/4Δ30, rDEN3/2Δ30, rDEN4Δ30,
(122) rDEN1/2Δ30, rDEN2/4Δ30, rDEN3/2Δ30, rDEN4/1Δ30,
(123) rDEN1/2Δ30, rDEN2/4Δ30, rDEN3/2Δ30, rDEN4/2Δ30,
(124) rDEN1/2Δ30, rDEN2/4Δ30, rDEN3/2Δ30, rDEN4/3Δ30,
(125) rDEN1/2Δ30, rDEN2/4Δ30, rDEN3/4Δ30, rDEN4Δ30,
(126) rDEN1/2Δ30, rDEN2/4Δ30, rDEN3/4Δ30, rDEN4/1Δ30,
(127) rDEN1/2Δ30, rDEN2/4Δ30, rDEN3/4Δ30, rDEN4/2Δ30, (128) rDEN1/2Δ30, rDEN2/4Δ30, rDEN3/4Δ30, rDEN4/3Δ30,
(129) rDEN1/3Δ30, rDEN2Δ30, rDEN3Δ30, rDEN4Δ30,
(130) rDEN1/3Δ30, rDEN2Δ30, rDEN3Δ30, rDEN4/1Δ30,
(131) rDEN1/3Δ30, rDEN2Δ30, rDEN3Δ30, rDEN4/2Δ30,
(132) rDEN1/3Δ30, rDEN2Δ30, rDEN3Δ30, rDEN4/3Δ30,
(133) rDEN1/3Δ30, rDEN2Δ30, rDEN3/1Δ30, rDEN4Δ30,
(134) rDEN1/3Δ30, rDEN2Δ30, rDEN3/1Δ30, rDEN4/1Δ30,
(135) rDEN1/3Δ30, rDEN2Δ30, rDEN3/1Δ30, rDEN4/2Δ30,
(136) rDEN1/3Δ30, rDEN2Δ30, rDEN3/1Δ30, rDEN4/3Δ30,
(137) rDEN1/3Δ30, rDEN2Δ30, rDEN3/2Δ30, rDEN4Δ30,
(138) rDEN1/3Δ30, rDEN2Δ30, rDEN3/2Δ30, rDEN4/1Δ30,
(139) rDEN1/3Δ30, rDEN2Δ30, rDEN3/2Δ30, rDEN4/2Δ30,
(140) rDEN1/3Δ30, rDEN2Δ30, rDEN3/2Δ30, rDEN4/3Δ30,
(141) rDEN1/3Δ30, rDEN2Δ30, rDEN3/4Δ30, rDEN4Δ30,
(142) rDEN1/3Δ30, rDEN2Δ30, rDEN3/4Δ30, rDEN4/1Δ30,
(143) rDEN1/3Δ30, rDEN2Δ30, rDEN3/4Δ30, rDEN4/2Δ30,
(144) rDEN1/3Δ30, rDEN2Δ30, rDEN3/4Δ30, rDEN4/3Δ30,
(145) rDEN1/3Δ30, rDEN2/1Δ30, rDEN3Δ30, rDEN4Δ30,
(146) rDEN1/3Δ30, rDEN2/1Δ30, rDEN3Δ30, rDEN4/1Δ30,
(147) rDEN1/3Δ30, rDEN2/1Δ30, rDEN3Δ30, rDEN4/2Δ30,
(148) rDEN1/3Δ30, rDEN2/1Δ30, rDEN3Δ30, rDEN4/3Δ30,
(149) rDEN1/3Δ30, rDEN2/1Δ30, rDEN3/1Δ30, rDEN4Δ30,
(150) rDEN1/3Δ30, rDEN2/1Δ30, rDEN3/1Δ30, rDEN4/1Δ30,
(151) rDEN1/3Δ30, rDEN2/1Δ30, rDEN3/1Δ30, rDEN4/2Δ30,
(152) rDEN1/3Δ30, rDEN2/1Δ30, rDEN3/1Δ30, rDEN4/3Δ30,
(153) rDEN1/3Δ30, rDEN2/1Δ30, rDEN3/2Δ30, rDEN4Δ30,
(154) rDEN1/3Δ30, rDEN2/1Δ30, rDEN3/2Δ30, rDEN4/1Δ30,
(155) rDEN1/3Δ30, rDEN2/1Δ30, rDEN3/2Δ30, rDEN4/2Δ30,
(156) rDEN1/3Δ30, rDEN2/1Δ30, rDEN3/2Δ30, rDEN4/3Δ30,
(157) rDEN1/3Δ30, rDEN2/1Δ30, rDEN3/4Δ30, rDEN4Δ30,
(158) rDEN1/3Δ30, rDEN2/1Δ30, rDEN3/4Δ30, rDEN4/1Δ30,
(159) rDEN1/3Δ30, rDEN2/1Δ30, rDEN3/4Δ30, rDEN4/2Δ30,
(160) rDEN1/3Δ30, rDEN2/1Δ30, rDEN3/4Δ30, rDEN4/3Δ30,
(161) rDEN1/3Δ30, rDEN2/3Δ30, rDEN3Δ30, rDEN4Δ30, (162) rDEN1/3Δ30, rDEN2/3Δ30, rDEN3Δ30, rDEN4/1Δ30,
(163) rDEN1/3Δ30, rDEN2/3Δ30, rDEN3Δ30, rDEN4/2Δ30,
(164) rDEN1/3Δ30, rDEN2/3Δ30, rDEN3Δ30, rDEN4/3Δ30,
(165) rDEN1/3Δ30, rDEN2/3Δ30, rDEN3/1Δ30, rDEN4Δ30,
(166) rDEN1/3Δ30, rDEN2/3Δ30, rDEN3/1Δ30, rDEN4/1Δ30,
(167) rDEN1/3Δ30, rDEN2/3Δ30, rDEN3/1Δ30, rDEN4/2Δ30,
(168) rDEN1/3Δ30, rDEN2/3Δ30, rDEN3/1Δ30, rDEN4/3Δ30,
(169) rDEN1/3Δ30, rDEN2/3Δ30, rDEN3/2Δ30, rDEN4Δ30,
(170) rDEN1/3Δ30, rDEN2/3Δ30, rDEN3/2Δ30, rDEN4/1Δ30,
(171) rDEN1/3Δ30, rDEN2/3Δ30, rDEN3/2Δ30, rDEN4/2Δ30,
(172) rDEN1/3Δ30, rDEN2/3Δ30, rDEN3/2Δ30, rDEN4/3Δ30,
(173) rDEN1/3Δ30, rDEN2/3Δ30, rDEN3/4Δ30, rDEN4Δ30,
(174) rDEN1/3Δ30, rDEN2/3Δ30, rDEN3/4Δ30, rDEN4/1Δ30,
(175) rDEN1/3Δ30, rDEN2/3Δ30, rDEN3/4Δ30, rDEN4/2Δ30,
(176) rDEN1/3Δ30, rDEN2/3Δ30, rDEN3/4Δ30, rDEN4/3Δ30,
(177) rDEN1/3Δ30, rDEN2/4Δ30, rDEN3Δ30, rDEN4Δ30,
(178) rDEN1/3Δ30, rDEN2/4Δ30, rDEN3Δ30, rDEN4/1Δ30,
(179) rDEN1/3Δ30, rDEN2/4Δ30, rDEN3Δ30, rDEN4/2Δ30,
(180) rDEN1/3Δ30, rDEN2/4Δ30, rDEN3Δ30, rDEN4/3Δ30,
(181) rDEN1/3Δ30, rDEN2/4Δ30, rDEN3/1Δ30, rDEN4Δ30,
(182) rDEN1/3Δ30, rDEN2/4Δ30, rDEN3/1Δ30, rDEN4/1Δ30,
(183) rDEN1/3Δ30, rDEN2/4Δ30, rDEN3/1Δ30, rDEN4/2Δ30,
(184) rDEN1/3Δ30, rDEN2/4Δ30, rDEN3/1Δ30, rDEN4/3Δ30,
(185) rDEN1/3Δ30, rDEN2/4Δ30, rDEN3/2Δ30, rDEN4Δ30,
(186) rDEN1/3Δ30, rDEN2/4Δ30, rDEN3/2Δ30, rDEN4/1Δ30,
(187) rDEN1/3Δ30, rDEN2/4Δ30, rDEN3/2Δ30, rDEN4/2Δ30,
(188) rDEN1/3Δ30, rDEN2/4Δ30, rDEN3/2Δ30, rDEN4/3Δ30,
(189) rDEN1/3Δ30, rDEN2/4Δ30, rDEN3/4Δ30, rDEN4Δ30,
(190) rDEN1/3Δ30, rDEN2/4Δ30, rDEN3/4Δ30, rDEN4/1Δ30,
(191) rDEN1/3Δ30, rDEN2/4Δ30, rDEN3/4Δ30, rDEN4/2Δ30,
(192) rDEN1/3Δ30, rDEN2/4Δ30, rDEN3/4Δ30, rDEN4/3Δ30,
(193) rDEN1/4Δ30, rDEN2Δ30, rDEN3Δ30, rDEN4Δ30,
(194) rDEN1/4Δ30, rDEN2Δ30, rDEN3Δ30, rDEN4/1Δ30,
(195) rDEN1/4Δ30, rDEN2Δ30, rDEN3Δ30, rDEN4/2Δ30,
(196) rDEN1/4Δ30, rDEN2Δ30, rDEN3Δ30, rDEN4/3Δ30,
(197) rDEN1/4Δ30, rDEN2Δ30, rDEN3/1Δ30, rDEN4Δ30,
(198) rDEN1/4Δ30, rDEN2Δ30, rDEN3/1Δ30, rDEN4/1Δ30,
(199) rDEN1/4Δ30, rDEN2Δ30, rDEN3/1Δ30, rDEN4/2Δ30,
(200) rDEN1/4Δ30, rDEN2Δ30, rDEN3/1Δ30, rDEN4/3Δ30,
(201) rDEN1/4Δ30, rDEN2Δ30, rDEN3/2Δ30, rDEN4Δ30,
(202) rDEN1/4Δ30, rDEN2Δ30, rDEN3/2Δ30, rDEN4/1Δ30,
(203) rDEN1/4Δ30, rDEN2Δ30, rDEN3/2Δ30, rDEN4/2Δ30,
(204) rDEN1/4Δ30, rDEN2Δ30, rDEN3/2Δ30, rDEN4/3Δ30,
(205) rDEN1/4Δ30, rDEN2Δ30, rDEN3/4Δ30, rDEN4Δ30,
(206) rDEN1/4Δ30, rDEN2Δ30, rDEN3/4Δ30, rDEN4/1Δ30,
(207) rDEN1/4Δ30, rDEN2Δ30, rDEN3/4Δ30, rDEN4/2Δ30,
(208) rDEN1/4Δ30, rDEN2Δ30, rDEN3/4Δ30, rDEN4/3Δ30,
(209) rDEN1/4Δ30, rDEN2/1Δ30, rDEN3Δ30, rDEN4Δ30,
(210) rDEN1/4Δ30, rDEN2/1Δ30, rDEN3Δ30, rDEN4/1Δ30,
(211) rDEN1/4Δ30, rDEN2/1Δ30, rDEN3Δ30, rDEN4/2Δ30,
(212) rDEN1/4Δ30, rDEN2/1Δ30, rDEN3Δ30, rDEN4/3Δ30,
(213) rDEN1/4Δ30, rDEN2/1Δ30, rDEN3/1Δ30, rDEN4Δ30,
(214) rDEN1/4Δ30, rDEN2/1Δ30, rDEN3/1Δ30, rDEN4/1Δ30,
(215) rDEN1/4Δ30, rDEN2/1Δ30, rDEN3/1Δ30, rDEN4/2Δ30,
(216) rDEN1/4Δ30, rDEN2/1Δ30, rDEN3/1Δ30, rDEN4/3Δ30,
(217) rDEN1/4Δ30, rDEN2/1Δ30, rDEN3/2Δ30, rDEN4Δ30,
(218) rDEN1/4Δ30, rDEN2/1Δ30, rDEN3/2Δ30, rDEN4/1Δ30,
(219) rDEN1/4Δ30, rDEN2/1Δ30, rDEN3/2Δ30, rDEN4/2Δ30,
(220) rDEN1/4Δ30, rDEN2/1Δ30, rDEN3/2Δ30, rDEN4/3Δ30,
(221) rDEN1/4Δ30, rDEN2/1Δ30, rDEN3/4Δ30, rDEN4Δ30,
(222) rDEN1/4Δ30, rDEN2/1Δ30, rDEN3/4Δ30, rDEN4/1Δ30,
(223) rDEN1/4Δ30, rDEN2/1Δ30, rDEN3/4Δ30, rDEN4/2Δ30,
(224) rDEN1/4Δ30, rDEN2/1Δ30, rDEN3/4Δ30, rDEN4/3Δ30,
(225) rDEN1/4Δ30, rDEN2/3Δ30, rDEN3Δ30, rDEN4Δ30,
(226) rDEN1/4Δ30, rDEN2/3Δ30, rDEN3Δ30, rDEN4/1Δ30,
(227) rDEN1/4Δ30, rDEN2/3Δ30, rDEN3Δ30, rDEN4/2Δ30,
(228) rDEN1/4Δ30, rDEN2/3Δ30, rDEN3Δ30, rDEN4/3Δ30, (229) rDEN1/4Δ30, rDEN2/3Δ30, rDEN3/1Δ30, rDEN4Δ30, (230) rDEN1/4Δ30, rDEN2/3Δ30, rDEN3/1Δ30, rDEN4/1Δ30, (231) rDEN1/4Δ30, rDEN2/3Δ30, rDEN3/1Δ30, rDEN4/2Δ30, (232) rDEN1/4Δ30, rDEN2/3Δ30, rDEN3/1Δ30, rDEN4/3Δ30, (233) rDEN1/4Δ30, rDEN2/3Δ30, rDEN3/2Δ30, rDEN4Δ30, (234) rDEN1/4Δ30, rDEN2/3Δ30, rDEN3/2Δ30, rDEN4/1Δ30, (235) rDEN1/4Δ30, rDEN2/3Δ30, rDEN3/2Δ30, rDEN4/2Δ30, (236) rDEN1/4Δ30, rDEN2/3Δ30, rDEN3/2Δ30, rDEN4/3Δ30, (237) rDEN1/4Δ30, rDEN2/3Δ30, rDEN3/4Δ30, rDEN4Δ30, (238) rDEN1/4Δ30, rDEN2/3Δ30, rDEN3/4Δ30, rDEN4/1Δ30, (239) rDEN1/4Δ30, rDEN2/3Δ30, rDEN3/4Δ30, rDEN4/2Δ30, (240) rDEN1/4Δ30, rDEN2/3Δ30, rDEN3/4Δ30, rDEN4/3Δ30, (241) rDEN1/4Δ30, rDEN2/4Δ30, rDEN3Δ30, rDEN4Δ30, (242) rDEN1/4Δ30, rDEN2/4Δ30, rDEN3Δ30, rDEN4/1Δ30, (243) rDEN1/4Δ30, rDEN2/4Δ30, rDEN3Δ30, rDEN4/2Δ30, (244) rDEN1/4Δ30, rDEN2/4Δ30, rDEN3Δ30, rDEN4/3Δ30, (245) rDEN1/4Δ30, rDEN2/4Δ30, rDEN3/1Δ30, rDEN4Δ30, (246) rDEN1/4Δ30, rDEN2/4Δ30, rDEN3/1Δ30, rDEN4/1Δ30, (247) rDEN1/4Δ30, rDEN2/4Δ30, rDEN3/1Δ30, rDEN4/2Δ30, (248) rDEN1/4Δ30, rDEN2/4Δ30, rDEN3/1Δ30, rDEN4/3Δ30, (249) rDEN1/4Δ30, rDEN2/4Δ30, rDEN3/2Δ30, rDEN4Δ30, (250) rDEN1/4Δ30, rDEN2/4Δ30, rDEN3/2Δ30, rDEN4/1Δ30, (251) rDEN1/4Δ30, rDEN2/4Δ30, rDEN3/2Δ30, rDEN4/2Δ30, (252) rDEN1/4Δ30, rDEN2/4Δ30, rDEN3/2Δ30, rDEN4/3Δ30, (254) rDEN1/4Δ30, rDEN2/4Δ30, rDEN3/4Δ30, rDEN4/1Δ30, (255) rDEN1/4Δ30, rDEN2/4Δ30, rDEN3/4Δ30, rDEN4/2Δ30, and (256) rDEN1/4Δ30, rDEN2/4Δ30, rDEN3/4Δ30, rDEN4/3Δ30.

* * * * *